United States Patent
Walder et al.

(10) Patent No.: US 10,227,641 B2
(45) Date of Patent: *Mar. 12, 2019

(54) RNASE H-BASED ASSAYS UTILIZING MODIFIED RNA MONOMERS

(71) Applicant: Integrated DNA Technologies, Inc., Coralville, IA (US)

(72) Inventors: Joseph Alan Walder, Chicago, IL (US); Mark Aaron Behlke, Coralville, IA (US); Scott D. Rose, Coralville, IA (US); Joseph R. Dobosy, Coralville, IA (US); Susan M. Rupp, Marion, IA (US)

(73) Assignee: INTEGRATED DNA TECHNOLOGIES, INC., Coralville, IA (US)

(*) Notice: Subject to any disclaimer, the term of this patent is extended or adjusted under 35 U.S.C. 154(b) by 342 days.

This patent is subject to a terminal disclaimer.

(21) Appl. No.: 14/123,944

(22) PCT Filed: Dec. 2, 2013

(86) PCT No.: PCT/US2013/072690
§ 371 (c)(1),
(2) Date: Apr. 24, 2015

(87) PCT Pub. No.: WO2014/143228
PCT Pub. Date: Sep. 18, 2014

(65) Prior Publication Data
US 2015/0307917 A1    Oct. 29, 2015

Related U.S. Application Data

(63) Continuation-in-part of application No. 13/959,637, filed on Aug. 5, 2013, now Pat. No. 9,644,198, which is a continuation-in-part of application No. 13/839,334, filed on Mar. 15, 2013, now abandoned, which is a continuation-in-part of application No. 12/507,142, filed on Jul. 22, 2009, now Pat. No. 8,911,948, which is a continuation-in-part of application No. 12/433,896, filed on Apr. 30, 2009, now abandoned.

(60) Provisional application No. 61/049,204, filed on Apr. 30, 2008.

(51) Int. Cl.
*C12P 19/34* (2006.01)
*C12Q 1/686* (2018.01)
*C12N 9/22* (2006.01)
*C12Q 1/6844* (2018.01)

(52) U.S. Cl.
CPC ............... *C12Q 1/686* (2013.01); *C12N 9/22* (2013.01); *C12Q 1/6844* (2013.01); *C12Y 301/26004* (2013.01)

(58) Field of Classification Search
CPC ............ C12Q 1/6844; C12Q 2521/327; C12Q 2525/186; C12Q 1/686; C12N 9/22; C12Y 301/26004
USPC ........................................................ 435/91.2
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 5,494,810 A | 2/1996 | Barany et al. |
| 5,677,152 A | 10/1997 | Birch et al. |
| 5,744,308 A | 4/1998 | Guillou-Bonnici et al. |
| 5,763,181 A | 6/1998 | Han et al. |
| 5,773,258 A | 6/1998 | Birch et al. |
| 5,830,664 A | 11/1998 | Rosemeyer et al. |
| 6,251,600 B1 * | 6/2001 | Winger ............... C07H 21/00 435/6.1 |
| 7,112,406 B2 | 9/2006 | Behlke et al. |
| 7,135,291 B2 | 11/2006 | Sagawa et al. |
| 2002/0132243 A1 * | 9/2002 | Callen ............... C12N 9/1252 435/6.1 |
| 2009/0068643 A1 | 3/2009 | Behlke et al. |
| 2010/0167353 A1 | 7/2010 | Walder et al. |

FOREIGN PATENT DOCUMENTS

| | | |
|---|---|---|
| EP | 1367136 | 12/2003 |
| WO | 9001069 | 2/1990 |
| WO | 0121813 | 3/2001 |
| WO | 0132887 A1 | 5/2001 |

(Continued)

OTHER PUBLICATIONS

Wu et al., "Properties of Cloned and Expressed Human RNase H1," J. Biol. Chem. 274:28270-28278 (1999).

(Continued)

*Primary Examiner* — Cynthia B Wilder
(74) *Attorney, Agent, or Firm* — Klintworth & Rosenblat IP LLP

(57) ABSTRACT

Methods and compositions are provided for improving specificity during amplification of a target DNA sequence. The methods and compositions rely upon the use of an RNase H enzyme, a polymerase, and RNase H enzyme-sensitive, blocked-cleavable oligonucleotide primers in the amplification reactions, wherein the reaction mixtures include either an optimized final concentration of a divalent metal salt comprising 2.0 mM or less of free $Mg^{++}$ cation and/or an optimized final concentration of a non-ionic detergent comprising at least about 0.001% polyethylene glycol hexadecyl ether.

55 Claims, 52 Drawing Sheets
Specification includes a Sequence Listing.

(56) References Cited

FOREIGN PATENT DOCUMENTS

| WO | 2004059012 | | 7/2004 |
|---|---|---|---|
| WO | 2006081426 | | 8/2006 |
| WO | 2007062495 | | 6/2007 |
| WO | 2009135093 | A2 | 11/2009 |
| WO | 2010065924 | A1 | 6/2010 |
| WO | 2011045744 | A2 | 4/2011 |
| WO | 2012135053 | A2 | 10/2012 |
| WO | 2013123238 | A1 | 8/2013 |
| WO | 2013142364 | A1 | 9/2013 |

OTHER PUBLICATIONS

Wu et al., "Investigating the Structure of Human RNase H1 by Site-directed Mutagenesis," J. Biol. Chem. 276:23547-23553 (2001).
Yazbeck et al., "Molecular requirements for degradation of a modified sense RNA strand by Escherichia coli ribonuclease H1," Nucleic Acids Res. 30:3015-3025 (2002).
Search report and written opinion from corresponding Singapore application No. 11201507512Q dated Sep. 5, 2016, 14 pages.
Communication from corresponding EP Application No. 13811693.4 dated Feb. 2, 2017, five pages.
Barany, "Genetic disease detection and DNA amplification using cloned thermostable ligase," Proc. Natl. Acad. Sci. 88:189-193 (1991).
Beaucage et al., "Deoxynucleoside Phosphoramidites—a New Class of Key Intermediates for Deoxypolynucleotide Synthesis," Tetrahedron lett. 22:1859-1862 (1981).
Brown et al., "Chemical Synthesis and Cloning of a Tyrosine tRNA Gene," Meth. Enzymol. 68:109-151 (1979).
Cariello et al., "Fidelity of Thermococcus litoralis DNA polymerase (Vent™) in PCR determined by denaturing gradient gel electrophoresis," Nucleic Acids Res. 19:4193-4198 (1991).
Cerritelli et al., "Cloning, Expression, and Mapping of Ribonucleases H of Human and Mouse Related to Bacterial RNase HI,"Genomics 53:300-307 (1998).
Chien et al., "Deoxyribonucleic Acid Polymerase from the Extreme Thermophile Thermus aquaticus," J. Bacteriol. 127(3):1550-1557 (1976).
Chou et al., "Prevention of pre-PCR mis-priming and primer dimerization improves low-copy-number amplifications," Nucl. Acids Res. 20(7):1717-1723 (1992).
Crooke et al., "Kinetic characterics of Excherichia coli RNase H1: cleavage of various antisense oligonucleotide—RNA duplexes," Biochem J. 312:599-608 (1995).
Diaz et al., "Accuracy of replication in the polymerase chain reaction. Comparison between Thermotoga maritima DNA polymerase and Thermus aquaticus DNA polymerase," Braz. J. Med. Res. 31:1239-1242 (1998).
Dobosy et al., "RNAse H-dependent PCR (rhPCR): improved specificity and single nucleotide polymorphism detection using blocked cleavable primers," BMC Biotechnology 11:80 (2011).
Eder et al., "Ribonuclease H from K562 Human Erythroleukemia Cells," J. Biol. Chem. 266:6472-6479 (1991).
Eder et al., "Substrate specificity of human RNase H1 and its role in excision repair of ribose residues misincorporated in DNA," Biochimie 75:123-126 (1993).
Federoff et al., "Structure of a DNA: RNA Hybrid Duplex Why RNase H Does Not Cleave Pure RNA," J. Mol. Biol. 233:509-523 (1993).
Goodchild et al., "Conjugates of oligonucleotides and modified oligonucleotides: a review of their synthesis and properties," Bioconjugate Chem. 1(3):165-187 (1990).
Haruki et al., "Gene Cloning and Characterization of Recombinant RNase HII from a Hyperthermophilic Archaean," J. Bacteriol. 180:6207-6214 (1998).
Hogrefe et al., "Kinetic Analysis of Escherichia coli RNase H Using DNA-RNA-DNA/DNA Substrates," J. Biol. Chem. 265:5561-5566 (1990).
Innis et al., eds., PCR Protocols: A Guide to Methods and Applications, "Optimization of PCRs," 1990.
Itaya, "Isolation and characterization of a second RNase H (RNase HII) of Escherichia coli K-12 encoded by the mhB gene," Proc. Natl. Acad. Sci. USA 87:8587-8591 (1990).
Kanaya, "Prokaryotic Type 2 RNases H," Methods Enzymol. 341:377-394 (2001).
Kataynagi et al., "Three-dimensional structure of ribonuclease H from E. coli," Nature 347:306-309 (1990).
Lai et al., "Crystal structure of archael RNase HIII: a homologue of human major RNase H," Structure 8:897-904 (2000).
Lai et al., "Metal Ion Binding and Enzymatic Mechanism of Methanococcus jannaschii RNase HII," Biochemistry 42:785-791 (2003).
Lecomte et al., "Selective inactivation of the 3' to 5' exonuclease activity of Escherichia coli DNA polymerase I by heat," Nucleic Acids Res. 11(21):7505-7515 (1983).
Lima et al., "Binding Affinity and Specificity of Escherichia coli RNase H1: Impact on the Kinetics of Catalysis of Antisense Oligonucleotide-RNA Hybrids," Biochemistry 36:390-398 (1997).
Lima et al., "The Influence of Antisense Oligonucleotide-induced RNA Strucgture on Escherichia coli RNase H1 Activity," J. Biol. Chem. 272:18191-18199 (1997).
Lima et al., "Cleavage of Single Strand RNA Adjacent to RNA-DNA Duplex Regions by Escherichia coli RNase H1," J. Biol. Chem. 272:27513-27516 (1997).
Lima et al., "Human RNase H1 Activity Is Regulated by a Unique Redox Switch Formed between Adjacent Cysteines," J. Biol. Chem. 278:14906-14912 (2003).
Lima et al., "Human RNase H1 Uses One Tryptophan and Two Lysines to Position to Enzyme at the 3'-DNA/5'—RNA Terminus of the Heteroduplex Substrate," J. Biol. Chem. 278:49860-49867 (2003).
Lima et al., "The Positional Influence of the Helical Geometry of the Heteroduplex Substrate on Human RNase H1 Catalysis," Mol. Pharmacol. 71:73-82 (2007).
Lima et al., "Human RNase H1 Discriminates between Subtle Variations in the Structure of the Heteroduplex Substrate," Mol. Pharmacol. 71:83-91 (2007).
Longo et al., "Short Communications: use of uracil DNA glycosylase to control carry-over contamination in polymerase chain reactions," Gene 93(1):125-128 (1990).
Lundberg et al., "High-fidelity amplification using a thermostable DNA polymerase isolated from Pyrococcus furiosus," Gene 108:1-6 (1991).
Mukaiyama et al., "Kinetically Robust Monomeric Protein from a Hyperthermophile," Biochemistry 43:13859-13866 (2004).
Myers et al., "Reverse Transcription and DNA Amplification by a Thermus thermophilus DNA Polymerase," biochemistry 30(31):7661-7666 (1991).
Nakamura et al., "How does RNase H recognize a DNA-RNA hybrid?," Proc. Natl. Acad. Sci. USA 88:11535-11539 (1991).
Narang et al., "Improved Phosphotriester Method for the Synthesis of Gene Fragments," Meth. Enzymol. 68:90-99 (1979).
Nordstrom et al., "Characterization of Bacteriophage T7 DNA Polymerase Purified to Homogeneity by Antithioredoxin Immunoadsorbent Chromatography," J. Biol. Chem. 256:3112-3117 (1981).
Ohtani et al., "Identification of the Genes Encoding Mn2+-Dependent RNase HII and Mg2+-Dependent RNase HIII from Bacillus subtilis: Classification of RNases H into Three Families," J. Biol. Chem. 256:3112, 1999.
Ohtani et al., "Molecular Diversities of RNases H," J. Biosci. Bioeng. 88:12-19 (1999).
Ohtani et al., "Characterization of Ribonuclease HIII from Escherichia coli Overproduced in a Soluble Form," J. Biochem. 127:895-899 (2000).
Ohtani et al., "Identification of the first archaeal Type 1 RNase H gene from Halobacterium sp. NRC-1: archaeal RNase H1 can cleave an RNA-DNA junction," Biochem J. 381:795-802 (2004).
Owczarzy et al., "Stability and Mismatch Discrimination of Locked Nucleic Acid-DNA Duplexes," Biochemistry 47:5336-5353 (2008).

(56) References Cited

OTHER PUBLICATIONS

Rys et al., "Preventing False Positives: Quantitative Evaluation of Three Protocols for Inactivation of Polymerase Chain Reaction Amplification Products," J. Clin. Microbiol. 31(9):2356-2360 (1993).
Sarkar et al., "Shedding light on PCR contamination," Nature 343:27 (1990).
Sato et al., "Cooperative regulation for Okazaki fragment processing by RNase HII and FEN-1 purified from a hyperthermophilic archaeon, Pyrococcus furiosus," Biochem. Biophys. Res. Commun. 309:247-252 (2003).
Stenesh et al., "DNA Polymerase from Mesophilic and Thermophilic Bacteria, III. Lack of Fidelity in the Replication of Synthetic Polydeoxyribonucleotides by DNA Polymerase from Bacillus Licheniformis and Bacillus Stearothermophilus," Biochim. Biophys. Acta. 475:32-41 (1977).
Takagi et al., "Characterization of DNA Polymerase from *Pyrococcus* sp. Strain KOD1 and its Application to PCR," Appl. Environ. Microbiol. 63:4504-4510 (1997).
Wetmur, "DNA Probes: Applications of the Principles of Nucleic Acid Hybridization," Critical Review in Biochem. and Mol. Biol. 26(3/4):227-259 (1991).
Wu et al., "The Ligation Amplification Reaction (LAR)—Amplification of Specific DNA Sequences Using Sequential Rounds of Template-Dependent Ligation," Genomics 4:560-569 (1989).
Wu et al., "Molecular Cloning and Express of cDNA for Human RNase H," Antisense Nucleic Acid Drug Dev. 8:53-61 (1998).
Itaya M. et al: "Molecular cloning of a ribonuclease H (RNase HI) gene from an extreme thermophile Thermus thermophilus HB8: a thermostable RNase H can functionally replace the *Escherichia coli* enzyme in vivo", Nucleic Acids Research Aug. 25, 1991, vol. 19, No. 16, pp. 4443-4449.
International Search Report and Written Opinion dated Feb. 17, 2014, 16 pages.

\* cited by examiner

A)
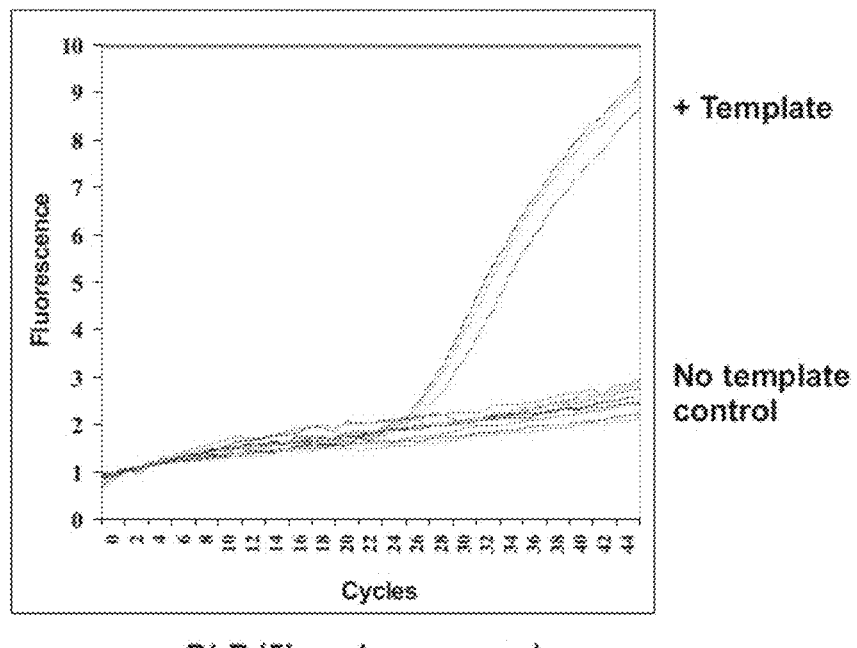
DLP (5'-nuclease assay)
B)
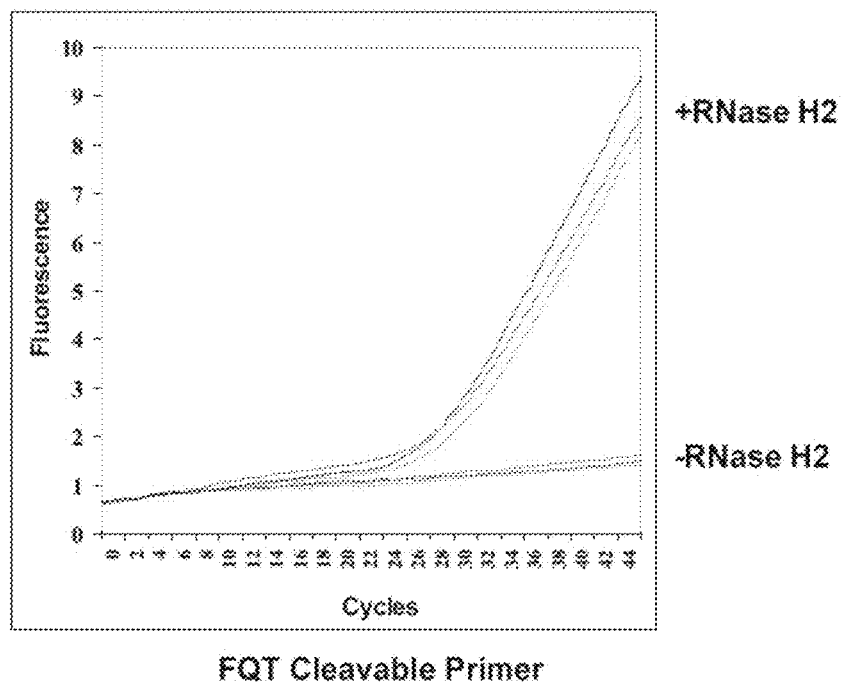
FQT Cleavable Primer
FIG. 32

SNP — Site of mutation in primer to cause "double mismatch"

SMAD7-For rC Series:

```
5'  CAGCCTCATCCAAAAGAGGAAAcAGGA-SpC3      3'
5'  CAGCCTCATCCAAAAGAGGAAAcAAGA-SpC3
5'  CAGCCTCATCCAAAAGAGGAAAcATGA-SpC3
5'  CAGCCTCATCCAAAAGAGGAAAcACGA-SpC3
    |||||||||||||||||||||||:|:||
3'  GTCGGAGTAGGTTTTCTCCTTTGTCCTGGGGTC... 5'  Target
                            A
```

SMAD7-For rU Series:

```
5'  CAGCCTCATCCAAAAGAGGAAAuAGGA-SpC3      3'
5'  CAGCCTCATCCAAAAGAGGAAAuAAGA-SpC3
5'  CAGCCTCATCCAAAAGAGGAAAuATGA-SpC3
5'  CAGCCTCATCCAAAAGAGGAAAuACGA-SpC3
    |||||||||||||||||||||||:|:||
3'  GTCGGAGTAGGTTTTCTCCTTTATCCTGGGGTC... 5'  Target
                            G
```

FIG. 33

8mer cleavable ligation probes   pAaGCTXXX-FAM
X = 5-nitroindole   pAaGCXXXX-FAM 5' CCCTGTTTGCTGTTTTTCCTTCTC
   ||||||||||||||||||||||||
3' GGGACAAACGACAAAAAGGAAGAGTTCGACTTCTCGTTTGTGA ↓ DNA Ligase 5' CCCTGTTTGCTGTTTTTCCTTCTCAaGCTXXX-FAM
   ||||||||||||||||||||||||||||||||
3' GGGACAAACGACAAAAAGGAAGAGATCGACTTCTCGTTTGTGA vs.

5' CCCTGTTTGCTGTTTTTCCTTCTCAaGCXXXX-FAM
   ||||||||||||||||||||||||||||||||
3' GGGACAAACGACAAAAAGGAAGAGATCGACTTCTCGTTTGTGA

FIG. 38

Traditional OLA Assay: 3 Oligos
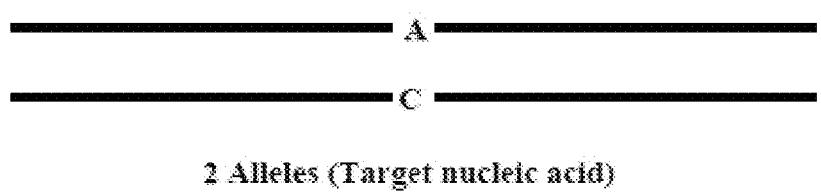
2 Alleles (Target nucleic acid)
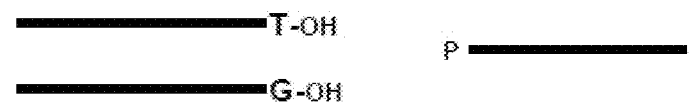
3 Synthetic Probe Oligos
Similar length / Tm
FIG. 41A

New RNase H2 OLA Assay: 4 Oligos
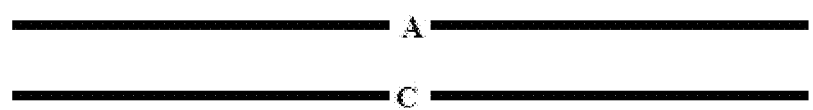
2 Alleles (Target nucleic acids)
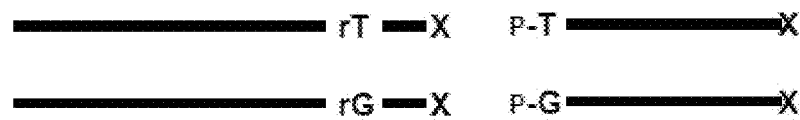
4 Synthetic Probe Oligos
Different length / Tm
FIG. 42A Single allele-specific blocked-cleavable primer, "For" orientation

RNASE H-BASED ASSAYS UTILIZING MODIFIED RNA MONOMERS

CROSS-REFERENCE TO RELATED APPLICATIONS

This application is the national stage entry of International Patent Application No. PCT/US13/72690, filed Dec. 2, 2013, which is a continuation in part of U.S. application Ser. No. 13/959,637 filed on Aug. 5, 2013, now U.S. Pat. No. 9,644,198, which is a continuation in part of U.S. application Ser. No. 13/839,334, filed Mar. 15, 2013, now abandoned, which is a continuation in part of U.S. application Ser. No. 12/507,142, filed Jul. 22, 2009, now U.S. Pat. No. 8,911,948, which is a continuation in part of U.S. application Ser. No. 12/433,896, filed Apr. 30, 2009, now abandoned, which claims benefit of priority to U.S. provisional application No. 61/049,204 filed on Apr. 30, 2008, which is incorporated by reference in its entirety.

SEQUENCE LISTING

The instant application contains a Sequence Listing which has been submitted in ASCII format via EFS-Web and is hereby incorporated by reference in its entirety. Said ASCII copy, created on Nov. 29, 2013, is named IDT01-004-PCT_ST25.txt, and is 101,119 bytes in size.

FIELD OF THE INVENTION

This invention pertains to methods of cleaving a nucleic acid strand to initiate, assist, monitor or perform biological assays.

BACKGROUND OF THE INVENTION

The specificity of primer-based amplification reactions, such as the polymerase chain reaction (PCR), largely depends on the specificity of primer hybridization with a DNA template. Under the elevated temperatures used in a typical amplification reaction, the primers ideally hybridize only to the intended target sequence and form primer extension products to produce the complement of the target sequence. However, amplification reaction mixtures are typically assembled at room temperature, well below the temperature needed to insure primer hybridization specificity. Under lower temperature conditions, the primers may bind non-specifically to other partially complementary nucleic acid sequences or to other primers and initiate the synthesis of undesired extension products, which can be amplified along with the target sequence. Amplification of non-specific primer extension products can compete with amplification of the desired target sequences and can significantly decrease the efficiency of the amplification of the desired sequence. Non-specific amplification can also give rise in certain assays to a false positive result.

One frequently observed type of non-specific amplification product in PCR is a template independent artifact of the amplification reaction known as "primer dimers". Primer dimers are double-stranded fragments whose length typically is close to the sum of the two primer lengths and are amplified when one primer is extended over another primer. The resulting duplex forms an undesired template which, because of its short length, is amplified efficiently.

Non-specific amplification can be reduced by reducing the formation of primer extension products (e.g., primer dimers) prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension at lower temperatures. Manual hot-start methods, in which the reaction tubes are opened after the initial high temperature incubation step and the missing reagents are added, are labor intensive and increase the risk of contamination of the reaction mixture.

Alternatively, a heat sensitive material, such as wax, can be used to separate or sequester reaction components, as described in U.S. Pat. No. 5,411,876, and Chou et al., 1992, Nucl. Acids Res. 20(7):1717-1723. In these methods, a high temperature pre-reaction incubation melts the heat sensitive material, thereby allowing the reagents to mix.

Another method of reducing the formation of primer extension products prior to the start of PCR relies on the heat-reversible inactivation of the DNA polymerase. U.S. Pat. Nos. 5,773,258 and 5,677,152, both incorporated herein by reference, describe DNA polymerases reversibly inactivated by the covalent attachment of a modifier group. Incubation of the inactivated DNA polymerase at high temperature results in cleavage of the modifier-enzyme bond, thereby releasing an active form of the enzyme. Non-covalent reversible inhibition of a DNA polymerase by DNA polymerase-specific antibodies is described in U.S. Pat. No. 5,338,671, incorporated herein by reference.

One objective of the present invention can be used, for example, to address the problem of carry-over cross contamination which is a significant concern in amplification reactions, especially PCR wherein a large number of copies of the amplified product are produced. In the prior art, attempts have been made to solve this problem in a number of ways. For example, direct UV irradiation can effectively remove contaminating DNA (Rys & Persing, 1993, J Clin Microbiol. 31(9):2356-60 and Sarkar & Sommer, 1990 Nature. 343(6253):27) but the irradiation of the PCR reagents must take place before addition of polymerase, primers, and template DNA. Furthermore, this approach may be inefficient because the large numbers of mononucleotides present in the reaction will absorb much of the UV light. An alternative, the "UNG method", incorporates dUTP into the amplified fragments to alter the composition of the product so that it is different from native, naturally occurring DNA (Longo et al. 1990, Gene, 93(1): 125-128). The enzyme Uracil-N-Glycosylase (UNG) is added together with the other components of the PCR mixture. The UNG enzyme will cleave the uracil base from DNA strands of contaminating amplicons before amplification, and render all such products unable to act as a template for new DNA synthesis without affecting the sample DNA. The UNG enzyme is then heat-inactivated and PCR is then carried out. The requirement for dUTP and the UNG enzyme adds significantly to the cost of performing PCR.

Another objective of the present invention is to provide PCR assays in which a hot-start reaction is achieved through a coupled reaction sequence with a thermostable RNase H.

Ribonuclease Enzymes

Ribonucleases (RNases) are enzymes that catalyze the hydrolysis of RNA into smaller components. The enzymes are present internally; in bodily fluids; on the surface of skin; and on the surface of many objects, including untreated laboratory glassware. Double-stranded RNases are present in nearly all intracellular environments and cleave RNA-containing, double-stranded constructs. Single-stranded RNases are ubiquitous in extracellular environments, and are therefore extremely stable in order to function under a wide range of conditions.

The RNases H are a conserved family of ribonucleases which are present in all organisms examined to date. There are two primary classes of RNase H: RNase H1 and RNase H2. Retroviral RNase H enzymes are similar to the prokaryotic RNase H1. All of these enzymes share the characteristic that they are able to cleave the RNA component of an RNA:DNA heteroduplex. The human and mouse RNase H1 genes are 78% identical at the amino acid level (Cerritelli, et al., (1998) *Genomics*, 53, 300-307). In prokaryotes, the genes are named rnha (RNase H1) and rnhb (RNase H2). A third family of prokaryotic RNases has been proposed, rnhc (RNase H3) (Ohtani, et al. (1999) *Biochemistry*, 38, 605-618).

Evolutionarily, "ancient" organisms (archaeal species) in some cases appear to have only a single RNase H enzyme which is most closely related to the modern RNase H2 enzymes (prokaryotic) (Ohtani, et al., *J Biosci Bioeng*, 88, 12-19). Exceptions do exist, and the archaeal *Halobacterium* has an RNase H1 ortholog (Ohtani, et al., (2004) *Biochem J*, 381, 795-802). An RNase H1 gene has also been identified in *Thermus thermophilus* (Itaya, et al., (1991) *Nucleic Acids Res*, 19, 4443-4449). RNase H2 enzymes appear to be present in all living organisms. Although all classes of RNase H enzymes hydrolyze the RNA component of an RNA:DNA heteroduplex, the substrate and co-factor requirements are different. For example, the Type II enzymes utilize $Mg^{++}$, $Mn^{++}$, $Co^{++}$ (and sometimes $Ni^{++}$) as cofactor, while the Type I enzymes require $Mg^{++}$ and can be inhibited by $Mn^{++}$ ions. The reaction products are the same for both classes of enzymes: the cleaved products have a 3'-OH and 5'-phosphate (See FIG. 1). RNase III class enzymes which cleave RNA:RNA duplexes (e.g., Dicer, Ago2, Drosha) result in similar products and contain a nuclease domain with similarity to RNase H. Most other ribonucleases, and in particular single stranded ribonucleases, result in a cyclic 2',3'-phosphate and 5'-OH products (see FIG. 2).

Type I RNase H

*E. coli* RNase H1 has been extensively characterized. A large amount of work on this enzyme has been carried out, focusing on characterization of substrate requirements as it impacts antisense oligonucleotide design; this has included studies on both the *E. coli* RNase H1 (see Crooke, et al., (1995) *Biochem J*, 312 (Pt 2), 599-608; Lima, et al., (1997) *J Biol Chem*, 272, 27513-27516; Lima, et al., (1997) *Biochemistry*, 36, 390-398; Lima, et al., (1997) *J Biol Chem*, 272, 18191-18199; Lima, et al., (2007) *Mol Pharmacol*, 71, 83-91; Lima, et al., (2007) *Mol Pharmacol*, 71, 73-82; Lima, et al., (2003) *J Biol Chem*, 278, 14906-14912; Lima, et al., (2003) *J Biol Chem*, 278, 49860-49867) and the Human RNase H1 (see Wu, et al., (1998) *Antisense Nucleic Acid Drug Dev*, 8, 53-61; Wu, et al., (1999) *J Biol Chem*, 274, 28270-28278; Wu, et al., (2001) *J Biol Chem*, 276, 23547-23553). In tissue culture, overexpression of human RNase H1 increases potency of antisense oligos (ASOs) while knockdown of RNase H1 using either siRNAs or ASOs decreases potency of antisense oligonucleotides.

Type I RNase H requires multiple RNA bases in the substrate for full activity. A DNA/RNA/DNA oligonucleotide (hybridized to a DNA oligonucleotide) with only 1 or 2 RNA bases is inactive. With *E. coli* RNase H1 substrates with three consecutive RNA bases show weak activity. Full activity was observed with a stretch of four RNA bases (Hogrefe, et al., (1990) *J Biol Chem*, 265, 5561-5566). An RNase H1 was cloned from *Thermus thermophilus* in 1991 which has only 56% amino acid identity with the *E. coli* enzyme but which has similar catalytic properties (Itaya, et al., (1991) *Nucleic Acids Res*, 19, 4443-4449). This enzyme was stable at 65° C. but rapidly lost activity when heated to 80° C.

The human RNase H1 gene (Type I RNase H) was cloned in 1998 (*Genomics*, 53, 300-307 and *Antisense Nucleic Acid Drug Dev*, 8, 53-61). This enzyme requires a 5 base RNA stretch in DNA/RNA/DNA chimeras for cleavage to occur. Maximal activity was observed in 1 mM $Mg^{++}$ buffer at neutral pH and $Mn^{++}$ ions were inhibitory (*J Biol Chem*, 274, 28270-28278). Cleavage was not observed when 2'-modified nucleosides (such as 2'-OMe, 2'-F, etc.) were substituted for RNA.

Three amino acids (Asp-10, Glu-48, and Asp-70) make up the catalytic site of *E. coli* RNase H1 which resides in the highly conserved carboxy-terminal domain of the protein (Katayanagi, et al., (1990) *Nature*, 347, 306-309); this domain has been evaluated by both site directed mutagenesis and crystal structure determination. The same amino acids are involved in coordination of the divalent ion cofactor.

Interestingly, 2'-modification of the substrate duplex alters the geometry of the helix and can adversely affect activity of RNase H1. 2'-O-(2-methoxyl)ethyl (MOE) modifications flanking the RNA segment reduce cleavage rates, presumably due to alterations in the sugar conformation and helical geometry. Locked nucleic acid (LNA) bases perturb helical geometry to a greater degree and impacted enzyme activity to a greater extent (*Mol Pharmacol*, 71, 83-91 and *Mol Pharmacol*, 71, 73-82). Damha (McGill University) has studied the effects of 2'-F modified nucleosides (2'-deoxy-2'-fluoro-b-D-ribose) when present in the substrate duplex and finds that this group cannot be cleaved by RNase H1 (Yazbeck, et al., (2002) *Nucleic Acids Res*, 30, 3015-3025). Formulas A and B illustrate the two different mechanisms that have been proposed for RNase H1 cleavage, both of which require participation of the 2'OH group.

Formulas A and B

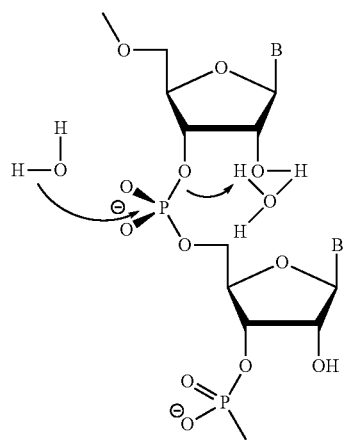

A

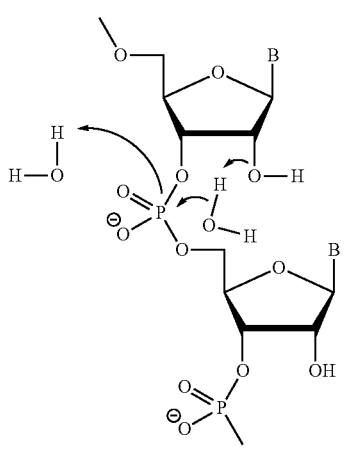

Damha's studies are consistent with the known active site of the enzyme, wherein the reaction mechanism involves the 2'-OH group. The enzyme active site resides within a cluster of lysine residues which presumably contribute to electrostatic binding of the duplex. Interaction between the binding surface and negatively charged phosphate backbone is believed to occur along the minor grove of the RNA:DNA heteroduplex (Nakamura, et al., (1991) *Proc Natl Acad Sci USA*, 88, 11535-11539); changes in structure that affect the minor groove should therefore affect interactions between the substrate and the active site. For example, the minor groove width is 7.5 Å in a B-form DNA:DNA duplex, is 11 Å in a pure A-form RNA:RNA duplex, and is 8.5 Å in the hybrid A-form duplex of an RNA:DNA duplex (Fedoroff et al., (1993) *J Mol Biol*, 233, 509-523). 2'-modifications protrude into the minor groove, which may account for some of the behavior of these groups in reducing or eliminating activity of modified substrates for cleavage by RNase H1. Even a 2'-F nucleoside, which is the most "conservative" RNA analog with respect to changing chemical structure, adversely affects activity.

Type II RNase H

The human Type II RNase H was first purified and characterized by Eder and Walder in 1991 (Eder, et al., (1991) *J Biol Chem*, 266, 6472-6479). This enzyme was initially designated human RNase H1 because it had the characteristic divalent metal ion dependence of what was then known as Class I RNases H. In the current nomenclature, it is a Type II RNase H enzyme. Unlike the Type I enzymes which are active in $Mg^{++}$ but inhibited by $Mn^{++}$ ions, the Type II enzymes are active with a wide variety of divalent cations. Optimal activity of human Type II RNase H is observed with 10 mM $Mg^{++}$, 5 mM $Co^{++}$, or 0.5 mM $Mn^{++}$.

Importantly, the substrate specificity of the Type II RNase H (hereafter referred to as RNase H2) is different from RNase H1. In particular, this enzyme can cleave a single ribonucleotide embedded within a DNA sequence (in duplex form) (Eder, et al., (1993) *Biochimie*, 75, 123-126). Interestingly, cleavage occurs on the 5' side of the RNA residue (See FIG. 3). See a recent review by Kanaya for a summary of prokaryotic RNase H2 enzymes (Kanaya (2001) *Methods Enzymol*, 341, 377-394).

The *E. coli* RNase H2 gene has been cloned (Itaya, M. (1990) *Proc Natl Acad Sci USA*, 87, 8587-8591) and characterized (Ohtani, et al., (2000) *J Biochem (Tokyo)*, 127, 895-899). Like the human enzyme, the *E. coli* enzyme functions with $Mn^{++}$ ions and is actually more active with manganese than magnesium.

RNase H2 genes have been cloned and the enzymes characterized from a variety of eukaryotic and prokaryotic sources. The RNase H2 from *Pyrococcus kodakaraensis* (KOD1) has been cloned and studied in detail (Haruki, et al., (1998) *J Bacteriol*, 180, 6207-6214; Mukaiyama, et al., (2004) *Biochemistry*, 43, 13859-13866). The RNase H2 from the related organism *Pyrococcus furious* has also been cloned but has not been as thoroughly characterized (Sato, et al., (2003) *Biochem Biophys Res Commun*, 309, 247-252).

The RNase H2 from *Methanococcus jannaschii* was cloned and characterized by Lai (Lai, et al., (2000) *Structure*, 8, 897-904; Lai et al., (2003) *Biochemistry*, 42, 785-791). Isothermal titration calorimetry was used to quantitatively measure metal ion binding to the enzyme. They tested binding of $Mn^{++}$, $Mg^{++}$, $Ca^{++}$, and $Ba^{++}$ and in all cases observed a 1:1 molar binding ratio, suggesting the presence of only a single divalent metal ion cofactor in the enzyme's active site. The association constant for $Mn^{++}$ was 10-fold higher than for $Mg^{++}$. Peak enzyme activity was seen at 0.8 mM $MnCl_2$.

Nucleic acid hybridization assays based on cleavage of an RNA-containing probe by RNase H such as the cycling probe reaction (Walder et al., U.S. Pat. No. 5,403,711) have been limited in the past by background cleavage of the oligonucleotide by contaminating single-stranded ribonucleases and by water catalyzed hydrolysis facilitated by $Mg^{2+}$ and other divalent cations. The effect of single-stranded ribonucleases can be mitigated to a certain degree by inhibitors such as RNasin that block single-stranded ribonucleases but do not interfere with the activity of RNase H.

Single-stranded ribonucleases cleave 3' of an RNA residue, leaving a cyclic phosphate group at the 2' and 3' positions of the ribose (See FIG. 2). The same products are produced by spontaneous water catalyzed hydrolysis. In both cases, the cyclic phosphate can hydrolyze further forming a 3'-monophosphate ester in the enzyme catalyzed reaction, or a mixture of the 3'- and 2'-monophosphate esters through spontaneous hydrolysis. The difference between the cleavage products formed by RNase H (FIG. 1) and those formed by nonspecific cleavage of the probe (FIG. 2) provides a basis for distinguishing between the two pathways. This difference is even more pronounced when comparing cleavage by RNase H2 and single-stranded ribonucleases with substrates having only a single RNA residue. In that case, RNase H2 and single-stranded ribonucleases attack at different positions along the phosphate backbone (See FIG. 3).

RNase H has been used as a cleaving enzyme in cycling probe assays, in PCR assays (Han et al., U.S. Pat. No. 5,763,181; Sagawa et al., U.S. Pat. No. 7,135,291; and Behlke and Walder, U.S. Pat. App. No. 20080068643) and in polynomial amplification reactions (Behlke et al., U.S. Pat. No. 7,112,406). Despite improvements offered by these assays, there remain considerable limitations. The PCR assays utilize a hot-start DNA polymerase which adds substantially to the cost. Moreover, each time an alternative DNA polymerase is required a new hot-start version of the enzyme must be developed. In addition, the utility of these various assays has been limited by undesirable cleavage of the oligonucleotide probe or primer used in the reaction, including water and divalent metal ion catalyzed hydrolysis 3' to RNA residues, hydrolysis by single-stranded ribonucleases and atypical cleavage reactions catalyzed by Type II RNase H enzymes at positions other than the 5'-phosphate of an RNA residue. The present invention overcomes these limitations and offers further advantages and new assay formats for use of RNase H in biological assays.

The current invention provides novel biological assays that employ RNase H cleavage in relation to nucleic acid amplification, detection, ligation, sequencing, and synthesis. Additionally, the invention provides new assay formats to utilize cleavage by RNase H and novel oligonucleotide substrates for such assays. The compounds, kits, and methods of the present invention provide a convenient and economic means of achieving highly specific primer-based amplification reactions that are substantially free of nonspecific amplification impurities such as primer dimers. The methods and kits of the present invention avoid the need for reversibly inactivated DNA polymerase and DNA ligase enzymes.

BRIEF SUMMARY OF THE INVENTION

One objective of the present invention is to enable hot start protocols in nucleic acid amplification and detection assays including but not limited to PCR, OLA (oligonucleotide ligation assays), LCR (ligation chain reaction), polynomial amplification and DNA sequencing, wherein the hot start component is a thermostable RNase H or other nicking enzyme that gains activity at the elevated temperatures employed in the reaction. Such assays employ a modified oligonucleotide of the invention that is unable to participate in the reaction until it hybridizes to a complementary nucleic acid sequence and is cleaved to generate a functional 5'- or 3'-end. Compared to the corresponding assays in which standard unmodified DNA oligonucleotides are used the specificity is greatly enhanced. Moreover the requirement for reversibly inactivated DNA polymerases or DNA ligases is eliminated.

In the case of assays involving primer extension (e.g., PCR, polynomial amplification and DNA sequencing) the modification of the oligonucleotide inhibiting activity is preferably located at or near the 3'-end. In some embodiments where the oligonucleotides are being used as primers, the oligonucleotide inhibiting activity may be positioned near the 3' end of the oligonucleotide, e.g., up to about 10 bases from the 3' end of the oligonucleotide of the invention. In other embodiments, the oligonucleotide inhibiting activity may be positioned near the 3' end, e.g., about 1-6 bases from the 3' end of the oligonucleotide of the invention. In other embodiments, the oligonucleotide inhibiting activity may be positioned near the 3' end, e.g., about 1-5 bases from the 3' end of the oligonucleotide of the invention. In other embodiments, the oligonucleotide inhibiting activity may be positioned near the 3' end, e.g., about 1-3 bases from the 3' end of the oligonucleotide of the invention. In other embodiments, the precise position (i.e., number of bases) from the 3' end where the oligonucleotide inhibiting activity may be positioned will depend upon factors influencing the ability of the oligonucleotide primer of the invention to hybridize to a shortened complement of itself on the target sequence (i.e., the sequence for which hybridization is desired). Such factors include but are not limited to Tm, buffer composition, and annealing temperature employed in the reaction(s).

For ligation assays (e.g., OLA and LCR) the modification inhibiting activity may be located at or near either the 3'- or 5'-end of the oligonucleotide. In other embodiments, for ligation assays, modification inhibitory activity, if used, is preferably placed within the domain that is 3' to the cleavable RNA base in the region that is removed by probe cleavage. In other embodiments, for ligation assays, C3 spacers may be positioned close to the RNA base in the oligonucleotide probes of the invention to improve specificity that is helpful for improving mismatch discrimination. In other embodiments, in an OLA assay, where readout depends upon a PCR assay to amplify the product of a ligation event, any blocking group may be placed in the domain of the oligonucleotide of the invention that is removed by RNase H cleavage. In such embodiments, in an OLA assay where readout depends upon a PCR assay to amplify the product of a ligation event, the precise position of the blocking group in the RNase H cleavable domain may be adjusted to alter specificity for cleavage and precise placement of the blocking group relative to the cleavable RNA bases may alter the amount of enzyme needed to achieve optimal cleavage rates.

Yet a further objective of the present invention is to provide novel modifications of oligonucleotides to interfere with primer extension and ligation.

Yet a further objective of the present invention is to provide modifications of oligonucleotides that prevent the oligonucleotide from serving as a template for DNA synthesis and thereby interfere with PCR.

Yet a further objective of the invention is to provide modified oligonucleotide sequences lacking RNA that are cleaved by RNase H. In one such embodiment, the oligonucleotide contains a single 2'-fluoro residue and cleavage is mediated by a Type II RNase H enzyme. In a more preferred embodiment the oligonucleotide contains two adjacent 2'-fluoro residues.

Yet a further objective of the present invention is to provide oligonucleotides for use in the above mentioned assays that are modified so as to inhibit undesired cleavage reactions including but not limited to water and divalent metal ion catalyzed hydrolysis 3' to RNA residues, hydrolysis by single-stranded ribonucleases and atypical cleavage reactions catalyzed by Type II RNase H enzymes at positions other than the 5'-phosphate of an RNA residue (see FIG. 3). In one such embodiment the 2'-hydroxy group of an RNA residue is replaced with an alternative functional group such as fluorine or an alkoxy substituent (e.g., O-methyl). In another such embodiment the phosphate group 3' to an RNA residue is replaced with a phosphorothioate or a dithioate linkage. In yet another embodiment the oligonucleotide is modified with nuclease resistant linkages further downstream from the 3'-phosphate group of an RNA residue or on the 5'-side of an RNA residue to prevent aberrant cleavage by RNase H2. Nuclease resistant linkages useful in such embodiments include phosphorothioates, dithioates, methylphosphonates, and abasic residues such as a C3 spacer. Incorporation of such nuclease resistant linkages into oligonucleotide primers used in PCR assays of the present invention has been found to be particularly beneficial (see Examples 25, 27 and 28).

Yet a further objective of the invention is to provide oligonucleotides for use in the above-mentioned assays that are modified at positions flanking the cleavage site to provide enhanced discrimination of variant alleles. Such modifications include but are not limited to 2'-O-methyl RNA residues and secondary mismatch substitutions (see Example 23).

Yet a further objective is to provide oligonucleotides and assay formats for use in the present invention wherein cleavage of the oligonucleotide can be measured by a change in fluorescence. In one such embodiment a primer cleavable by RNase H is labeled with a fluorophore and a quencher and the assay is monitored by an increase in fluorescence (see Examples 19-21).

Yet a further objective of the invention is to provide RNase H compositions and protocols for their use in which the enzyme is thermostable and has reduced activity at lower temperatures.

In yet a further embodiment a Type II RNase H is employed in a cycling probe reaction in which the RNA residue in the probe is replaced with a 2'-fluoro residue. In a more preferred embodiment a probe with two adjacent 2'-fluoro residues is used.

Many of the aspects of the present invention relating to primer extension assays, ligation assays and cycling probe reactions are summarized in Tables 1, 2, and 3, respectively.

In yet a further embodiment of the invention Type II RNase H enzymes are used in novel methods for DNA sequencing.

In yet a further embodiment of the invention Type II RNase H enzymes are used in novel methods for DNA synthesis.

Yet a further objective is to increase the ability of the assays of the present invention to distinguish the presence of a base mismatch between the primer sequence and the target nucleic acid by providing sets of overlapping blocked primers. In one embodiment of the present invention, the RNA base of the blocked-cleavable primer is positioned at the site of a single base polymorphism (the SNP). It is readily appreciated by one with skill in the art that a primer which overlays a polymorphic site can be made specific to the top or bottom (sense or antisense) strand of a duplex DNA target nucleic acid. In one embodiment of the present invention a single blocked-cleavable primer is employed having the RNA residue positioned directly at the site of the SNP (single nucleotide polymorphism) so that hybridization to a target having a perfect match with the primer results in efficient cleavage by RNase H2 whereas hybridization to a target having a mismatch at this site results in inefficient cleavage by RNase H2. When paired with a second unmodified primer that is positioned a suitable distance from the first primer, an allele-specific amplification reaction can be performed using PCR where a significant delay is observed in detection of product when using a mismatched target compared with a matched target. In another embodiment of the invention, two blocked-cleavable primers are paired, one corresponding to the top strand and the second corresponding to the bottom strand, with the SNP site positioned at the RNA base. The two primers overlap and, following activation by RNase H2 cleavage, function as a PCR primer pair and preferentially amplify a matched target over a mismatched target. By incorporating upstream and downstream blocked primers that overlap at the mutation site, the selectivity of the assay is further enhanced.

In another object of the invention, a method of improving specificity during amplification of a target DNA sequence is provided. The method includes four steps. The first step includes providing a reaction mixture. The reaction mixture includes: (i) an oligonucleotide primer having a cleavage domain, which is cleavable by an RNase H enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis; (ii) a sample nucleic acid that may or may not the target sequence; (iii) a DNA polymerase, and (iv) an RNase H enzyme wherein said RNase H enzyme is thermostable and has at least a 10-fold decrease in activity at 30° C. as compared to 70° C. The second step includes hybridizing the oligonucleotide primer to the target DNA sequence to form a double-stranded substrate. The third step includes cleaving the hybridized oligonucleotide primer with said RNase H enzyme at a cleavage site within or adjacent to the cleavage domain to remove the blocking group from the oligonucleotide primer. The fourth step includes extending the oligonucleotide primer with the DNA polymerase. The reaction mixture includes a concentration of a divalent cation such that a ΔCp of at least about 5.0 or greater or about 50% or greater is obtained for the amplification of the target DNA as adjudged by a 3'-mismatch discrimination assay.

In another object of the invention, a method of amplifying a target DNA sequence is provided. The method includes four steps. The first step includes providing a reaction mixture. The reaction mixture includes: (i) an oligonucleotide primer having a cleavage domain, which is cleavable by an RNase H enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis; (ii) a sample nucleic acid that may or may not the target sequence; (iii) a DNA polymerase, and (iv) an RNase H enzyme wherein said RNase H enzyme is thermostable and has at least a 10-fold decrease in activity at 30° C. as compared to 70° C. The second step includes hybridizing the oligonucleotide primer to the target DNA sequence to form a double-stranded substrate. The third step includes cleaving the hybridized oligonucleotide primer with said RNase H enzyme at a cleavage site within or adjacent to the cleavage domain to remove the blocking group from the oligonucleotide primer. The fourth step includes extending the oligonucleotide primer with the DNA polymerase. The reaction mixture includes a divalent cation and a non-ionic detergent comprising polyethylene glycol hexadecyl ether.

In another object of the invention, a kit for performing amplification of a target DNA sequence is provided. The kit has a reaction buffer that includes a metal salt comprising a divalent cation and associated counterion. The divalent cation comprises $Mg^{++}$, and the reaction buffer provides a final concentration of the metal salt no greater than about 2.0 mM free $Mg^{++}$ in the reaction mixture for performing amplification of the target DNA.

BRIEF DESCRIPTION OF THE FIGURES

FIG. 4A shows induced protein for *Pyrococcus furiosus* and *Pyrococus abyssi*. FIG. 4B shows induced protein for *Methanocaldococcus jannaschii, Sulfolobus solfataricus, Pyrococcus kodadarensis*.

FIG. 32 shows amplification plots of qPCR reactions done with primers specific for the human Drosha gene using HeLa cell cDNA. A) Reactions performed using unmodified primers and a fluorescence-quenched dual-labeled probe (DLP), 5'-nuclease assay format. The reaction was performed with or without template (HeLa cDNA) as indicated. B) Reactions performed using a fluorescence-quenched FQT For primer and an unmodified Rev primer in a primer-probe assay format. Reactions were performed with or without the addition of RNase H2 as indicated. Cycle number is shown on the X-axis and relative fluorescence intensity is shown on the Y-axis.

FIG. 33 shows the sequences of cleavable-blocked primers that are either perfect match or contain a mismatch at position +2 relative to the single RNA base (2 bases 3'- to the ribonucleotide). SMAD7 target sequences at SNP site rs4939827 are aligned below the primers to indicate how this strategy results in the presence of a single mismatch when primers hybridize with one allele vs. a double mismatch when hybridize with the second allele. DNA bases are uppercase, RNA bases are lowercase, and SpC3 is a Spacer C3 modification. FIG. 33 discloses SEQ ID NOS: 231-232, 234, 233, 303, 235-236, 238, 237 and 303, respectively, in order of appearance.

FIG. 38 shows the scheme for hybridization and ligation of RNA-containing cleavable ligation probes containing either three or four 5-nitroindole residues. FIG. 38 discloses SEQ ID NOS: 257, 260, 307, 258, 308 and 258, respectively, in order of appearance.

DETAILED DESCRIPTION OF THE INVENTION

Figure 1:
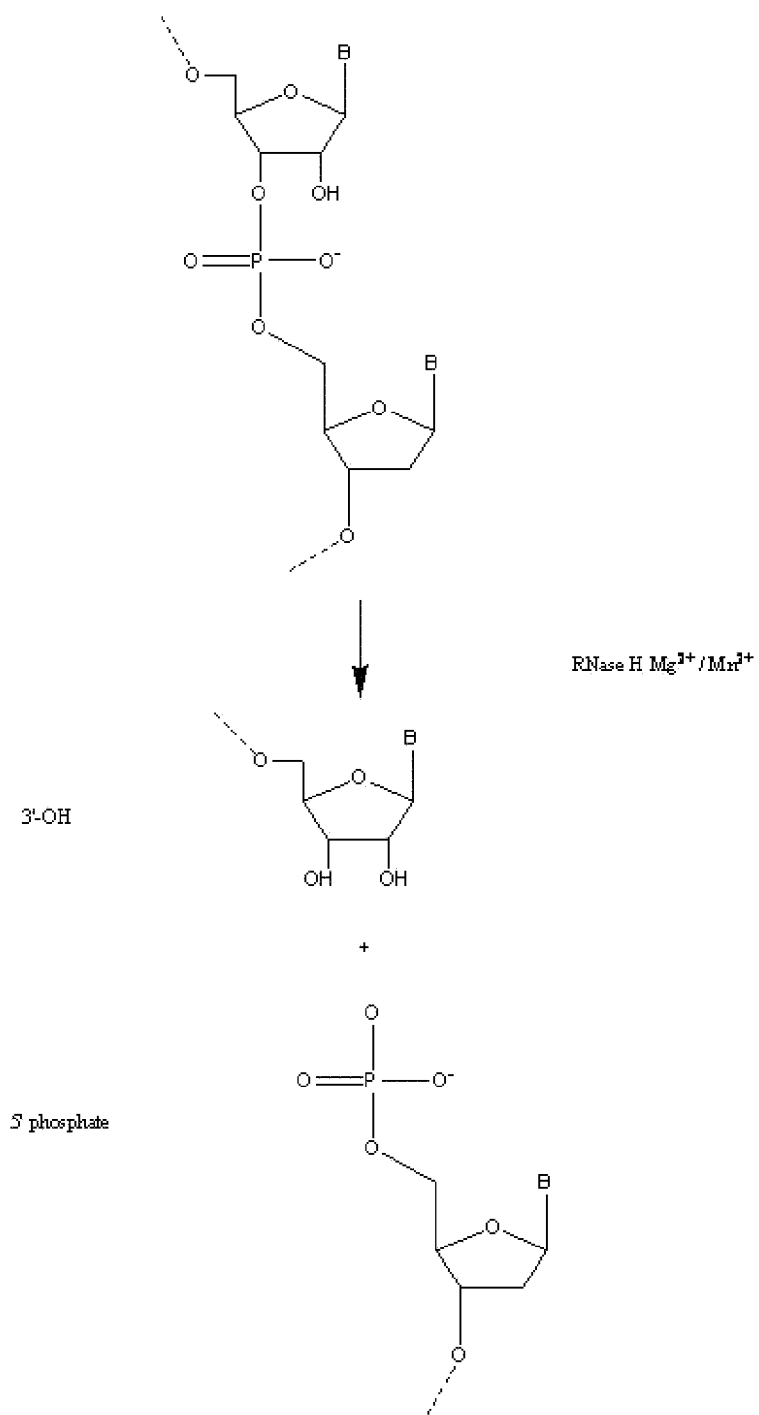
FIG. 1 depicts the cleavage pattern that occurs with an RNase H enzyme on a substrate containing multiple RNA bases.
Figure 2:
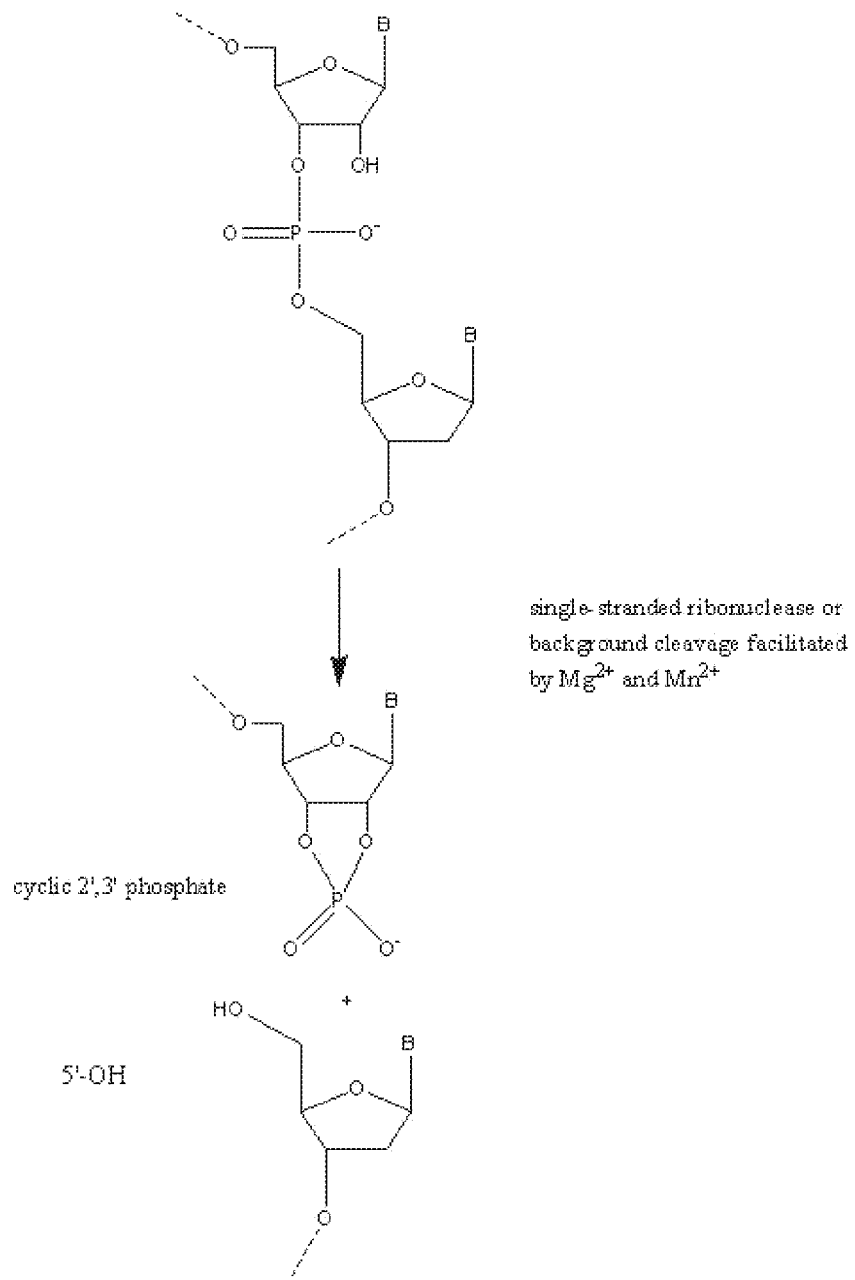
FIG. 2 depicts the cleavage pattern that occurs with a single-stranded ribonuclease enzyme or through water catalyzed hydrolysis, wherein the end-product results in a cyclic phosphate group at the 2' and 3' positions of the ribose.

The current invention provides novel nucleic acid compounds having a cleavage domain and a 3' or 5' blocking group. These compounds offer improvements to existing methods for nucleic acid amplification, detection, ligation, sequencing and synthesis. New assay formats comprising the use of these novel nucleic acid compounds are also provided.

Definitions

To aid in understanding the invention, several terms are defined below.

The terms "nucleic acid" and "oligonucleotide," as used herein, refer to polydeoxyribonucleotides (containing 2-deoxy-D-ribose), polyribonucleotides (containing D-ribose), and to any other type of polynucleotide which is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature. Primer extension can also be carried out in the absence of one or more of the nucleotide triphosphates in which case an extension product of limited length is produced. As used herein, the term "primer" is intended to encompass the oligonucleotides used in ligation-mediated reactions, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product. The region of the primer which is sufficiently complementary to the template to hybridize is referred to herein as the hybridizing region.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two step cycles have a high temperature denaturation step followed by a hybridization/elongation (or ligation) step. Three step cycles comprise a denaturation step followed by a hybridization step followed by a separate elongation or ligation step.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites.

The term "non-specific amplification," as used herein, refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions, or in situations where there is a variant allele in the sample having a very closely related sequence to the true target as in the case of a single nucleotide polymorphism (SNP).

The term "3'-mismatch discrimination" refers to a property of a DNA polymerase to distinguish a fully complementary sequence from a mismatch-containing (nearly complementary) sequence where the nucleic acid to be extended (for example, a primer or other oligonucleotide) has a mismatch at the 3' end of the nucleic acid compared to the template to which the nucleic acid hybridizes. In some embodiments, the nucleic acid to be extended comprises a mismatch at the 3' end relative to the fully complementary sequence.

The term "3'-mismatch discrimination assay" refers to an assay to discern the present of improved specificity in amplification of a target DNA sequence when the target DNA sequence is interrogated with two primers having substantially identical sequence except for the occurrence of one of more nucleotide residue having different base composition at or near their respective 3'-ends. For example, a first primer having 3'-end sequences with perfect complementarity to the target DNA sequence is considered a 3'-matched primer and a second primer having a 3'-end sequences having at least one nucleotide base non-complementarity to the target DNA sequence is considered a 3'-mismatched primer. An example of a 3'-mismatch discrimination assay is provided in many of the examples, such as EXAMPLES 36 and 37, among others.

The term "primer dimer," as used herein, refers to a template-independent non-specific amplification product, which is believed to result from primer extensions wherein another primer serves as a template. Although primer dimers frequently appear to be a concatamer of two primers, i.e., a dimer, concatamers of more than two primers also occur. The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the invention.

For the purposes of this invention, the terms "non-activated" or "inactivated," as used herein, refer to a primer or other oligonucleotide that is incapable of participating in a primer extension reaction or a ligation reaction because either DNA polymerase or DNA ligase cannot interact with the oligonucleotide for their intended purposes. In some embodiments when the oligonucleotide is a primer, the non-activated state occurs because the primer is blocked at or near the 3'-end so as to prevent primer extension. When specific groups are bound at or near the 3'-end of the primer, DNA polymerase cannot bind to the primer and extension cannot occur. A non-activated primer is, however, capable of hybridizing to a substantially complementary nucleotide sequence.

For the purposes of this invention, the term "activated," as used herein, refers to a primer or other oligonucleotide that is capable of participating in a reaction with DNA polymerase or DNA ligase. A primer or other oligonucleotide becomes activated after it hybridizes to a substantially complementary nucleic acid sequence and is cleaved to generate a functional 3'- or 5'-end so that it can interact with a DNA polymerase or a DNA ligase. For example, when the oligonucleotide is a primer, and the primer is hybridized to a template, a 3'-blocking group can be removed from the primer by, for example, a cleaving enzyme such that DNA polymerase can bind to the 3' end of the primer and promote primer extension.

The term "cleavage domain" or "cleaving domain," as used herein, are synonymous and refer to a region located between the 5' and 3' end of a primer or other oligonucleotide that is recognized by a cleavage compound, for example a cleavage enzyme, that will cleave the primer or other oligonucleotide. For the purposes of this invention, the cleavage domain is designed such that the primer or other oligonucleotide is cleaved only when it is hybridized to a complementary nucleic acid sequence, but will not be cleaved when it is single-stranded. The cleavage domain or sequences flanking it may include a moiety that a) prevents or inhibits the extension or ligation of a primer or other oligonucleotide by a polymerase or a ligase, b) enhances discrimination to detect variant alleles, or c) suppresses undesired cleavage reactions. One or more such moieties may be included in the cleavage domain or the sequences flanking it.

The term "RNase H cleavage domain," as used herein, is a type of cleavage domain that contains one or more ribonucleic acid residue or an alternative analog which provides a substrate for an RNase H. An RNase H cleavage domain can be located anywhere within a primer or oligonucleotide, and is preferably located at or near the 3'-end or the 5'-end of the molecule.

An "RNase H1 cleavage domain" generally contains at least three residues. An "RNase H2 cleavage domain" may contain one RNA residue, a sequence of contiguously linked RNA residues or RNA residues separated by DNA residues or other chemical groups. In one embodiment, the RNase H2 cleavage domain is a 2'-fluoronucleoside residue. In a more preferred embodiment the RNase H2 cleavable domain is two adjacent 2'-fluoro residues.

The terms "cleavage compound," or "cleaving agent" as used herein, refers to any compound that can recognize a cleavage domain within a primer or other oligonucleotide, and selectively cleave the oligonucleotide based on the presence of the cleavage domain. The cleavage compounds utilized in the invention selectively cleave the primer or other oligonucleotide comprising the cleavage domain only when it is hybridized to a substantially complementary nucleic acid sequence, but will not cleave the primer or other oligonucleotide when it is single stranded. The cleavage compound cleaves the primer or other oligonucleotide within or adjacent to the cleavage domain. The term "adjacent," as used herein, means that the cleavage compound cleaves the primer or other oligonucleotide at either the 5'-end or the 3' end of the cleavage domain. Cleavage reactions preferred in the invention yield a 5'-phosphate group and a 3'-OH group.

In a preferred embodiment, the cleavage compound is a "cleaving enzyme." A cleaving enzyme is a protein or a ribozyme that is capable of recognizing the cleaving domain when a primer or other nucleotide is hybridized to a substantially complementary nucleic acid sequence, but that will not cleave the complementary nucleic acid sequence (i.e., it provides a single strand break in the duplex). The cleaving enzyme will also not cleave the primer or other oligonucleotide comprising the cleavage domain when it is single stranded. Examples of cleaving enzymes are RNase H enzymes and other nicking enzymes.

The term "nicking," as used herein, refers to the cleavage of only one strand of the double-stranded portion of a fully or partially double-stranded nucleic acid. The position where the nucleic acid is nicked is referred to as the "nicking site" (NS). A "nicking agent" (NA) is an agent that nicks a partially or fully double-stranded nucleic acid. It may be an enzyme or any other chemical compound or composition. In certain embodiments, a nicking agent may recognize a particular nucleotide sequence of a fully or partially double-stranded nucleic acid and cleave only one strand of the fully or partially double-stranded nucleic acid at a specific position (i.e., the NS) relative to the location of the recognition sequence. Such nicking agents (referred to as "sequence specific nicking agents") include, but are not limited to, nicking endonucleases (e.g., N.BstNB).

A "nicking endonuclease" (NE), as used herein, thus refers to an endonuclease that recognizes a nucleotide sequence of a completely or partially double-stranded nucleic acid molecule and cleaves only one strand of the nucleic acid molecule at a specific location relative to the recognition sequence. In such a case the entire sequence from the recognition site to the point of cleavage constitutes the "cleavage domain".

The term "blocking group," as used herein, refers to a chemical moiety that is bound to the primer or other oligonucleotide such that an amplification reaction does not occur. For example, primer extension and/or DNA ligation does not occur. Once the blocking group is removed from the primer or other oligonucleotide, the oligonucleotide is capable of participating in the assay for which it was designed (PCR, ligation, sequencing, etc). Thus, the "blocking group" can be any chemical moiety that inhibits recognition by a polymerase or DNA ligase. The blocking group may be incorporated into the cleavage domain but is generally located on either the 5'- or 3'-side of the cleavage domain. The blocking group can be comprised of more than one chemical moiety. In the present invention the "blocking group" is typically removed after hybridization of the oligonucleotide to its target sequence.

The term "fluorescent generation probe" refers either to a) an oligonucleotide having an attached fluorophore and quencher, and optionally a minor groove binder or to b) a DNA binding reagent such as SYBR® Green dye.

The terms "fluorescent label" or "fluorophore" refers to compounds with a fluorescent emission maximum between about 350 and 900 nm. A wide variety of fluorophores can be used, including but not limited to: 5-FAM (also called 5-carboxyfluorescein; also called Spiro(isobenzofuran-1 (3H), 9'-(9H)xanthene)-5-carboxylic acid, 3',6'-dihydroxy-3-oxo-6-carboxyfluorescein); 5-Hexachloro-Fluorescein; ([4,7,2',4',5',7'-hexachloro-(3',6'-dipivaloyl-fluoresceinyl)-6-carboxylic acid]); 6-Hexachloro-Fluorescein; ([4,7,2',4',5',7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetrachloro-Fluorescein; ([4,7,2',7'-tetrachloro-(3',6'-dipivaloyl-fluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-proprionic acid); Quasar®-670 dye (Biosearch Technologies); Cal Fluor® Orange dye (Biosearch Technologies); Rox dyes; Max dyes (Integrated DNA Technologies), as well as suitable derivatives thereof.

As used herein, the term "quencher" refers to a molecule or part of a compound, which is capable of reducing the emission from a fluorescent donor when attached to or in proximity to the donor. Quenching may occur by any of several mechanisms including fluorescence resonance energy transfer, photo-induced electron transfer, paramagnetic enhancement of intersystem crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more. A number of commercially available quenchers are known in the art, and include but are not limited to DABCYL, Black Hole™ Quenchers (BHQ-1, BHQ-2, and BHQ-3), Iowa Black® FQ and Iowa Black® RQ. These are so-called dark quenchers. They have no native fluorescence, virtually eliminating background problems seen with other quenchers such as TAMRA which is intrinsically fluorescent.

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3' hydroxyl group of one polynucleotide to the 5' phosphate group of a second polynucleotide. Examples of ligases include *E. coli* DNA ligase, T4 DNA ligase, etc.

The ligation reaction can be employed in DNA amplification methods such as the "ligase chain reaction" (LCR), also referred to as the "ligase amplification reaction" (LAR), see Barany, Proc. Natl. Acad. Sci., 88:189 (1991); and Wu and Wallace, Genomics 4:560 (1989) incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. In the presence of the target sequence, DNA ligase will covalently link each set of hybridized molecules. Importantly, in LCR, two oligonucleotides are ligated together only when they base-pair with sequences without gaps. Repeated cycles of denaturation, hybridization and ligation amplify a short segment of DNA. A mismatch at the junction between adjacent oligonucleotides inhibits ligation. As in other oligonucleotide ligation assays this property allows LCR to be used to distinguish between variant alleles such as SNPs. LCR has also been used in combination with PCR to achieve enhanced detection of single-base changes, see Segev, PCT Public. No. WO9001069 (1990).

Novel Oligonucleotides and Compounds of the Present Invention.

In one embodiment, the novel oligonucleotides of the present invention are primers for DNA replication, as for example in PCR, DNA sequencing and polynomial amplification, to name a few such applications. In this embodiment, the primers have an inactive configuration wherein DNA replication (i.e., primer extension) is blocked, and an activated configuration wherein DNA replication proceeds. The inactive configuration of the primer is present when the primer is either single-stranded, or the primer is hybridized to the DNA sequence of interest and primer extension remains blocked by a chemical moiety that is linked at or near to the 3' end of the primer. The activated configuration of the primer is present when the primer is hybridized to a nucleic acid sequence of interest and subsequently acted upon by RNase H or other cleaving agent to remove the blocking group and allow for an enzyme (e.g., a DNA polymerase) to catalyze primer extension.

A number of blocking groups are known in the art that can be placed at or near the 3' end of the oligonucleotide (e.g., a primer) to prevent extension. A primer or other oligonucleotide may be modified at the 3'-terminal nucleotide to prevent or inhibit initiation of DNA synthesis by, for example, the addition of a 3' deoxyribonucleotide residue (e.g., cordycepin), a 2',3'-dideoxyribonucleotide residue, non-nucleotide linkages or alkane-diol modifications (U.S. Pat. No. 5,554,516). Alkane diol modifications which can be used to inhibit or block primer extension have also been described by Wilk et al., (1990, Nucleic Acids Res., 18 (8):2065), and by Arnold et al., (U.S. Pat. No. 6,031,091). Additional examples of suitable blocking groups include 3' hydroxyl substitutions (e.g., 3'-phosphate, 3'-triphosphate or 3'-phosphate diesters with alcohols such as 3-hydroxypropyl), a 2'3'-cyclic phosphate, 2' hydroxyl substitutions of a terminal RNA base (e.g., phosphate or sterically bulky groups such as triisopropyl silyl (TIPS) or tert-butyl dimethyl silyl (TBDMS)). 2'-alkyl silyl groups such as TIPS and TBDMS substituted at the 3'-end of an oligonucleotide are described by Laikhter et al., U.S. patent application Ser. No. 11/686,894 which is incorporated herein by reference. Bulky substituents can also be incorporated on the base of the 3'-terminal residue of the oligonucleotide to block primer extension.

Blocking groups to inhibit primer extension can also be located upstream, that is 5', from the 3'-terminal residue. Sterically bulky substituents which interfere with binding by the polymerase can be incorporated onto the base, sugar or phosphate group of residues upstream from the 3'-terminus Such substituents include bulky alkyl groups like t-butyl, triisopropyl and polyaromatic compounds including fluorophores and quenchers, and can be placed from one to about 10 residues from the 3'-terminus. Alternatively abasic residues such as a C3 spacer may be incorporated in these locations to block primer extension. In one such embodiment two adjacent C3 spacers have been employed (see Examples 27 and 28).

In the case of PCR, blocking moieties upstream of the 3'-terminal residue can serve two functions: 1) to inhibit primer extension, and 2) to block the primer from serving as a template for DNA synthesis when the extension product is copied by synthesis from the reverse primer. The latter is sufficient to block PCR even if primer extension can occur. C3 spacers placed upstream of the 3'-terminal residue can function in this manner (see Examples 26 and 27).

A modification used as a blocking group may also be located within a region 3' to the priming sequence that is non-complementary to the target nucleic acid sequence.

The oligonucleotide further comprises a cleavage domain located upstream of the blocking group used to inhibit primer extension. An RNase H cleavage domain is preferred. An RNase H2 cleavage domain comprising a single RNA residue or replacement of the RNA base with one or more alternative nucleosides is most preferred.

In one embodiment, RNase H2 can be used to cleave duplexes containing a single 2'-fluoro residue. Cleavage occurs on the 5' side of the 2'-fluoro residue. In a preferred embodiment, an RNase H2 cleavage domain comprising two adjacent 2'-fluoro residues is employed (see Example 6). The activity is enhanced when two consecutive 2'-fluoro modifications are present. In this embodiment cleavage occurs preferentially between the 2'-fluoro residues. Unlike oligonucleotides containing unmodified RNA residues, oligonucleotides with 2'-fluoro groups are not cleaved by single-stranded ribonucleases and are resistant to water catalyzed cleavage and completely stable at high temperatures. Enhanced cleavage has also been found when a 2'-fluoro modified RNA residue is used with a 2' LNA modified RNA residue. 2'-fluoro-containing oligonucleotides have been found to be further advantageous in certain applications compared to RNA-containing oligonucleotides in offering greater discrimination with respect to mismatches between the oligonucleotide and the target sequence.

Alternatives to an RNA residue that can be used in the present invention wherein cleavage is mediated by an RNase H enzyme include but are not limited to 2'-O-alkyl RNA nucleosides, preferably 2'-O-methyl RNA nucleosides, 2'-fluoronucleosides, locked nucleic acids (LNA), 2'-ENA residues (ethylene nucleic acids), 2'-alkyl nucleosides, 2'-aminonucleosides and 2'-thionucleosides. The RNase H cleavage domain may include one or more of these modified residues alone or in combination with RNA bases. DNA bases and abasic residues such as a C3 spacer may also be included to provide greater performance.

If the cleaving agent is an RNase H1 enzyme a continuous sequence of at least three RNA residues is preferred. A continuous sequence of four RNA residues generally leads to maximal activity. If the cleaving agent is an RNase H2 enzyme a single RNA residue or 2 adjacent 2'-fluoro residues are preferred.

Figure 3:
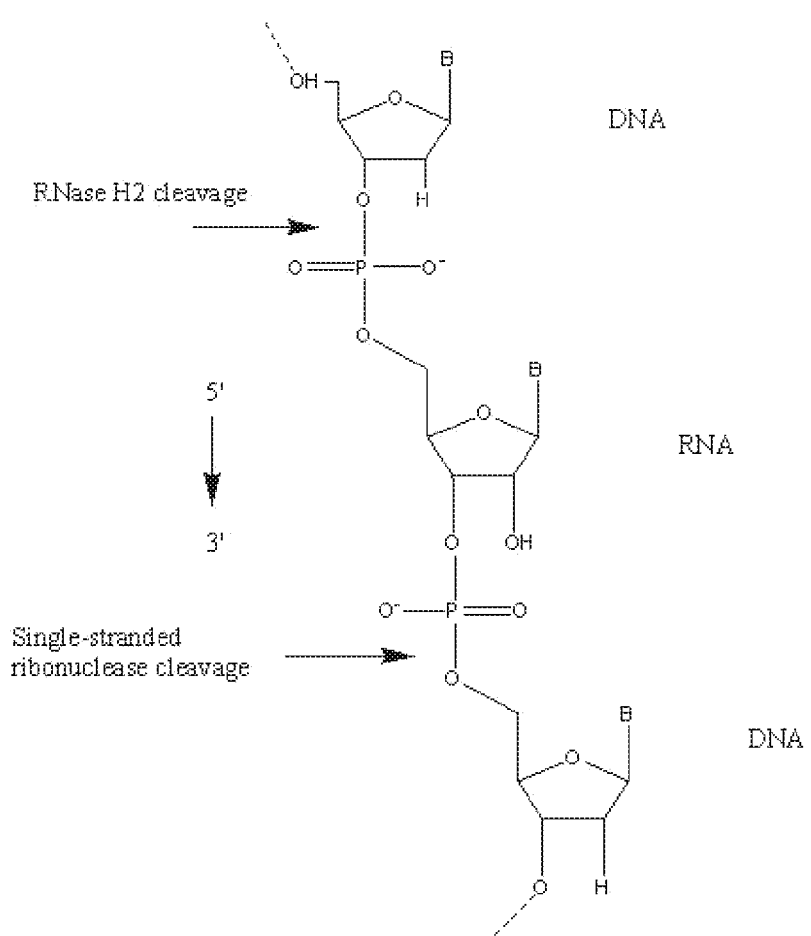
FIG. 3 depicts the cleavage sites for RNase H2 and single-stranded ribonucleases on a substrate containing a single RNA base.

One objective of incorporating modified residues within an RNase H cleavage domain is to suppress background cleavage of a primer or probe due to water catalyzed hydrolysis or cleavage by single stranded ribonucleases. Replacement of the 2'-hydroxyl group with a substituent that cannot attack the adjacent phosphate group of an RNA residue can accomplish this goal. Examples of this approach include the use of the 2'-substituted nucleosides listed above, such as 2'-fluoro and 2'-O-methyl nucleosides. This is particularly advantageous when cleavage is mediated by RNase H2 and there is a single RNA residue within the cleavage domain. As shown in FIG. 3, in this case cleavage by single stranded ribonucleases or water catalyzed hydrolysis occurs at a different position than cleavage by RNase H2.

Other examples of modifications that can be used to suppress cleavage by single stranded ribonucleases and water catalyzed hydrolysis at RNA residues include substitution of the 5' oxygen atom of the adjacent residue (3'- to the RNA base) with an amino group, thiol group, or a methylene group (a phosphonate linkage). Alternatively one or both of the hydrogen atoms on the 5' carbon of the adjacent residue can be replaced with bulkier substituents such as methyl groups to inhibit background cleavage of a ribonucleotide residue. In another such embodiment, the phosphate group at the 3'-side of an RNA residue can be replaced with a phosphorothioate, phosphorodithioates or boronate linkage. In the case of a phosphorothioate the S stereoisomer is preferred. Combinations of these various modifications may also be employed.

It should be noted that background cleavage at RNA residues by single stranded ribonucleases or water catalyzed hydrolysis leads to a blocked 3'-end (see FIG. 3) that cannot serve as a primer for DNA synthesis. This mitigates the occurrence of false positive results even if such cleavage does occur.

The cleavage domain may include the blocking group provided that cleavage occurs on the 5'-side of the blocking group and generates a free 3'-OH. Generally however the cleavage domain and the blocking group are separated by one to about 15 bases. After cleavage takes place the portion of the primer 3' from the cleavage site containing the blocking group dissociates from the template and a functional 3'-hydroxyl group is exposed, capable of being acted on by a polymerase enzyme. The optimal distance between the cleavage site and the blocking group will depend on the cleaving agent and the nature of the blocking group. When cleavage of the oligonucleotide is mediated by RNase H2 at a single RNA residue a distance of 3 to about 8 bases between the cleavage site and the blocking group is preferred. If the blocking group is sterically small, for example a phosphodiester at the 3' terminal nucleotide as in the following structure

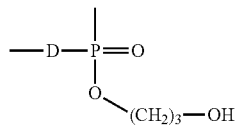

a cleavage site 5 bases from the 3'-end is generally optimal. If the blocking group is larger it is advantageous to position the cleavage site further from it.

In a preferred embodiment, a thermophilic RNase H2 enzyme is utilized to cleave the oligonucleotide. In yet a more preferred embodiment, a thermophilic RNase H2 enzyme is used which is less active at room temperature than at elevated temperatures. This allows a hot-start type of reaction to be achieved in PCR and other primer extension assays using the blocked primers of the present invention without actually requiring a hot start, i.e., reversibly inactivated, DNA polymerase. Standard less expensive DNA polymerase polymerases such as Taq polymerase can be used instead of the much more expensive hot start versions of the enzyme. Moreover, for different applications alternative DNA polymerases may be preferred. Utilizing RNase H as the hot start component of the assay obviates the need to develop a new reversibly inactivated analog of each different DNA polymerase.

Hot start properties of the enzyme may be intrinsic to the protein as in the case of *Pyrococcus abysii* RNase H2 (see Example 4). Alternatively the enzyme may be reversibly inactivated by chemical modification using, for example, maleic acid anhydride analogs such as citroconic anhydride. These compounds react with amino groups of the protein and at high temperature are released restoring activity. In yet another embodiment antibodies against an RNase H which block the enzyme may be employed which are denatured at elevated temperatures.

In yet another embodiment, the oligonucleotide of the present invention has a cleavage domain that is recognized and cleaved by a sequence specific nicking agent, e.g., a nicking enzyme. The nicking agent also can be designed to cleave an oligonucleotide (e.g., a primer) at a modified nucleic acid or grouping of modified nucleic acids. In this embodiment, the oligonucleotide is designed to be recognized by a nicking agent upon hybridization with the target nucleic acid, and the nicking of the oligonucleotide/target duplex can be used to remove a blocking group and allow for oligonucleotide extension. The nicking site (NS) is preferably located at or near the 3'-end of the oligonucleotide, specifically, one to about 15 bases from the 3'-end of the oligonucleotide.

Exemplary nicking agents include, without limitation, single strand nicking restriction endonucleases that recognize a specific sequence such as N.BstNBI; or repair enzymes such as Mut H, MutY (in combination with an AP endonuclease), or uracil-N-glycosylase (in combination with an AP Lyase and AP endonucleases); and the geneII protein of bacteriophage f1.

The blocked primers of the present invention minimize non-specific reactions by requiring hybridization to the target followed by cleavage before primer extension. If a primer hybridizes incorrectly to a related sequence, cleavage of the primer is inhibited especially when there is a mismatch that lies at or near the cleavage site. This reduces the frequency of false priming at such locations and thereby increases the specificity of the reaction. It should be noted that with *Pyrococcus abysii* Type II RNase H and other RNase H enzymes used in the present invention some cleavage does occur even when there is a mismatch at the cleavage site. Reaction conditions, particularly the concentration of RNase H and the time allowed for hybridization and extension in each cycle, can be optimized to maximize the difference in cleavage efficiencies between the primer hybridized to its true target and when there is a mismatch. This allows the methods of the present invention to be used very effectively to distinguish between variant alleles, including SNPs (see Examples 12-14, 22-25).

As noted above, background cleavage of the primer does not lead to false-positive priming when RNA residues are incorporated into the oligonucleotide, because the 2',3'-cyclic phosphate (or 2' or 3'-phosphate) formed at the 3' end of the cleaved primer blocks primer extension. A freely accessible 3' OH group is needed to form a substrate for DNA polymerase. The formation of primer-dimers, a common side reaction occurring in PCR, can also be inhibited using the 3' blocked primers of the present invention. This allows for a greater degree of multiplexing in PCR (e.g., detecting multiple target sequences in the case of a DNA detection/amplification assay).

Without being bound by any theory, it has been observed that atypical cleavage can occur at a low frequency 3' to an RNA residue when there is a mismatch, presumably catalyzed by RNase H2, to generate a free 3'-OH and lead to primer extension. This can result in a decrease in the specificity of the reaction. To mitigate this effect nuclease resistant residues can be incorporated into the primer 3' to the RNA residue (see Example 22, 25 and 28). Such groups include but are not limited to one or more phosphorothioates, phosphorodithioates, methyl phosphonates and abasic residues such as a C3 spacer.

Other substitutions both 5' and 3' to the RNA residue can also be utilized to enhance the discrimination and detection of variant alleles in the methods of the present invention. Such substitutions include but are not limited to 2'-O-methyl RNA and secondary mismatches (see Example 23).

The nature of the blocking group which prevents primer extension is not critical. It can be placed at the 3'-terminal residue or upstream from it. Labeling groups can be incorporated within the blocking group or attached at other positions on the 3'-segment of the oligonucleotide primer which dissociates from the template after cleavage occurs. Such labeling groups include, but are not limited to, fluorophores, quenchers, biotin, haptens such as digoxigenin, proteins including enzymes and antibodies, mass tags which alter the mass of the cleavage fragment for detection by mass spectrometry, and radiolabels such as $^{14}C$, $^{3}H$, $^{35}S$, $^{32}P$ and $^{33}P$. These labeling groups can also be attached to the primer 5' to the cleavage site, in which case they will be incorporated within the extension product.

In one embodiment, the blocking group at or near the 3'-end of the oligonucleotide can be a fluorescent moiety. In this case, release of the fluorescent molecule can be used to monitor the progress of the primer extension reaction. This is facilitated if the oligonucleotide also contains a quencher moiety on the 5'-side of the cleavage site. Cleavage of the oligonucleotide during the reaction separates the fluorophore from the quencher and leads to an increase in fluorescence. If the quencher is itself a fluorophore, such as Tamra, a decrease in its fluorescence may also be observed.

In yet a further embodiment, the oligonucleotide is labeled with a fluorescent molecule on the 5'-side of the cleavage domain, and the blocking group located at or near the 3'-end of the molecule is a quencher such as Iowa Black®, Black Hole™, or Tamra to name a few. Again, cleavage of the quencher from the oligonucleotide (e.g., a primer) leads to an increase in fluorescence which can be used to monitor the progress of the oligonucleotide extension reaction. Moreover, in this case, the primer extension product is fluorescently labeled.

In yet a further embodiment, the blocked primers of the present invention are used for nucleic acid sequencing. As in the case of DNA amplification reactions, the specificity of primer extension for DNA sequencing is also increased when using the oligonucleotides of the present invention. In one sequencing embodiment, 2',3' dideoxynucleotide triphosphates that are fluorescently labeled and used as chain terminators and the nested fragments produced in the reaction are separated by electrophoresis, preferably capillary electrophoresis.

In yet another embodiment, an oligonucleotide primer of the present invention is labeled with a fluorescent group and the 3' dideoxynucleotide triphosphate chain terminators are unlabeled. In this embodiment, the blocking group can be a quencher, in which case background fluorescence is reduced because the primer itself is not fluorescent. Only the extension products are fluorescent.

Another aspect of the invention includes the incorporation of alternative divalent cations such as $Mn^{2+}$, $Ni^{2+}$ or $Co^{2+}$, with or without $Mg^{2+}$, into the assay buffer. In certain embodiments of the invention, when such alternative divalent cations are present, the effectiveness of the particular assay is increased due to enhanced cleavage by RNase H2. In one embodiment, when two adjacent 2'-fluoronucleoside residues constitute the RNase H2 cleavable domain, 0.3-1 mM $MnCl_2$ with 2-4 mM $MgCl_2$ gave optimal performance in the assay (see Example 3).

THE METHODS OF THE PRESENT INVENTION

The primers, probes and other novel oligonucleotides described herein can be utilized in a number of biological assays. Although the following list is not comprehensive, the majority of the methods of the present invention fall into six general categories: (1) primer extension assays (including PCR, DNA sequencing and polynomial amplification), (2) oligonucleotide ligation assays (OLA), (3) cycling probe reactions, (4) sequencing by ligation, (5) sequencing by generation of end-labeled fragments using RNase H enzymes, and (6) synthesis by ligation.

The primers, probes and other novel oligonucleotides described herein can be utilized in a number of primer extension assays.

Primer Extension Assays

In one embodiment of the present invention, a method of amplifying a target DNA sequence of interest is provided. The method comprises the steps of:
(a) providing a reaction mixture comprising a primer having a cleavage domain and a blocking group linked at or near to the 3' end of the primer which prevents primer extension, a sample nucleic acid having the target DNA sequence of interest, a cleaving enzyme and a polymerase;
(b) hybridizing the primer to the target DNA sequence to form a double-stranded substrate;
(c) cleaving the hybridized primer with the cleaving enzyme at a point within or adjacent to the cleavage domain to remove the blocking group from the primer; and
(d) extending the primer with the polymerase.

PCR in General

When used in PCR, a 3'-blocked primer containing a cleavage domain first hybridizes to the target sequence. In this embodiment, the primer cannot extend until cleavage of the 3' blocking group occurs after hybridization to the complementary DNA sequence. For example, when an RNase H cleavage domain is present in the primer, an RNase H enzyme will recognize the double-stranded substrate formed by the primer and target and cleave the primer within or adjacent to the cleavage domain. The primer can then extend and amplification of the target can then occur. Because the primer needs to be recognized and cleaved by RNase H before extension, non-specific amplification is reduced.

In conventional PCR, a "hot start" polymerase is often used to reduce primer dimers and decrease non-specific amplification. Blocked primers of the present invention requiring cleavage by RNase H can confer the same advantage. A thermophilic RNase H enzyme with little or no activity at lower temperatures is preferred. Activation of the primers occurs only after hybridization to the target sequence and cleavage at elevated temperatures. Advantages of this approach compared to the use of a hot start reversibly inactivated DNA polymerase have been described above. Of course a hot start RNase H enzyme and a hot start DNA polymerase can be used in conjunction, if desired.

Three types of hot start RNase H enzymes are described here (see Tables 1, 2, and 3): 1) a thermostable RNase H enzyme that has intrinsically little or no activity at reduced temperatures as in the case of *Pyrococcus abysii* RNase H2;

2) a thermostable RNase H reversibly inactivated by chemical modification; and 3) a thermostable RNase H reversibly inactivated by a blocking antibody. In addition, through means well-known in the art, such as random mutagenesis, mutant versions of RNase H can be synthesized that can further improve the traits of RNase H that are desirable in the assays of the present invention. Alternatively, mutant strains of other enzymes that share the characteristics desirable for the present invention could be used.

In one embodiment, the cleavage domain within the primer is cleavable by RNase H. In yet a further embodiment, the RNase H cleavage domain consists of a single RNA residue and cleavage of the primer is mediated by a Type II RNase H enzyme, preferably by a thermophilic Type II RNase H enzyme, and even more preferably a thermophilic Type II RNase H enzyme which is less active at room temperature than at elevated temperatures. In yet a further embodiment, the RNase H2 cleavage domain consists of two adjacent 2'-fluoro nucleoside residues. In yet a more preferred embodiment of the present invention in which the cleavage domain consists of two adjacent 2'-fluoro nucleoside residues, the PCR is carried out in buffers containing alternative divalent cations, including but not limited to, $Mn^{2+}$, $Ni^{2+}$ or $Co^{2+}$ in addition to $Mg^{2+}$. In an additional embodiment, the novel 3'-blocked primers of the present invention comprising a cleavage domain can be utilized in a variation of hot start PCR in which a thermophilic nicking enzyme is used and the cleavage domain is a nicking site.

Alternatively, a cleavage enzyme that lacks hot start characteristics can be used in the present invention with traditional hot-start methods such as adding the enzyme at an elevated temperature, encasing a necessary reagent or enzyme in wax, or with a hot start reversibly inactivated DNA polymerase.

The increased specificity of the present invention, when used in amplification reactions, enables real-time PCR applications to achieve more specific results, as compared to conventional real-time PCR with standard DNA primers. For example, double-stranded DNA-binding dye assays, such as SYBR® Green assays, have a disadvantage in that a signal is produced once the dye binds to any double-stranded product produced by PCR (e.g., a primer dimer) and can thereby give rise to a false positive result. But when a primer of the current invention is used, non-specific amplification and primer-dimer formation is reduced, and the intensity of the signal of the double-stranded DNA-binding dye will reflect amplification only of the desired target (see Example 17).

The reagent concentrations and reaction conditions of the assay can be varied to maximize its utility. The relative efficiency of PCR using the blocked primers of the present invention relates to the concentration of the unblocking enzyme and the dwell time at the anneal/extend reaction temperature (where unblocking proceeds). With low amounts of enzyme and short dwell times, cleavage can be incomplete and the reactions with blocked primers have lower efficiency than those with unblocked primers. As either enzyme concentration or dwell time increases, the reaction efficiency with blocked primers increases and becomes identical to unblocked primers. The use of even more enzyme or longer dwell times can decrease the specificity of the assay and lessen the ability of the system to discriminate mismatches at the cleavage site or within the surrounding sequence (see Example 4). This results because there is an increase in the efficiency of cleavage of the primer when it is hybridized to a mismatch sequence. Cleavage at the true target site cannot be further increased because it is already at 100% each cycle. Thus the assay can be tuned for SNP assays requiring higher specificity, or for quantitation of expression levels of mRNA requiring less specificity. Specificity can also be adjusted by varying composition of the reaction buffer. For example, a $Mg^{++}$ ion concentration of 3 mM may support a very robust, high efficiency assay; lowering $Mg^{++}$ ion concentration to 2.5 mM, 2.0 mM, or lower may increase specificity of SNP discrimination, but may also lead to a slightly lower reaction efficiency (See Examples 36 and 37). Certain DNA polymerase enzymes may require use of higher $Mg^{++}$ ion concentrations. Therefore optimization of $Mg^{++}$ ion concentration can be used to adjust performance as the assay to suit specific needs, and this process is familiar to all with skill in the art. Some DNA polymerase enzymes perform better when small amounts of detergent are present in the buffer. *Pyrococcus abyssi* RNase H2, and likely other RNase H2 enzymes, similarly has higher reaction rates when small amounts of detergent are present in the buffer. Detergent content can be adjusted within a wide range and still be compatible with PCR amplification, using non-ionic detergents (e.g., Triton-X-100, Brij-58, etc.) or select ionic detergents (e.g., CTAB) (see Examples 18 and 38).

In another embodiment, a primer pair having one blocked primer and one unblocked primer, can be used. In another embodiment, an enzyme can be selected that has less sequence specificity and can cleave various sequences. In yet another embodiment, an additional mismatch flanking the cleavage site can be added to increase the ability to discriminate variant alleles. Modified bases such as 2'-O-methyl nucleosides can also be introduced into the primer on either side of the cleavage site to increase specificity (see Example 23).

The reactions of the various assays described herein can be monitored using fluorescent detection, detection by mass tags, enzymatic detection, and via labeling the probe or primer with a variety of other groups including biotin, haptens, radionucleotides and antibodies to name a few. In one embodiment, the progress of PCR using the modified primers of the present invention is monitored in real time using a dye intercalating assay with, for example, SYBR® Green. In yet a further embodiment, the progress of PCR using the modified primers of the present invention is monitored using a probe labeled with a fluorophore and a quencher such as a molecular beacon or, as in the 5' nuclease assay where cleavage of the probe occurs. Alternatively, a dual labeled probe which is cleavable by RNase H2 may be employed. In the latter case, cleavage of both the hybridized primers and the probe can be mediated by the same enzyme. The RNase H cleavage domain within the probe may comprise only RNA residues. In general, all of the combinations of residues useful in the cleavage domain of the blocked primers of the present invention can be used as the cleavage domain within the probe. In particular, when RNase H2 is used as the cleavage enzyme, a single RNA residue or two adjacent 2'-F residues are preferred as the cleavage domain within the probe. Such a modified oligonucleotide probe is particularly useful in real-time PCR and can be employed with standard DNA primers or with the blocked primers of the present invention. In such real-time PCR assays, thermophilic versions of RNase H2 are preferred, especially thermophilic RNase H2 enzymes having lower activity at reduced temperatures. In the examples provided herein, a number of thermophilic RNase H2 enzymes have been isolated and have shown to be stable under thermocycling conditions and useful in PCR. When used with the blocked primers of the present invention, the need for a specific hot-start DNA polymerase can be eliminated. This results in a significant decrease in assay cost.

In another embodiment, the blocked primers of the present invention can be used in the primer-probe assay format for PCR described in U.S. Patent App. 2009/0068643. In this case, the primer also contains a label domain on the 5' end of the oligonucleotide which may or may not be complementary to the target nucleic acid. The product generated by extension of the primer serves as a template for synthesis by the reverse primer in the next cycle of PCR. This converts the label domain into a double stranded structure. In one such embodiment a fluorophore and a quencher are attached to the label domain and the reaction is monitored by an increase in fluorescence resulting from an increase in the distance between the fluorophore and quencher in the double stranded form compared to the single stranded state. In yet another such embodiment the label domain contains a cleavage domain located between the fluorophore and quencher. Cleavage occurs only when the cleavage domain is double stranded. Again the reaction is monitored by an increase in fluorescence. In this instance the cleaving agent may be one that cleaves both strands, the primer and its complement, such as a restriction enzyme. Alternatively the cleaving agent may be a nicking agent that cleaves only the primer, preferably an RNase H enzyme, and even more preferably a thermostable RNase H2 enzyme. There are two cleavage domains within the primer in this assay format: one 5' of the blocking group at which cleavage occurs to activate the primer and allow extension and the second within the label domain. Cleavage at both sites can be mediated by the same cleaving agent. The label domain may also contain other labeling groups including but not limited to biotin, haptens and enzymes to name a few. Alternatively the 5' fragment released by cleavage within the label domain may serve as a mass tag for detection by mass spectrometry.

In yet another embodiment, the blocked primers of the present invention can be used in the template-probe assay format for PCR described in U.S. Patent App. 2009/0068643.

In another embodiment of the invention, RNase H2 cleavable blocked oligonucleotides are used to detect 5-methylcytosine residues by PCR analysis of sodium bisulfite treated nucleic acids, including but not limited to DNA and RNA. Previous work has established that treatment of nucleic acid template with bisulfite will rapidly deaminate cytosines that are not methylated on the 5' carbon of the base. This deamination reaction converts the unmethylated cytosines into uracil, resulting in a functional C→T transition mutation in the nucleic acid sequence. It is also known that 5-methylcytosine is highly resistant to this deamination, resulting in preservation of the 5-methylcytosine nucleotide as a cytosine, rather than conversion to a thymine Numerous methods have been employed to detect 5' cytosine methylation modifications following the bisulfite conversion technique. Examples include, but are not limited to, standard mismatch-specific quantitative and non-quantitative PCR methods, as well as subcloning and sequencing of the generated sodium bisulfite reaction products.

In the present invention, the template is bisulfite treated by methods that are well known to those in the art. If the starting template was RNA, a complementary cDNA strand is generated by any well known reverse transcription method. Blocked cleavable oligonucleotides that will either match or discriminate against the target template cytosines (now converted to uracils) or 5-methylcytosines are added to a PCR reaction containing the RNase H2 enzyme and the bisulfite treated template. Amplification of the mismatched (converted cytosine>uracil or unconverted 5-methylcytosine>5-methylcytosine) base containing template is highly reduced relative to the matched base template due to the mismatch discrimination of RNase H2 cleavage reaction. Incomplete bisulfite conversion of cytosines to uracils, a consistent concern with the sodium bisulfite conversion technique, can be detected by the designing blocked cleavable oligonucleotides that target known non-5'-methylated cytosines in the bisulfite converted template. PCR amplification of unconverted cytosines with these primers should display greater discrimination relative to standard unblocked primers. The present invention is expected to significantly increase the discrimination of the methylated and unmethylated cytosines.

Allele Specific PCR

The blocked primers of the present invention can also be used in allele-specific PCR (AS-PCR). In general, AS-PCR is used to detect variant alleles of a gene, especially single base mutations such as SNPs (see for example U.S. Pat. No. 5,496,699). SNP locations in the genome, as well as sequences of mutated oncogenes, are known in the art and PCR primers can be designed to overlap with these regions.

Detection of single base mismatches is a critical tool in diagnosing and correlating certain diseases to a particular gene sequence or mutation. Although AS-PCR has been known in the biological arts for more than a decade (Bottema et al., 1993, Methods Enzymol., 218, pp. 388-402), tools are still needed to more accurately discriminate between particular mismatches and fully complementary sequences. The present invention addresses this need.

In AS-PCR a primer is utilized which overlaps the variant locus. Generally the primer is designed such that the 3'-terminal nucleotide is positioned over the mutation site. Alternatively, the mutation site is sometimes located over one or two bases from the 3'-end. If there is a mismatch at or near the 3'-end, primer extension and hence PCR are inhibited. The difference between the efficiency of amplification when there is an exact match with the primers versus an allelic variant where there is one or more mismatches can in some cases be measured by end point PCR in which case the final amplification products are analyzed by, for example, gel electrophoresis. More commonly real time PCR is used to determine the efficiency of amplification. A fluorescence based method of detection of the amplicon in real time such as a DNA dye binding assay or a dual labeled probe assay is most often used. The PCR cycle where fluorescence is first detectable above background levels (the Cp, or crossing point) provides a measure of amplification efficiency. If there is a mismatch between the primer and the target DNA, amplification efficiency is reduced and the Cp is delayed. Generally an increase in Cp of 4 to 5 cycles is sufficient for discrimination of SNPs.

In one AS-PCR embodiment of the present invention, the primer contains a single RNA residue, and the mismatch can be aligned directly over the RNA residue of the primer. The difference in crossing point (Cp) values between a perfect match and a mismatch, correlating to a cleavage differential, is readily apparent (see Example 13). In some instances, aligning the mismatch one base to either the 5' side or the 3' side of the RNA residue increases the difference in Cp values. When the mismatch is located on the 5' side of the RNA residue, the subsequent RNase H2 cleavage would leave the mismatch as the last base of the 3' end of the cleaved primer. Surprisingly, having the mismatch directly on top of the RNA residue is more effective in most cases than locating the mismatch to the 5' side of the RNA residue.

In another embodiment, the primer contains multiple RNA residues or two adjacent 2'-fluoro residues and detection of the mismatch follows the same principles as with a primer containing one RNA residue; the mismatch preferably is located near or on top of the expected point of cleavage.

In another embodiment, a second mismatch is used to increase the sensitivity of the assay. In yet a further embodiment, the second mismatch is placed to the 3' side of the mismatch directly over the SNP site. In yet a further embodiment, the second mismatch is placed one or two bases from the mismatch directly over the SNP site (see Example 23).

In yet another embodiment, modified residues are incorporated into the primer on the 5'- or 3'-side of the base located over the mutation site. In one such embodiment of the present invention a 2'-O-methyl ribonucleoside is placed immediately 5' to the RNA base within the primer (see Example 22).

The sensitivity of the assay can also be increased through incorporation of nuclease resistant analogs into the primer on the 3'-side of the base over the mutation site. Such nuclease resistant analogs include, but are not limited to, phosphorothioates, phosphorodithioates, methylphosphonates and abasic residues such as a C3 spacer. In one such embodiment of the present invention, phosphorothioate internucleotide linkages are incorporated at each position from the RNA base over the mutation site to the 3'-end of the primer. In yet another such embodiment phosphorothioate linkages or phosphorodithioate are incorporated at all positions from the base on the 3'-side of the RNA residue to the 3'-end of the primer. In yet another such embodiment a single phosphorothioate or phosphorodithioates is introduced on the 3'-side of the residue immediately downstream from the RNA base within the primer. In one embodiment, the phosphorothioate bonds are placed between each monomer 3' to the RNA monomer directly over the SNP site, as well as between the RNA monomer and the base 3' to the RNA base (see Example 25).

The assay sensitivity can also be improved by optimizing the placement of the 3' blocking group or groups. In one embodiment, a blocking group is placed internal to the 3' end of the oligonucleotide. In a further embodiment, more than on blocking group is placed internal to the 3' terminus. In yet a further embodiment, an RNA monomer sits directly over the SNP site, with a DNA monomer 3' to the RNA monomer, followed by two C3 spacers, and finally followed by a 3' terminal base (see Example 28). The assay sensitivity and specificity also be improved by optimization of magnesium ion concentration in the reaction buffer, wherein lower magnesium levels (e.g., 1.5 mM or 2.0 or 2.5 mM, etc.) may confer higher specificity and higher magnesium levels (e.g., 3.0 mM, 3.5 mM, etc.) may confer lower specificity but with higher amplification efficiency (see Examples 36 and 37).

One convenient, quantitative measure of improved specificity during amplification of a target DNA sequence is the observed change in Cp value (ΔCp) for amplifying a target DNA sequence with a matched primer vs. a mismatched primer. A preferred ΔCp of at least about 5 or greater or a relative increase of ΔCp of at least about 50% or greater is indicative of improved specificity by optimization of magnesium ion concentration. More typically, however, as revealed by the Examples, preferred ΔCp can be much greater, such as ΔCp values of at least about 10-20 or greater or a relative increase of ΔCp of at least about 100% or greater. The observed ΔCp indicative of improved specificity by optimization of magnesium ion concentration can depend upon primer design and the particular target DNA sequence being interrogated.

In one embodiment of the allele-specific PCR, the primers can be designed to detect more than one mismatch. For example, the forward primer can detect a first mismatch, and the reverse primer could detect a second mismatch. In this embodiment, the assay can be used to indicate whether two mismatches occur on the same gene or chromosome being analyzed. This assay would be useful in applications such as determining whether a bacterium of interest is both pathogenic and antibiotic resistant.

In another embodiment, the forward and reverse primers are both blocked and overlap at the mismatch. In a further embodiment, the blocking groups are internal to the 3' end of the oligonucleotide. In yet a further embodiment, for one or both the forward and reverse primers, an RNA monomer sits directly over the SNP site, with a DNA monomer 3' to the RNA monomer, followed by two C3 spacers, and finally followed by a 3' terminal base.

Reverse Transcriptase PCR (RT-PCR)

In yet another embodiment the methods of the present invention can be used in coupled reverse transcription-PCR (RT-PCR). In one such embodiment reverse transcription and PCR are carried out in two distinct steps. First a cDNA copy of the sample mRNA is synthesized using either an oligo dT primer or a sequence specific primer. Random hexamers and the like can also be used to prime cDNA synthesis. The resulting cDNA is then used as the substrate for PCR employing the blocked primers and methods of the present invention.

Alternatively reverse transcription and PCR can be carried out in a single closed tube reaction. In one such embodiment three primers are employed, one for reverse transcription and two for PCR. The primer for reverse transcription binds to the mRNA 3' to the position of the PCR amplicon. Although not essential, the reverse transcription primer can include RNA residues or modified analogs such as 2'-O-methyl RNA bases which will not form a substrate for RNase H when hybridized to the mRNA. Preferably an RNase H2 enzyme which has decreased activity at lower temperatures is used as the cleaving agent.

In the three primer RT-PCR assay it is desirable to inhibit the RT-primer from participating in the PCR reaction. This can be accomplished by utilizing an RT-primer having a lower Tm than the PCR primers so it will not hybridize under the PCR conditions. Alternatively, a non-replicable primer incorporating, for example, two adjacent C3 spacers can be used as the RT-primer (as in polynomial amplification, see U.S. Pat. No. 7,112,406). In this case when the cDNA is copied by extension of the forward PCR primer it will not include the binding site for the RT-primer.

In one embodiment, only the reverse PCR primer is blocked utilizing the compositions and methods of the present invention. In yet another embodiment both the forward and reverse PCR primers are blocked. The reverse PCR primer is blocked in the 3 primer RT-PCR assay to prevent it from being utilized for reverse transcription. If desired, modified bases such as 2'-O-methyl RNA residues can be incorporated in the reverse PCR primer although any such modification must allow the primer sequence to serve as a template for DNA synthesis and be copied.

In the two primer RT-PCR assays of the present invention, only the forward PCR is blocked. The reverse PCR primer also serves as the RT-primer and therefore can not be blocked.

While not comprehensive, Table 1 illustrates how variations in the blocking groups, labeling groups, cleavage site embodiments, modifications to the cleavage site or other regions of the oligonucleotide, buffer conditions and enzyme can further optimize assay formats depending on their particular application. Examples of assay formats and applications include PCR; real-time PCR utilizing double-stranded DNA-binding dyes such as SYBR® Green, 5' nuclease assays (Taqman™ assays) or molecular beacons; primer-probe and template-probe assays (see U.S. Patent Application 2009/0068643); polynomial or linked linear amplification assays; gene construction or fragment assembly via PCR; allele-specific PCR and other methods used to detect single nucleotide polymorphisms and other variant alleles; nucleic acid sequencing assays; and strand displacement amplification. In these various assays, cleavage of the primers of the present invention can be used to enhance the specificity of the particular reaction.

TABLE 1

| | | | | PCR/Primer Extension/Polyamp | | | | | |
|---|---|---|---|---|---|---|---|---|---|
| Primer Blocking Group | Labeling Group | RNase H Cleavage Site | Flanking sequence modifications | Divalent cation | DNA Polymerase | RNase H | Sample | Use | Assay Format |
| None | None<br>Fluorophore<br>Fluorophore/Quencher<br>Enzyme<br>1. Horseradish peroxidase<br>2. Alkaline phosphatase | RNA<br>1. Single RNA residue<br>2. Multiple RNA residues | None<br>Nuclease-resistant linkages<br>1. Phosphorothioate<br>2. Dithioate<br>3. Methyl-phosphonate<br>4. Non-nucleotide spacers | $Mg^{2+}$ | Hot Start<br>1. Ab<br>2. Chemically modified | RNase H1<br>RNase H2<br>1. Non-thermostable<br>2. Thermostable<br>A. Hot Start<br>  i. Intrinsic<br>  ii. Ab<br>  iii. Chemically modified<br>B. Non-Hot Start | Genomic DNA<br>Mitochondrial/chloroplast DNA | Sample Prep<br>Coupled amplification to reverse transcription<br>Quantification of target nucleic acid sequence<br>1. Chromosomal copy number<br>2. mRNA | No additional probe<br>1. Detection of primer cleavage<br>  A. Fluorescence<br>  B. Mass Spec<br>  C. Electrophoresis<br>2. Dye-binding assay<br>  A. Sybr Green |
| Modification of 3'-terminal residue<br>1. C3 spacer | Biotin<br>Hapten<br>1. Deoxigenin | Modified residues:<br>1. 2 adjacent 2' F residues | 2'OMe | Alternative divalent cation +/− $Mg^{2+}$ | Non-Hot Start | RNase H3 and other catalysts that cleave RNA/DNA heteroduplexes | cDNA | Detection of variant allele | With an internal probe<br>1. Taqman ®<br>2. Fluorescence-quenched linear probe<br>3. Molecular beacon<br>4. RNase H-cleavable probe |
| Upstream modification<br>1. Adjacent to the 3'-terminal residue<br>2. Further upstream | Antibody<br>Mass Tag<br>Radiolabel<br>$^{32}P$, $^{14}C$, $^{3}H$, $^{35}S$, etc. | | Secondary mismatches | | | RNase H mutants having altered cleavage specificity<br>1. Enhanced cleavage of 2'-F substrates | RNA<br>1. mRNA | Gene/Fragment construction | Tempro Assay<br>1. RNase H2-cleavable probe |

Cycling Probe Reactions

Cycling probe reactions are another technique for detecting specific nucleic acid sequences (see U.S. Pat. No. 5,403,711). The reaction operates under isothermal conditions or with temperature cycling. Unlike PCR products accumulate in a linear fashion.

Table 2 illustrates a non-comprehensive set of possible elements of the current invention to improve assays based on the cycling probe reaction. New features of the invention include 1) use of a hot start RNase H enzyme; 2) cleavage of novel sequences by RNase H enzymes (e.g., cleavage of substrates containing 2'-fluoronucleosides by Type II RNases H); and 3) introduction of modifications and secondary mismatches flanking an RNase H cleavage domain to enhance specificity and/or suppress nonspecific cleavage reactions. Such modifications and secondary mismatches are particularly useful when cleavage is mediated by a Type II RNase H and the cleavage domain is a single RNA residue or two adjacent 2'-fluoro residues.

TABLE 2

| | | | | Cycling Probe Reaction | | | | |
|---|---|---|---|---|---|---|---|---|
| Primer Extension Blocking Group | Labeling Group | RNase H Cleavage Site | Flanking sequence mods | Divalent cation | RNase H | Sample | Use | Assay Format |
| None | None | RNA | None | Mg$^{2+}$ | RNase H1 RNase H2 1. Non-thermostable 2. Thermostable A. Hot Start i. Intrinsic ii. Ab iii. Chemically modified B. Non-Hot Start | Genomic DNA Mito-chondrial/ chloroplast DNA | Quantification of target nucleic acid sequence 1. Chromosomal copy number 2. mRNA | Stand-alone 1. Isothermal 2. Temperature cycling |
| Modification of 3'-terminal residue 1. C3 spacer | Fluorophore Fluorophore/ Quencher | 1. Single RNA residue 2. Multiple RNA residues | Nuclease-resistant linkages 1. Phos-phorothioate 2. Dithioate 3. Methyl-phosphonate 4. Non-nucleotide spacers | | | | | |
| Upstream modification 1. Adjacent to the 3'-terminal residue 2. Further upstream | Enzyme 1. Horseradish peroxidase 2. Alkaline phosphatase | Modified residues: 1. 2 adjacent 2' F residues | 2'OMe | Alternative divalentcation +/− Mg$^{2+}$ | RNase H3 and other catalyst that cleave RNA/DNA heteroduplexes | | Detection of variant allele | Coupled to Amplification 1. PCR 2. LCR 3. Polyamp |
| | Biotin | | Secondary mismatches | | RNase H mutants having altered cleavage specificity 1. Enhanced cleavage of 2'-F substrates | cDNA | | |
| | Hapten | | | | | | | |
| | 1. Deoxigenin Antibody | | | | | | | |
| | Mass Tag | | | | | | | |
| | Radiolabel $^{32}$P, $^{14}$C, $^{3}$H, $^{35}$S, etc. | | | | | | | |

DNA Ligation Assays

The present invention can also serve to increase the specificity of DNA ligation assays. Donor and/or acceptor oligonucleotides of the present invention can be designed which bind adjacent to one another on a target DNA sequence and are modified to prevent ligation. Blocking groups on the acceptor oligonucleotide useful to inhibit ligation are the same as those used to prevent primer extension. Blocking the donor oligonucleotide can be readily accomplished by capping the 5'-OH group, for example as a phosphodiester, e.g.:

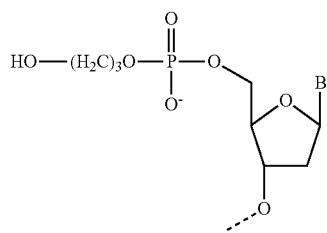

Other 5' blocking groups include 5'-O-alkyl substituents such as 5'-O-methyl or 5'-O-trityl groups, 5'-O-heteroalkyl groups such as 5'-OCH$_2$CH$_2$OCH$_3$, 5'-O-aryl groups, and 5'-O-silyl groups such as TIPS or TBDMS. A 5' deoxy residue can also be used to block ligation.

Sterically bulky groups can also be placed at or near the 5'-end of the oligonucleotide to block the ligation reaction. A 5'-phosphate group cannot be used to block the 5'-OH as this is the natural substrate for DNA ligase. Only after hybridization to the target DNA sequence are the blocking groups removed by, for example cleavage at an RNase H cleavable domain, to allow ligation to occur. Preferably cleavage is mediated by an RNase H Type II enzyme, and even more preferably a thermophilic Type II RNase H enzyme. More preferably, a thermophilic Type II RNase H enzyme which is less active at room temperature than at elevated temperature is utilized to mediate cleavage and thereby activation of the acceptor and/or donor oligonucleotide. Alternatively, a sequence specific nicking enzyme, such as a restriction enzyme, may be utilized to mediate cleavage of the donor and/or acceptor oligonucleotide.

In a further embodiment, the cleaving reaction is first carried out at a higher temperature at which only one of the two oligonucleotides hybridizes to the target sequence. The temperature is then lowered, and the second oligonucleotide hybridizes to the target, and the ligation reaction then takes place.

In yet a further embodiment in which there is a cleavage domain located in the donor oligonucleotide, this oligonucleotide is not blocked at or near the 5'-end, but simply has a free 5'-OH. This oligonucleotide cannot serve as a donor in the ligation reaction; to do so requires a 5'-phosphate group. Thus, the 5'-end is functionally blocked. Cleavage by RNase H generates a 5'-phosphate group allowing the donor oligonucleotide to participate in the ligation reaction.

An important advantage of the present invention is that it allows double interrogation of the mutation site, and hence greater specificity, than standard ligation assays. There is an opportunity for discrimination of a variant allele both at the cleavage step and the ligation step.

Table 3 illustrates a non-comprehensive set of possible elements of the current invention to improve oligonucleotide ligation assays.

TABLE 3

Oligonucleotide Ligation Assay

| Donor Oligonucleotide Blocking Group | Acceptor Oligonucleotide Blocking Group | Labeling Group | RNase H Cleavage Site | Flanking sequence mods | Divalent cation | DNA Ligase | RNase H | Sample | Use | Reaction Conditions | Assay Format |
|---|---|---|---|---|---|---|---|---|---|---|---|
| None (5'-phosphate) | None | None | RNA 1. Single RNA residue 2. Multiple RNA residues | None | $Mg^{2+}$ | Hot Start 1. Ab 2. Chemically modified | RNase H1 | Genomic DNA | Quantification of target nucleic acid sequence | RNase H cleavage and DNA ligation at single temperature | Stand-alone 1. Single cycle 2. Linear Amplification 3. LCR |
| 5'-OH (Functional block) | Modification of 3'-terminal residue | Fluorophore | | Nuclease-resistant linkages 1. Phosphorothioate 2. Dithioate 3. Methylphosphonate 4. Non-nucleotide spacers | | | RNase H2 1. Non-thermostable 2. Thermostable A. Hot Start   i. Intrinsic   ii. Ab   iii. Chemically modified B. Non-Hot Start | Mitochondrial/ chloroplast DNA | 1. Chromosomal copy number 2. mRNA | | |
| Modification of 5'-residue 1. C3 spacer | 1. C3 spacer | Fluorophore/ Quencher | | | | | RNase H3 and other catalysts that cleave RNA/DNA heteroduplexes | | | | |
| Downstream modification 1. Adjacent to the 5'-terminal residue 2. Further downstream | Upstream modification 1. Adjacent to the 3'-terminal residue 2. Further upstream | Enzyme 1. Horse-radish peroxidase 2. Alkaline phosphatase Biotin Hapten 1. Deoxigenin Antibody Mass Tag Radiolabel $^{32}P$, $^{14}C$, $^{3}H$, $^{35}S$, etc. | Modified residues: 1. 2 adjacent 2'-F residues | 2'OMe Secondary mismatches | Alternative divalent cation +/- $Mg^{2+}$ | Non-Hot Start | RNase H mutants having altered cleavage specificity 1. Enhanced cleavage of 2'-F substrates | cDNA | Detection of variant allele | RNase H cleavage at elevated temperature (reduced temperature for DNA ligation) | Coupled to primer extension 1. PCR 2. Reverse transcription 3. Polyamp |

DNA Sequencing Reactions

In one embodiment, a method of sequencing a target DNA of interest is provided. The method entails
(a) providing a reaction mixture comprising a primer having a cleavage domain and a blocking group linked at or near to the 3' end of the primer which prevents primer extension, a sample nucleic acid comprising the target DNA sequence of interest, a cleaving enzyme, nucleotide triphosphate chain terminators (e.g., 3' dideoxynucleotide triphosphates) and a polymerase,
(b) hybridizing the primer to the target nucleic acid to form a double-stranded substrate;
(c) cleaving the hybridized primer with the cleaving enzyme at a point within or adjacent to the cleavage domain to remove the blocking group from the primer; and
(d) extending the primer with the polymerase.

In one embodiment, the invention is used in a "next generation" sequencing platform. One type of next generation sequencing is "sequencing by synthesis", wherein genomic DNA is sheared and ligated with adapter oligonucleotides or amplified by gene-specific primers, which then are hybridized to complementary oligonucleotides that are either coated onto a glass slide or are placed in emulsion for PCR. The subsequent sequencing reaction either incorporates dye-labeled nucleotide triphosphates or is detected by chemiluminescence resulting from the reaction of pyrophosphate released in the extension reaction with ATP sulfurylase to generate ATP and then the ATP-catalyzed reaction of luciferase and its substrate luciferin to generate oxyluciferin and light.

A second type of next generation sequencing is "sequencing by ligation", wherein four sets of oligonucleotides are used, representing each of the four bases. In each set, a fluorophore-labeled oligonucleotide of around 7 to 11 bases is employed in which one base is specified and the remaining are either universal or degenerate bases. If, for example, an 8-base oligonucleotide is used containing 3 universal bases such as inosine and 4 degenerate positions, there would be $4^4$ or 256 different oligonucleotides in each set each with a specified base (A, T, C or G) at one position and a fluorescent label attached to either the 5'- or 3'-end of the molecule or at an internal position that does not interfere with ligation. Four different labels are employed, each specific to one of the four bases. A mixture of these four sets of oligonucleotides is allowed to hybridize to the amplified sample DNA. In the presence of DNA ligase the oligonucleotide hybridized to the target becomes ligated to an acceptor DNA molecule. Detection of the attached label allows the determination of the corresponding base in the sample DNA at the position complementary to the base specified within the oligonucleotide.

In one embodiment of the present invention, a donor oligonucleotide of about 7-11 bases contains a specified base at the 5' end of the oligonucleotide. The remaining bases are degenerate or universal bases, and a label specific to the specified base is incorporated on the 3' side of the specified base. The 3' end of the probe is irreversibly blocked to prevent the donor oligonucleotide from also acting as an acceptor. In some cases this may be accomplished by the labeling group. The second base from the 5' end of the oligonucleotide, i.e., the residue next to the specified base is a degenerate mixture of the 4 RNA bases. Alternatively, any analog recognized by RNase H2, such as a 2'-fluoronucleoside may be substituted at this position. A universal base such as riboinosine or ribo-5-nitroindole, may also be incorporated at this location. The probe first hybridizes to the target sequence and becomes ligated to the acceptor DNA fragment as in the standard sequencing by ligation reaction. After detection of the specified base, RNase H2 is added which cleaves the probe on the 5'-side of the RNA residue leaving the specified base attached to the 3' end of the acceptor fragment. The end result is that the acceptor fragment is elongated by one base and now is in position to permit the determination of the next base within the sequence. The cycle is repeated over and over, in each case moving the position of hybridization of the donor oligonucleotide one base 3' down the target sequence. The specificity is increased compared to traditional sequencing by ligation because the specified base is always positioned at the junction of the ligation reaction.

The donor oligonucleotide probe can optionally contain universal bases including, but not limited to, 5-nitroindole, ribo-5'-nitroindole, 2'-O-methyl-5-nitroindole, inosine, riboinosine, 2'-O-methylriboinosine and 3-nitropyrrole. This reduces the number of different oligonucleotides in each set required for the assay by a factor of four for every degenerate position on the probe substituted with a universal base. The method can also include a capping step between the ligation reaction and the RNase H2 cleaving step. The capping reaction can be performed by introducing a DNA polymerase and a chain terminator, thereby capping any of the acceptor fragment molecules that did not ligate with a donor oligonucleotide probe in the previous step.

In the above example the ligation reactions and hence the sequencing readout proceeds in the 5'- to 3'-direction one base at a time. Alternatively the donor oligonucleotide can be designed so that two bases are determined in each cycle. In this case the first two bases on the 5'-end of the donor oligonucleotide are specified (for example, pA-C-R-N-N-N-I-I-X, where R=a degenerate mixture of all 4 RNA bases, N=a degenerate DNA base, I=inosine, and X is a fluorophore). As in all cases there is a 5'-phosphate (p) to permit ligation of the donor oligonucleotide to the acceptor. Sixteen such oligonucleotide sets are required, one for each of the sixteen possible dinucleotides. Each of the sixteen can be labeled with a different fluorophore. Alternatively ligation reactions can be carried out with 4 separate pools each having four such sets of oligonucleotides. In that case, only four different fluorophores are required.

In another embodiment for sequencing in the 5'- to 3'-direction a donor oligonucleotide of the following type can be used: pA-N-R-N-N-N-I-I-X wherein p, N, R, I and X are as defined in the previous example. One base is determined at each cycle but at alternate positions: 1, 3, 5, etc. This may be adequate for identification of the sequence if compared to a reference database. If desired, the remaining bases (positions 2, 4, 6, etc.) can be determined by repeating the sequencing reaction on the same template with the original acceptor oligonucleotide shifted one base upstream or downstream. In a related example a donor oligonucleotide of the following type can be used: p-A-F-FN-N-N-I-I-X wherein p, N, I and X are as defined above and F is a degenerate mixture of all four 2'-fluoronucleosides. Following ligation, cleavage by RNase H2 results in the addition of two bases to the 3'-end of the acceptor (i.e., AF). After the next ligation reaction, the sequence at the 3'-end of the acceptor would be . . . A-F-S-F-F-N-N-N-I-I-X where S is the specified base at position 3, and X would be a different fluorophore from the previous cycle if the specified base were not A. Cleavage with RNase H2 next occurs between the two 2'-fluororesidues. Cleavage by RNase H2 at the isolated 2'-fluororesidue occurs much more slowly and can be avoided by adjusting the RNase H2 concentration and reaction time.

A variant of the above method can be performed in which sequencing proceeds in the 3'- to 5'-direction. In this case an acceptor oligonucleotide is added at each cycle as in the following structure: X-I-I-N-N-N-F-F-S-OH wherein the specified base (S) is at the 3'-end of the oligonucleotide. The 5'-end is blocked to prevent the oligonucleotide from acting as a donor. Cleavage by RNase H2 leaves the sequence pF-S at the 5'-end of the donor fragment which is prepared for the next sequencing cycle. A capping step can be included in the cycle before the cleavage reaction using a phosphatase to remove the 5'-phosphate of the donor oligonucleotide if ligation to the acceptor failed to occur.

In a further embodiment, the invention provides an improvement for DNA sequencing using ribotriphosphates (or alternative analogs which provide a substrate for RNase H2, such as 2'-fluoronucleoside triphosphates) in conjunction with a fluorescently labeled primer. Similar to traditional sequencing methods known in the art, the triphosphate residue would be incorporated by a DNA polymerase. The concentration of the ribo triphosphate, or the alternative analog providing a substrate for RNase H2, is adjusted to a concentration such that on average one such base is incorporated randomly within each extension product produced by the polymerase. The nested family of fragments originating from the primer is generated by cleavage with RNase H2 and then separated by electrophoresis as in standard DNA sequencing methods. Alternatively, multiple RNA residues or modified nucleosides such as 2'-fluoronucleosides may be incorporated into the extension product and the subsequent digestion with RNase H2 is limited so that on average each strand is cut only once. Four separate reactions are run, each substituting one of the bases with a different ribotriphosphate (A, C, T or G) or other RNase H2 cleavable analog. In this assay, use of expensive fluorescently labeled dideoxy triphosphate chain terminators is obviated.

Next Generation DNA Sequencing (NGS)

Modern next generation sequencing (NGS) methods typically involve PCR amplification of sub-fragments of a target nucleic acid sample prior to performing the actual sequencing reactions and base identity interrogation. Selective amplification of regions adjacent to SNP sites could be achieved using the blocked-cleavable primers with RNase H2 method of the present invention, enriching these sequences for input into NGS analysis. Further, NGS methods can involve the need for multiplex PCR reactions to enrich for many specific sequences of interest, and primer-dimer and other unwanted reactions can occur which contribute unwanted fragments into the sequencing workflow, decreasing useful information content, increasing cost, and lowering throughput. These unwanted side reactions could be suppressed using the blocked-cleavable primers with RNase H2 method of the present invention. Typically, PCR amplification preformed as part of the work flow of NGS employs high fidelity DNA polymerases, which can have 10-100 fold lower base incorporation error rate than Taq DNA polymerase. Many high fidelity DNA polymerases possess a 3'-exonuclease proofreading activity, which can in some cases remove a non-nucleotide blocking group from the 3'-end of a modified primer. Certain designs of blocked-cleavable primers, particularly those with internal template blocking groups (e.g., internal C3 spacers) having an unmodified DNA 3'-end are not recognized by the 3'-exonuclease activity of the high fidelity polymerase and permit linked use of blocked-cleavable primers and RNase H2 with amplification reactions employing a high fidelity DNA polymerase (see Examples 39 and 40).

Oligonucleotide Synthesis

In another embodiment of the present invention, an improved method for oligonucleotide synthesis is provided. Using similar techniques as described above, a composition acting as a donor oligonucleotide can be ligated to an acceptor fragment in order to add additional bases to the 3'-end of the acceptor fragment. It is the acceptor fragment that is the growing polynucleotide undergoing synthesis. In this case, the composition of the donor fragment is preferably a single-stranded oligonucleotide that forms a hairpin to provide a double-stranded region with an overhang of about 1-8 bases on the 3'-end. The base at the 5' end would be the desired base to add to the growing acceptor fragment. For synthesis of a polynucleotide containing all four bases (A, C, T and G), four different donor fragments are employed which can have the identical sequence except varying in the 5' base. Preferably the donor is blocked at the 3'-end so it cannot react as an acceptor. The blocking group placed at or near the 3'-end of the donor can be a label to allow monitoring of the reaction. Four different labels can be used corresponding to the four different bases at the 5'-end of the donor. The base adjacent to the desired base at the 5'-end is a RNA base or an alternative analog such as a 2'-fluoronucleoside which provides a substrate for RNase H2. The overhang at the 3'-end can be random (degenerate) bases or universal bases or a combination of both. The donor fragment binds to the acceptor fragment, through hybridization of the 3'-end of the acceptor to the 3'-overhang of the donor oligonucleotide. A DNA ligase enzyme is then used to join the two fragments. Next a Type II RNase H is used to cleave the product on the 5'-side of the RNase H2 cleavage site, transferring the 5' base of the donor to the 3'-end of the acceptor. Optionally, a third step can be included in the cycle between the ligase and RNase H2 cleavage reactions in which molecules of the growing polynucleotide chain which may have failed to ligate are capped by reaction with a dideoxynucleotide triphosphate (or other chain terminator) catalyzed by a DNA polymerase. In one embodiment the DNA polymerase is a deoxynucleotide terminal transferase. The cycle is repeated, and the acceptor fragment can continue to be extended in a 5' to 3' direction. To facilitate isolation of the growing polynucleotide at each step the acceptor can be attached to a solid support such as controlled pore glass or polystyrene Similar to the sequence method described above, a donor oligonucleotide can be used to add two bases to the 3'-end of the acceptor oligonucleotide at each cycle. In this case the RNase H2 cleavable residue would be positioned 3' from the 5' end of the donor. This enzymatic synthesis method is particularly advantageous for synthesis of longer DNA molecules. The hairpin reagents corresponding to each base can be collected for reuse in further cycles or additional syntheses. Because the system does not use organic solvents, waste disposal is simplified.

Kits of the Present Invention

The present invention also provides kits for nucleic acid amplification, detection, sequencing, ligation or synthesis that allow for use of the primers and other novel oligonucleotides of the present invention in the aforementioned methods. In some embodiments, the kits include a container containing a cleavage compound, for example a nicking enzyme or an RNase H enzyme; another container containing a DNA polymerase and/or a DNA ligase and preferably there is an instruction booklet for using the kits. In certain embodiments, the kits include a container containing both a nicking enzyme or an RNase H enzyme combined with a DNA polymerase or DNA ligase. Optionally, the modified oligonucleotides used in the assay can be included with the enzymes. The cleavage enzyme agent, DNA polymerase and/or DNA ligase and oligonucleotides used in the assay are preferably stored in a state where they exhibit long-term stability, e.g., in suitable storage buffers or in a lyophilized or freeze dried state. In addition, the kits may further comprise a buffer for the nicking agent or RNase H, a buffer for the DNA polymerase or DNA ligase, or both buffers. Alternatively, the kits may further comprise a buffer suitable for both the nicking agent or RNase H, and the DNA polymerase or DNA ligase. Buffers may include RNasin and other inhibitors of single stranded ribonucleases. Descriptions of various components of the present kits may be found in preceding sections related to various methods of the present invention.

Optionally, the kit may contain an instruction booklet providing information on how to use the kit of the present invention for amplifying or ligating nucleic acids in the presence of the novel primers and/or other novel oligonucleotides of the invention. In certain embodiments, the information includes one or more descriptions on how to use and/or store the RNase H, nicking agent, DNA polymerase, DNA ligase and oligonucleotides used in the assay as well as descriptions of buffer(s) for the nicking agent or RNase H and the DNA polymerase or DNA ligase, appropriate reaction temperature(s) and reaction time period(s), etc.

Accordingly, in one embodiment, a kit for the selective amplification of a nucleic acid from a sample is provided. The kit comprises
(a) a first and a second oligonucleotide primer, each having a 3' end and 5' end, wherein each oligonucleotide is complementary to a portion of a nucleic acid to be amplified or its complement, and wherein at least one oligonucleotide comprises a RNase H cleavable domain, and a blocking group linked at or near to the 3' end of the oligonucleotide to prevent primer extension and/or to prevent the primer from being copied by DNA synthesis directed from the opposite primer;
(b) an RNase H enzyme; and
(c) an instruction manual for amplifying the nucleic acid. The kit may optionally include a DNA polymerase.

In a further embodiment, the kit for selective amplification of a nucleic acid includes an oligonucleotide probe having a 3' end and a 5' end comprising an RNase H cleavable domain, a fluorophore and a quencher, wherein the cleavable domain is positioned between the fluorophore and the quencher, and wherein the probe is complementary to a portion of the nucleic acid to be amplified or its complement.

In yet another embodiment, the present invention is directed to a kit for the ligation of an acceptor oligonucleotide and a donor oligonucleotide in the presence of a target nucleic acid sequence. The kit comprises
(a) a donor oligonucleotide and an acceptor oligonucleotide in which one or both of the oligonucleotides comprise an RNase H cleavable domain and a blocking group preventing ligation;
(b) an RNase H enzyme; and
(c) an instruction manual for ligating the acceptor and donor oligonucleotides in the presence of a target nucleic acid sequence.

In a further embodiment, the kit may optionally include a DNA ligase enzyme.

In a further ligation kit embodiment, the donor oligonucleotide contains an RNase H cleavage domain, but lacks a blocking group at or near the 5'-end and instead has a free 5'-OH.

Blocking Group Designs

In several embodiments, oligonucleotide primers are provided that include a cleavage domain, which is cleavable by an RNase H enzyme, positioned 5' of a blocking group. The blocking group can b e linked at or near the 3'-end of the oligonucleotide primer. The blocking group prevents primer extension and/or inhibits the oligonucleotide primer from serving as a template for DNA synthesis. The blocking group can encompass one of several designs selected from the group consisting of RDDDDx, RDDDDMx, RDxxD, RDxxDM, RDDDDxxD, RDDDDxxDM and DxxD, wherein R is an RNA residue, D is a DNA residue, M is a mismatched residue and x is a C3 spacer. When an oligonucleotide that includes a blocking group having an M (for examples, RDDDDMx, RDxxDM, RDDDDxxDM) is hybridized to the target DNA sequence to form a double-stranded substrate, a mismatch exists at the location of the M in the blocking group oligonucleotide and its pairing partner in the target DNA sequence.

EXAMPLES

The present invention is further illustrated by reference to the following Examples. However, it should be noted that these Examples, like the embodiments described above, are illustrative and are not to be construed as restricting the enabled scope of the invention in any way.

Example 1—Cloning of Codon Optimized RNase H2 Enzymes from Thermophilic Organisms This example describes the cloning of codon optimized RNase H2 enzymes from thermophilic organisms.

To search for functional novel RNase H2 enzymes with potentially new and useful activities, candidate genes were identified from public nucleotide sequence repositories from Archaeal hyperthermophilic organisms whose genome sequences had previously been determined. While RNase H2 enzymes do share some amino acid homology and have several highly conserved residues present, the actual homology between the identified candidate genes was low and it was uncertain if these represented functional RNase H2 enzymes or were genes of unknown function or were non-functional RNase H2 genes. As shown in Table 4, five genes were selected for study, including two organisms for which the RNase H2 genes have not been characterized and three organisms to use as positive controls where the RNase H2 genes (rnhb) and functional proteins have been identified and are known to be functional enzymes. Although two uncharacterized predicted rnhb genes were selected for this initial study, many more Archaeal species have had their genome sequences determined whose rnhb genes are uncharacterized which could similarly be studied.

TABLE 4

Five candidate RNase H2 (rnhb) genes from thermophilic bacteria

| Organism | Accession # | Length | Comments |
|---|---|---|---|
| Pyrococcus kodakaraensis | AB012613 | 687 bp, 228 AA | See References (1-3) below |
| Pyrococcus furiosus | AE010276 | 675 bp, 224 AA | See Reference (4) below and UA20040038366A1 |
| Methanocaldococcus jannaschii | U67470 | 693 bp, 230 AA | See References (5, 6) below |
| Pyrococcus abyssi | AJ248284 | 675 bp, 224 AA | uncharacterized |

TABLE 4-continued

Five candidate RNase H2 (rnhb) genes from thermophilic bacteria

| Organism | Accession # | Length | Comments |
|---|---|---|---|
| Sulfolobus solfataricus | AE006839 | 639 bp, 212 AA | uncharacterized |

Bp = base pairs;
AA = amino acids

References 1-6: 1) Haruki, M., Hayashi, K., Kochi, T., Muroya, A., Koga, Y., Morikawa, M., Imanaka, T. and Kanaya, S. (1998) Gene cloning and characterization of recombinant RNase HII from a hyperthermophilic archaeon. *J Bacteriol*, 180, 6207-6214; 2) Haruki, M., Tsunaka, Y., Morikawa, M. and Kanaya, S. (2002) Cleavage of a DNA-RNA/DNA chimeric substrate containing a single ribonucleotide at the DNA-RNA junction with prokaryotic RNases HII. *FEBS Lett*, 531, 204-208; 3) Mukaiyama, A., Takano, K., Haruki, M., Morikawa, M. and Kanaya, S. (2004) Kinetically robust monomeric protein from a hyperthermophile. *Biochemistry*, 43, 13859-13866 4) Sato, A., Kanai, A., Itaya, M. and Tomita, M. (2003) Cooperative regulation for Okazaki fragment processing by RNase HII and FEN-1 purified from a hyperthermophilic archaeon, *Pyrococcus furiosus*. *Biochem Biophys Res Commun*, 309, 247-252; 5) Lai, B., Li, Y., Cao, A. and Lai, L. (2003) Metal ion binding and enzymatic mechanism of *Methanococcus jannaschii* RNase HII. *Biochemistry*, 42, 785-791; and 6) Lai, L., Yokota, H., Hung, L. W., Kim, R. and Kim, S. H. (2000) Crystal structure of archaeal RNase HII: a homologue of human major RNase H. *Structure*, 8, 897-904.

The predicted physical properties of the proteins encoded by the rnhb genes listed above are shown in Table 5 (Pace, C. N. et al., (1995) Protein Sci., 4, p. 2411).

TABLE 5

Characteristics of five RNase H2 enzymes

| Organism | Mol. weight | Molecules/µg protein | # residues Trp, Tyr, Cys | $\epsilon$ 280 nm $M^{-1}cm^{-1}$ |
|---|---|---|---|---|
| Pyrococcus kodakarensis | 25800.5 | 2.3E13 | 1, 7, 0 | 15930 |
| Pyrococcus furiosus | 25315.2 | 2.4E13 | 2, 8, 0 | 22920 |
| Methanocaldococcus jannaschii | 26505.8 | 2.3E13 | 1, 9, 3 | 19285 |
| Pyrococcus abysii | 25394.2 | 2.4E13 | 3, 7, 0 | 26930 |
| Sulfolobus solfataricus | 23924.8 | 2.5E13 | 3, 10, 0 | 31400 |

The amino acid similarity between RNase H2 enzymes (or candidate enzymes) from different Archaeal species within this set of 5 sequences ranges from 34% to 65%. An amino-acid identity matrix is shown in Table 6 below.

TABLE 6

Amino acid identity between five Archaeal RNase H2 proteins

| | P. kod. | P. fur. | M. jann. | P. ab. | S. solf. |
|---|---|---|---|---|---|
| P. kodakarensis | — | 0.570 | 0.595 | 0.358 | 0.333 |
| P. furiosus | 0.570 | — | 0.654 | 0.410 | 0.362 |
| M. jannaschii | 0.595 | 0.654 | — | 0.380 | 0.363 |
| P. abysii | 0.358 | 0.410 | 0.380 | — | 0.336 |
| S. solfataricus | 0.333 | 0.362 | 0.363 | 0.336 | — |

Codons of the native gene sequence were optimized for expression in *E. coli* using standard codon usage tables. The following sequences were assembled and cloned into plasmids as artificial genes made from synthetic oligonucleotides using standard methods. DNA sequence identity was verified on both strands. Sequences of the artificial DNA constructs are shown below. Lower case letters represents linker sequences, including a Bam HI site on the 5'-end and a Hind III site on the 3'-end. Upper case letters represents coding sequences and the ATG start codons are underlined.

SEQ ID NO: 1 - codon optimized rnhb gene from
*Pyrococcus kodakaraensis*
ggatccg<u>ATG</u>AAGATTGCTGGCATCGATGAAGCCGGCCGTGGCCCGGTAA

TTGGTCCAATGGTTATCGCTGCGGTAGTCGTGGACGAAAACAGCCTGCCA

AAACTGGAAGAGCTGAAAGTGCGTGACTCCAAGAAACTGACCCCGAAGCG

CCGTGAAAAGCTGTTTAACGAAATTCTGGGTGTCCTGGACGATTATGTGA

TCCTGGAGCTGCCGCCTGATGTTATCGGCAGCCGCGAAGGTACTCTGAAC

GAGTTCGAGGTAGAAAACTTCGCTAAAGCGCTGAATTCCCTGAAAGTTAA

ACCGGACGTAATCTATGCTGATGCGGCTGACGTTGACGAGGAACGTTTTG

CCCGCGAGCTGGGTGAACGTCTGAACTTTGAAGCAGAGGTTGTTGCCAAA

CACAAGGCGGACGATATCTTCCCAGTCGTGTCCGCGGCGAGCATTCTGGC

TAAAGTCACTCGTGACCGTGCGGTTGAAAAACTGAAGGAAGAATACGGTG

AAATCGGCAGCGGTTATCCTAGCGATCCTCGTACCCGTGCGTTTCTGGAG

AACTACTACCGTGAACACGGTGAATTCCCGCCGATCGTACGTAAAGGTTG

GAAAACCCTGAAGAAATCGCGGAAAAAGTTGAATCTGAAAAAAAAGCTG

AAGAACGTCAAGCAACTCTGGACCGTTATTTCCGTAAAGTgaagctt

SEQ ID NO: 2 - codon optimized rnhb gene from
*Pyrococcus furiosus*
ggatccg<u>ATG</u>AAGATTGGTGGCATCGACGAAGCCGGCCGTGGTCCGGCGA

TCGGTCCGCTGGTAGTAGCTACTGTTGTAGTGGATGAAAAAAACATCGAA

AAACTGCGTAACATCGGCGTAAAAGACTCCAAACAGCTGACGCCGCACGA

ACGTAAAAACCTGTTTTCCCAGATCACCTCCATTGCGGATGATTACAAGA

TCGTAATCGTGTCTCCGGAAGAAATTGACAACCGTAGCGGTACCATGAAC

GAGCTGGAAGTTGAAAAATTCGCGCTGGCGCTGAACTCTCTGCAGATCAA

GCCGGCTCTGATCTACGCAGACGCAGCAGATGTTGATGCAAACCGCTTCG

CATCCCTGATCGAACGTCGCCTGAACTATAAAGCCAAAATCATCGCGGAA

CACAAAGCAGACGCAAAGTACCCGGTCGTTTCTGCGGCGAGCATTCTGGC

GAAGGTTGTGCGTGACGAAGAAATCGAAAAGCTGAAAAAGCAATATGGCG

ACTTTGGCAGCGGTTACCCGAGCGACCCGAAAACGAAGAAATGGCTGGAG

GAGTATTACAAGAAACATAACAGCTTCCCACCGATCGTTCGTCGTACGTG

GGAAACTGTCCGCAAAATTGAAGAGTCCATCAAAGCCAAAAAGTCCCAGC

TGACCCTGGATAAATTCTTCAAGAAACCGaagctt

SEQ ID NO: 3 - codon optimized rnhb gene from
*Methanocaldococcus jannaschii*
ggatccgATGATTATCATTGGTATCGATGAAGCTGGCCGTGGTCCTGTAC

TGGGCCCGATGGTTGTATGTGCGTTCGCTATCGAGAAGGAACGTGAAGAA

GAACTGAAAAAGCTGGGCGTTAAAGATTCTAAAGAACTGACGAAGAATAA

ACGCGCGTACCTGAAAAAGCTGCTGGAGAACCTGGGCTACGTGGAAAAGC

GCATCCTGGAGGCTGAGGAAATTAACCAGCTGATGAACAGCATTAACCTG

AACGACATTGAAATCAACGCATTCAGCAAGGTAGCTAAAAACCTGATCGA

AAAGCTGAACATTCGCGACGACGAAATCGAAATCTATATCGACGCTTGTT

CTACTAACACCAAAAAGTTCGAAGACTCTTTCAAAGATAAAATCGAAGAT

ATCATTAAAGAACGCAATCTGAATATCAAAATCATTGCCGAACACAAAGC

AGACGCCAAGTACCCAGTAGTGTCTGCGGCGAGCATTATCGCGAAAGCAG

AACGCGACGAGATCATCGATTATTACAAGAAAATCTACGGTGACATCGGC

TCTGGCTACCCATCTGACCCGAAAACCATCAAATTCCTGGAAGATTACTT

TAAAAAGCACAAGAAACTGCCGGATATCGCTCGCACTCACTGGAAAACCT

GCAAACGCATCCTGGACAAATCTAAACAGACTAAACTGATTATCGAAaag ctt

SEQ ID NO: 4 - codon optimized rnhb gene from
*Pyrococcus abysii*
ggatccgATGAAAGTTGCAGGTGCAGATGAAGCTGGTCGTGGTCCAGTTA

TTGGTCCGCTGGTTATTGTTGCTGCTGTTGTGGAGGAAGACAAAATCCGC

TCTCTGACTAAGCTGGGTGTTAAAGACTCCAAACAGCTGACCCCGGCGCA

ACGTGAAAAACTGTTCGATGAAATCGTAAAAGTACTGGATGATTACTCTG

TGGTCATTGTGTCCCCGCAGGACATTGACGGTCGTAAGGGCAGCATGAAC

GAACTGGAGGTAGAAAACTTCGTTAAAGCCCTGAATAGCCTGAAAGTTAA

GCCGGAAGTTATTTACATTGATTCCGCTGATGTTAAAGCTGAACGTTTCG

CTGAAAACATTCGCAGCCGTCTGGCGTACGAAGCGAAAGTTGTAGCCGAA

CATAAAGCGGATGCGAAGTATGAGATCGTATCCGCAGCCTCTATCCTGGC

AAAAGTTATCCGTGACCGCGAGATCGAAAAGCTGAAAGCCGAATACGGTG

ATTTTGGTTCCGGTTACCCGTCTGATCCGCGTACTAAGAAATGGCTGGAA

GAATGGTATAGCAAACACGGCAATTTCCCGCCGATCGTGCGTCGTACTTG

GGATACTGCAAAGAAAATCGAAGAAAAATTCAAACGTGCGCAGCTGACCC

TGGACAACTTCCTGAAGCGTTTTCGCAACaagctt

SEQ ID NO: 5 - codon optimized rnhb gene from
*Sulfolobus solfataricus*
ggatccgATGCGCGTTGGCATCGATGAAGCGGGTCGCGGTGCCCTGATCG

GCCCGATGATTGTTGCTGGTGTTGTAATCTCTGACACTAAACTGAAGTTT

CTGAAAGGCATCGGCGTAAAAGACTCTAAACAGCTGACTCGCGAGCGTCG

TGAAAAGCTGTTTGATATTGTTGCTAACACTGTGGAAGCATTCACTGTCG

TTAAAGTTTTCCCTTATGAAATCGACAACTATAACCTGAATGACCTGACC

TACGACGCAGTTTCTAAAATCATCCTGAGCCTGTCTAGCTTTAACCCAGA

AATTGTAACGGTTGATAAAGTGGGCGATGAGAAACCGGTTATCGAACTGA

TTAATAAGCTGGGCTACAAAAGCAACGTCGTACACAAGGCAGATGTACTG

TTTGTAGAAGCCTCCGCTGCTAGCATCATTGCGAAAGTTATTCGTGATAA

CTACATTGACGAACTGAAACAAGTATACGGTGACTTTGGTAGCGGTTACC

CAGCTGATCCTCGCACTATCAAATGGCTGAAATCTTTCTACGAAAAGAAT

CCGAATCCGCCGCCAATCATTCGTCGTTCCTGGAAGATTCTGCGTTCTAC

CGCCCCGCTGTATTACATTTCCAAAGAAGGTCGCCGTCTGTGGaagctt

Example 2—Expression of Recombinant RNase H2 Peptides

The following example demonstrates the expression of recombinant RNase H2 peptides.

The five synthetic gene sequences from Example 1 were subcloned using unique Bam HI and Hind III restriction sites into the bacterial expression vector pET-27b(+) (Novagen, EMD Biosciences, La Jolla, Calif.). This vector places six histidine residues (which together comprise a "His-tag") (SEQ ID NO: 313) at the carboxy terminus of the expressed peptide (followed by a stop codon). A "His-tag" permits use of rapid, simple purification of recombinant proteins using Ni affinity chromatography, methods which are well known to those with skill in the art. Alternatively, the synthetic genes could be expressed in native form without the His-tag and purified using size exclusion chromatography, anion-exchange chromatography, or other such methods, which are also well known to a person of ordinary skill in the art.

BL21(DE3) competent cells (Novagen) were transformed with each plasmid and induced with 0.5 mM isopropyl-β-D-thio-galactoside (IPTG) for 4.5 hours at 25° C. For all clones, 5 mL of IPTG induced culture was treated with Bugbuster® Protein Extraction Reagent and Benzonase® Nuclease (Novagen) to release soluble proteins and degrade nucleic acids according to the manufacturer's instructions. The recovered protein was passed over a Ni affinity column (Novagen) and eluted with buffer containing 1M imidazole according to protocols provided by the manufacturer.

Figure 4A:
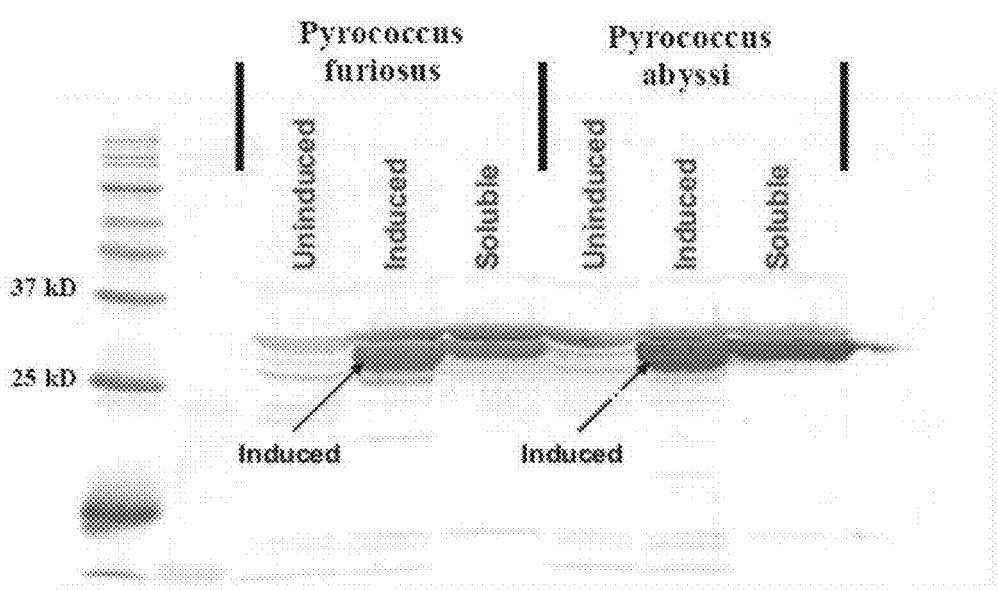
FIGS. 4A and 4B are photographs of SDS 10% polyacrylamide gels that illustrate the induced protein produced from five Archaeal RNase H2 synthetic genes.
Figure 4B:
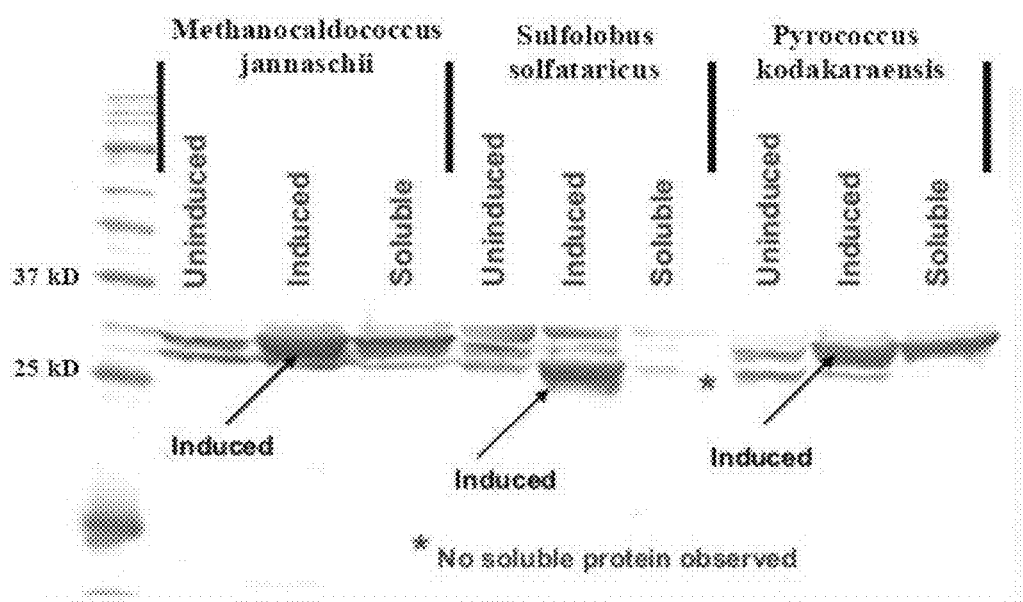

Both "total" and "soluble" fractions of the bacterial lysate were examined using SDS 10% polyacrylamide gel electrophoresis. Proteins were visualized with Coomassie Blue staining. Following IPTG induction, large amounts of recombinant proteins were produced from all 5 Archaeal RNase H2 synthetic genes. Using this method of purification, protein was recovered in the soluble fraction for 4 enzymes, *Pyrococcus kodakaraensis, Pyrococcus furiosus, Methanocaldococcus jannaschii*, and *Pyrococcus abyssi*. No soluble protein was recovered for *Sulfolobus solfataricus* RNase H2 using this lysis procedure. Examples of induced RNase H2 proteins are shown in FIGS. 4A and 4B.

Improved methods to produce and purify the recombinant proteins were developed to produce small scale amounts of the proteins for characterization as follows. To maximize the amount of soluble protein obtained for each clone, an induction temperature of 37° C. is used for 6 hours. For *Pyrococcus kodakaraensis, Methanocaldococcus jannaschii*, and *Sulfolobus solfataricus*, CelLytic™ B 10× lysis reagent (Sigma-Aldrich, St. Louis, Mo.) is used for lysis. A 10 fold dilution in 500 mM NaCl, 20 mM TrisHCl, 5 mM imidazole, pH 7.9 is made and 10 mL is used per 0.5 g of pelleted bacterial paste from induced cultures. For *Pyrococcus furiosus* and *Pyrococcus abyssi*, 5 mL of Bugbuster® Protein Extraction Reagent (Novagen) per 100 mL of induced culture is used for cell lysis. In addition, per 100 mL induced culture for all clones, 5KU rLysozyme™ (Novagen) and 250 U DNase I (Roche Diagnostics, Indianapolis, Ind.)

is used to enhance bacterial cell lysis and decrease the viscosity of the solution. Following centrifugation to remove cell debris, the lysates are heated for 15 minutes at 75° C. to inactive the DNase I and any other cellular nucleases present. The lysates are then spun at 16,000×g for 20 minutes to sediment denatured protein following heat treatment. The centrifugation step alone provides a large degree of functional purification of the recombinant thermostable enzymes.

The resulting soluble supernatant is passed over a Ni affinity column containing His•Bind® Resin (Novagen) and eluted with an elution buffer containing 200 mM imidazole. The purified protein is then precipitated in the presence of 70% ammonium sulfate and resuspended in storage buffer (10 mM Tris pH 8.0, 1 mM EDTA, 100 mM NaCl, 0.1% Triton X-100, 50% Glycerol) to concentrate and stabilize the protein for long term storage. The concentrated protein is dialyzed 2×2 hours (×250 volumes each) against the same storage buffer to remove residual salts. The final purified protein is stored at −20° C. Using these protocols, for *Pyrococcus abysii*, 200 mL of IPTG induced culture yields ~2 mg of soluble protein. After passing over a Ni column, ~0.7 mg of pure protein is recovered. For functional use, the concentrated enzyme stocks were diluted in storage buffer and added 1:10 in all enzymatic reactions studied. Therefore all reaction buffers contain 0.01% Triton X-100 and 5% Glycerol.

Figure 5:
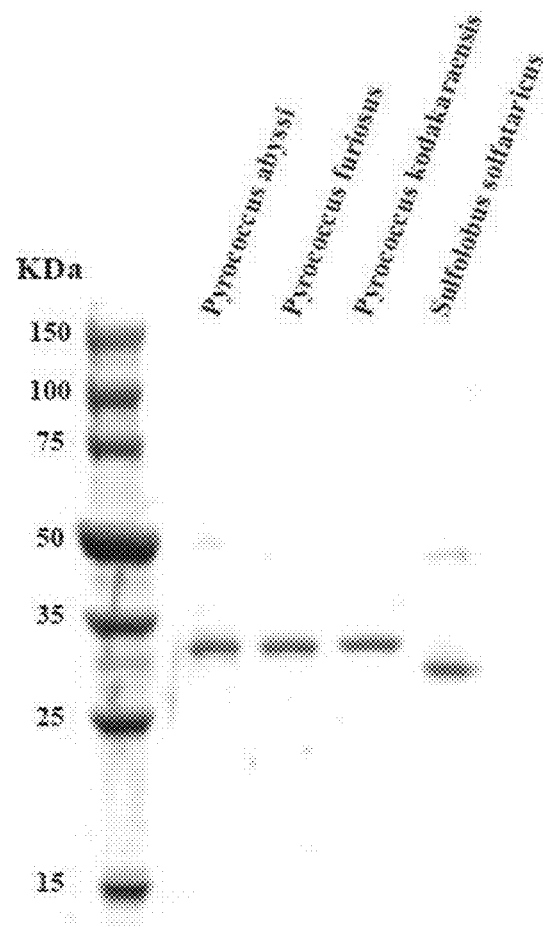
FIG. 5 shows a Coomassie Blue stained protein gel showing pure, single bands after purification using nickel affinity chromatography of recombinant His tag RNase H2 proteins.
Figure 6:
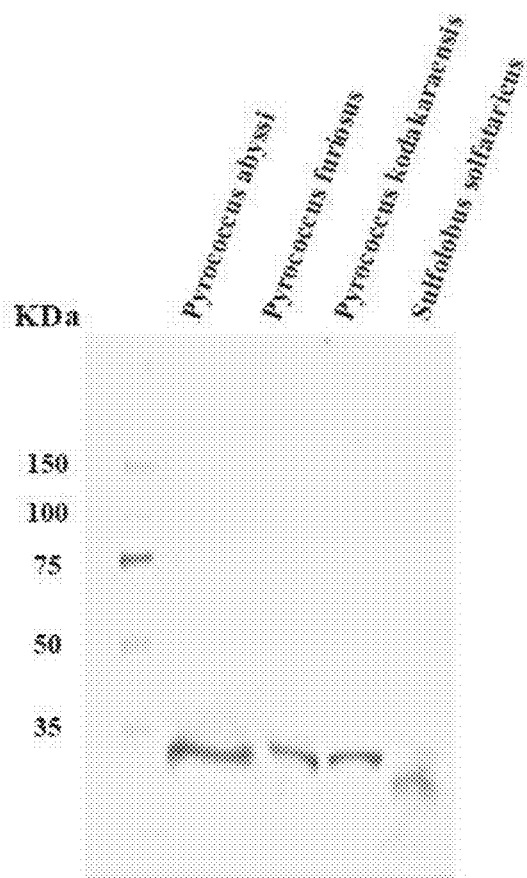
FIG. 6 shows a Western blot done using anti-His tag antibodies using the protein gel from FIG. 5.

Recombinant protein was made and purified for each of the cloned RNase H2 enzymes as outlined above. Samples from *Pyrococcus kodakaraensis*, *Pyrococcus furiosus*, *Pyrococcus abyssi*, and *Sulfolobus solfataricus* were examined using SDS 10% polyacrylamide gel electrophoresis. Proteins were visualized with Coomassie Blue staining. Results are shown in FIG. 5. If the expression and purification method functioned as predicted, these proteins should all contain a 6× Histidine tag (SEQ ID NO: 313), which can be detected using an anti-His antibody by Western blot. The gel shown in FIG. 5 was electroblot transferred to a nylon membrane and a Western blot was performed using an anti-His antibody. Results are shown in FIG. 6. All of the recombinant proteins were recognized by the anti-His antibody, indicating that the desired recombinant protein species were produced and purified.

Large scale preparations of the recombinant proteins can be better expressed using bacterial fermentation procedures well known to those with skill in the art. Heat treatment followed by centrifugation to sediment denatured proteins will provide substantial purification and final purification can be accomplished using size exclusion or anion exchange chromatography without the need for a His-tag or use of Ni-affinity chromatography.

Example 3—RNase H2 Activity for the Recombinant Peptides

The following example demonstrates RNase H2 activity for the recombinant peptides.

RNase H enzymes cleave RNA residues in an RNA/DNA heteroduplex. All RNase H enzymes can cleave substrates of this kind when at least 4 sequential RNA residues are present. RNase H1 enzymes rapidly lose activity as the RNA "window" of a chimeric RNA/DNA species is shortened to less than 4 residues. RNase H2 enzymes, on the other hand, are capable of cleaving an RNA/DNA heteroduplex containing only a single RNA residue. In all cases, the cleavage products contain a 3'-hydroxyl and a 5'-phosphate (see FIG. 1). When multiple RNA residues are present, cleavage occurs between RNA bases, cleaving an RNA-phosphate linkage. When only a single RNA residue is present, cleavage occurs only with Type II RNase H enzymes. In this case cleavage occurs on the 5'-side of the RNA base at a DNA-phosphate linkage (see FIG. 3). RNase H enzymes require the presence of a divalent metal ion cofactor. Typically, RNase H1 enzymes require the presence of $Mg^{++}$ ions while RNase H2 enzymes can function with any of a number of divalent cations, including but not limited to $Mg^{++}$, $Mn^{++}$, $Co^{++}$ and $Ni^{++}$.

The recombinant RNase H2 proteins described in Example 2 were tested for both types of RNase H activity and were examined for the characteristics listed above.

Cleavage of a Substrate with Multiple RNA Bases.

The following synthetic 30 bp substrate was used to test the activity of these enzymes for cleavage of a long RNA domain. The substrate is an "11-8-11" design, having 11 DNA bases, 8 RNA bases, and 11 DNA bases on one strand and a perfect match DNA complement as the other strand. The oligonucleotides employed are indicated below, where upper case letters represent DNA bases and lower case letters represent RNA bases.

```
                                         SEQ ID NO: 6
        5'-CTCGTGAGGTGaugcaggaGATGGGAGGCG-3'

SEQ ID NO: 7
        5'-CGCCTCCCATCTCCTGCATCACCTCACGAG-3'
```

When annealed, these single-stranded (ss) oligonucleotides form the following "11-8-11" double-stranded (ds) substrate:

SEQ ID NOS: 6 and 7, respectively, in order of appearance

```
        5'-CTCGTGAGGTGaugcaggaGATGGGAGGCG-3'

3'-GAGCACTCCACTACGTCCTCTACCCTCCGC-5'
```

Aliquots of each of the recombinant protein products were incubated with single-stranded or double-stranded oligonucleotide substrates in an 80 μl reaction volume in buffer 50 mM NaCl, 10 mM $MgCl_2$, and 10 mM Tris pH 8.0 for 20 minutes at 45° C. or 70° C. Reactions were stopped with the addition of gel loading buffer (formamide/EDTA) and separated on a denaturing 7M urea, 15% polyacrylamide gel. Gels were stained using GelStar' (Lonza, Rockland, Me.) and visualized with UV excitation. All 5 recombinant peptides showed the ability to cleave an 8 base RNA sequence in an RNA/DNA heteroduplex (11-8-11) substrate. Importantly, the recombinant proteins did not degrade the single stranded RNA-containing oligonucleotide (SEQ ID NO: 6), indicating that a double-stranded substrate was required. Further, a dsDNA substrate was not cleaved.

Cleavage was not observed in the absence of a divalent cation (e.g., no activity was observed if $Mg^{++}$ was absent from the reaction buffer). A $Mg^{++}$ titration was performed and high enzyme activity was observed between 2-8 mM $MgCl_2$. Optimal activity was observed between 3-6 mM $MgCl_2$. Cleavage activity was also detected using other divalent cations including $Mn^{++}$ and $Co^{++}$. In $MnCl_2$, good activity was seen from 0.3 mM to 10 mM divalent cation concentration. Enzyme activity was optimal in the range of 300 nM to 1 mM. For $CoCl_2$, activity was seen in the range of 0.3 mM to 2 mM, with optimal activity in the range of 0.5-1 mM. The isolated enzymes therefore show RNase H activity, and divalent cation requirements that are characteristic of the RNase H2 class.

Figure 7:
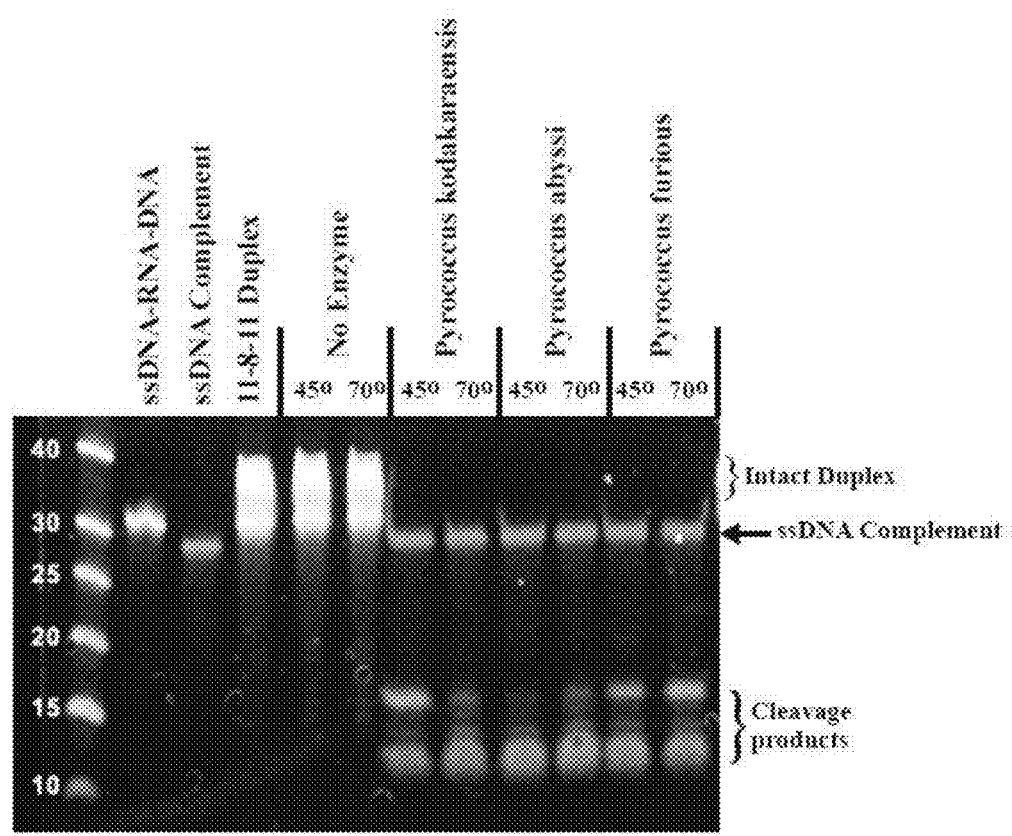
FIG. 7 is a photograph of a gel that shows the digestion of a duplex, containing a chimeric 11 DNA-8 RNA-11 DNA strand and a complementary DNA strand, by recombinant RNase H2 enzymes from *Pyrococcus kodakaraensis*, *Pyrococcus furiosus*, and *Pyrococcus abyssi*.

Digestion of the 11-8-11 substrate by recombinant RNase H2 enzymes from *Pyrococcus kodakaraensis*, *Pyrococcus furiosus*, and *Pyrococcus abyssi* is shown in FIG. 7.

Substrate cleavage by RNase H enzymes is expected to result in products with a 3'-OH and 5'-phosphate. The identity of the reaction products from the new recombinant RNase H2 proteins was examined by mass spectrometry. Electrospray ionization mass spectrometry (ESI-MS) has near single Dalton resolution for nucleic acid fragments of this size (accuracy of +/−0.02%). The oligonucleotide 11-8-11 substrate (SEQ ID NOS: 6 and 7) was examined by ESI-MS both before and after digestion with the three *Pyrococcus* sp. RNase H enzymes. The primary masses observed are reported in Table 7 along with identification of nucleic acid species consistent with the observed masses.

TABLE 7

Mass of species observed after RNase H2 digestion of SEQ ID NOS: 6 and 7

| RNase H2 Treatment | Sequence | | Predicted Mol Wt | Observed Mol Wt |
|---|---|---|---|---|
| None (control) | 5' CTCGTGAGGTGaugcaggaGATGGGAGGCG | (SEQ ID NO: 6) | 9547 | 9548 |
|  | 3' GAGCACTCCACTACGTCCTCTACCCTCCGC | (SEQ ID NO: 7) | 8984 | 8984 |
| *Pyrococcus kodakaraensis* | 5' CTCGTGAGGTGa | (SEQ ID NO: 8) | 3717 | 3719 |
|  | 5' P-aGATGGGAGGCG | (SEQ ID NO: 9) | 3871 | 3871 |
|  | 3' GAGCACTCCACTACGTCCTCTACCCTCCGC | (SEQ ID NO: 7) | 8984 | 8984 |
| *Pyrococcus furiosus* | 5' CTCGTGAGGTGa | (SEQ ID NO: 8) | 3717 | 3719 |
|  | 5' P-aGATGGGAGGCG | (SEQ ID NO: 9) | 3871 | 3872 |
|  | 3' GAGCACTCCACTACGTCCTCTACCCTCCGC | (SEQ ID NO: 7) | 8984 | 8984 |
| *Pyrococcus abyssi* | 5' CTCGTGAGGTGa | (SEQ ID NO: 8) | 3717 | 3719 |
|  | 5' P-aGATGGGAGGCG | (SEQ ID NO: 9) | 3871 | 3872 |
|  | 3' GAGCACTCCACTACGTCCTCTACCCTCCGC | (SEQ ID NO: 7) | 8984 | 8984 |

Major species identified are shown. DNA bases are indicated with upper case letters, RNA bases are indicated with lower case letters, and phosphate="P". Molecular weights are rounded to the nearest Dalton. In the absence of other notation, the nucleic acids strands end in a 5'-hydroxyl or 3'-hydroxyl.

In all cases, the DNA complement strand was observed intact (non-degraded). The RNA-containing strands were efficiently cleaved and the observed masses of the reaction products are consistent with the following species being the primary fragments produced: 1) a species which contained undigested DNA residues and a single 3'-RNA residue with a 3'-hydroxyl groups (SEQ ID No: 8), and 2) a species with a 5'-phosphate, a single 5'-RNA residue, and undigested DNA residues (SEQ ID No: 9). The observed reaction products are consistent with the known cleavage properties of both RNase H1 and RNase H2 enzymes.

SEQ ID NO: 8
5' CTCGTGAGGTGa 3'

SEQ ID NO: 9
5' P-aGATGGGAGGCG 3'

Cleavage of a Substrate with a Single RNA Base.

RNase H2 enzymes characteristically cleave a substrate that contains a single RNA residue while RNase H1 enzymes cannot. The following synthetic 30 bp substrates were used to test the activity of these enzymes for cleavage at a single RNA residue. The substrates are a "14-1-15" design, having 14 DNA bases, 1 RNA base, and 15 DNA bases on one strand and a perfect match DNA complement as the other strand. Four different substrates were made from 8 component single-stranded oligonucleotides comprising each of the 4 RNA bases: C, G, A, and U. The oligonucleotides employed are indicated below, where upper case letters represent DNA bases and lower case letters represent RNA bases.

For rC:

SEQ ID NO: 10
5'-CTCGTGAGGTGATGcAGGAGATGGGAGGCG-3'

SEQ ID NO: 11
5'-CGCCTCCCATCTCCTGCATCACCTCACGAG-3'

When annealed, these single-stranded (ss) oligonucleotides form the following "14-1-15 rC" double-stranded (ds) substrate:

SEQ ID NOS: 10 and 11, respectively, in order of appearance

5'-CTCGTGAGGTGATGcAGGAGATGGGAGGCG-3'

3'-GAGCACTCCACTACGTCCTCTACCCTCCGC-5'

For rG:

SEQ ID NO: 12
5'-CTCGTGAGGTGATGgAGGAGATGGGAGGCG-3'

SEQ ID NO: 13
5'-CGCCTCCCATCTCCTCCATCACCTCACGAG-3'

When annealed, these single-stranded (ss) oligonucleotides form the following "14-1-15 rG" double-stranded (ds) substrate:

SEQ ID NOS: 12 and 13, respectively, in order of appearance

5'-CTCGTGAGGTGATGgAGGAGATGGGAGGCG-3'

3'-GAGCACTCCACTACCTCCTCTACCCTCCGC-5'

For rA:

```
                                        SEQ ID NO: 14
    5'-CTCGTGAGGTGATGaAGGAGATGGGAGGCG-3'

SEQ ID NO: 15
    5'-CGCCTCCCATCTCCTTCATCACCTCACGAG-3'
```

When annealed, these single-stranded (ss) oligonucleotides form the following "14-1-15 rA" double-stranded (ds) substrate:

SEQ ID NOS: 14 and 15, respectively, in order of appearance

```
    5'-CTCGTGAGGTGATGaAGGAGATGGGAGGCG-3'

3'-GAGCACTCCACTACTTCCTCTACCCTCCGC-5'
```

For rU:

```
                                        SEQ ID NO: 16
    5'-CTCGTGAGGTGATGuAGGAGATGGGAGGCG-3'

SEQ ID NO: 17
    5'-CGCCTCCCATCTCCTACATCACCTCACGAG-3'
```

When annealed, these single-stranded (ss) oligonucleotides form the following "14-1-15 rU" double-stranded (ds) substrate:

SEQ ID NOS: 16 and 17, respectively, in order of appearance

```
    5'-CTCGTGAGGTGATGuAGGAGATGGGAGGCG-3'

3'-GAGCACTCCACTACATCCTCTACCCTCCGC-5'
```

Aliquots of each of the recombinant protein products were incubated with the single-stranded and double-stranded oligonucleotide substrates indicated above in an 80 µl reaction volume in buffer 50 mM NaCl, 10 mM MgCl$_2$, and 10 mM Tris pH 8.0 for 20 minutes at 70° C. Reactions were stopped with the addition of gel loading buffer (formamide/EDTA) and separated on a denaturing 7M urea, 15% polyacrylamide gel. Gels were stained using GelStar™ (Lonza, Rockland, Me.) and visualized with UV excitation. All 5 recombinant peptides showed the ability to cleave a single RNA base in an RNA/DNA heteroduplex (14-1-15). Each of the 4 RNA bases functioned as a cleavable substrate with these enzymes. Importantly, the recombinant proteins did not degrade the single stranded RNA-containing oligonucleotides (SEQ ID NOS: 10, 12, 14, 16), indicating that a double-stranded substrate was required. The isolated enzymes therefore show RNase H2 activity. Titration of divalent cations was tested and results were identical to those obtained previously using the 8-11-8 substrate.

Figure 8A:
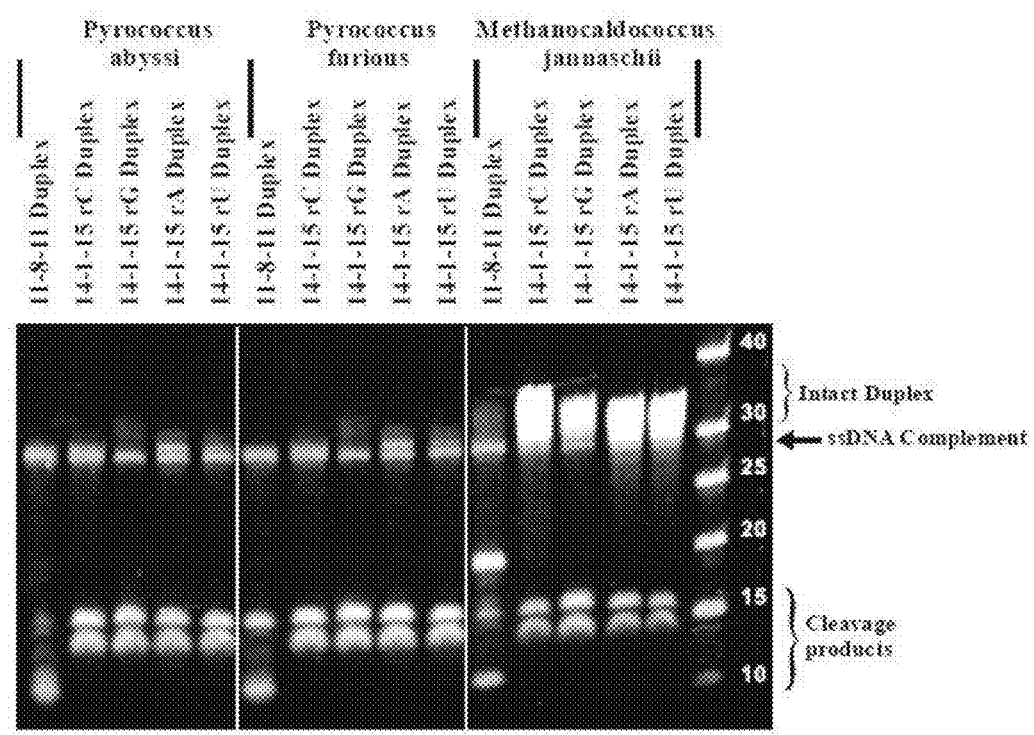
FIGS. 8A and 8B are photographs of gels that show the digestion of a duplex, containing a chimeric 14 DNA-1 RNA-15 DNA strand and a complementary DNA strand, by recombinant RNase H2 enzymes from *Pyrococcus abyssi*, *Pyrococcus furiosus*, and *Methanocaldococcus jannaschii* (FIG. 8A) and *Pyrococcus kodakaraensis* (FIG. 8B).
Figure 8B:
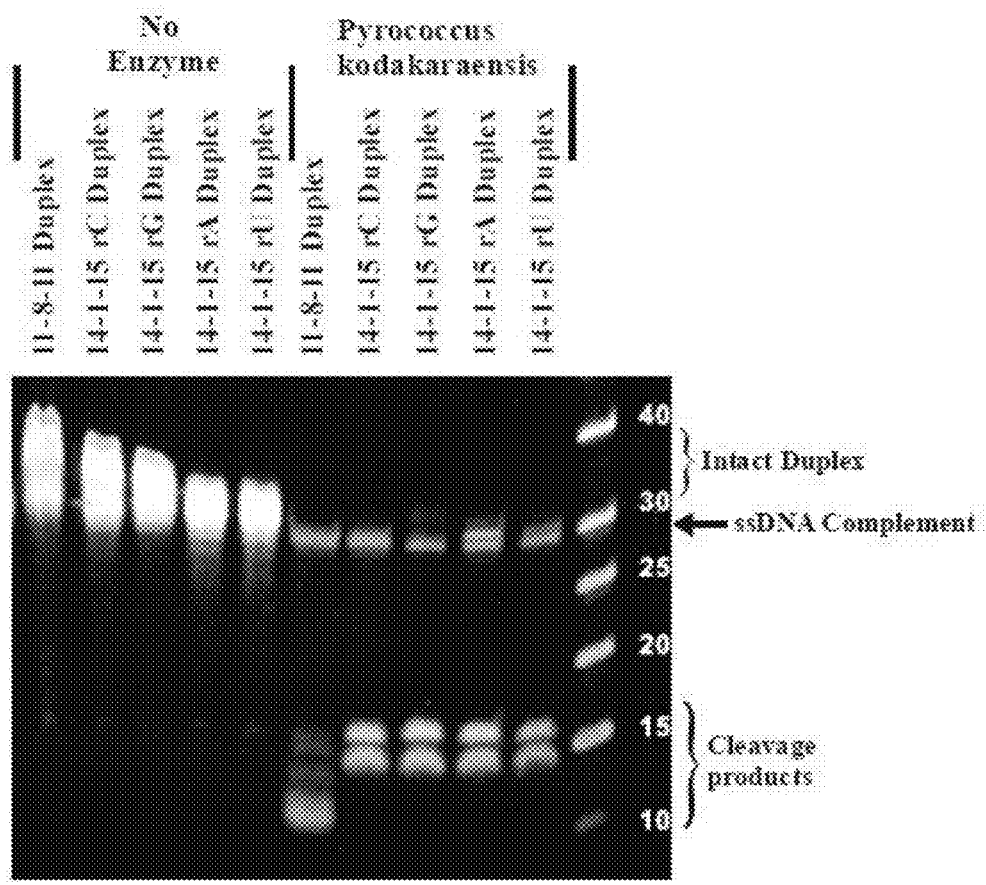

Digestion of the four 14-1-15 substrates (SEQ ID NOS: 10-11, 12-13, 14-15 and 16-17) and the 11-8-11 substrate (SEQ ID NOS: 6 and 7) by recombinant RNase H2 enzymes from *Pyrococcus abyssi*, *Pyrococcus furiosus*, and *Methanocaldococcus jannaschii* is shown in FIG. 8A and from *Pyrococcus kodakaraensis* in FIG. 8B.

Substrate cleavage by RNase H enzymes is expected to result in products with a 3'-OH and 5'-phosphate. Further, cleavage of a substrate containing a single ribonucleotide by RNase H2 enzymes characteristically occurs at the DNA linkage 5'- to the RNA residue. The identity of the reaction products using a single ribonucleotide substrate from the new recombinant RNase H2 proteins was examined by mass spectrometry. The oligonucleotide 14-1-15 rC substrate (SEQ ID NOS: 10 and 11) was examined by ESI-MS both before and after digestion with the three *Pyrococcus* sp. RNase H2 enzymes and the *Methanocaldococcus jannaschii* enzyme. The primary masses observed are reported in Table 8 along with identification of nucleic acid species consistent with the observed masses.

TABLE 8

Mass of species observed after RNase H2 digestion of SEQ ID NOS: 10 and 11

| RNase H2 Treatment | Sequence | Predicted Mol Wt | Observed Mol Wt |
|---|---|---|---|
| None (control) | 5' CTCGTGAGGTGATGcAGGAGATGGGAGGCG (SEQ ID NO: 10) | 9449 | 9450 |
|  | 3' GAGCACTCCACTACGTCCTCTACCCTCCGC (SEQ ID NO: 11) | 8984 | 8984 |
| *Pyrococcus kodakaraensis* | 5' CTCGTGAGGTGATG (SEQ ID NO: 18) | 4334 | 4335 |
|  | 5' P-cAGGAGATGGGAGGCG (SEQ ID NO: 19) | 5132 | 5133 |
|  | 3' GAGCACTCCACTACGTCCTCTACCCTCCGC (SEQ ID NO: 11) | 8984 | 8984 |
| *Pyrococcus furiosus* | 5' CTCGTGAGGTGATG (SEQ ID NO: 18) | 4334 | 4335 |
|  | 5' P-cAGGAGATGGGAGGCG (SEQ ID NO: 19) | 5132 | 5132 |
|  | 3' GAGCACTCCACTACGTCCTCTACCCTCCGC (SEQ ID NO: 11) | 8984 | 8984 |
| *Pyrococcus abyssi* | 5' CTCGTGAGGTGATG (SEQ ID NO: 18) | 4334 | 4335 |
|  | 5' P-cAGGAGATGGGAGGCG (SEQ ID NO: 19) | 5132 | 5133 |
|  | 3' GAGCACTCCACTACGTCCTCTACCCTCCGC (SEQ ID NO: 11) | 8984 | 8984 |
| *Methanocaldococcus jannaschii* | 5' CTCGTGAGGTGATG (SEQ ID NO: 18) | 4334 | 4335 |
|  | 5' P-cAGGAGATGGGAGGCG (SEQ ID NO: 19) | 5132 | 5133 |
|  | 3' GAGCACTCCACTACGTCCTCTACCCTCCGC (SEQ ID NO: 11) | 8984 | 8984 |

Major species identified are shown. DNA bases are indicated with upper case letters, RNA bases are indicated with lower case letters, and phosphate="P". Molecular weights are rounded to the nearest Dalton. In the absence of other notation, the nucleic acids strands end in a 5'-hydroxyl or 3'-hydroxyl.

In all cases, the DNA complement strand was observed intact (non-degraded). The RNA-containing strands were efficiently cleaved and the observed masses of the reaction products are consistent with the following species being the primary fragments produced: 1) a species which contained undigested DNA residues with a 3'-hydroxyl (SEQ ID NO: 18), and 2) a species with a 5'-phosphate, a single 5'-RNA residue, and undigested DNA residues (SEQ ID NO: 19). The observed reaction products are consistent with the known cleavage properties of RNase H2 class enzymes.

SEQ ID NO: 18
5' CTCGTGAGGTGATG 3'

SEQ ID NO: 19
5' P-cAGGAGATGGGAGGCG 3'

In summary, the cloned, codon-optimized rnhb genes predicted to encode RNase H2 enzymes from 5 Archaeal species all produced recombinant protein products which displayed enzyme activities consistent with that expected for members of the RNase H2 family. 1) The enzymes required divalent cation to function (the experiments presented here were done using $Mg^{++}$). Activity is also present using $Mn^{++}$ or $Co^{++}$ ions; 2) Single-stranded nucleic acids are not degraded; 3) Double-stranded heteroduplex nucleic acids are substrates where one strand contains one or more RNA bases; 4) For substrates containing 2 or more consecutive RNA bases, cleavage occurs in a DNA-RNA-DNA chimera between RNA linkages; for substrates containing a single RNA base, cleavage occurs immediately 5'- to the RNA base in a DNA-RNA-DNA at a DNA linkage; and 6) Reaction products have a 3-hydroxyl and 5'-phosphate.

Example 4—Reaction Temperature Optimization and Thermal Stability of *Pyrococcus abyssi* RNase H2

For this example and all subsequent work, the amount of the enzyme employed was standardized based upon the following unit definition, where:
1 unit is defined as the amount of enzyme that results in the cleavage of 1 nmole of a heteroduplex substrate containing a single rC residue per minute at 70° C. in a buffer containing 4 mM Mg' at pH 8.0.

SEQ ID NOS: 10 and 11 were employed for characterizing RNase H2 enzyme preparation for the purpose of normalizing unit concentration. The following standardized buffer was employed unless otherwise noted. "Mg Cleavage Buffer": 4 mM $MgCl_2$, 10 mM Tris pH 8.0, 50 mM NaCl, 10 µg/ml BSA (bovine serum albumin), and 300 nM oligo-dT (20mer poly-dT oligonucleotide). The BSA and oligo-dT serve to saturate non-specific binding sites on plastic tubes and improve the quantitative nature of assays performed.

Figure 9:
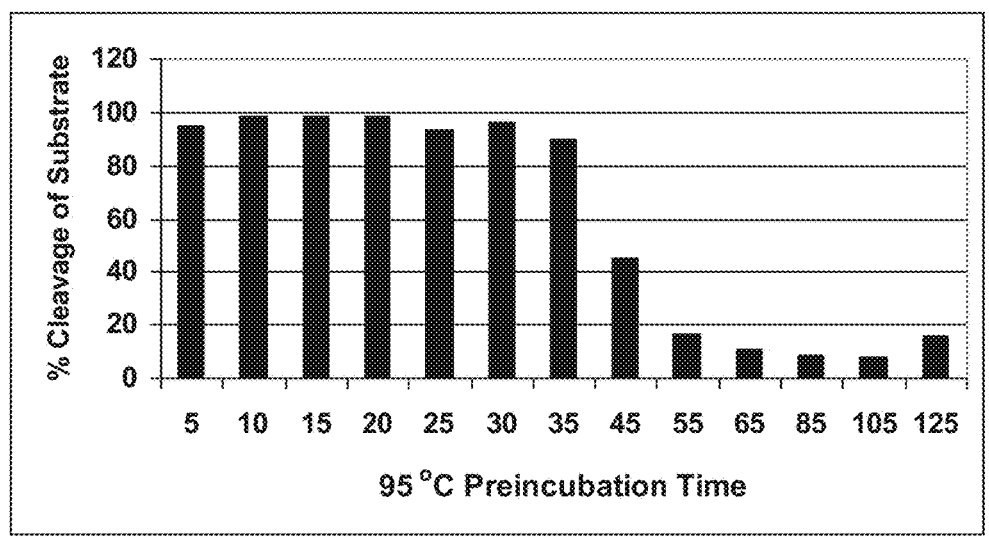
FIG. 9 shows the effects of incubation at 95° C. for various times on the activity of the *Pyrococcus abyssi* RNase H2 enzyme.

Purified recombinant *Pyrococcus abyssi* RNase H2 enzyme was studied for thermal stability. Aliquots of enzyme were incubated at 95° C. for various periods of time and then used to cleave the single rC containing substrate SEQ ID NOS: 10 and 11. The RNA strand of the substrate was radiolabeled with $^{32}P$ using 6000 Ci/mmol γ-$^{32}P$-ATP and the enzyme T4 Polynucleotide Kinase (Optikinase, US Biochemical). Trace label was added to reaction mixtures (1:50). Reactions were performed using 100 nM substrate with 100 microunits (µU) of enzyme in Mg Cleavage Buffer. Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified using the manufacturer's image analysis software and results plotted as a fraction of total substrate cleaved. Results are shown in FIG. 9. The enzyme retained full activity for over 30 minutes at 95° C. Activity was reduced to 50% after 45 minutes incubation and to 10% after 85 minutes incubation.

These results demonstrate that the *Pyrococcus abyssi* RNase H2 enzyme is sufficiently thermostable to survive prolonged incubation at 95° C. and would therefore survive conditions typically employed in PCR reactions.

Figure 10:
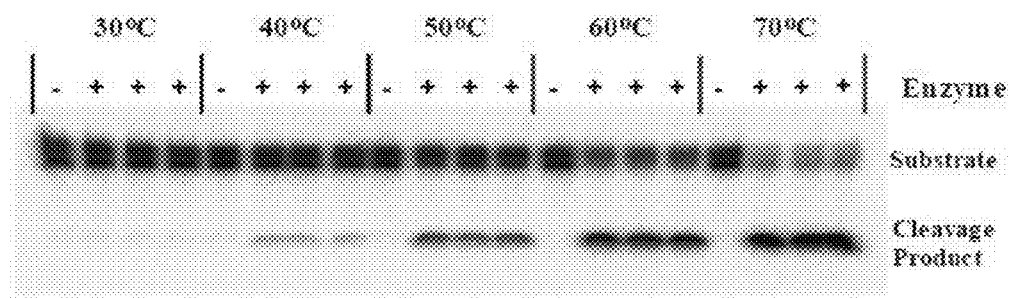
FIG. 10 is a photograph of a gel that shows the relative amounts of cleavage of a single ribonucleotide-containing substrate by *Pyrococcus abyssi* RNase H2 at various incubation temperatures.
Figure 11:
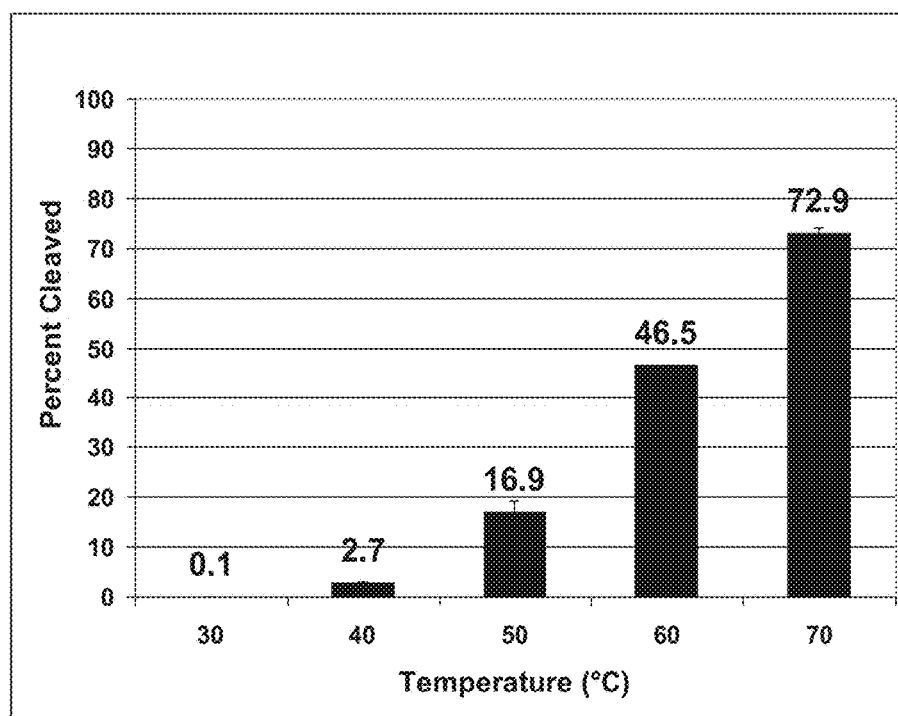
FIG. 11 is a graph showing the actual quantity of substrate cleaved in the gel from FIG. 10.

The temperature dependence of the activity of the *Pyrococcus abyssi* RNase H2 enzyme was next characterized. The activity was studied over a 40° C. temperature range from 30° C. to 70° C. The RNA strand of the rC substrate SEQ ID NOS: 10 and 11 was radiolabeled as described above. Reactions were performed using 100 nM substrate with 200 microunits (µU) of enzyme in Mg Cleavage Buffer. Reactions were incubated at 30° C., 40° C., 50° C., 60° C., or 70° C. for 10 minutes. Reactions were stopped with the addition of cold EDTA containing formamide gel loading buffer. Reaction products were then separated using denaturing 7M urea, 15% polyacrylamide gel electrophoresis (PAGE) and visualized using a Packard Cyclone™ Storage Phosphor System (phosphorimager). The resulting gel image is shown in FIG. 10. The relative intensity of each band was quantified using the manufacturer's image analysis software and results plotted as a fraction of total substrate cleaved (see FIG. 11). The enzyme shows only ~0.1% activity at 30° C. and does not attain appreciable activity until about 50 to 60° C.

Therefore, for practical purposes the enzyme is functionally inactive at room temperature. Reactions employing this enzyme can therefore be set up on ice or even at room temperature and the reactions will not proceed until temperature is elevated. If *Pyrococcus abyssi* RNase H2 cleavage were linked to a PCR reaction, the temperature dependent activity demonstrated herein would effectively function to provide for a "hot start" reaction format in the absence of a modified DNA polymerase.

Example 5—Cleavage at Non-Standard Bases by RNase H2

The natural biological substrates for RNase H1 and RNase H2 are duplex DNA sequences containing one or more RNA residues. Modified bases containing substitutions at the 2'-position other than hydroxyl (RNA) have not been observed to be substrates for these enzymes. The following example demonstrates that the *Pyrococcus abyssi* RNase H2 enzyme has activity against modified RNA-containing substrates.

The following 14-1-15 substrates containing modified bases were tested to determine if RNase H2 could recognize single non-RNA 2'-modified bases as sites for cleavage. The modifications are located on the 2' position of the base and include locked nucleic acid (LNA), 2'-O-methyl (2'OMe), and 2'-fluoro (2'F); the single ribo-C containing substrate was employed as positive control. Hereafter, LNA bases will be designated with a "+" prefix (+N), 2'OMe bases will be designated with a "m" prefix (mN), 2'F bases will be designated with a "f" prefix (fN), and 2'-amino bases with an "a" prefix (aN).

Ribo-C Substrate
SEQ ID NOS: 10 and 11, respectively, in order of appearance

```
5'-CTCGTGAGGTGATGcAGGAGATGGGAGGCG-3'
3'-GAGCACTCCACTACGTCCTCTACCCTCCGC-5'
```

LNA-C Substrate
SEQ ID NOS: 20 and 274, respectively, in order of appearance

```
5'-CTCGTGAGGTGATG(+C)AGGAGATGGGAGGCG-3'
3'-GAGCACTCCACTAC  G TCCTCTACCCTCCGC-5'
```

2'OMe-C Substrate
SEQ ID NOS: 21 and 274, respectively, in order of appearance

```
5'-CTCGTGAGGTGATG(mC)AGGAGATGGGAGGCG-3'
3'-GAGCACTCCACTAC  G TCCTCTACCCTCCGC-5'
```

2'F-C Substrate
SEQ ID NOS: 22 and 274, respectively, in order of appearance

```
5'-CTCGTGAGGTGATG(fC)AGGAGATGGGAGGCG-3'
3'-GAGCACTCCACTAC  G TCCTCTACCCTCCGC-5'
```

Figure 12:
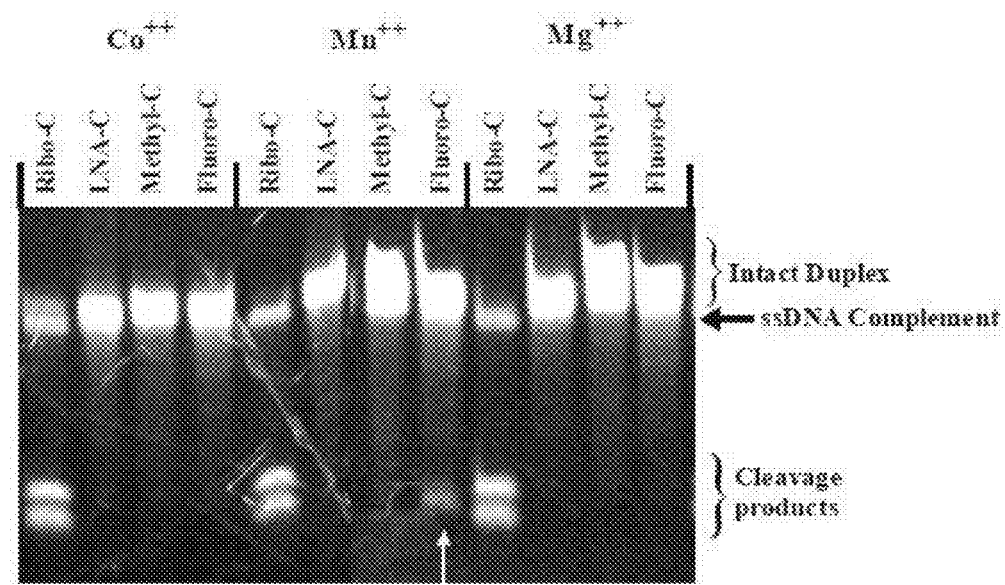
FIG. 12 is a photograph of a gel that shows cleavage by *Pyrococcus abysii* RNase H2 of various single 2' modified substrates in the presence of different divalent cations.

The above 4 substrates were incubated in an 80 µl reaction volume in various buffers for 20 minutes at 70° C. with the recombinant *Pyrococcus abyssi* RNase H2 enzyme. Buffers tested included 50 mM NaCl, 10 mM Tris pH 8.0 with either 10 mM MgCl$_2$, 10 mM CoCl$_2$, or 10 mM MnCl$_2$. Reactions were stopped with the addition of gel loading buffer (formamide/EDTA) and separated on a denaturing 7M urea, 15% polyacrylamide gel. Gels were stained using GelStar™ (Lonza, Rockland, Me.) and visualized with UV excitation. Results are shown in FIG. 12. The control substrate with a single ribo-C residue was 100% cleaved. The substrates containing a single LNA-C or a single 2'OMe-C residue were not cleaved. However, the substrate containing a single 2'-F-C residue was cleaved to a small extent. This cleavage occurred only in the manganese containing buffer and was not seen in either cobalt or magnesium buffers.

Cleavage at a 2'-F-C base was unexpected. Cleavage of 2'-fluoro bases was investigated further using the following substrates.

Ribo-C Substrate
SEQ ID NOS: 10 and 11, respectively, in order of appearance

```
5'-CTCGTGAGGTGATGcAGGAGATGGGAGGCG-3'
3'-GAGCACTCCACTACGTCCTCTACCCTCCGC-5'
```

2'F-C Substrate
SEQ ID NOS: 22 and 274, respectively, in order of appearance

```
5'-CTCGTGAGGTGATG(fC)AGGAGATGGGAGGCG-3'
3'-GAGCACTCCACTAC  G TCCTCTACCCTCCGC-5'
```

2'F-U Substrate
SEQ ID NOS: 23 and 275, respectively, in order of appearance

```
5'-CTCGTGAGGTGATG(fU)AGGAGATGGGAGGCG-3'
3'-GAGCACTCCACTAC  A TCCTCTACCCTCCGC-5'
```

2'F-C+2'FU (fCfU) Substrate
SEQ ID NOS: 24 and 276, respectively, in order of appearance

```
5'-CTCGTGAGGTGATG(fCfU)GGAGATGGGAGGCG-3'
3'-GAGCACTCCACTAC  G A CCTCTACCCTCCGC-5'
```

Figure 13:
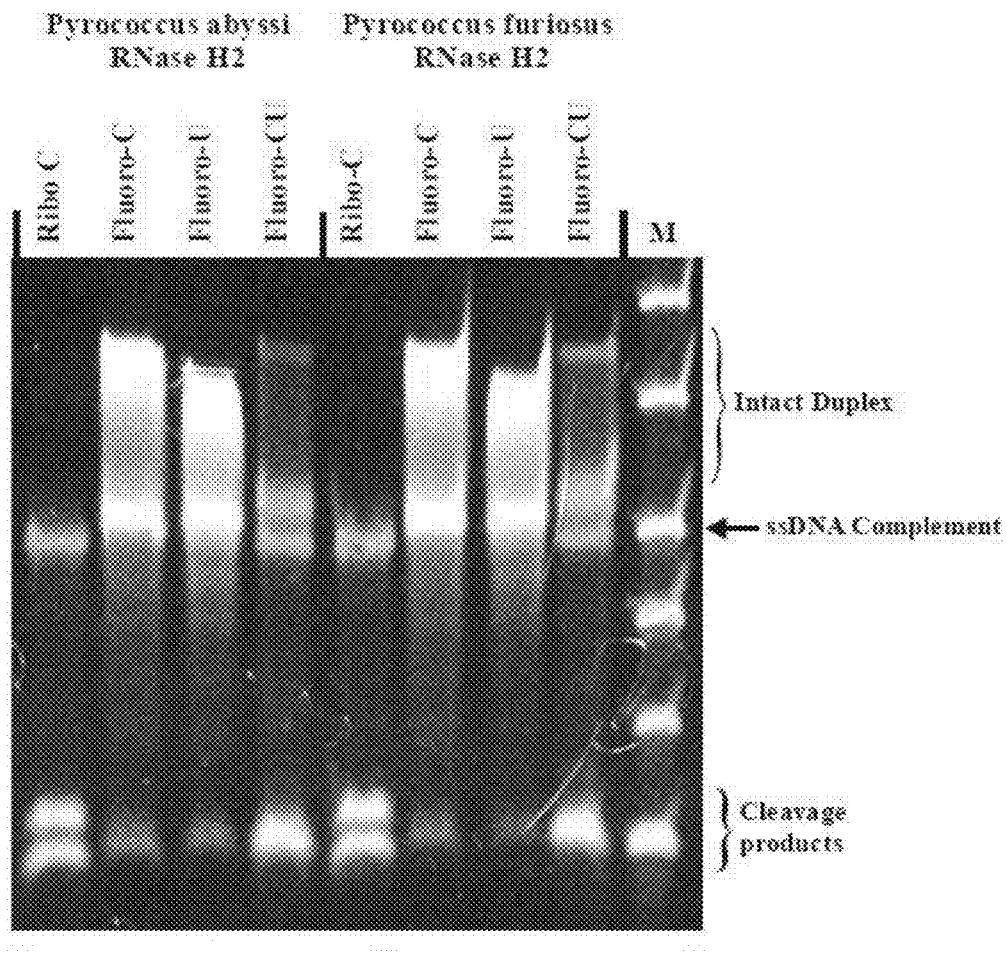
FIG. 13 is a photograph of a gel that shows cleavage by *Pyrococcus abyssi* RNase H2 of single 2'-fluoro or double 2'-fluoro (di-fluoro) modified substrates. The divalent cation present was $Mn^{++}$.

The above 4 substrates were incubated in an 80 µl reaction volume in a buffer containing 50 mM NaCl, 10 mM Tris pH 8.0 and 10 mM MnCl$_2$ for 20 minutes at 70° C. with either the recombinant *Pyrococcus abyssi* RNase H2 enzyme or the recombinant *Pyrococcus furiosus* RNase H2 enzyme. Reactions were stopped with the addition of gel loading buffer (formamide/EDTA) and separated on a denaturing 7M urea, 15% polyacrylamide gel. Gels were stained using GelStar™ (Lonza, Rockland, Me.) and visualized with UV excitation. Results are shown in FIG. 13. The control substrate with a single ribo-C residue was 100% cleaved. The substrates containing a single 2'-F-C or single 2'-F-U residue were cleaved to a small extent. The di-fluoro substrate containing adjacent 2'-F-C and 2'-F-U residues (fCfU) was cleaved nearly 100%. Further, both the *Pyrococcus abyssi* and *Pyrococcus furiosus* RNase H2 enzymes cleaved the modified substrate in an identical fashion. This example demonstrates that the unexpected cleavage of the fC group was not restricted to fC but also occurred with fU. More importantly, a combination of 2 sequential 2'-fluoro modified bases was a far better substrate for RNase H2. This novel cleavage property was seen for both the *P. abyssi* and *P. furiosus* enzymes. Cleavage of such atypical substrates may be a property common to all Archaeal RNase H2 enzymes.

The identity of the cleavage products of the di-fluoro fCfU substrate was studied using mass spectrometry using the methods described in Example 3. Using traditional ribonucleotide substrates, cleavage by RNase H enzymes results in products with a 3'-OH and 5'-phosphate. The fCfU substrate (SEQ ID NOS: 24 and 276) were examined by ESI-MS both before and after digestion by the recombinant *Pyrococcus abyssi* RNase H2 enzyme. The primary masses observed are reported in Table 9 along with identification of nucleic acid species consistent with the observed masses.

TABLE 9

Mass of species observed after RNase H2 digestion of SEQ ID NOS: 24 and 276

| RNase H2 Treatment | Sequence | | Predicted Mol Wt | Observed Mol Wt |
|---|---|---|---|---|
| None (control) | 5'-CTCGTGAGGTGATG(fCfU)GGAGATGGGAGGCG-3' | (SEQ ID NO: 24) | 9446 | 9446 |
|  | 3'-GAGCACTCCACTAC  G A CCTCTACCCTCCGC-5' | (SEQ ID NO: 276) | 8993 | 8994 |
| Pyrococcus abyssi | 5' CTCGTGAGGTGATG(fC) | (SEQ ID NO: 277) | 4642 | 4643 |
|  | 5' P-(fU)GGAGATGGGAGGCG | (SEQ ID NO: 278) | 4822 | 4823 |
|  | 3' GAGCACTCCACTAC  G  A CCTCTACCCTCCGC | (SEQ ID NO: 276) | 8993 | 8994 |

Major species identified are shown. DNA bases are indicated with upper case letters, 2'-F bases are indicated as fC or fU, and phosphate="P". Molecular weights are rounded to the nearest Dalton. In the absence of other notation, the nucleic acids strands end in a 5'-hydroxyl or 3'-hydroxyl.

The mass spectrometry data indicates that digestion of a di-fluoro substrate such as the fCfU duplex studied above by RNase H2 results in cleavage between the two fluoro bases. Further, the reaction products contain a 3'-hydroxyl and 5'-phosphate, similar to the products resulting from digestion of RNA containing substrates.

Cleavage of the modified bases was not observed in the absence of a divalent cation. A titration was performed and enzyme activity was observed between 0.25-10 mM MnCl$_2$ and 0.25-1.5 mM CoCl$_2$. Enzyme activity was optimal in the range of 0.5 mM to 1 mM for both MnCl$_2$ and CoCl$_2$. Hereafter 0.6 mM MnCl$_2$ was employed in reactions or 0.5 mM CoCl$_2$. Reduced activity for cleavage of the modified substrate was observed using Mg buffers. Overall, optimum activity was observed using Mn buffers for cleavage of the di-fluoro (fNfN) substrates whereas Mg buffers were superior for cleavage of ribonucleotide (rN) substrates.

The ability of the RNase H2 enzymes to cleave at single or double 2'-F bases was unexpected. The Pyrococcus abyssi RNase H2 enzyme was next tested for the ability to cleave a greater variety of modified substrates using the same methods described above in this example. The modified strand of the substrate was radiolabeled as described above. Reactions were performed using 100 nM substrate and 480-1000 mU of recombinant enzyme in Mn Cleavage Buffer (10 mM Tris pH 8.0, 50 mM NaCl, 0.6 mM MnCl$_2$, 10 µg/ml BSA). Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified using the manufacturer's image analysis software and results plotted as a fraction of total substrate cleaved are shown in Table 10.

TABLE 10

Cleavage of substrates containing 2'-modification by Pyrococcus abyssi RNase H2 using increased amounts of enzyme

| 2'-Mod | Oligo Sequence | SEQ ID NOS: | Cleavage |
|---|---|---|---|
| fN-fN | 5'-CTCGTGAGGTGAT(fNfN)AGGAGATGGGAGGCG-3' | 25 | +++++ |
|  | 3'-GAGCACTCCACTA  N N TCCTCTACCCTCCGC-5' | 279 | |
| fU-LNA-C | 5'-CTCGTGAGGTGAT(fU+C)AGGAGATGGGAGGCG-3' | 26 | ++++ |
|  | 3'-GAGCACTCCACTA  A G TCCTCTACCCTCCGC-5' | 280 | |
| mU-fC | 5'-CTCGTGAGGTGAT(mUfC)AGGAGATGGGAGGCG-3' | 27 | +++ |
|  | 3'-GAGCACTCCACTA  A G TCCTCTACCCTCCGC-5' | 280 | |
| mU-LNA-C | 5'-CTCGTGAGGTGAT(mU+C)AGGAGATGGGAGGCG-3' | 28 | ++ |
|  | 3'-GAGCACTCCACTA  A G TCCTCTACCCTCCGC-5' | 279 | |
| mU-mN | 5'-CTCGTGAGGTGAT(mUmN)AGGAGATGGGAGGCG-3' | 29 | ++ |
|  | 3'-GAGCACTCCACTA  A N TCCTCTACCCTCCGC-5' | 281 | |
| Amino-U-LNA-C | 5'-CTCGTGAGGTGAT(aU+C)AGGAGATGGGAGGCG-3' | 30 | + |
|  | 3'-GAGCACTCCACTA  A G TCCTCTACCCTCCGC-5' | 280 | |
| fN | 5'-CTCGTGAGGTGATG(fN)AGGAGATGGGAGGCG-3' | 31 | + |
|  | 3'-GAGCACTCCACTAC  N TCCTCTACCCTCCGC-5' | 282 | |
| mU-Amino-C | 5'-CTCGTGAGGTGAT(mUaC)AGGAGATGGGAGGCG-3' | 32 | +/− |
|  | 3'-GAGCACTCCACTA  A G TCCTCTACCCTCCGC-5' | 280 | |
| LNA-T-fC | 5'-CTCGTGAGGTGAT(+TfC)AGGAGATGGGAGGCG-3' | 33 | − |
|  | 3'-GAGCACTCCACTA  A G TCCTCTACCCTCCGC-5' | 280 | |
| Amino-U | 5'-CTCGTGAGGTGATG(aU)AGGAGATGGGAGGCG-3' | 34 | − |
|  | 3'-GAGCACTCCACTAC  A TCCTCTACCCTCCGC-5' | 275 | |
| LNA-T-LNA-C | 5'-CTCGTGAGGTGAT(+T+C)AGGAGATGGGAGGCG-3' | 35 | − |
|  | 3'-GAGCACTCCACTA  A G TCCTCTACCCTCCGC-5' | 280 | |

TABLE 10-continued

Cleavage of substrates containing 2'-modification by *Pyrococcus abyssi* RNase H2 using increased amounts of enzyme

| 2'-Mod | Oligo Sequence | SEQ ID NOS: | Cleavage |
|---|---|---|---|
| fU-mC | 5'-CTCGTGAGGTGAT(fUmC)AGGAGATGGGAGGCG-3'<br>3'-GAGCACTCCACTA   A G TCCTCTACCCTCCGC-5' | 36<br>280 | – |
| LNA-T-mC | 5'-CTCGTGAGGTGAT(+TmC)AGGAGATGGGAGGCG-3'<br>3'-GAGCACTCCACTA   A G TCCTCTACCCTCCGC-5' | 37<br>280 | – |

Uppercase letters = DNA;
fN = 2'-F bases,
+N = LNA bases,
mN = 2'OMe bases,
aN = 2'-amino bases
Use of "N" base indicates that every possible base (A, G, C, U/T) was tested with the appropriate perfect match complement.
Efficiency of cleavage was rated from "+++++" (100% cleavage) to "–" (no cleavage).
The mUmN substrates did not cleave equally well and the "++" rating applies to the best cleaving dinucleotide pair, mUmU.
The rank order of cleavage for this substrate design was mUmU > mUmA > mUmC > mUmG.

It is clear from the above results that many different 2'-modifications can be cleaved by RNase H2 enzymes that were not heretofore appreciated. Of the 2'-modified substrates, the di-fluoro compounds (those with 2 sequential 2'-fluoro bases) were most active. Additional substrates were tested, including some with 3 or 4 sequential 2'-fluoro bases. No increase in activity was seen when increasing the 2'-fluoro content above 2 residues.

A similar series of experiments was performed using lower amounts of enzyme. The experiment below was conducted using an identical protocol except that 148 µU of recombinant *Pyrococcus abyssi* RNase H2 was employed instead of the 480 mU previously employed (3000-fold less enzyme) and the buffer contained a mixture of divalent cations (3 mM $MgCl_2$+0.6 mM $MnCl_2$). Under these conditions, a substrate containing a single ribonucleotide residue is completely cleaved whereas modified substrates are not. Results are shown in Table 11. RNase H2 is more active in cleaving substrates containing an RNA base than in cleaving the 2'-modified bases.

fluoro (fNfN) containing substrates performed best. Use of the modified substrates generally requires increased amounts of enzyme, however the enzyme is catalytically very potent and it presents no difficulty to employ sufficient enzyme to achieve 100% cleavage of a di-fluoro substrate.

The 2'-modified substrate described in this example are not susceptible to cleavage by typical RNase enzymes. As such they can be employed in novel assay formats where cleavage events are mediated by RNase H2 using substrates that are completely resistant to cleavage by other RNase enzymes, particularly single stranded ribonucleases.

Example 6—Base Preferences for Cleavage of the Di-Fluoro fNfN Substrate

The following example demonstrates that all 16 possible 2'-fluoro dinucleotides can be cleaved by RNase H2. Distinct base preferences are observed.

The modified strand of each substrate was radiolabeled as described above. Reactions were performed using 100 nM

TABLE 11

Cleavage of substrates containing 2'-modification by *Pyrococcus abyssi* RNase H2 using small amounts of enzyme

| 2'-Mod | Oligo Sequence | SEQ ID NOS: | Cleavage |
|---|---|---|---|
| rN | 5'-CTCGTGAGGTGATGnAGGAGATGGGAGGCG-3'<br>3'-GAGCACTCCACTACNTCCTCTACCCTCCGC-5' | 38<br>282 | +++++ |
| fU-rC | 5'-CTCGTGAGGTGAT(fUrC)AGGAGATGGGAGGCG-3'<br>3'-GAGCACTCCACTA   A G TCCTCTACCCTCCGC-5' | 39<br>275 | +++++ |
| rU-fC | 5'-CTCGTGAGGTGAT(rUfC)AGGAGATGGGAGGCG-3'<br>3'-GAGCACTCCACTA   A G TCCTCTACCCTCCGC-5' | 40<br>275 | ++++ |
| fN-fN | 5'-CTCGTGAGGTGAT(fNfN)AGGAGATGGGAGGCG-3'<br>3'-GAGCACTCCACTA   N N TCCTCTACCCTCCGC-5' | 25<br>279 | + |
| fN | 5'-CTCGTGAGGTGATG(fN)AGGAGATGGGAGGCG-3'<br>3'-GAGCACTCCACTAC   N TCCTCTACCCTCCGC-5' | 31<br>282 | – |

Uppercase letters = DNA;
fN = 2'-F bases.
Use of "N" base indicates that every possible base (A, G, C, U/T) was tested with the appropriate perfect match complement.
Efficiency of cleavage was rated from "+++++" (100% cleavage) to "–" (no cleavage).

Figure 14:
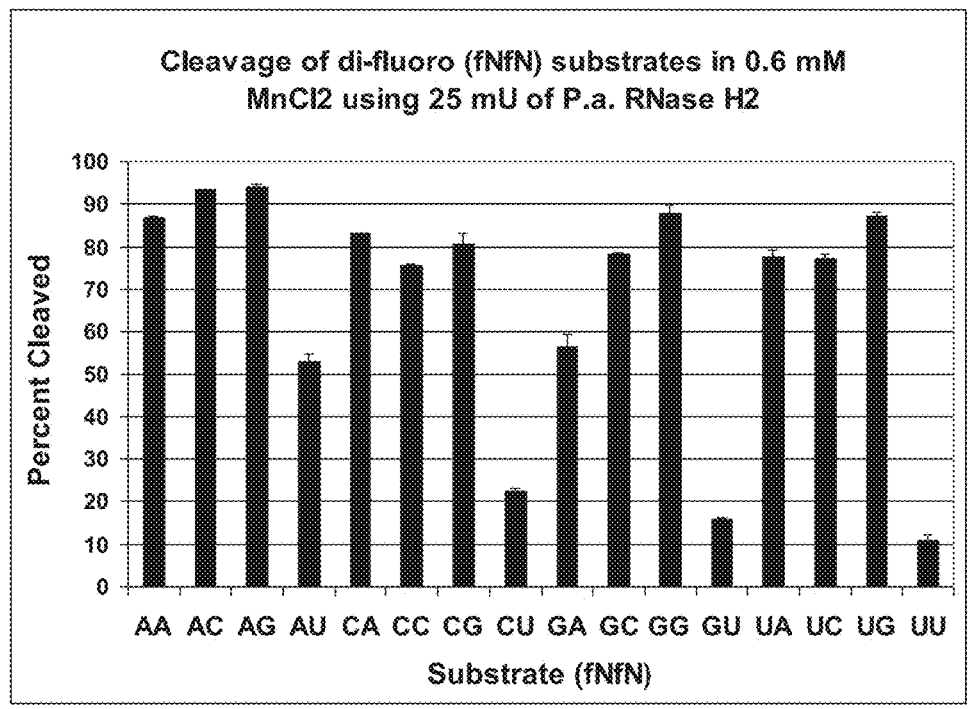
FIG. 14 is a graph quantifying the relative cleavage by *Pyrococcus abyssi* RNase H2 of all 16 possible di-fluoro modified substrates.

Thus, *Pyrococcus abyssi* RNase H2 can be used to cleave substrates which do not contain any RNA bases but instead contain 2'-modified bases. Of the compounds studied, disubstrate with 25 mU of recombinant enzyme in Mn Cleavage Buffer (10 mM Tris pH 8.0, 50 mM NaCl, 0.6 mM $MnCl_2$, 10 µg/ml BSA). Reactions were incubated at 70° C.

for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified, and results plotted as a fraction of total substrate cleaved are shown in FIG. 14. The enzyme amount was titrated so that the most active substrate cleaved at 90-95% without having excess enzyme present so that accurate assessment could be made of relative cleavage efficiency for less active substrates.

All 16 dinucleotide fNfN pairs were cleaved by RNase H2, however clear substrate preferences were observed. In general, substrates having the sequence fNfU performed worse, indicating that placement of a fU base at the 3'-position of the dinucleotide pair was unfavorable. The least active substrate was fUfU, which showed 10% cleavage under conditions that resulted in >90% cleavage of fAfC or fAfG substrates.

Using greater amounts of enzyme, the relative differences of cleavage efficiency between substrates is minor and 100% cleavage can readily be achieved for all substrates studied here.

Example 7—Optimization of 3'- and 5'-Base Lengths for Cleavage of rN and fNfN Substrates The following example shows the optimization of the placement of the cleavable domain relative to the 3' and 5' ends of a primer or probe sequence. In the prior examples, the substrates all had 14 or 15 DNA bases on both the 5'- and 3'-sides flanking the cleavable domain. For use in designing cleavable probes and primers, it may at times be beneficial to make these flanking sequences as short as possible, in order to control Tm (hybridization temperature) or to improve specificity of priming reactions. It is therefore important to define the minimum length of duplex needed to obtain efficient enzymatic cleavage.

In this experiment, the synthetic substrate duplexes shown in Table 13 were made having a single rC cleavable base, a fixed domain of 25 DNA bases 5'-flanking the ribonucleotide and a variable number of bases on the 3'-side.

TABLE 13

| 3'-End Sequence (rC) | | SEQ ID NOS: |
|---|---|---|
| 3'-D1 | 5'-CTGAGCTTCATGCCTTTACTGTCCTcT-3'<br>3'-GACTCGAAGTACGGAAATGACAGGACA-5' | 43<br>283 |
| 3'-D2 | 5'-CTGAGCTTCATGCCTTTACTGTCCTcTC-3'<br>3'-GACTCGAAGTACGGAAATGACAGGACAG-5' | 44<br>284 |
| 3'-D3 | 5'-CTGAGCTTCATGCCTTTACTGTCCTcTCC-3'<br>3'-GACTCGAAGTACGGAAATGACAGGACAGG-5' | 45<br>285 |
| 3'-D5 | 5'-CTGAGCTTCATGCCTTTACTGTCCTcTCCTT-3'<br>3'-GACTCGAAGTACGGAAATGACAGGACAGGAA-5' | 46<br>286 |
| 3'-D6 | 5'-CTGAGCTTCATGCCTTTACTGTCCTcTCCTTC-3'<br>3'-GACTCGAAGTACGGAAATGACAGGACAGGAAG-5' | 47<br>287 |

Figure 15:
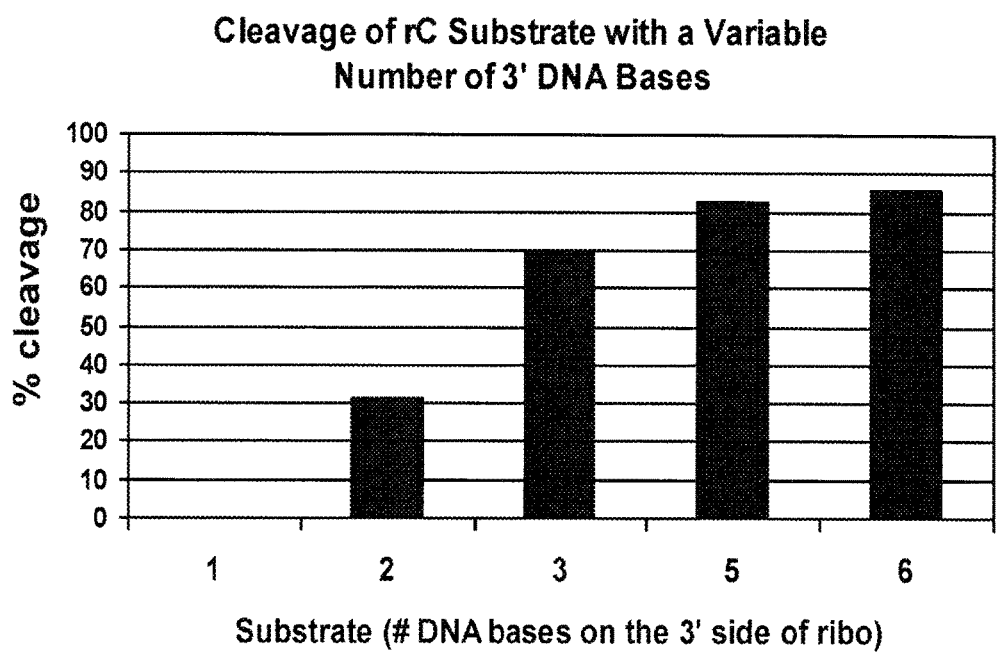
FIG. 15 is a graph quantifying the relative cleavage by *Pyrococcus abyssi* RNase H2 of rN substrates with a variable number of 3' DNA bases (i.e., number of DNA bases on the 3' side of the RNA residue).

The modified strand of each substrate was radiolabeled as described above Reactions were performed using 100 nM substrate with 100 μU of recombinant enzyme in Mg Cleavage Buffer (10 mM Tris pH 8.0, 50 mM NaCl, 4 mM $MgCl_2$, 10 μg/ml BSA). Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified, and results plotted as a fraction of total substrate cleaved are shown in FIG. 15. Maximal cleavage occurred with 4-5 DNA bases flanking the ribonucleotide on the 3'-side.

In the next experiment, the synthetic substrate duplexes shown in Table 14 were made having a single rU cleavable base with a fixed domain of 25 base-pairs flanking the ribonucleotide on the 3'side and 2-14 base-pairs on the 5'-side. A minimum of 5 unpaired bases (dangling ends) were left on the unmodified complement to simulate hybridization to a long nucleic acid sample.

TABLE 14

| 5'-End Sequence (rU) | | SEQ ID NOS: |
|---|---|---|
| 5'-D1 | 5'-CuCCTGAGCTTCATGCCTTTACTGTCC-3'<br>3'-ACGTAGAATGGACAGAAGGAGGACTCGAAGTACGGAAATGACAGGACGTA-5' | 48<br>288 |
| 5'-D2 | 5'-CCuCCTGAGCTTCATGCCTTTACTGTCC-3'<br>3'-ACGTAGAATGGACAGAAGGAGGACTCGAAGTACGGAAATGACAGGACGTA-5' | 49<br>288 |
| 5'-D3 | 5'-TCCuCCTGAGCTTCATGCCTTTACTGTCC-3'<br>3'-ACGTAGAATGGACAGAAGGAGGACTCGAAGTACGGAAATGACAGGACGTA-5' | 50<br>288 |
| 5'-D4 | 5'-TTCCuCCTGAGCTTCATGCCTTTACTGTCC-3'<br>3'-ACGTAGAATGGACAGAAGGAGGACTCGAAGTACGGAAATGACAGGACGTA-5' | 51<br>288 |
| 5'-D5 | 5'-CTTCCuCCTGAGCTTCATGCCTTTACTGTCC-3'<br>3'-ACGTAGAATGGACAGAAGGAGGACTCGAAGTACGGAAATGACAGGACGTA-5' | 52<br>288 |
| 5'-D6 | 5'-TCTTCCuCCTGAGCTTCATGCCTTTACTGTCC-3'<br>3'-ACGTAGAATGGACAGAAGGAGGACTCGAAGTACGGAAATGACAGGACGTA-5' | 53<br>288 |
| 5'-D8 | 5'-TGTCTTCCuCCTGAGCTTCATGCCTTTACTGTCC-3'<br>3'-ACGTAGAATGGACAGAAGGAGGACTCGAAGTACGGAAATGACAGGACGTA-5' | 54<br>288 |
| 5'-D10 | 5'-CCTGTCTTCCuCCTGAGCTTCATGCCTTTACTGTCC-3'<br>3'-ACGTAGAATGGACAGAAGGAGGACTCGAAGTACGGAAATGACAGGACGTA-5' | 55<br>288 |
| 5'-D12 | 5'-TACCTGTCTTCCuCCTGAGCTTCATGCCTTTACTGTCC-3'<br>3'-ACGTAGAATGGACAGAAGGAGGACTCGAAGTACGGAAATGACAGGACGTA-5' | 56<br>288 |

TABLE 14-continued

| 5'-End | Sequence (rU) | SEQ ID NOS: |
|---|---|---|
| 5'-D14 | 5'-CTTACCTGTCTTCCuCCTGAGCTTCATGCCTTTACTGTCC-3'<br>3'-ACGTAGAATGGACAGAAGGAGGACTCGAAGTACGGAAATGACAGGACGTA-5' | 57<br>288 |

Figure 16:
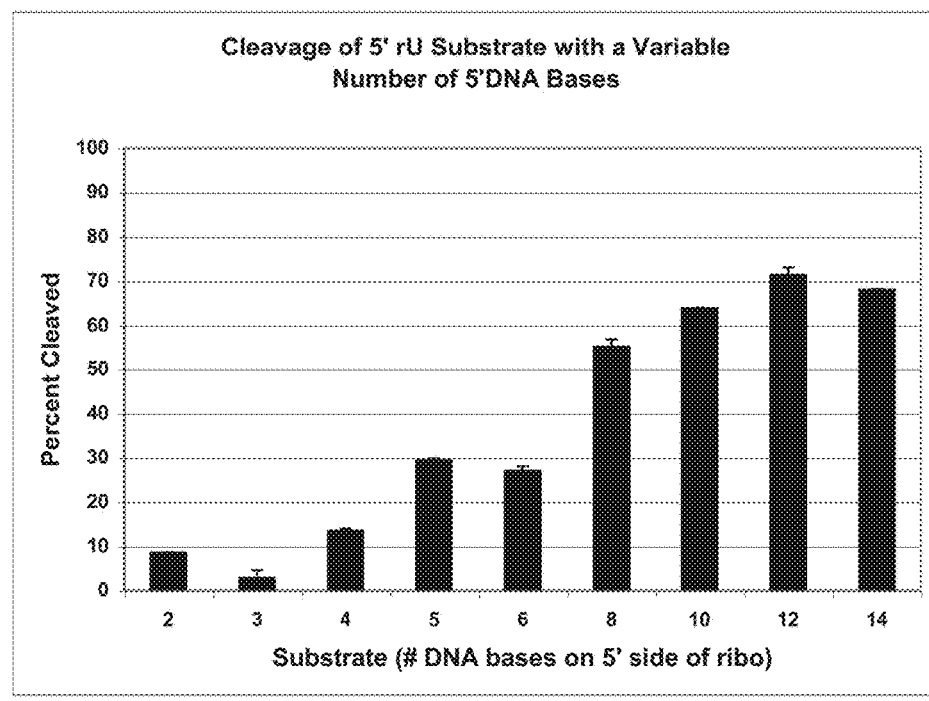
FIG. 16 is a graph quantifying the relative cleavage by *Pyrococcus abyssi* RNase H2 of rN substrates with a variable number of 5' DNA bases (i.e., number of DNA bases on the 5' side of the RNA residue).

The modified strand of each substrate was radiolabeled as previously described. Reactions were performed using 100 nM substrate with 123 µU of recombinant enzyme in a mixed buffer containing both Mg and Mn cations (10 mM Tris pH 8.0, 50 mM NaCl, 0.6 mM $MnCl_2$, 3 mM $MgCl_2$, 10 µg/ml BSA). Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified and the results plotted as a fraction of total substrate cleaved in FIG. 16. Little cleavage was seen with the short substrates. Activity increased with length of the 5'-DNA domain until maximum cleavage was obtained at around 10-12 bases of duplex flanking the rU base on the 5'-side.

Figure 17:
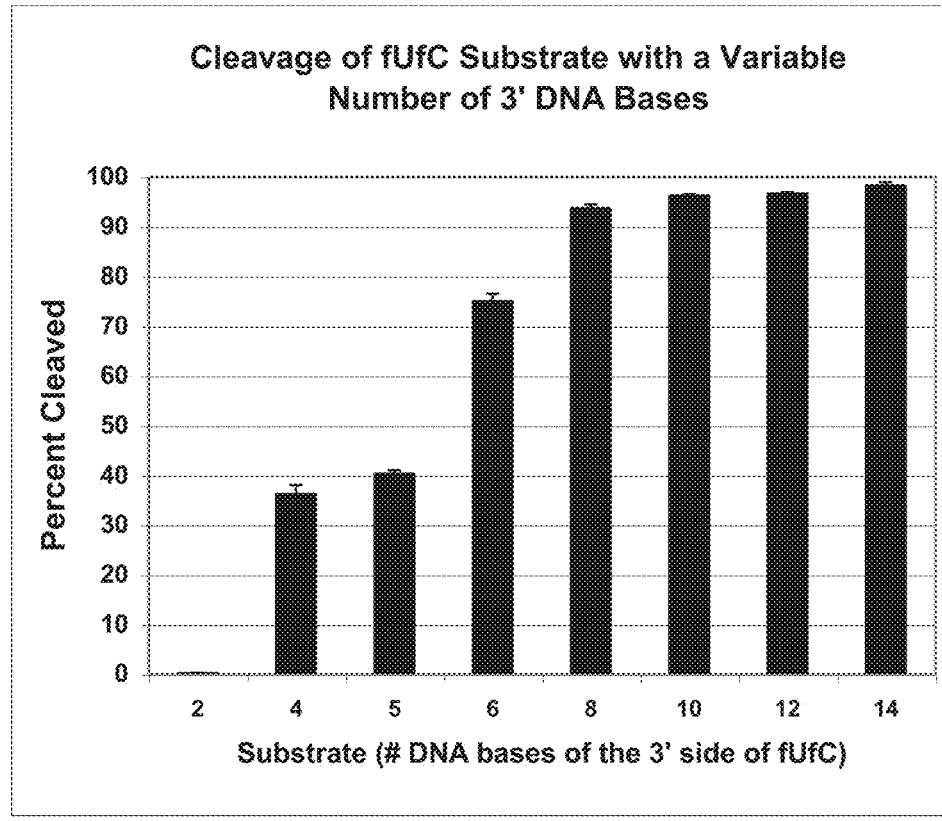
FIG. 17 is a graph quantifying the relative cleavage by *Pyrococcus abyssi* RNase H2 of di-fluoro substrates with a variable number of 3' DNA bases (i.e., number of DNA bases on the 3' side of the fUfC residues).

Similar experiments were done to determine the optimal length of the 3'-DNA domain needed for cleavage of di-fluoro (fNfN) substrates. The duplexes shown in Table 15 were synthesized and tested to functionally define the length of DNA bases needed at the 3'-end of a fUfC di-fluoro substrate. A fixed domain of 22 base pairs was positioned at the 5'-end and the 3'-domain was varied from 2-14 bases.

cleaved in FIG. 17. No cleavage was seen with the substrate having 2 DNA bases on the 3'-side of the cleavable domain. Cleavage was seen with 4 DNA bases and steadily increased until maximal cleavage was obtained when 8-10 DNA bases were present on the 3'-side of the fUfC cleavage domain. Interestingly, the optimal length of DNA bases on the 3'-side of the cleavage domain is longer for the di-fluoro substrates (8-10 bases) compared with the single ribonucleotide substrates (4-5 bases).

In summary, for ribonucleotide containing substrates, maximal cleavage activity is seen when at least 4-5 DNA residues are positioned on the 3'-side and 10-12 DNA residues are positioned on the 5'-side of the cleavable domain. For di-fluoro substrates, maximal cleavage activity is seen when at least 8-10 DNA residues are positioned on the 3'-side of the cleavable domain; from prior examples it is clear that activity is high when 14-15 DNA residues are positioned on the 5'-side of the cleavable domain.

TABLE 15

| 3'-End | Sequence (fUfC) | SEQ ID NOS: |
|---|---|---|
| 3'-D2 | 5'-CTGAGCTTCATGCCTTTACTGT(fUfC)CC-SpC3-3'<br>3'-GACTCGAAGTACGGAAATGACA  A G GGGCTGTGTGTCGAG-5' | 58<br>289 |
| 3'-D4 | 5'-CTGAGCTTCATGCCTTTACTGT(fUfC)CCCG-SpC3-3'<br>3'-GACTCGAAGTACGGAAATGACA  A G GGGCTGTGTGTCGAG-5' | 59<br>289 |
| 3'-D5 | 5'-CTGAGCTTCATGCCTTTACTGT(fUfC)CCCGA-SpC3-3'<br>3'-GACTCGAAGTACGGAAATGACA  A G GGGCTGTGTGTCGAG-5' | 60<br>289 |
| 3'-D6 | 5'-CTGAGCTTCATGCCTTTACTGT(fUfC)CCCGAC-SpC3-3'<br>3'-GACTCGAAGTACGGAAATGACA  A G GGGCTGTGTGTCGAG-5' | 61<br>289 |
| 3'-D8 | 5'-CTGAGCTTCATGCCTTTACTGT(fUfC)CCCGACAC-SpC3-3'<br>3'-GACTCGAAGTACGGAAATGACA  A G GGGCTGTGTGTCGAG-5' | 62<br>289 |
| 3'-D10 | 5'-CTGAGCTTCATGCCTTTACTGT(fUfC)CCCGACACAC-SpC3-3'<br>3'-GACTCGAAGTACGGAAATGACA  A G GGGCTGTGTGTCGAG-5' | 63<br>289 |
| 3'-D12 | 5'-CTGAGCTTCATGCCTTTACTGT(fUfC)CCCGACACACAG-SpC3-3'<br>3'-GACTCGAAGTACGGAAATGACA  A G GGGCTGTGTGTCGAG-5' | 64<br>289 |
| 3'-D14 | 5'-CTGAGCTTCATGCCTTTACTGT(fUfC)CCCGACACACAGCT-SpC3-3'<br>3'-GACTCGAAGTACGGAAATGACA  A G GGGCTGTGTGTCGAG-5' | 65<br>289 |

Figure 18:
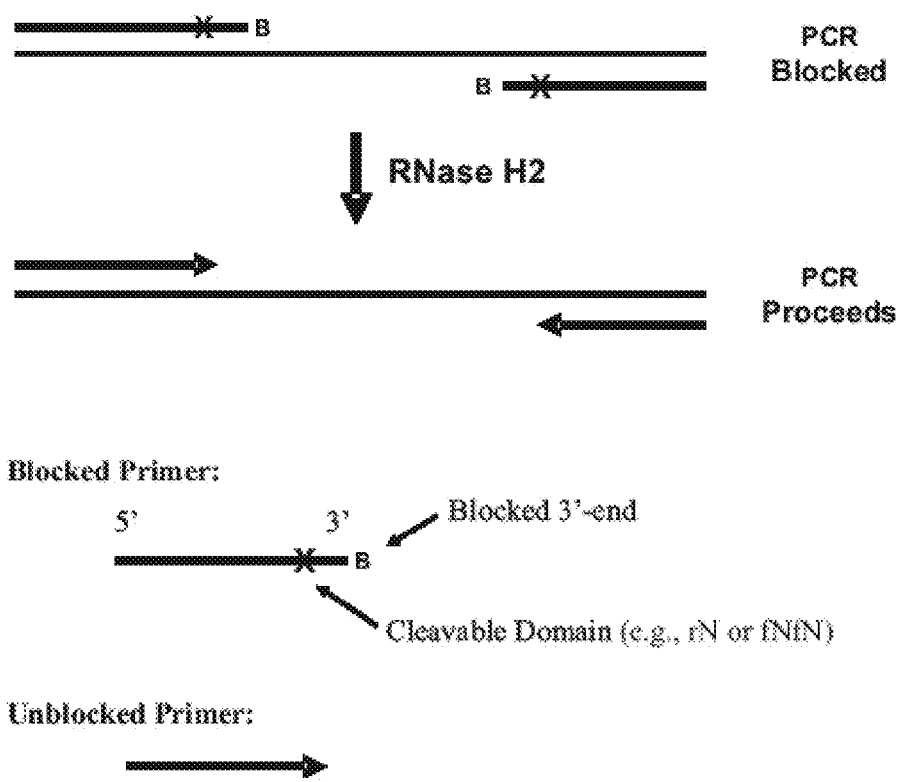
FIG. 18 is a reaction schematic of RNase H2 activation of blocked PCR primers.

The modified strand of each substrate was radiolabeled as above. Reactions were performed using 100 nM substrate with 37 mU of recombinant enzyme in a mixed buffer containing both Mg and Mn cations (10 mM Tris pH 8.0, 50 mM NaCl, 0.6 mM $MnCl_2$, 3 mM $MgCl_2$, 10 µg/ml BSA). Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified and the results plotted as a fraction of total substrate Example 8—Application to DNA Primers: Primer Extension Assay Format and Potential Utility in DNA Sequencing The examples above characterized the ability of a thermostable RNase H2 enzyme to cleave a duplex nucleic acid at a single internal ribonucleotide or at a 2'-fluoro dinucleotide. Example 7 establishes parameters for designing short oligonucleotides which will be effective substrates in this cleavage reaction. These features can be combined to make cleavable primers that function in primer extension assays, such as DNA sequencing, or PCR. A single stranded oligonucleotide is not a substrate for the cleavage reaction, so a modified oligonucleotide primer will be functionally "inert" until it hybridizes to a target sequence. If a cleavable domain is incorporated into an otherwise unmodified oligonucleotide, this oligonucleotide could function to prime PCR and will result in an end product wherein a sizable portion of the primer domain could be cleaved from the final PCR product, resulting in sterilization of the reaction (lacking the priming site, the product will no longer be a template for PCR using the original primer set). If the cleavable domain is incorporated into an oligonucleotide which is blocked at the 3'-end, then this primer will not be active in PCR until cleavage has occurred. Cleavage will "activate" the blocked primer. As such, this format can confer a "hot start" to a PCR reaction, as no DNA synthesis can occur prior to the cleavage event. Example 4 showed that this cleavage event is very inefficient with *Pyrococcus abysii* RNase H2 until elevated temperatures are attained. Additionally, the linkage between the cleavage reaction and primer extension confer added specificity to the assay, since both steps require enzymatic recognition of the duplex formed when the primer hybridizes to the template. A schematic of this reaction is shown in FIG. 18. Note that this schema applies to both simple primer extension reactions as well as PCR. It can also be exploited in other kinds of enzymatic assays such as ligation reactions.

The following example demonstrates the use of an RNase H2 cleavable primer for DNA sequencing. The most common method of DNA sequencing in use today involves sequential DNA synthesis reactions (primer extension reactions) done in the presence of dideoxy terminator nucleotides. The reaction is done in a thermal cycling format where multiple cycles of primer extension are performed and product accumulates in a linear fashion.

DNA sequencing was done using the Big Dye™ Terminator V3.1 Cycle Sequencing Kit (Applied Biosystems, Foster City, Calif.). The following primers were used:

```
M13(-27)
                                         SEQ ID No. 66
5'-CAGGAAACAGCTATGAC-3'

M13(-27)-rC
                                         SEQ ID No. 67
5'-CAGGAAACAGCTATGACcATGA-SpC3-3'
```

As before, DNA bases are indicated in upper case, RNA bases are indicated in lower case, and SpC3 is a spacer C3 blocking group placed at the 3'-end of the oligonucleotide. The blocked cleavable primer contains 17 DNA bases on the 5'-side of the ribonucleotide and 4 DNA bases on the 3'-side of the ribonucleotide (17-1-4 design) and so conforms to the optimized design rules established in Example 7.

Sequencing reactions were set up in 20 µl volume comprising 0.75×ABI Reaction buffer, 160 nM primer, 0.5× Big Dye Terminators and 230 ng plasmid DNA template. Optionally, 4 mM additional $MgCl_2$ was supplemented into the reaction, with or without 14, 1.4, or 0.14 mU of recombinant *Pyrococcus abyssi* RNase H2. The following cycle sequencing program was employed: 96° C. for 30 seconds followed by 25 cycles of [96° C. for 5 seconds, 50° C. for 10 seconds, 55° C. for 4 minutes]. The DNA sequencing reactions were run on an Applied Biosystems model 3130xl Genetic Analyzer. The resulting sequencing traces were examined for quality and read length. Results are summarized in Table 16 below.

TABLE 16

Results of cycle sequencing using a rC blocked cleavable primer

| Primer | RNase H2 | Read length in ABI Buffer | Read length in ABI Buffer + 4 mM $MgCl_2$ |
|---|---|---|---|
| M13(-27) | 0 | >800 | ~500 |
| SEQ ID NO: 66 | 0.14 mU | >800 | >800 |
|  | 1.4 mU | >800 | >800 |
|  | 14 mU | >800 | >800 |
| M13(-27)-rC | 0 | 0 | 0 |
| SEQ ID NO: 67 | 0.14 mU | 0 | 0 |
|  | 1.4 mU | 0 | ~300 |
|  | 14 mU | ~300 | >800 |

Control reactions using an unmodified primer resulted in high quality DNA sequence traces with usable read lengths slightly exceeding 800 bases. The addition of RNase H2 enzyme to these reactions did not compromise reaction quality. The manufacturer (Applied Biosystems) does not disclose the cation content of the buffer provided in the sequencing kits, so actual reaction conditions are not certain. Supplementation of the reactions with an additional 4 mM $MgCl_2$ had no effect. The rC blocked cleavable primer did not support DNA sequencing without the addition of RNase H2. With the addition of RNase H2, high quality sequencing reactions were obtained using 14 mU of enzyme in the 20 µl reaction. Use of lower amounts enzyme resulted in lower quality reactions or no functional reaction at all. Supplementing magnesium content of the reaction buffer was necessary to obtain cleavage and primer extension reactions using the blocked primers. The amount of enzyme employed here is 100-fold higher than is needed to achieve 100% cleavage of a rN substrate under optimal conditions (70° C., 20 minute incubation). In the cycle sequencing reactions performed herein, primer annealing was run at 50° C. and extension reactions were run at 55° C. for 10 seconds and 4 minutes, respectively. These lower temperatures are suboptimal for *Pyrococcus abyssi* RNase H2 (see Example 4 above). Performing the cycle sequencing reaction at higher temperatures will require less enzyme but is not necessary.

This example demonstrates that blocked primers containing an internal cleavage site for RNase H2 can be used with primer-extension based sequencing methods, such as dideoxy (Sanger) sequencing, and are compatible with use of existing high throughput fluorescent sequencing protocols. Use of blocked primers and the method of the present invention can confer added specificity to the sequencing reaction, thus permitting sequencing to be performed for more cycles and on highly complex nucleic acid samples that work poorly with unmodified primers.

Example 9—Application to DNA Primers: rN Primers in PCR and Quantitative Real-Time PCR Example 8 demonstrated that RNase H2 could be used to cleave a blocked primer and that this system could be linked to DNA synthesis and primer extension reactions, including DNA sequencing. The following example demonstrates the utility of this method in PCR. The first system demonstrates use in an end point PCR format and the second system demonstrates use in a quantitative real-time PCR format.

The primers shown in Table 17, were made for use in a synthetic end-point PCR assay. The Syn-For and Syn-Rev primers are unmodified control primers specific for an artificial amplicon (a synthetic oligonucleotide template). The Syn-For primer is paired with the unmodified control Syn-Rev primer or the different modified Syn-Rev primers. A set of modified Syn-Rev primers were made which contain a single rU (cleavable) base followed by 2-6 DNA bases, all ending with a dideoxy-C residue (ddC). The ddC residue functions as a blocking group that prevents primer function. The ddC blocking group is removed with cleavage of the primer at the rU base by the action of RNase H2 (the unblocking step, shown in FIG. 18). The synthetic template is a 103-base long oligonucleotide, shown below (SEQ ID NO: 75). Primer binding sites are underlined.

TABLE 17

| Name | Sequence | SEQ ID NO: |
|---|---|---|
| Syn-For | 5'-AGCTCTGCCCAAAGATTACCCTG-3' | SEQ ID NO: 68 |
| Syn-Rev | 5'-CTGAGCTTCATGCCTTTACTGT-3' | SEQ ID NO: 69 |
| Syn-Rev-rU-2D | 5'-CTGAGCTTCATGCCTTTACTGTuCC-ddC-3' | SEQ ID NO: 70 |
| Syn-Rev-rU-3D | 5'-CTGAGCTTCATGCCTTTACTGTuCCC-ddC-3' | SEQ ID NO: 71 |
| Syn-Rev-rU-4D | 5'-CTGAGCTTCATGCCTTTACTGTuCCCC-ddC-3' | SEQ ID NO: 72 |
| Syn-Rev-rU-5D | 5'-CTGAGCTTCATGCCTTTACTGTuCCCCG-ddC-3' | SEQ ID NO: 73 |
| Syn-Rev-rU-6D | 5'-CTGAGCTTCATGCCTTTACTGTuCCCCGA-ddC-3' | SEQ ID NO: 74 |

DNA bases are shown in uppercase.
RNA bases are shown in lowercase.
ddC indicates a dideoxy-C residue which functions as a blocking group.

Synthetic Template

SEQ ID NO: 75
AGCTCTGCCCAAAGATTACCCTGACAGCTAAGTGGCAGTGGAAGTTGGCC
TCAGAAGTAGTGGCCAGCTGTGTGTCGGGGAACAGTAAAGGCATGAAGCT
CAG

Figure 19:
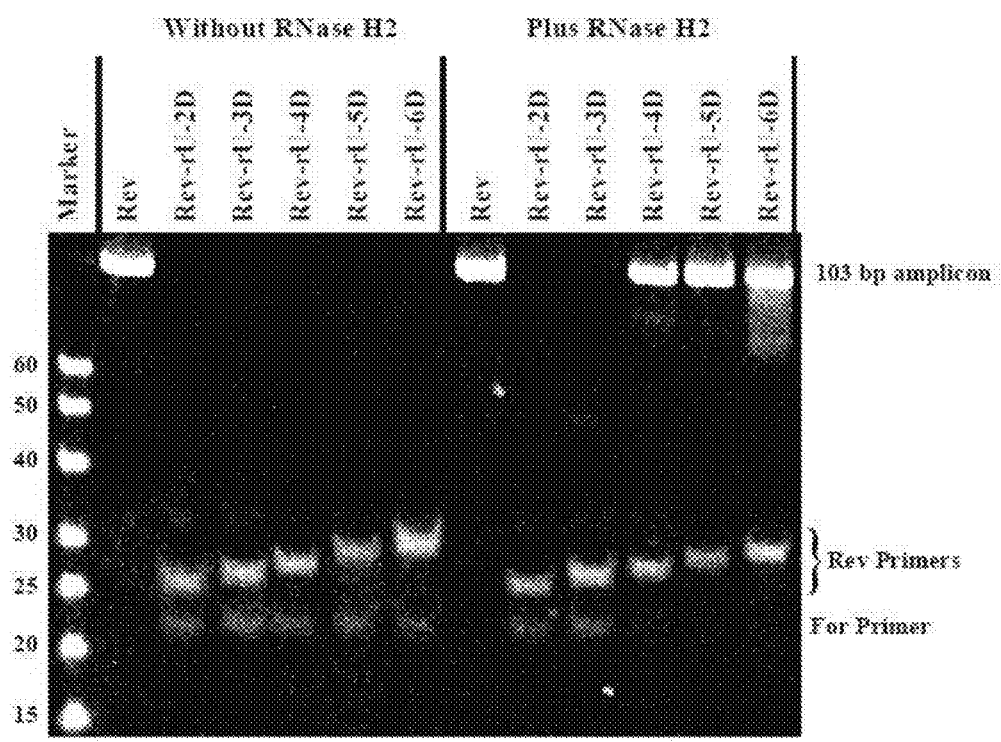
FIG. 19 is a photograph of a gel that shows the products of an end point PCR reaction performed with a single rU-containing blocked primer. The suffix 2D, 3D, etc. represents the number of DNA bases between the rU residues and the 3'-end of the primer. The primer is blocked with a dideoxy C residue.

PCR reactions were performed in 20 µl volume using 200 nM primers, 2 ng template, 200 µM of each dNTP (800 µM total), 1 unit of Immolase (a thermostable DNA polymerase, Bioline), 50 mM Tris pH 8.3, 50 mM KCl, and 3 mM $MgCl_2$. Reactions were run either with or without 100 µU of Pyrococcus abyssi RNase H2. Reactions were started with a soak at 95° C. for 5 minutes followed by 35 cycles of [95° C. for 10 seconds, 60° C. for 30 seconds, and 72° C. for 1 second]. Reaction products were separated on a 10% non-denaturing polyacrylamide gel and visualized using GelStar staining. Results are shown in FIG. 19. Unmodified control primers produced a strong band of the correct size. 3'-end blocked rU primers did not produce any products in the absence of RNase H2. In the presence of RNase H2, blocked primers produced a strong band of the correct size using the D4, D5, and D6 primers. No signal was seen using the D2 or D3 primers. This example demonstrates that blocked primers can be used in PCR reactions using the method of the present invention. Further, this example is consistent with results obtained using cleavage of preformed duplex substrates in Example 7, where the presence of 4-5 3'-DNA bases were found to be optimal for cleavage of rN containing primers.

The same synthetic PCR amplicon assay system described above was next tested in a quantitative real-time PCR assay using SYBR® Green detection. Reactions were done in 384 well format using a Roche Lightcycler® 480 platform. Reactions comprised 1×BIO-RAD iQ™ SYBR® Green Supermix (BIO-RAD, Hercules, Calif.), 200 nM of each primer (for+rev), $2×10^6$ copies of synthetic template oligonucleotide (SEQ ID NO: 75), and 5 mU of Pyrococcus abyssi RNase H2 in 10 µl volume. Thermal cycling parameters included an initial 5 minutes soak at 95° C. and then 45 cycles were performed of [95° C. for 10 seconds+60° C. for 20 seconds+72° C. for 30 seconds]. All reactions were run in triplicate and reactions employed the same unmodified For primer (SEQ ID NO: 68). The Rev primer was varied between the unmodified and 2-6D modified primers (SEQ ID NOS: 69-74). Cp values, the PCR cycle number where a positive reaction is first detected, in these experiments are shown in Table 18 below. The Cps were essentially identical for control reactions done using unmodified For+Rev primers and the coupled cleavage PCR reactions performed using the D4, D5, or D6 blocked primers in the presence of RNase H2. In the absence of RNase H2, no positive signal was detected using the blocked primers. As was seen in the end point assay, performance was reduced for the primers having shorter 3'-DNA domains (D2 or D3).

TABLE 18

Cp values for SYBR® Green qPCR reactions using cleavable blocked primers in a synthetic amplicon system with RNase H2 present

| Reverse Primer | SEQ ID NO: | Cp Value |
|---|---|---|
| Syn-Rev (Control) | SEQ ID NO: 69 | 17.7 |
| Syn-Rev-rU-2D | SEQ ID NO: 70 | 23.4 |
| Syn-Rev-rU-3D | SEQ ID NO: 71 | 23.0 |
| Syn-Rev-rU-4D | SEQ ID NO: 72 | 16.8 |
| Syn-Rev-rU-5D | SEQ ID NO: 73 | 16.6 |
| Syn-Rev-rU-6D | SEQ ID NO: 74 | 16.9 |

All reactions used the same unmodified For primer, SEQ ID NO: 68.

The following example demonstrates use of RNase H2 cleavage using rN blocked primers (both For and Rev) in a quantitative real-time PCR assay format using an endogenous human gene target and HeLa cell cDNA as template. The primers shown in Table 19 specific for the human HRAS gene (NM_176795) were designed and synthesized. In this case a C3 spacer was used as the blocking group.

TABLE 19

| Name | Sequence | SEQ ID NO: |
|---|---|---|
| HRAS-618-For | 5'-ACCTCGGCCAAGACCC-3' | SEQ ID NO: 76 |
| HRAS-916-Rev | 5'-CCTTCCTTCCTTCCTTGCTTCC-3' | SEQ ID NO: 77 |
| HRAS-618-For-rG-D4 | 5'-ACCTCGGCCAAGACCCgGCAG-SpC3-3' | SEQ ID NO: 78 |
| HRAS-916-Rev-rG-D4 | 5'-CCTTCCTTCCTTCCTTGCTTCCgTCCT-SpC3-3' | SEQ ID NO: 79 |

Uppercase represents DNA bases, lowercase represents RNA bases.
SpC3 is a spacer C3 placed as a blocking group on the 3'-end.

These primers define a 340 bp amplicon within the HRAS gene as shown below. Primer binding sites are underlined.
HRAS Assay Amplicon SEQ ID NO: 80
<u>ACCTCGGCCAAGACCC</u>GGCAGGGCAGCCGCTCTGGCTCTAGCTCCAGCTC -continued
CGGGACCCTCTGGGACCCCCCGGGACCCATGTGACCCAGCGGCCCCTCGC

GCTGGAGTGGAGGATGCCTTCTACACGTTGGTGCGTGAGATCCGGCAGCA

CAAGCTGCGGAAGCTGAACCCTCCTGATGAGAGTGGCCCCGGCTGCATGA

GCTGCAAGTGTGTGCTCTCCTGACGCAGCACAAGCTCAGGACATGGAGGT

GCCGGATGCAGGAAGGAGGTGCAGACGGAAGGAGGAGGAAGGAAGGAC<u>GG

AAGCAAGGAAGGAAGG</u>

Figure 20:
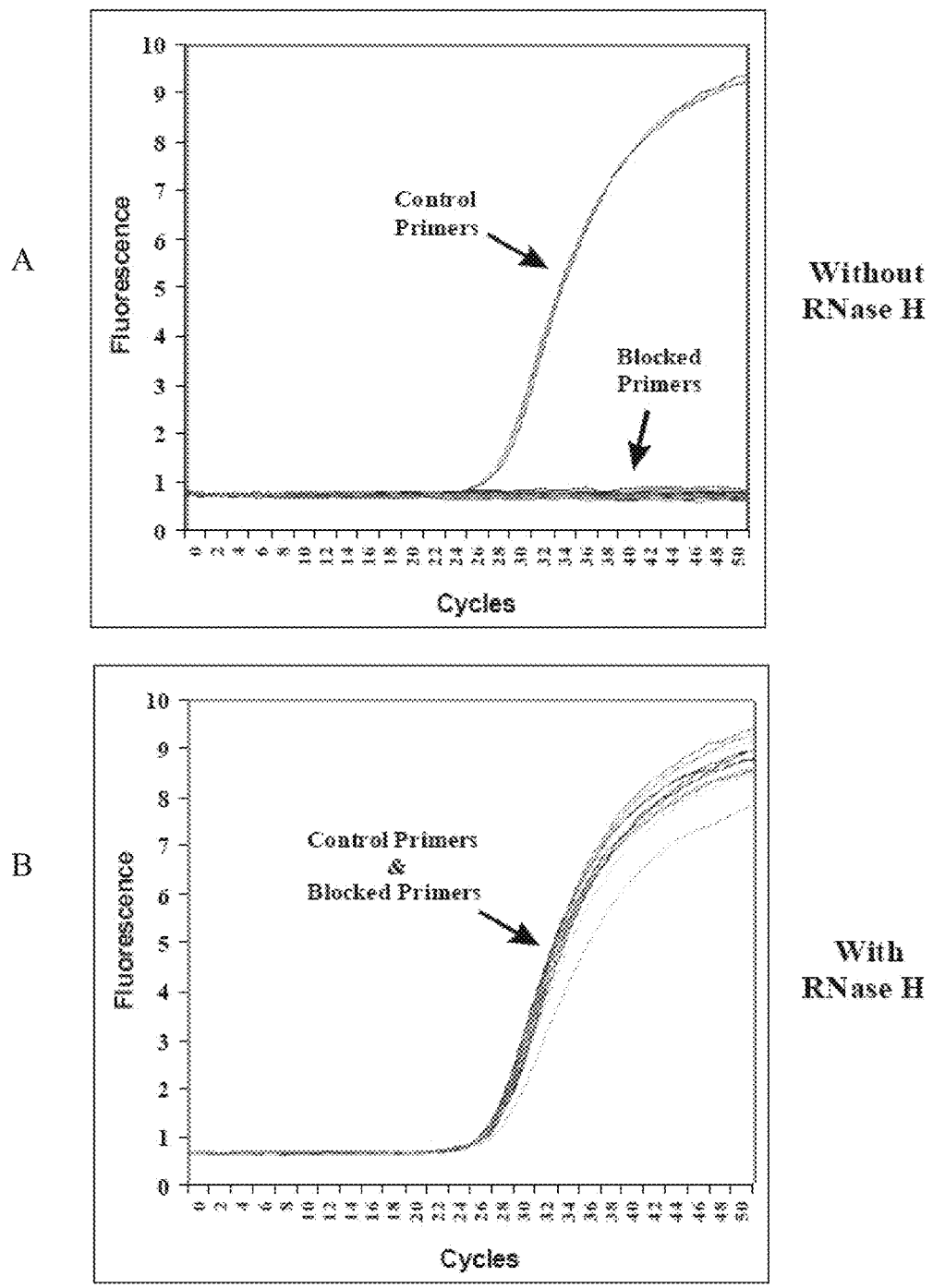
FIGS. 20A-B are PCR amplification plots for a 340 bp amplicon within the human HRAS gene, using both unmodified and blocked rN primers, without RNase H2 (20A) and with RNase H2 (20B). Cycle number is shown on the X-axis and relative fluorescence intensity is shown on the Y-axis.

Reactions were performed in 10 l volume in 384 well format using a Roche Lightcycler® 480 platform. Reactions comprised 1×BIO-RAD iQ™ SYBR® Green Supermix (BIO-RAD, Hercules, Calif.) using the iTAQ DNA polymerase at 25 U/ml, 3 mM MgCl$_2$, 200 nM of each primer (for+rev), 2 ng cDNA (made from HeLa cell total RNA), with or without 5 mU of *Pyrococcus abyssi* RNase H2. Thermal cycling parameters included an initial 5 minutes soak at 95° C. and then 50 cycles were performed of [95° C. for 10 seconds+60° C. for 20 seconds+72° C. for 30 seconds]. All reactions were run in triplicate. Using unmodified primers, the crossing point (Cp) occurred at cycle 27. In the absence of RNase H2, reactions done with blocked primers did not support PCR and no fluorescence signal was detected during the 50 cycle reaction. In the presence of RNase H2, reactions done with blocked primers produced detectable signal at cycle 27.4, essentially identical to the control unblocked primers. Real time PCR fluorescence plots are shown in FIG. 20.

The following example demonstrates use of RNase H2 cleavage using rN blocked primers in a quantitative real-time PCR assay format using another endogenous human gene target and HeLa cell cDNA as the template. The primers specific for the human ETS2 gene (NM_005239) shown in Table 20 were designed and synthesized.

TABLE 20

| Name | Sequence | SEQ ID NO: |
|---|---|---|
| ETS2-300-For | 5'-CCCTGTTTGCTGTTTTTCCTTCTC-3' | SEQ ID NO: 81 |
| ETS2-463-Rev | 5'-CGCCGCTGTTCCTTTTTGAAG-3' | SEQ ID NO: 82 |
| ETS2-300-For-rU-D4 | 5'-CCCTGTTTGCTGTTTTTCCTTCTCuAAAT-SpC3-3' | SEQ ID NO: 83 |
| ETS2-463-Rev-rC-D4 | 5'-CGCCGCTGTTCCTTTTTGAAGcCACT-SpC3-3' | SEQ ID NO: 84 |

Uppercase represents DNA bases, lowercase represents RNA bases.
SpC3 is a spacer C3 placed as a blocking group on the 3'-end These primers define a 184 bp amplicon within the ETS2 gene as shown below. Primer binding sites are underlined.
ETS2 Assay Amplicon SEQ ID NO: 85
<u>CCCTGTTTGCTGTTTTTCCTTCTC</u>TAAATGAAGAGCAAACACTGCAAGAA

GTGCCAACAGGCTTGGATTCCATTTCTCATGACTCCGCCAACTGTGAATT

GCCTTTGTTAACCCCGTGCAGCAAGGCTGTGATGAGTCAAGCCTTAAAAG

CTACCTTCAGTGG<u>CTTCAAAAAGGAACAGCGGCG</u>

Figure 21:
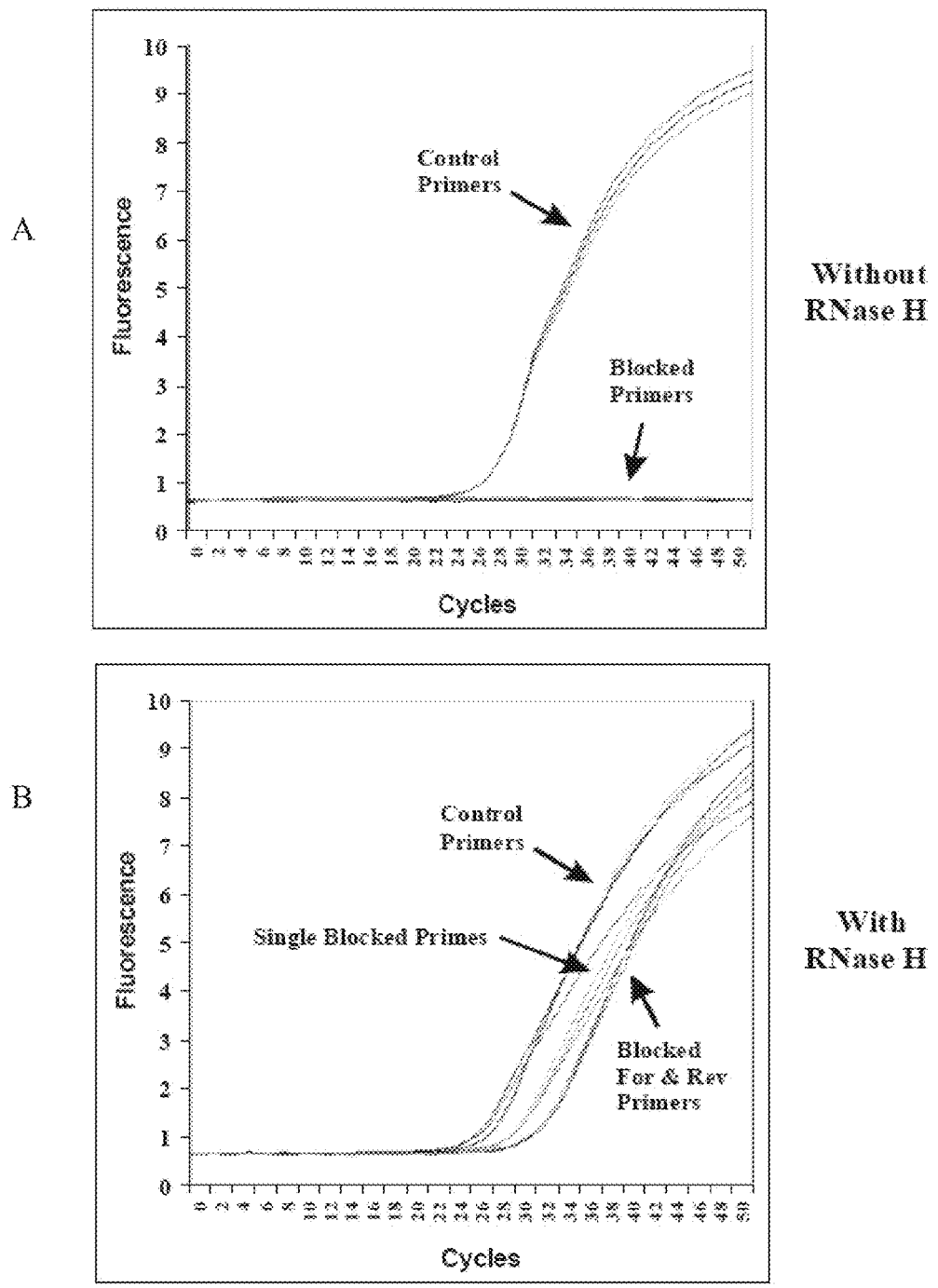
FIGS. 21A-B are PCR amplification plots for a 184 bp amplicon within the human ETS2 gene, using both unmodified and blocked rN primers, without RNase H2 (21A) and with RNase H2 (21B). Cycle number is shown on the X-axis and relative fluorescence intensity is shown on the Y-axis.

Reactions were performed in 10 μl volume in 384 well format using a Roche Lightcycler® 480 platform. Reactions comprised 1×BIO-RAD iQ™ SYBR® Green Supermix (BIO-RAD, Hercules, Calif.) using the iTAQ DNA polymerase at 25 U/ml, 3 mM MgCl$_2$, 200 nM of each primer (for+rev), 2 ng cDNA (made from HeLa cell total RNA), with or without 5 mU of *Pyrococcus abyssi* RNase H2. Thermal cycling parameters included an initial 5 minutes soak at 95° C. and then 50 cycles were performed of [95° C. for 10 seconds+60° C. for 20 seconds+72° C. for 30 seconds]. All reactions were run in triplicate. Using unblocked primers, the Cp occurred at cycle 25.7. In the absence of RNase H2, reactions done with blocked primers did not support PCR and no fluorescence signal was detected out to 50 cycles. In the presence of RNase H2, reactions done with blocked primers produced detectable signal at cycle 31.7, a delay of 6 cycles from the unmodified control primers. Reactions done using one blocked primer (unmodified For+ blocked Rev or blocked For+unmodified Rev) showed intermediate Cp values. Real time PCR fluorescence plots are shown in FIG. 21.

Using the present reaction conditions, the HRAS assay performed identically using unmodified vs. blocked primers. However, the ETS2 assay showed a delay between unmodified vs. blocked primers. In the setting of a PCR reaction where rapid thermal cycling occurs, primer hybridization and cleavage kinetics play a significant role in the efficiency of the overall reaction for reactions which employ the blocked primers. DNA synthesis is linked to the unblocking event, and unblocking requires hybridization, binding of RNase H2, and substrate cleavage before primers become activated and are capable of priming DNA synthesis. It should be possible to increase the amount of cleaved primer produced each cycle by either increasing the amount of RNase H2 enzyme present or by increasing the anneal time of the reaction. DNA synthesis occurs at the anneal temperature (60° C.) nearly as well as at the extension temperature (72° C.) used in the above examples. However, unblocking can only take place during the duration of the anneal step (60° C.) and not during the extend step (72° C.) due to the Tm of the primers employed which only permit formation of a double-stranded substrate for RNase H2 during the anneal step but not at 72° C. (where the primers only exist in single-stranded form).

PCR cycle parameters were changed to a 2 step reaction with anneal/extend as a single event done at 60° C. and the duration of the anneal/extend step was varied to see if changing these reaction parameters could allow the blocked ETS2 primers to perform with similar efficiency as the unmodified control primers. Reactions were done in 10 µl volume in 384 well format using a Roche Lightcycler® 480 platform. Reactions comprised 1×BIO-RAD iQ™ SYBR® Green Supermix (BIO-RAD, Hercules, Calif.) using the iTAQ DNA polymerase at 25 U/ml, 3 mM MgCl$_2$, 200 nM of each primer (for+rev), 2 ng cDNA (made from HeLa cell total RNA), with or without 5 mU of *Pyrococcus abyssi* RNase H2. Thermal cycling parameters included an initial 5 minutes soak at 95° C. and then 45 cycles were performed of [95° C. for 10 seconds+60° C. for 20-120 seconds]. All reactions were run in triplicate. The differences between the Cp values obtained for the blocked primers and the unmodified control primers (ΔCp) are summarized in Table 21 below.

TABLE 21

ΔCp values for SYBR ® Green qPCR ETS2 reactions comparing unmodified and cleavable blocked primers

| Combined time at 60° C. (anneal/extend) | ΔCp Value |
|---|---|
| 20 seconds | 6.1 |
| 60 seconds | 1.2 |
| 90 seconds | 0.6 |
| 120 seconds | 0.4 |

Minor adjustment of the cycling parameters and increasing the duration of the 60° C. anneal step from 20 seconds to 1-2 minutes led to uniform performance between the blocked-cleavable primers and the control unmodified primers. Similar experiments were performed keeping the cycling parameters fixed and increasing enzyme. As predicted, it was possible to improve performance of the blocked primers using higher amounts of enzyme. Doubling the amount of enzyme employed to 10 mU RNase H resulted in minimal difference between control unblocked and blocked cleaveable primers when using a 30 second anneal step at 60° C.

The above example demonstrates that blocked primers containing a single ribonucleotide residue of the optimized design taught in Example 7 can be used with RNase H2 in quantitative real-time PCR assays.

Example 10—Application to DNA Primers: fNfN Primers in PCR and Quantitative Real-Time PCR Example 9 above demonstrated utility of RNase H2 mediated cleavage for use of rN blocked primers in end point and quantitative real time PCR assays. The present example demonstrates utility using fNfN blocked primers in quantitative real time PCR assays.

Since cleavage of the di-fluoro substrate by RNase H2 results in a species having a 3'-OH end, this product should also be able to support PCR reactions using the same reaction format as described in Example 9, assuming that primers bearing a single 2'-F base (fN) are capable of priming DNA synthesis. Cleavage of a di-fluoro substrate proceeds best in the presence of manganese cations, whereas PCR reactions generally are performed in the presence of magnesium cations. PCR reactions using unmodified primers were tested using standard qPCR buffer containing 3 mM MgCl$_2$ and a modified buffer containing 3 mM MgCl$_2$+0.6 mM MnCl$_2$. Reaction performance was identical and the presence of this low amount of manganese did not adversely affect the quantitative nature of the reaction.

The ability of a terminal 3'-fN primer to function in PCR was investigated using the synthetic PCR amplicon system described in example 9. The following primers shown in Table 22 were tested:

TABLE 22

| Name | Sequence | SEQ ID NO: |
|---|---|---|
| Syn-For | 5'-AGCTCTGCCCAAAGATTACCCTG-3' | SEQ ID NO: 68 |
| Syn-Rev | 5'-CTGAGCTTCATGCCTTTACTGT-3' | SEQ ID NO: 69 |
| Syn-Rev-fU | 5'-CTGAGCTTCATGCCTTTACTGT(fU)-3' | SEQ ID NO: 86 |

DNA bases are shown in uppercase.
2'-fluoro bases are indicated as fN.

Synthetic Template

SEQ ID NO: 75
AGCTCTGCCCAAAGATTACCCTGACAGCTAAGTGGCAGTGGAAGTTGGCC

TCAGAAGTAGTGGCCAGCTGTGTGTCGGGGAACAGTAAAGGCATGAAGCT

CAG

Figure 22:
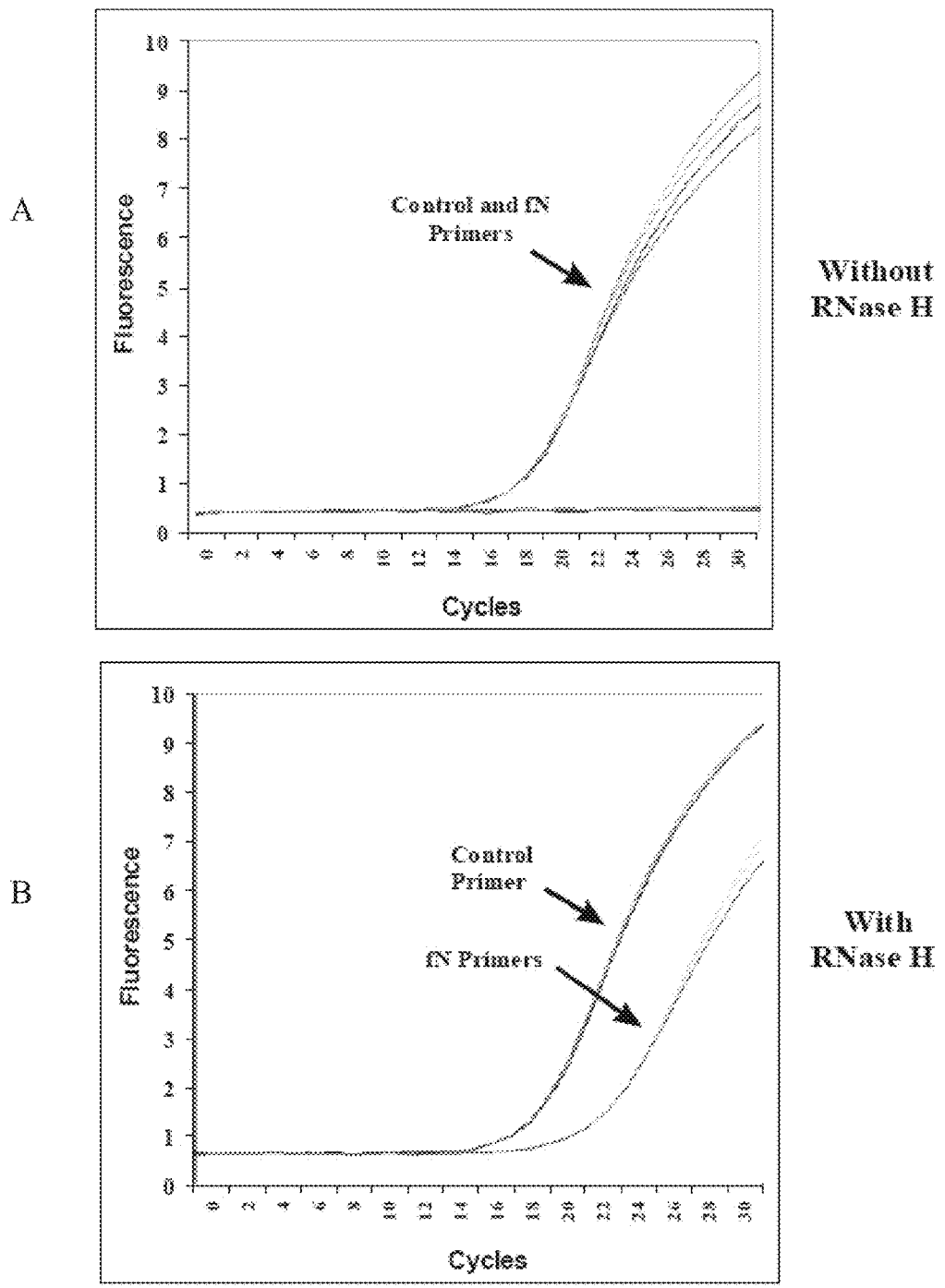
FIGS. 22A-B are PCR amplification plots for a synthetic 103 bp amplicon, using both unmodified and 3'-fN modified primers, without RNase H2 (22A) and with RNase H2 (22B).

Reactions were done in 10 µl volume in 384 well format using a Roche Lightcycler® 480 platform. Reactions comprised 1×BIO-RAD iQ™ SYBR® Green Supermix (BIO-RAD, Hercules, Calif.) using the iTAQ DNA polymerase at 25 U/ml, 3 mM MgCl$_2$, 0.6 mM MnCl$_2$, 200 nM of each primer (for+rev), 2×10$^6$ copies of synthetic oligonucleotide target, with or without 1.75 U of *Pyrococcus abyssi* RNase H2. Thermal cycling parameters included an initial 5 minutes soak at 95° C. and then 30 cycles were performed of [95° C. for 10 seconds+60° C. for 120 seconds+72° C. for 120 seconds]. All reactions were run in triplicate. Results are shown in FIG. 22. In the absence of RNase H2, the primer having a 2'-F base at the 3'-end supported PCR with identical efficiency compared with the unmodified primer. However, in the presence of RNase H2, the 2'-F modified primer showed a 3.5 Cp delay compared with the unmodified primer. This results not from the inhibition of DNA synthesis by RNase H2, but from a low level of cleavage of the primer from the amplification product by RNase H2. Following DNA synthesis, incorporation of a fN-containing primer into the newly formed DNA product creates a potential substrate for RNase H2 (see example 5 above). Cleavage at the 2'-F base will remove the priming site from this strand of the amplicon, effectively sterilizing this product so that any products made from it will be incapable of further priming events. It is this reaction sequence which occurs in polynomial amplification. Cleavage of substrates containing a single 2'-F residue is relatively inefficient, however, so only a modest decrease in PCR reaction efficiency is seen. Extending incubation at 72° C. following PCR should result in total cleavage of the primer from the amplification product, completely blocking the ability of further amplification to occur and thereby sterilizing the product. This should be useful in cross-contamination control of PCR reactions.

Given that the cleavage of a single 2'-F residue is inefficient, use of lower amounts of enzyme, or eliminating the 72° C. elongation step permits cleavage of a difluoro blocked primer by RNase H2 without significantly cleaving the primer extension reaction product containing a single 2' fluoro residue. Alternatively, it should be possible to block this cleavage event by selective placement of a phosphorothioate modification between the terminal 2'-F residue and the adjacent DNA base.

The ability of a di-fluoro blocked primer to support qPCR was demonstrated using the primers shown in Table 23, in the synthetic oligonucleotide amplicon system, described in Example 9 above.

TABLE 23

| Name | Sequence | SEQ ID NO: |
|---|---|---|
| Syn-For | 5'-AGCTCTGCCCAAAGATTACCCTG-3' | SEQ ID NO: 68 |
| Syn-Rev-fU | 5'-CTGAGCTTCATGCCTTTACTGT(fU)-3' | SEQ ID NO: 86 |
| Syn-Rev-fUfC-D10 | 5'-CTGAGCTTCATGCCTTTACTGT(fUfC)CCCGACACAC-SpC3-3' | SEQ ID NO: 87 |

DNA bases are shown in uppercase.
2'-F bases are indicated as fN.
SpC3 indicates a spacer C3 group employed to block the 3'-end Synthetic Template

SEQ ID NO: 75
AGCTCTGCCCAAAGATTACCCTGACAGCTAAGTGGCAGTGGAAGTTGGCC

TCAGAAGTAGTGGCCAGCTGTGTGTCGGGGAACAGTAAAGGCATGAAGCT

CAG

Reactions were done in 10 μl volume in 384 well format using a Roche Lightcycler® 480 platform. Reactions comprised 1×BIO-RAD iQ™ SYBR® Green Supermix (BIO-RAD, Hercules, Calif.) using the iTAQ DNA polymerase at 25 U/ml, 3 mM MgCl$_2$, 0.6 mM MnCl$_2$, 200 nM of each primer (for+rev), 2×10$^6$ copies of synthetic oligonucleotide target, with or without 1.75 U of Pyrococcus abyssi RNase H2. Thermal cycling parameters included an initial 5 minutes soak at 95° C. and then 45 cycles were performed of [95° C. for 10 seconds+60° C. for 120 seconds+72° C. for 120 seconds]. All reactions were run in triplicate. The reactions run with the control primer having a single 2'-fluoro base at the 3'-end (which mimics the cleavage product of the fNfN blocked primer) had a Cp of 20. Reactions run with the blocked fUfC primer also had a Cp of 20.

The amount of RNase H2 enzyme needed in the di-fluoro primer cleavage assay was next studied in more detail. Reactions were done in 10 μl volume in 384 well format using a Roche Lightcycler® 480 platform. Reactions comprised 1×BIO-RAD iQ™ SYBR® Green Supermix (BIO-RAD, Hercules, Calif.) using the iTAQ DNA polymerase at 25 U/ml, 3 mM MgCl$_2$, 0.6 mM MnCl$_2$, 200 nM of each primer (for+rev), 2×10$^6$ copies of synthetic oligonucleotide target. The same unmodified Syn-For primer was used in all reactions. Recombinant Pyrococcus abyssi RNase H2 was added from 0 to 600 mU per reaction. Thermal cycling parameters included an initial 5 minutes soak at 95° C. and then 45 cycles were performed of [95° C. for 10 seconds+ 60° C. for 120 seconds+72° C. for 120 seconds]. All reactions were run in triplicate. Cp values corresponding to the varying amounts of RNase H2 for each primer are shown in Table 24.

TABLE 24

Optimization of the amount of RNase H2 for qPCR reactions using a fUfC blocked primer

| | Amount of RNase H2 used per reaction | | | | |
|---|---|---|---|---|---|
| Primer | 600 mU | 400 mU | 200 mU | 100 mU | 0 mU |
| Syn-Rev | 17.9 | 17.7 | 17.2 | 17.1 | 17.0 |
| Syn-Rev-fU | 25.6 | 23.2 | 19.9 | 18.5 | 17.0 |
| Syn-Rev-fUfC-D10 | 24.6 | 22.9 | 21.3 | 21.9 | ND |

ND = not detected.

The optimal amount of RNase H2 is 200 mU (Cp=21.3 shown in bold and underlined). At higher concentrations of RNase H2 PCR reaction is less efficient, and to a similar degree, with both the 3' fluoroU primer and the blocked difluoro primer. Presumably this is due to a low level of cleavage at the fU set within the PCR product as discussed above.

Generally about 200 mU of *Pyrococcus abysii* RNase H2 per 10 μl is the optimal enzyme concentration for a coupled RNase H2-PCR with blocked primers wherein the RNase H2 cleavage domain is two consecutive 2'-fluoronucleosides. An increase in Cp compared to standard unmodified DNA primers of between 2 and 6 cycles is typically observed. This small difference has no effect on assay performance because results are always compared to a standard curve of Cp vs. target copy number generated with the same primers as used to test unknown samples.

In conclusion, this example has demonstrated that blocked fNfN primers can support qPCR reactions using RNase H2 cleavage with the methods of the present invention and defines optimal amounts of RNase H2 and cycling conditions to employ.

Example 11—Improved Specificity Using rN Blocked Primers in PCR Reactions

In theory, PCR has an almost unlimited potential for amplification and a PCR reaction should only be limited by consumption of reagents in the reaction mix. In actual practice, PCR reactions are typically limited to 40-45 cycles to help preserve specificity. The amplification power of PCR is enormous and, as cycle number exceeds 40-45, it becomes increasingly common for mispriming events to give rise to amplification of undesired products and false positive signals. This example demonstrates how use of cleavable blocked primers with the methods of the present invention improves reaction specificity and permits use of a greater number of PCR cycles, thereby increasing the potential sensitivity of PCR.

In this example, we studied PCR reactions specific for 3 human genes and compared the specificity of each set of primer pairs in amplification using human and rat cDNA as the template. Traditional unmodified oligonucleotides were compared with the new cleavable blocked primers of the present invention. The following primers, as shown in Table 25, were employed. DNA bases are shown in upper case, RNA bases in lower case, and the 3'-blocking group employed was a C3 spacer (SpC3). The gene targets studied were human ETS2, NM_005239 (rat homolog NM_001107107), human HRAS, NM_176795 (rat homolog NM_001061671), and human ACACA, NM_198834 (rat homolog NM_022193).

PCR reactions were done in 384 well format using a Roche Lightcycler® 480 platform. Reactions comprised 1×BIO-RAD iQ™ SYBR® Green Supermix (BIO-RAD, Hercules, Calif.), 200 nM of each primer (For+Rev), and 1.3 mU of *Pyrococcus abyssi* RNase H2 in 10 μl volume. Template DNA was either 2 ng of human HeLa cell cDNA or 2 ng of rat spinal cord cDNA. Thermal cycling parameters included an initial 5 minutes soak at 95° C. and then 60 cycles were performed of [95° C. for 10 seconds+60° C. for 90 seconds]. Under these conditions, the Cp value observed for human cDNA represents a true positive event. If any signal was detected using rat cDNA, it was recorded as a false positive event. For these 3 genes, the human and rat sequences are divergent at the primer binding sites. Therefore detection of a PCR product in rat cDNA using human gene specific primers is an undesired, false positive result that originates from mispriming Results are shown in Table 26 below.

TABLE 26

False detection of products in rat cDNA using human gene specific primers in a 60 cycle qRT-PCR reaction

| Primers (For/Rev) | Observed Cp Human cDNA | Observed Cp Rat cDNA | ΔCp |
| --- | --- | --- | --- |
| ETS2 | 23.6 | 56.4 | 32.8 |
| ETS2-blocked | 24.9 | ND | >assay |
| HRAS | 25.2 | 35.5 | 10.3 |
| HRAS-blocked | 26.1 | ND | >assay |
| ACACA | 26.2 | 52.3 | 26.1 |
| ACACA-blocked | 26.3 | ND | >assay |

ND = not detected

Using unmodified primers, detection of the human targets in human cDNA was successful and Cp's of 23-26 were observed. For all 3 PCR assays, the human gene-specific primers also detected products in rat cDNA when cycling was continued, and Cp's of 35-56 were observed. These represent undesired false positive signals which limit the ability of the PCR assays to detect low levels of true positive signal.

Using modified primers, detection of the desired product in human cDNA was successful and Cp's were all within 1 of the values obtained for unmodified primers. However, no false positive signals were seen using rat cDNA with the modified primers, even at 60 cycles. Use of the RNase H2 blocked-cleavable primers resulted in improved specificity, permitting use of longer, more sensitive PCR reactions (in this case up to 60 cycles) without detection of false priming

TABLE 25

| Gene | Primer | SEQ ID NO: | Sequence |
| --- | --- | --- | --- |
| ETS2 | hETS2-For | SEQ ID NO: 88 | CCCTGTTTGCTGTTTTTCCTTCTC |
|  | hETS2-For-rU | SEQ ID NO: 89 | CCCTGTTTGCTGTTTTTCCTTCTCuAAAT-SpC3 |
|  | hETS2-Rev | SEQ ID NO: 90 | CGCCGCTGTTCCTTTTTGAAG |
|  | hETS2-Rev-rC | SEQ ID NO: 91 | CGCCGCTGTTCCTTTTTGAAGcCACT-SpC3 |
|  |  |  |  |
| HRAS | hHRAS-For | SEQ ID NO: 92 | ACCTCGGCCAAGACCC |
|  | hHRAS-For-rG | SEQ ID NO: 93 | ACCTCGGCCAAGACCCgGCAG-SpC3 |
|  | hHRAS-Rev | SEQ ID NO: 94 | CCTTCCTTCCTTCCTTGCTTCC |
|  | hHRAS-Rev-rG | SEQ ID NO: 95 | CCTTCCTTCCTTCCTTGCTTCCgTCCT-SpC3 |
|  |  |  |  |
| ACACA | hACACA-For | SEQ ID NO: 96 | GCATTTCTTCCATCTCCCCCTC |
|  | hACACA-For-rU | SEQ ID NO: 97 | GCATTTCTTCCATCTCCCCCTCuGCCT-SpC3 |
|  | hACACA-Rev | SEQ ID NO: 98 | TCCGATTCTTGCTCCACTGTTG |
|  | hACACA-Rev-rG | SEQ ID NO: 99 | TCCGATTCTTGCTCCACTGTTGgCTGA-SpC3 | events. This allows for a much greater ability to detect variant alleles in the presence of a larger excess of the wild type sequence.

Example 12—Mismatch Discrimination for a rC Substrate Under Steady State Conditions Example 11 demonstrated the ability of the methods of the invention to improve specificity of a qPCR reaction in the face of background mispriming events. The present example demonstrates the specificity of the RNase H2 cleavage reaction with respect to single-base differences (SNPs). The ability of the *Pyrococcus abyssi* RNase H2 enzyme to distinguish base mismatches in a duplex substrate containing a single rC base was tested under steady state conditions. The following substrates were $^{32}$P-end labeled and incubated in "Mg Cleavage Buffer" as described in Example 4 above. Reactions comprised 100 nM substrate with 100 µU of enzyme in 20 µL volume and were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified and results plotted as a fraction of total substrate cleaved.

Ten duplexes were studied, including the perfect match (rC:G, SEQ ID NOS: 10 and 11) as well as each possible base mismatch at the rC base (3 duplexes, SEQ ID NOS: 10 and 100-102), at position +1 relative to the rC (3 duplexes, SEQ ID NOS: 10 and 103-105), and at position −1 relative to the rC (3 duplexes, SEQ ID NOS: 10 and 106-108). Results were normalized for perfect match=100% and are shown in Table 27 below.

TABLE 27

Cleavage of rC substrates with and without mismatches under steady state conditions

| Duplex Identity SEQ ID NOS: | Substrate Sequence | Cleavage |
|---|---|---|
| 10 | 5' CTCGTGAGGTGATGcAGGAGATGGGAGGCG 3' | 100% |
| 11 | 3' GAGCACTCCACTACGTCCTCTACCCTCCGC 5' | |
| 10 | 5' CTCGTGAGGTGATGcAGGAGATGGGAGGCG 3' | 46% |
| 100 | 3' GAGCACTCCACTACATCCTCTACCCTCCGC 5' | |
| 10 | 5' CTCGTGAGGTGATGcAGGAGATGGGAGGCG 3' | 35% |
| 101 | 3' GAGCACTCCACTACTTCCTCTACCCTCCGC 5' | |
| 10 | 5' CTCGTGAGGTGATGcAGGAGATGGGAGGCG 3' | 23% |
| 102 | 3' GAGCACTCCACTACCTCCTCTACCCTCCGC 5' | |
| 10 | 5' CTCGTGAGGTGATGcAGGAGATGGGAGGCG 3' | 19% |
| 103 | 3' GAGCACTCCACTAAGTCCTCTACCCTCCGC 5' | |
| 10 | 5' CTCGTGAGGTGATGcAGGAGATGGGAGGCG 3' | 65% |
| 104 | 3' GAGCACTCCACTATGTCCTCTACCCTCCGC 5' | |
| 10 | 5' CTCGTGAGGTGATGcAGGAGATGGGAGGCG 3' | 22% |
| 105 | 3' GAGCACTCCACTAGGTCCTCTACCCTCCGC 5' | |
| 10 | 5' CTCGTGAGGTGATGcAGGAGATGGGAGGCG 3' | 61% |
| 106 | 3' GAGCACTCCACTACGACCTCTACCCTCCGC 5' | |
| 10 | 5' CTCGTGAGGTGATGcAGGAGATGGGAGGCG 3' | 91% |
| 107 | 3' GAGCACTCCACTACGCCCTCTACCCTCCGC 5' | |
| 10 | 5' CTCGTGAGGTGATGcAGGAGATGGGAGGCG 3' | 46% |
| 108 | 3' GAGCACTCCACTACGGCCTCTACCCTCCGC 5' | |

DNA bases are shown as uppercase.
RNA bases are shown as lowercase.
Mismatches are shown in bold font and are underlined.

*Pyrococcus* RNase H2 was able to discriminate between single base mismatches under these conditions. The precise degree of discrimination varied with which bases were paired in the mismatch. Interestingly, mismatches at position −1 (one base 5' to the rC base) showed relatively good mismatch discrimination while mismatches at position +1 (one base 3' to the rC base) were in general less effective. Although the selectivity appears relatively modest, it becomes greatly amplified with repeated cycles of PCR.

Example 13—Mismatch Discrimination for rN Substrates During Thermal Cycling

The ability of the *Pyrococcus abyssi* RNase H2 enzyme to distinguish base mismatches for a rC substrate under steady state conditions was described in Example 12. The ability of this enzyme to distinguish base mismatches for all rN containing substrates under conditions of thermal cycling was examined in the present example. In these conditions, the cleavable substrate is only available for processing by the enzyme for a short period of time before temperature elevation disrupts the duplex. Mismatch discrimination was assessed in the setting of a fluorescent quantitative real-time PCR assay. We found that base mismatch discrimination was greatly improved under these kinetically limited conditions than were observed under steady-state conditions.

The following nucleic acids were employed in this example. Oligonucleotides were synthesized to provide coverage for all nearest neighbor pairs and mismatches.

Unmodified For Primer:

SEQ ID NO: 68
5' AGCTCTGCCCAAAGATTACCCTG 3'

Blocked rN substrate rev primers (C3 spacer blocking group at the 3'-end) are shown below. DNA bases are uppercase and RNA bases are lower case. Regions of variation are indicated by bold and underlined. At total of 28 blocked primers containing a single RNA residue were synthesized.

rA Series:

rA series:
SEQ ID NO: 109
5' CTGAGCTTCATGCCTTTACTGTaCCCC-SpC3 3'

SEQ ID NO: 110
5' CTGAGCTTCATGCCTTTACTGAaCCCC-SpC3 3'

SEQ ID NO: 111
5' CTGAGCTTCATGCCTTTACTGCaCCCC-SpC3 3'

-continued

```
                                       SEQ ID NO: 112
5' CTGAGCTTCATGCCTTTACTGGaCCCC-SpC3 3'

SEQ ID NO: 113
5' CTGAGCTTCATGCCTTTACTGTaTCCC-SpC3 3'

SEQ ID NO: 114
5' CTGAGCTTCATGCCTTTACTGTaGCCC-SpC3 3'

SEQ ID NO: 115
5' CTGAGCTTCATGCCTTTACTGTaACCC-SpC3 3' rU series:
                                       SEQ ID NO: 116
5' CTGAGCTTCATGCCTTTACTGTuCCCC-SpC3 3'

SEQ ID NO: 117
5' CTGAGCTTCATGCCTTTACTGAuCCCC-SpC3 3'

SEQ ID NO: 118
5' CTGAGCTTCATGCCTTTACTGCuCCCC-SpC3 3'

SEQ ID NO: 119
5' CTGAGCTTCATGCCTTTACTGGuCCCC-SpC3 3'

SEQ ID NO: 120
5' CTGAGCTTCATGCCTTTACTGTuTCCC-SpC3 3'

SEQ ID NO: 121
5' CTGAGCTTCATGCCTTTACTGTuGCCC-SpC3 3'

SEQ ID NO: 122
5' CTGAGCTTCATGCCTTTACTGTuACCC-SpC3 3' rC series:
                                       SEQ ID NO: 123
5' CTGAGCTTCATGCCTTTACTGTcCCCC-SpC3 3'

SEQ ID NO: 124
5' CTGAGCTTCATGCCTTTACTGAcCCCC-SpC3 3'

SEQ ID NO: 125
5' CTGAGCTTCATGCCTTTACTGCcCCCC-SpC3 3'

SEQ ID NO: 126
5' CTGAGCTTCATGCCTTTACTGGcCCCC-SpC3 3'

SEQ ID NO: 127
5' CTGAGCTTCATGCCTTTACTGTcTCCC-SpC3 3'

SEQ ID NO: 128
5' CTGAGCTTCATGCCTTTACTGTcGCCC-SpC3 3'

SEQ ID NO: 129
5' CTGAGCTTCATGCCTTTACTGTcACCC-SpC3 3' rG series:
                                       SEQ ID NO: 130
5' CTGAGCTTCATGCCTTTACTGTgCCCC-SpC3 3'

SEQ ID NO: 131
5' CTGAGCTTCATGCCTTTACTGAgCCCC-SpC3 3'

SEQ ID NO: 132
5' CTGAGCTTCATGCCTTTACTGCgCCCC-SpC3 3'

SEQ ID NO: 133
5' CTGAGCTTCATGCCTTTACTGGgCCCC-SpC3 3'

SEQ ID NO: 134
5' CTGAGCTTCATGCCTTTACTGTgTCCC-SpC3 3'

SEQ ID NO: 135
5' CTGAGCTTCATGCCTTTACTGTgGCCC-SpC3 3'

SEQ ID NO: 136
5' CTGAGCTTCATGCCTTTACTGTgACCC-SpC3 3'
```

The unblocked control Rev primer (mimicing reaction product of blocked primers after cleavage by RNase H2) employed was:

```
                                       SEQ ID NO: 290
        5' CTGAGCTTCATGCCTTTACTG 3'
```

The following perfect-matched and mismatched synthetic templates were employed. The locations of varying bases are indicated in bold font with underline. Unique templates were made for each possible base variation at the ribonucleotide or one base 5' or one base 3' of the ribonucleotide. In total, 28 templates were synthesized and tested.

rA templates:
```
                                                 SEQ ID NO: 137
5'AGCTCTGCCCAAAGATTACCCTGACAGCTAAGTGGCAGTGGAAGT

TGGCCTCAGAAGTAGTGGCCAGCTGTGTGTCGGGGTACAGTAAAGGCATG

AAGCTCAG-3'

SEQ ID NO: 138
5'AGCTCTGCCCAAAGATTACCCTGACAGCTAAGTGGCAGTGGAAGT

TGGCCTCAGAAGTAGTGGCCAGCTGTGTGTCGGGGTCCAGTAAAGGCATG

AAGCTCAG-3'

SEQ ID NO: 139
5'AGCTCTGCCCAAAGATTACCCTGACAGCTAAGTGGCAGTGGAAGT

TGGCCTCAGAAGTAGTGGCCAGCTGTGTGTCGGGGTTCAGTAAAGGCATG

AAGCTCAG-3'

SEQ ID NO: 140
5'AGCTCTGCCCAAAGATTACCCTGACAGCTAAGTGGCAGTGGAAGT

TGGCCTCAGAAGTAGTGGCCAGCTGTGTGTCGGGGTGCAGTAAAGGCATG

AAGCTCAG-3'

SEQ ID NO: 141
5'AGCTCTGCCCAAAGATTACCCTGACAGCTAAGTGGCAGTGGAAGT

TGGCCTCAGAAGTAGTGGCCAGCTGTGTGTCGGGCTACAGTAAAGGCATG

AAGCTCAG-3'

SEQ ID NO: 142
5'AGCTCTGCCCAAAGATTACCCTGACAGCTAAGTGGCAGTGGAAGT

TGGCCTCAGAAGTAGTGGCCAGCTGTGTGTCGGGATACAGTAAAGGCATG

AAGCTCAG-3'

SEQ ID NO: 143
5'AGCTCTGCCCAAAGATTACCCTGACAGCTAAGTGGCAGTGGAAGT

TGGCCTCAGAAGTAGTGGCCAGCTGTGTGTCGGGTTACAGTAAAGGCATG

AAGCTCAG-3'
``` rU templates:
```
                                                 SEQ ID NO: 144
5'AGCTCTGCCCAAAGATTACCCTGACAGCTAAGTGGCAGTGGAAGT

TGGCCTCAGAAGTAGTGGCCAGCTGTGTGTCGGGGAACAGTAAAGGCATG

AAGCTCAG-3'

SEQ ID NO: 145
5'AGCTCTGCCCAAAGATTACCCTGACAGCTAAGTGGCAGTGGAAGT

TGGCCTCAGAAGTAGTGGCCAGCTGTGTGTCGGGGATCAGTAAAGGCATG

AAGCTCAG-3'

SEQ ID NO: 146
5'AGCTCTGCCCAAAGATTACCCTGACAGCTAAGTGGCAGTGGAAGT
```

TGGCCTCAGAAGTAGTGGCCAGCTGTGTGTCGGGGACCAGTAAAGGCATG

AAGCTCAG-3'

SEQ ID NO: 147
5'AGCTCTGCCCAAAGATTACCCTGACAGCTAAGTGGCAGTGGAAGT

TGGCCTCAGAAGTAGTGGCCAGCTGTGTGTCGGGGAGCAGTAAAGGCATG

AAGCTCAG-3'

SEQ ID NO: 148
5'AGCTCTGCCCAAAGATTACCCTGACAGCTAAGTGGCAGTGGAAGT

TGGCCTCAGAAGTAGTGGCCAGCTGTGTGTCGGGCAACAGTAAAGGCATG

AAGCTCAG-3'

SEQ ID NO: 149
5'AGCTCTGCCCAAAGATTACCCTGACAGCTAAGTGGCAGTGGAAGT

TGGCCTCAGAAGTAGTGGCCAGCTGTGTGTCGGGAAACAGTAAAGGCATG

AAGCTCAG-3'

SEQ ID NO: 150
5'AGCTCTGCCCAAAGATTACCCTGACAGCTAAGTGGCAGTGGAAGT

TGGCCTCAGAAGTAGTGGCCAGCTGTGTGTCGGGTAACAGTAAAGGCATG

AAGCTCAG-3' rG templates:

SEQ ID NO: 151
5'AGCTCTGCCCAAAGATTACCCTGACAGCTAAGTGGCAGTGGAAGT

TGGCCTCAGAAGTAGTGGCCAGCTGTGTGTCGGGGCACAGTAAAGGCATG

AAGCTCAG-3'

SEQ ID NO: 152
5'AGCTCTGCCCAAAGATTACCCTGACAGCTAAGTGGCAGTGGAAGT

TGGCCTCAGAAGTAGTGGCCAGCTGTGTGTCGGGGCTCAGTAAAGGCATG

AAGCTCAG-3'

SEQ ID NO: 153
5'AGCTCTGCCCAAAGATTACCCTGACAGCTAAGTGGCAGTGGAAGT

TGGCCTCAGAAGTAGTGGCCAGCTGTGTGTCGGGGCCCAGTAAAGGCATG

AAGCTCAG-3'

SEQ ID NO: 154
5'AGCTCTGCCCAAAGATTACCCTGACAGCTAAGTGGCAGTGGAAGT

TGGCCTCAGAAGTAGTGGCCAGCTGTGTGTCGGGGCGCAGTAAAGGCATG

AAGCTCAG-3'

SEQ ID NO: 155
5'AGCTCTGCCCAAAGATTACCCTGACAGCTAAGTGGCAGTGGAAGT

TGGCCTCAGAAGTAGTGGCCAGCTGTGTGTCGGGACACAGTAAAGGCATG

AAGCTCAG-3'

SEQ ID NO: 156
5'AGCTCTGCCCAAAGATTACCCTGACAGCTAAGTGGCAGTGGAAGT

TGGCCTCAGAAGTAGTGGCCAGCTGTGTGTCGGGTCACAGTAAAGGCATG

AAGCTCAG-3'

SEQ ID NO: 157
5'AGCTCTGCCCAAAGATTACCCTGACAGCTAAGTGGCAGTGGAAGT

TGGCCTCAGAAGTAGTGGCCAGCTGTGTGTCGGGCCACAGTAAAGGCATG

AAGCTCAG-3' rC templates

SEQ ID NO: 158
5'AGCTCTGCCCAAAGATTACCCTGACAGCTAAGTGGCAGTGGAAGT

TGGCCTCAGAAGTAGTGGCCAGCTGTGTGTCGGGGGACAGTAAAGGCATG

AAGCTCAG-3'

SEQ ID NO: 159
5'AGCTCTGCCCAAAGATTACCCTGACAGCTAAGTGGCAGTGGAAGT

TGGCCTCAGAAGTAGTGGCCAGCTGTGTGTCGGGGGTCAGTAAAGGCATG

AAGCTCAG-3'

SEQ ID NO: 160
5'AGCTCTGCCCAAAGATTACCCTGACAGCTAAGTGGCAGTGGAAGT

TGGCCTCAGAAGTAGTGGCCAGCTGTGTGTCGGGGGCCAGTAAAGGCATG

AAGCTCAG-3'

SEQ ID NO: 161
5'AGCTCTGCCCAAAGATTACCCTGACAGCTAAGTGGCAGTGGAAGT

TGGCCTCAGAAGTAGTGGCCAGCTGTGTGTCGGGGGGCAGTAAAGGCATG

AAGCTCAG-3'

SEQ ID NO: 162
5'AGCTCTGCCCAAAGATTACCCTGACAGCTAAGTGGCAGTGGAAGT

TGGCCTCAGAAGTAGTGGCCAGCTGTGTGTCGGGAGACAGTAAAGGCATG

AAGCTCAG-3'

SEQ ID NO: 163
5'AGCTCTGCCCAAAGATTACCCTGACAGCTAAGTGGCAGTGGAAGT

TGGCCTCAGAAGTAGTGGCCAGCTGTGTGTCGGGTGACAGTAAAGGCATG

AAGCTCAG-3'

SEQ ID NO: 164
5'AGCTCTGCCCAAAGATTACCCTGACAGCTAAGTGGCAGTGGAAGT

TGGCCTCAGAAGTAGTGGCCAGCTGTGTGTCGGGCGACAGTAAAGGCATG

AAGCTCAG-3'

Together, these nucleic acids (SEQ ID NOS: 68, 291, 116 and 69, respectively, in order of appearance) comprise PCR assays set up as indicated:

```
5'AGCTCTGCCCAAAGATTACCCTG →
::::::::::::::::::::::::
5'AGCTCTGCCCAAAGATTACCCTGACAGCTAAGT

GGCAGTGGAAGTTGGCCTCAGAAGTAGTGGCCAG

CTGTGTGTGTCGGGGAACAGTAAAGGCATGAAGCTCAG 3'
                  :::::::::::::::::::::::::::::
             X-CCCCuTGTCATTTCCGTACTTCGAGTC 5'
              ←TGTCATTTCCGTACTTCGAGTC 5'
```

The terminal C3 spacer group (indicated by "x") blocks the rU containing oligonucleotide to serve as a primer. When hybridized to the template, the duplex becomes a substrate for RNase H2 and cleavage occurs immediately 5'- to the rU residue, resulting in a functional primer as shown (←).

SEQ ID NOS: 109-136 and templates SEQ ID NOS: 137-164. Reactions were done in 384 well format using a Roche Lightcycler® 480 platform. Reactions comprised 1×BIO-RAD iQ™ SYBR® Green Supermix (BIO-RAD, Hercules, Calif.), 200 nM of each primer (for +rev), and 1.3 mU of *Pyrococcus abyssi* RNase H2 in 10 µl volume. Thermal cycling parameters included an initial 5 minutes soak at 95° C. and then 45 cycles were performed of [95° C. for 10 seconds+60° C. for 20 seconds+72° C. for 30 seconds]. Under these conditions, the Cp value was identical for control reactions done using For+Rev (unmodified) primers and control coupled RNase H2 cleavage-PCR reactions done using the perfect match For (unmodified)+rN Rev (blocked) primers. Thus the reaction conditions employed had sufficient incubation time and RNase H2 concentration to cleave the perfect match species within the kinetic constraints of the real time thermal cycling and any deviations from this point will represent a change in reaction efficiency imparted by base mismatches present between the blocked primer and the various templates.

Pairwise combinations of primers and templates were run as described above and results are summarized below showing ΔCp, which is the difference of cycle threshold observed between control and mismatch reactions. Since each Cp represents a cycle in PCR (which is an exponential reaction under these conditions), a ΔCp of 10 represents a real differential of $2^{10}$, or a 1024 fold change in sensitivity. A ΔCp of 4 to 5 cycles is generally sufficient to discriminate between SNPs in allele specific PCR assays.

Results for tests done varying bases at the central position over the rN base are shown below in Table 28 (SEQ ID NOS: 292 and 293, respectively, in order of appearance):

```
                            g
                            c
                            u
5'CTGAGCTTCATGCCTTTACTGTaCCCC-SpC3 3'  blocked
  ::::::::::::::::::::::::::::::::     primers
3'GACTCGAAGTACGGAAATGACATGGGG... 5'   templates
                            A
                            C
                            G
```

TABLE 28

ΔCp for all possible base mismatches at the rN position

| | Template | | | |
|---|---|---|---|---|
| | A | C | G | T |
| rA | 14.9 | 9.4 | 13.6 | 0 |
| rC | 7.4 | 9.2 | 0 | 6.6 |
| rG | 13.9 | 0 | 12.7 | 14.5 |
| rU | 0 | 12.2 | 10.9 | 5.3 |

Very large differences in reactive efficiency are seen in RNase H2 cleavage of a rN substrate under thermal cycling conditions, ranging from a difference of around 40-fold (ΔCp 5.3) to over a 30,000 fold difference (ΔCp 14.9). None of the assays showed a ΔCp less than 5 cycles. Thus the RNase H2 rN cleavage reaction shows far greater specificity in the setting of a kinetic assay (qPCR) than under steady state conditions and much greater selectivity than allele specific PCR with standard DNA primers. Added specificity may be conferred by the design of the primers as described in the detailed description of the invention and demonstrated in the examples below.

SEQ ID NOS: 294 and 295, respectively, in order of appearance):

```
                          G
                          C
                          A
5'CTGAGCTTCATGCCTTTACTGTuCCCC-SpC3 3'  blocked
  ::::::::::::::::::::::::::::::::     primers
3'GACTCGAAGTACGGAAATGACAAGGGG... 5'   templates
                          T
                          C
                          G
```

TABLE 29

ΔCp for all possible base mismatches at position −1 relative to a rU base

| | Template | | | |
|---|---|---|---|---|
| | A | C | G | T |
| A(rU) | 16.1 | 8.7 | 12.6 | 0 |
| C(rU) | 7.6 | 3.9 | 0 | 12.0 |
| G(rU) | 13.8 | 0 | 12.4 | 5.9 |
| T(rU) | 0 | 5.2 | 2.4 | 6.2 |

Results for tests done varying bases at the +1 position relative to the rN base are shown below in Table 30 (SEQ ID NOS: 296 and 297, respectively, in order of appearance):

```
                            G
                            T
                            A
5'CTGAGCTTCATGCCTTTACTGTuCCCC-SpC3 3'  blocked
  ::::::::::::::::::::::::::::::::     primers
3'GACTCGAAGTACGGAAATGACAAGGGG... 5'   templates
                         T
                         C
                         A
```

TABLE 30

ΔCp for all possible base mismatches at position +1 relative to a rU base

| | Template | | | |
|---|---|---|---|---|
| | A | C | G | T |
| (rU)A | 11.4 | 2.5 | 12.2 | 0 |
| (rU)C | 6.4 | 10.4 | 0 | 9.0 |
| (rU)G | 13.8 | 0 | 4.5 | 3.0 |
| (rU)T | 0 | 11.1 | 11.9 | 2.9 |

Pairwise combinations were similarly tested for all sequence variants listed above for the −1 and +1 positions relative to the rN base, including the rA, rC, and rG probes. Results are shown in Tables 31-36 below.

TABLE 31

ΔCp for all possible base mismatches at position −1 relative to a rA base

| | Template | | | |
|---|---|---|---|---|
| | A | C | G | T |
| A(rA) | 14.2 | 8.6 | 11.8 | 0 |
| C(rA) | 6.9 | 12.6 | 0 | 6.8 |
| G(rA) | 12.8 | 0 | 12.6 | 8.9 |
| T(rA) | 0 | 5.1 | 1.4 | 8.6 |

TABLE 32

ΔCp for all possible base mismatches at position +1 relative to a rA base

| | Template | | | |
|---|---|---|---|---|
| | A | C | G | T |
| (rA)A | 3.1 | 1.0 | 6.12 | 0 |
| (rA)C | 9.3 | 10.2 | 0 | 8.3 |
| (rA)G | 13.2 | 0 | 2.5 | 5.9 |
| (rA)T | 0 | 5.0 | 7.1 | 4.0 |

TABLE 33

ΔCp for all possible base mismatches at position −1 relative to a rC base

| | Template | | | |
|---|---|---|---|---|
| | A | C | G | T |
| A(rC) | 13.0 | 8.2 | 10.5 | 0 |
| C(rC) | 5.0 | 3.3 | 0 | 3.5 |
| G(rC) | 8.3 | 0 | 7.0 | 0.8 |
| T(rC) | 0 | 5.4 | 2.1 | 4.6 |

TABLE 34

ΔCp for all possible base mismatches at position +1 relative to a rC base

| | Template | | | |
|---|---|---|---|---|
| | A | C | G | T |
| (rC)A | 5.6 | 1.8 | 10.2 | 0 |
| (rC)C | 8.8 | 9.6 | 0 | 8.6 |
| (rC)G | 9.8 | 0 | 3.2 | 0.3 |
| (rC)T | 0 | 2.1 | 0.2 | 0.0 |

TABLE 35

ΔCp for all possible base mismatches at position −1 relative to a rG base

| | Template | | | |
|---|---|---|---|---|
| | A | C | G | T |
| A(rG) | 12.4 | 4.8 | 10.4 | 0 |
| C(rG) | 4.5 | 11.1 | 0 | 2.5 |
| G(rG) | 10.3 | 0 | 10.1 | 3.8 |
| T(rG) | 0 | 3.5 | 2.2 | 5.3 |

TABLE 36

ΔCp for all possible base mismatches at position +1 relative to a rG base

| | Template | | | |
|---|---|---|---|---|
| | A | C | G | T |
| (rG)A | 6.2 | 3.0 | 11.4 | 0 |
| (rG)C | 9.5 | 7.3 | 0 | 4.7 |
| (rG)G | 13.1 | 0 | 6.0 | 3.2 |
| (rG)T | 0 | 4.5 | 11.5 | 0.3 |

The relative change in reaction efficiency of cleavage of a rN substrate by *Pyrococcus abyssi* RNase H2 in the setting of a single base mismatch varies with the identity of the paired bases, the relative position of the mismatch to the cleavage site, and the neighboring bases. The mismatch charts defined in this example can be used to design optimal mismatch detection assays which maximize the expected differential (ΔCp) between mismatch and matched loci, and can be built into an algorithm to automate optimization of new assay designs.

Example 14—Mismatch Discrimination for fUfU Substrate Under Steady State Conditions The ability of the *Pyrococcus abyssi* RNase H2 enzyme to distinguish base mismatches in a duplex substrate containing a fUfU dinucleotide pair was tested under steady state conditions. The following substrates were $^{32}$P-end labeled and incubated in "Mn Cleavage Buffer" as described in Examples 5 and 6 above. Reactions comprised 100 nM substrate with 1 U of enzyme in 20 μL volume and were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified and results plotted as a fraction of total substrate cleaved.

Fourteen duplexes shown in Table 37, were studied, including the perfect match (SEQ ID NOS: 42 and 183), mismatches within the 2'-fluoro dinucleotide pair (SEQ ID NOS: 42 and 165-171), and mismatches adjacent to the 2'-fluoro dinucleotide pair (SEQ ID NOS: 42 and 172-177). Results were normalized for a perfect match=100%.

TABLE 37

Cleavage of fUfU substrates with and without mismatches under steady state conditions

| Duplex Identity SEQ ID NOS: | Substrate Sequence | Cleavage |
|---|---|---|
| SEQ ID NO: 42<br>SEQ ID NO: 183 | 5' CTCGTGAGGTGAT(fUfU)AGGAGATGGGAGGCG 3'<br>3' GAGCACTCCACTA  A A  TCCTCTACCCTCCGC 5' | 100% |
| SEQ ID NO: 42<br>SEQ ID NO: 165 | 5' CTCGTGAGGTGAT(fUfU)AGGAGATGGGAGGCG 3'<br>3' GAGCACTCCACTA  A <u>G</u> TCCTCTACCCTCCGC 5' | 5% |
| SEQ ID NO: 42<br>SEQ ID NO: 166 | 5' CTCGTGAGGTGAT(fUfU)AGGAGATGGGAGGCG 3'<br>3' GAGCACTCCACTA  A <u>C</u> TCCTCTACCCTCCGC 5' | 14% |

TABLE 37-continued

Cleavage of fUfU substrates with and without mismatches under steady state conditions

| Duplex Identity SEQ ID NOS: | | Substrate Sequence | Cleavage |
|---|---|---|---|
| SEQ ID NO: 42 | 5' | CTCGTGAGGTGAT(fUfU)AGGAGATGGGAGGCG 3' | 1% |
| SEQ ID NO: 167 | 3' | GAGCACTCCACTA  A T TCCTCTACCCTCCGC 5' | |
| SEQ ID NO: 42 | 5' | CTCGTGAGGTGAT(fUfU)AGGAGATGGGAGGCG 3' | 2% |
| SEQ ID NO: 168 | 3' | GAGCACTCCACTA  C T TCCTCTACCCTCCGC 5' | |
| SEQ ID NO: 42 | 5' | CTCGTGAGGTGAT(fUfU)AGGAGATGGGAGGCG 3' | 0% |
| SEQ ID NO: 169 | 3' | GAGCACTCCACTA  G G TCCTCTACCCTCCGC 5' | |
| SEQ ID NO: 42 | 5' | CTCGTGAGGTGAT(fUfU)AGGAGATGGGAGGCG 3' | 0% |
| SEQ ID NO: 170 | 3' | GAGCACTCCACTA  C C TCCTCTACCCTCCGC 5' | |
| SEQ ID NO: 42 | 5' | CTCGTGAGGTGAT(fUfU)AGGAGATGGGAGGCG 3' | 0% |
| SEQ ID NO: 171 | 3' | GAGCACTCCACTA  T T TCCTCTACCCTCCGC 5' | |
| SEQ ID NO: 42 | 5' | CTCGTGAGGTGAT(fUfU)AGGAGATGGGAGGCG 3' | 8% |
| SEQ ID NO: 172 | 3' | GAGCACTCCACTC  A A TCCTCTACCCTCCGC 5' | |
| SEQ ID NO: 42 | 5' | CTCGTGAGGTGAT(fUfU)AGGAGATGGGAGGCG 3' | 4% |
| SEQ ID NO: 173 | 3' | GAGCACTCCACTG  A A TCCTCTACCCTCCGC 5' | |
| SEQ ID NO: 42 | 5' | CTCGTGAGGTGAT(fUfU)AGGAGATGGGAGGCG 3' | 4% |
| SEQ ID NO: 174 | 3' | GAGCACTCCACTT  A A TCCTCTACCCTCCGC 5' | |
| SEQ ID NO: 42 | 5' | CTCGTGAGGTGAT(fUfU)AGGAGATGGGAGGCG 3' | 2% |
| SEQ ID NO: 175 | 3' | GAGCACTCCACTA  A A GCCTCTACCCTCCGC 5' | |
| SEQ ID NO: 42 | 5' | CTCGTGAGGTGAT(fUfU)AGGAGATGGGAGGCG 3' | 8% |
| SEQ ID NO: 176 | 3' | GAGCACTCCACTA  A A CCCTCTACCCTCCGC 5' | |
| SEQ ID NO: 42 | 5' | CTCGTGAGGTGAT(fUfU)AGGAGATGGGAGGCG 3' | 2% |
| SEQ ID NO: 177 | 3' | GAGCACTCCACTA  A A ACCTCTACCCTCCGC 5' | |

DNA bases are shown as uppercase. 2'-F bases are shown as fU.
Mismatches are shown in bold font and are underlined.

*Pyrococcus* RNase H2 was able to discriminate very efficiently between single base mismatches under these conditions. The precise degree of discrimination varied with which bases were paired in the mismatch. Interestingly, mismatches at both positions −1 and +1 (relative to the fUfU domain) were effective. Specificity for cleavage using the fUfU substrate was significantly higher under steady state assay conditions than was the rC substrate (Example 12 above).

The study above employed the fUfU dinucleotide pair, which was previously shown in Example 6 to be the least efficient di-fluoro substrate for cleavage of the 16 possible dinucleotide pairs. This may impact the mismatch results. Similar experiments were conducted using the same complement strands, substituting a fUfC di-fluoro substrate strand. RNase H2 was reduced to 20 mU due to the increased activity of cleavage seen for fUfC compared to fUfU substrates. Results are shown in Table 38 below.

TABLE 38

Cleavage of fUfC substrates with and without mismatches under steady state conditions

| Duplex Identity SEQ ID NOS: | | Substrate Sequence | Cleavage |
|---|---|---|---|
| SEQ ID NO: 41 | 5' | CTCGTGAGGTGAT(fUfC)AGGAGATGGGAGGCG 3' | 100% |
| SEQ ID NO: 298 | 3' | GAGCACTCCACTA  A G TCCTCTACCCTCCGC 5' | |
| SEQ ID NO: 41 | 5' | CTCGTGAGGTGAT(fUfC)AGGAGATGGGAGGCG 3' | 0% |
| SEQ ID NO: 178 | 3' | GAGCACTCCACTA  T G TCCTCTACCCTCCGC 5' | |
| SEQ ID NO: 41 | 5' | CTCGTGAGGTGAT(fUfC)AGGAGATGGGAGGCG 3' | 7% |
| SEQ ID NO: 179 | 3' | GAGCACTCCACTA  C G TCCTCTACCCTCCGC 5' | |
| SEQ ID NO: 41 | 5' | CTCGTGAGGTGAT(fUfC)AGGAGATGGGAGGCG 3' | 0% |
| SEQ ID NO: 180 | 3' | GAGCACTCCACTA  G G TCCTCTACCCTCCGC 5' | |
| SEQ ID NO: 41 | 5' | CTCGTGAGGTGAT(fUfC)AGGAGATGGGAGGCG 3' | 1% |
| SEQ ID NO: 181 | 3' | GAGCACTCCACTA  A T TCCTCTACCCTCCGC 5' | |
| SEQ ID NO: 41 | 5' | CTCGTGAGGTGAT(fUfC)AGGAGATGGGAGGCG 3' | 0% |
| SEQ ID NO: 182 | 3' | GAGCACTCCACTA  A C TCCTCTACCCTCCGC 5' | |

TABLE 38-continued

Cleavage of fUfC substrates with and without mismatches under steady state conditions

| Duplex Identity SEQ ID NOS: | Substrate Sequence | Cleavage |
|---|---|---|
| SEQ ID NO: 41<br>SEQ ID NO: 183 | 5' CTCGTGAGGTGAT(fUfC)AGGAGATGGGAGGCG 3'<br>3' GAGCACTCCACTA  A A TCCTCTACCCTCCGC 5' | 2% |
| SEQ ID NO: 41<br>SEQ ID NO: 184 | 5' CTCGTGAGGTGAT(fUfC)AGGAGATGGGAGGCG 3'<br>3' GAGCACTCCACTA  T C TCCTCTACCCTCCGC 5' | 0% |
| SEQ ID NO: 41<br>SEQ ID NO: 185 | 5' CTCGTGAGGTGAT(fUfC)AGGAGATGGGAGGCG 3'<br>3' GAGCACTCCACTT  A G TCCTCTACCCTCCGC 5' | 0% |
| SEQ ID NO: 41<br>SEQ ID NO: 186 | 5' CTCGTGAGGTGAT(fUfC)AGGAGATGGGAGGCG 3'<br>3' GAGCACTCCACTC  A G TCCTCTACCCTCCGC 5' | 4% |
| SEQ ID NO: 41<br>SEQ ID NO: 187 | 5' CTCGTGAGGTGAT(fUfC)AGGAGATGGGAGGCG 3'<br>3' GAGCACTCCACTG  A G TCCTCTACCCTCCGC 5' | 0% |
| SEQ ID NO: 41<br>SEQ ID NO: 188 | 5' CTCGTGAGGTGAT(fUfC)AGGAGATGGGAGGCG 3'<br>3' GAGCACTCCACTA  A G ACCTCTACCCTCCGC 5' | 2% |
| SEQ ID NO: 41<br>SEQ ID NO: 189 | 5' CTCGTGAGGTGAT(fUfC)AGGAGATGGGAGGCG 3'<br>3' GAGCACTCCACTA  A G CCCTCTACCCTCCGC 5' | 4% |
| SEQ ID NO: 41<br>SEQ ID NO: 190 | 5' CTCGTGAGGTGAT(fUfC)AGGAGATGGGAGGCG 3'<br>3' GAGCACTCCACTA  A G GCCTCTACCCTCCGC 5' | 2% |

DNA bases are shown as uppercase. 2'-F bases are shown as fU.
Mismatches are shown in bold font and are underlined.

Again, *Pyrococcus abyssi* RNase H2 was able to discriminate very efficiently between single base mismatches. The precise degree of discrimination varied with which bases were paired in the mismatch. As before, mismatches at both positions −1 and +1 (relative to the fUfC domain) were effective. Specificity for cleavage using the fUfC substrate was significantly higher under steady state assay conditions than was the rC substrate (Example 12 above) and also showed slightly greater specificity than the fUfU substrate. Under kinetic assay conditions during thermal cycling, mismatch assays using di-fluoro substrates may show even greater selectivity.

Example 15—Selective Placement of Phosphorothioate Internucleotide Modifications in the Substrate The effect of incorporation of a phosphorothioate internucleoside linkage was tested for several different substrates. Phosphorothioate (PS) bonds are typically considered relatively nuclease resistant and are commonly used to increase the stability of oligonucleotides in nuclease containing solutions, such as serum. PS bonds form two stereoisomers, Rp and Sp, which usually show different levels of stabilization for different nucleases.

The di-fluoro substrate was examined with a PS bond between the two modified bases. A mixture of both diastereomers was employed for the present study.
Unmodified fUfC Substrate:
SEQ ID NOS: 41 and 298, respectively, in order of appearance 5'-CTCGTGAGGTGAT(fUfC)AGGAGATGGGAGGCG-3'

3'-GAGCACTCCACTA  A G TCCTCTACCCTCCGC-5'

Modified fU*fC Substrate ("*"=PS Bond):
SEQ ID NOS: 191 and 299, respectively, in order of appearance 5'-CTCGTGAGGTGAT(fU*fC)AGGAGATGGGAGGCG-3'

3'-GAGCACTCCACTA  A G TCCTCTACCCTCCGC-5'

(note gaps in sequence are for alignment purposes)

The above substrates were incubated for 1 hour at 70° C. in "Mn Cleavage Buffer" using 160 pmoles of substrate in 120 µl volume (1.3 µM) and 4 units of the recombinant *Pyrococcus* RNase H2 enzyme. Reactions were stopped with the addition of gel loading buffer (formamide/EDTA) and separated on a denaturing 7M urea, 15% polyacrylamide gel. Gels were stained using GelStar™ (Lonza, Rockland, Me.) and visualized with UV excitation. The unmodified substrate was 100% cleaved under these conditions; however the PS-modified substrate was essentially uncleaved. The phosphorothioate modification can effectively block cleavage of a di-fluoro substrate.

A substrate containing a single rC residue was studied next, testing placement of the PS modification on either side of the RNA base (5'- or 3'-side as indicated). A mixture of both diastereomers were employed for the present study.

The above substrates were incubated for 1 hour at 70° C. in "Mg Cleavage Buffer" using 160 pmoles of substrate in 120 µl volume (1.3 µM) and 4 units of the recombinant *Pyrococcus* RNase H2 enzyme. Reactions were stopped with the addition of gel loading buffer (formamide/EDTA) and separated on a denaturing 7M urea, 15% polyacrylamide gel. Gels were stained using GelStar™ (Lonza, Rockland, Me.) and visualized with UV excitation. The unmodified substrate was 100% cleaved under these conditions. Both the 5'-*rC and 3'-rC* PS-modified substrates were approximately 50% cleaved under these conditions. These results are most consistent with one stereoisomer, Rp or Sp, being more resistant to cleavage than the other isomer.

The 3'-rC* substrate was studied in greater detail. Since RNase H2 cleaves this substrate on the 5'-side of the ribonucleotide while other RNases (such as RNase A, RNase 1, etc.) cleave this substrate on the 3'-side of the ribonucleotide, it may be possible to use the PS modification as a way of protecting the substrate from unwanted degradation by other nucleases while leaving it available as an RNase H2 substrate. It is well known that cleavage of RNA substrates by RNase A and other single-stranded ribonucleases is inhibited to a greater extent by the Sp phosphorothioate isomer than the Rp isomer. The relative effects of the Sp vs. Rp isomer on RNase H2 cleavage have not been known. Therefore the two stereoisomers were purified and the relative contributions of the Sp and Rp isomers on 3'-rC* substrate stability were studied.

Figure 23:
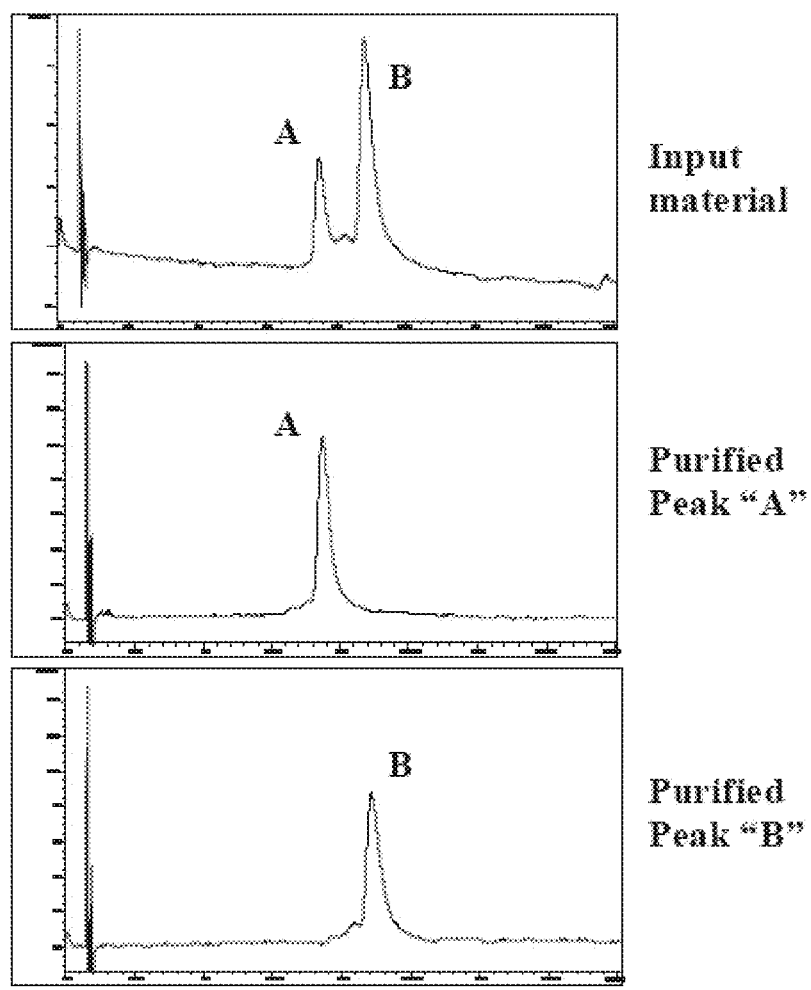
FIG. 23 shows HPLC traces of a rN primer containing a single phosphorothioate internucleoside modification (SEQ ID NO. 192). The top panel shows the original synthesis product demonstrating resolution of the two isomers. The middle panel is the purified Rp isomer and the bottom panel is the purified Sp isomer.

It is well known that phosphorothioate isomers can be separated by HPLC techniques and that this separation is readily done if only a single PS bond exists in an oligonucleotide. HPLC was therefore employed to purify the two PS isomers of the 3'-rC* substrate, SEQ ID NO: 192 (5'-CTCGTGAGGTGATTC(*)AGGAG ATGGGAGGCG-3'; FIG. 23). A mass of 7 nmoles of the single-stranded 3'-rC* containing oligonucleotide was employed. Characterization showed that the test material had a molecular weight of 9464 Daltons (calculated 9465) by ESI-MS with a molar purity of 95% by capillary electrophoresis. This material was injected into a 4.6 mm×50 mm Xbridge™ C18 column (Waters) with 2.5 micron particle size. Starting mobile phase (Buffer A) was 100 mM TEAA pH 7.0 with 5% acetonitrile and which was mixed with pure acetonitrile (Buffer B) at 35° C. The HPLC method employed clearly resolved two peaks in the sample which were collected and re-run to demonstrate purity. HPLC traces of the mixed isomer sample and purified specimens are shown in FIG. 23. Both the "A" and "B" peaks had an identical mass of 9464 Daltons by ESI-MS. From the original sample, 1.3 nmoles of peak "A" and 3.6 nmoles of peak "B" were recovered.

It was not possible based upon mass or HPLC data to identify which peak was the Rp and which peak was the Sp isomer. Relative resistance to degradation by RNase A was employed to assign isomer identity to the purification fractions. The Sp isomer is known to confer relatively greater resistance to RNase A degradation than the Rp isomer. Purified products were studied in the single-stranded form. The substrate was radiolabeled with $^{32}$P using 6000 Ci/mmol γ-$^{32}$P-ATP and the enzyme T4 Polynucleotide Kinase (Optikinase, US Biochemical). Trace label was added to reaction mixtures (1:50). Reactions were performed using 100 nM substrate in 20 μl volume with 1 pg (72 attomoles) of RNase A in Mg Cleavage Buffer. Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified and results plotted as a fraction of total substrate cleaved. Peak "A" was more completely degraded by RNase A than peak "B"; peak "A" was therefore assigned identity as the Rp isomer and peak "B" was assigned as the Sp isomer.

Figure 24:
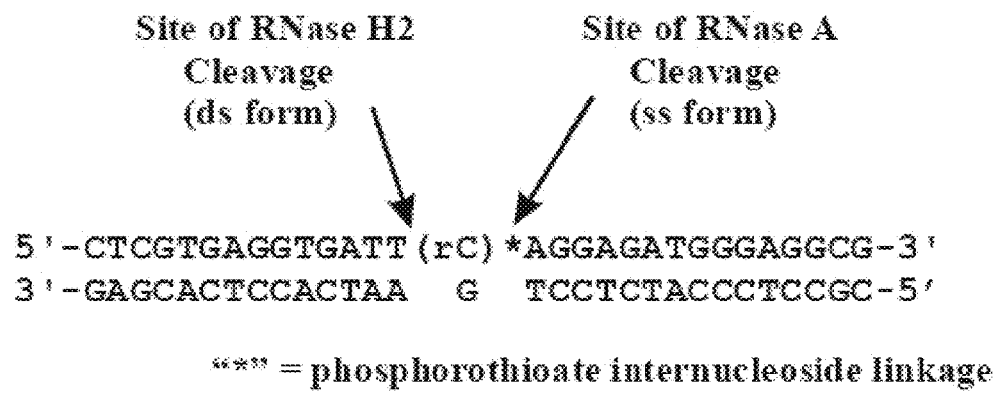
FIG. 24 shows the relationship between RNase H2 versus RNase A enzymatic cleavage with substrates having (SEQ ID NOS: 302 and 103, respectively, in order of appearance) having a single RNA base and different phosphorothioate stereoisomers.

The relative susceptibility of each stereoisomer to RNase H2 cleavage was studied. The RNA-containing strand of the substrate was radiolabeled with $^{32}$P using 6000 Ci/mmol γ-$^{32}$P-ATP and the enzyme T4 Polynucleotide Kinase (Optikinase, US Biochemical). Trace label was added to reaction mixtures (1:50). Reactions were performed using 100 nM substrate in 20 μl volume with 100 μU of recombinant *Pyrococcus abyssi* RNase H2 in Mg Cleavage Buffer. Substrates were employed in both single-stranded and duplex form. Reactions were incubated at 70° C. for 20 minutes. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified and results plotted as a fraction of total substrate cleaved. As expected, single-stranded substrates were not cleaved by the RNase H2 enzyme. The control unmodified rC duplex (SEQ ID NOS: 10 and 11) were 100% cleaved under the conditions employed. The Sp isomer 3'-rC* duplex substrate (peak "B") was cleaved ~30% whereas the Rp isomer (peak "A") was cleaved <10% under these conditions. Therefore the relative susceptibility to cleavage of racemically pure phosphorothioate modified substrates at this position (3'- to the ribonucleotide) is exactly opposite for RNase H2 vs. RNase A. The Sp isomer is more readily cleaved by RNase H2 while the Rp isomer is more readily cleaved by RNase A. Therefore single ribonucleotide containing substrates having a racemically pure Sp isomer phosphorothioate modification on the 3'-side of the ribonucleotide could be employed to protect this bond from unwanted degradation by single-stranded nucleases (such as RNase A) while still being a functional substrate for cleavage by RNase H2. The relationship between enzyme cleavage and phosphorothioate stereoisomer is summarized in FIG. 24.

Example 16—Utility of rN Containing Dual-Labeled Probes in qPCR Assays

The following example illustrates a real time PCR assay utilizing a rU-containing dual labeled probe. Previously, we demonstrated in Example 9 the feasibility for use of rN blocked primers in qPCR using a SYBR® Green detection format. Cleavage of blocked oligonucleotides using the method of the present invention can also be applied to the dual-labeled probe assay format. Use of RNase H1 to cleave a dual-labeled probe containing a 4 RNA base cleavage domain in an isothermal cycling probe assay format has been described by Harvey, J. J., et al. (Analytical Biochemistry, 333:246-255, 2004). Another dual-labeled probe assay using RNase H has been described, wherein a molecular beacon containing a single ribonucleotide residue was employed to detect polymorphisms in an end-point PCR format using RNase H2 (Hou, J., et al., Oligonucleotides, 17:433-443, 2007). In the present example we will demonstrate use of single ribonucleotide containing dual-labeled probes in a qPCR assay format that relies upon RNase H2 cleavage of the probe.

The following oligonucleotides shown in Table 39, were used as probes and primers in a qPCR assay with a dual-labeled fluorescence-quenched probe. The target was a synthetic oligonucleotide template.

TABLE 39

| Name | Sequence | SEQ ID NO: |
|---|---|---|
| Syn-For | 5'-AGCTCTGCCCAAAGATTACCCTG-3' | SEQ ID NO: 68 |
| Syn-Rev | 5'-CTGAGCTTCATGCCTTTACTGT-3' | SEQ ID NO: 69 |
| Syn-Probe | 5'-FAM-TTCTGAGGCCAACTCCACTGCC ACTTA-IBFQ-3' | SEQ ID NO: 193 |

TABLE 39-continued

| Name | Sequence | SEQ ID NO: |
|---|---|---|
| Syn-Probe-rU | 5'-FAM-TTCTGAGGCCAACuCCACTGCC ACTTA-IBFQ-3' | SEQ ID NO: 194 |

DNA bases are shown in uppercase.
RNA bases are shown in lowercase.
FAM is 6-carboxyfluorescein and IBFQ is a dark quencher (Integrated DNA Technologies).

Synthetic Template (Primer and Probe Binding Sites are Underlined).

SEQ ID NO: 75
AGCTCTGCCCAAAGATTACCCTGACAGCTAAGTGGCAGTGGAAGTTGGCC

TCAGAAGTAGTGGCCAGCTGTGTGTCGGGGAACAGTAAAGGCATGAAGCT

CAG

Quantitative real time PCR reactions were performed using unmodified primers SEQ ID NOS: 68 and 69 and probes Seq ID NOS: 193 and 194. Reactions were done in 384 well format using a Roche Lightcycler® 480 platform. Reactions comprised 200 nM of each primer (for+rev) and 200 nM probe, 2×10$^6$ copies of the synthetic template, and 5 mU of *Pyrococcus abyssi* RNase H2 in 10 µl volume. Thermal cycling parameters included an initial 10 minutes incubation at 95° C. and then 45 cycles were performed of [95° C. for 10 seconds+60° C. for 30 seconds+72° C. for 1 seconds]. The buffer employed varied with the polymerase used.

If PCR is performed using a thermostable DNA polymerase having 5'-exonuclease activity the polymerase will degrade the probe. Under these conditions, a DNA probe should perform the same as a rN modified probe. This reaction constitutes a positive control. If a DNA polymerase is employed which is lacking 5'-exonuclease activity, then neither probe should be degraded. This reaction constitutes a negative control. A PCR reaction using the exo-negative polymerase with RNase H2, however, should degrade the rN containing probe but not the DNA probe, demonstrating function of the invention. For the present study, the following two thermostable polymerases were used: Immolase (intact 5' nuclease activity, Bioline) and Vent Exo (5'-exonuclease negative mutant, New England Biolabs). Buffers employed were the manufacturer's recommended buffers for the DNA polymerases and were not optimized for RNase H2 activity. For Immolase, the buffer comprised 16 mM (NH$_4$)$_2$SO$_4$, 67 mM Tris pH 8.3, and 3 mM MgCl$_2$. For Vent Exo$^-$, the buffer comprised 10 mM (NH$_4$)$_2$SO$_4$, 20 mM Tris pH 8.8, 10 mM KCl, and 3 mM MgSO$_4$.

qPCR reactions were run as described and results are shown below in Table 40.

TABLE 40

Cp values of qPCR reactions comparing DNA or rU Dual-Labeled Probes

| Probe | Polymerase | Minus RNase H2 | Plus RNase H2 |
|---|---|---|---|
| Syn-Probe | Immolase Exo$^+$ | 21.1 | 21.0 |
| | Vent Exo$^-$ | ND | ND |
| Syn-Probe-rU | Immolase Exo$^+$ | 21.0 | 20.7 |
| | Vent Exo$^-$ | ND | 21.1 |

ND = not detectable

Using the exonuclease positive polymerase, both probes showed similar functional performance and gave similar Cp values, both with or without RNase H2. Using the exonuclease deficient mutant polymerase, however, the DNA probe did not produce any detectable fluorescent signal; the rU probe failed to produce fluorescent signal in the absence of RNase H2, but in the presence of RNase H2 was cleaved and resulted in signal at the expected Cp value. Similar results can be obtained using di-fluoro containing probes. If the RNase H2 cleavage domain is placed over a mutation site such probes can be used to distinguish variant alleles.

RNase H-cleavable probes can also be linked with the use of blocked primers of the present invention to additively increase the specificity of amplification based assay systems.

Example 17—Utility of rN Containing Blocked Primer to Prevent Primer-Dimer Formation Formation of primer-dimers or other small target independent amplicons can be a significant problem in both endpoint and real-time PCR. These products can arise even when the primers appear to be well designed. Further, it is sometimes necessary to employ primers which have suboptimal design because of sequence constraints for selection of primers which hybridize to specific regions. For example, PCR assays for certain viruses can be subtype or serotype specific if primers are chosen in areas that are variable between strains. Conversely, PCR reactions can be designed to broadly amplify all viral strains if primers are placed in highly conserved regions of the viral genome. Thus the sequence space available to choose primers may be very limited and "poor" primers may have to be employed that have the potential to form primer dimers. Use of "hot start" PCR methods may eliminate some but not all of these problems.

The following example derives from one such case cited in U.S. Pat. No. 6,001,611 where primer-dimers were found to be a significant problem during development of a PCR-based nucleic acid detection assay for the Hepatitis C virus (HCV) using sites in conserved domains that permit detection of a wide range of viral serotypes. We demonstrate herein that use of cleavable blocked primers can prevent unwanted primer dimer formation, specifically in the absence of a "hot-start" DNA polymerase.

The following oligonucleotides, as shown in Table 41, were used as primers in a PCR assay. The target was a cloned synthetic amplicon isolated from a plasmid.

TABLE 41

| Name | Sequence | SEQ ID NO: |
|---|---|---|
| ST280A-for | 5'-GCAGAAAGCGTCTAGCCATGGCGTTA | SEQ ID NO: 195 |
| ST778AA-rev | 5'-GCAAGCACCCTATCAGGCAGTACCACAA | SEQ ID NO: 196 |
| ST280A-for-B | 5'-GCAGAAAGCGTCTAGCCATGGCGTTAgT ATG-SpC3 | SEQ ID NO: 197 |
| ST778AA-rev-B | 5'-GCAAGCACCCTATCAGGCAGTACCACA AgGCCT-SpC3 | SEQ ID NO: 198 |

DNA bases are shown in uppercase.
RNA bases are shown in lowercase.
SpC3 is a C3 spacer.
The "B" designation indicates a blocked, cleavable primer.

Cloned Synthetic Target (Primer Binding Sites are Underlined).

```
Hepatitis C virus subtype 1b amplicon (242 bp):
                                      SEQ ID NO: 199
gcagaaagcgtctagccatggcgttagtatgagtgtcgtgcagcctccag gaccccccctcccgggagagccatagtggtctgcggaaccggtgagta caccggaattgccaggacgacccgggtcctttcttggactaaacccgctca atgcctggagatttgggcgtgccccccgcgagactgctagccgagtagtgt tgggtcgcgaaaggccttgtggtactgcctgatagggtgcttgc
```

Figure 25:
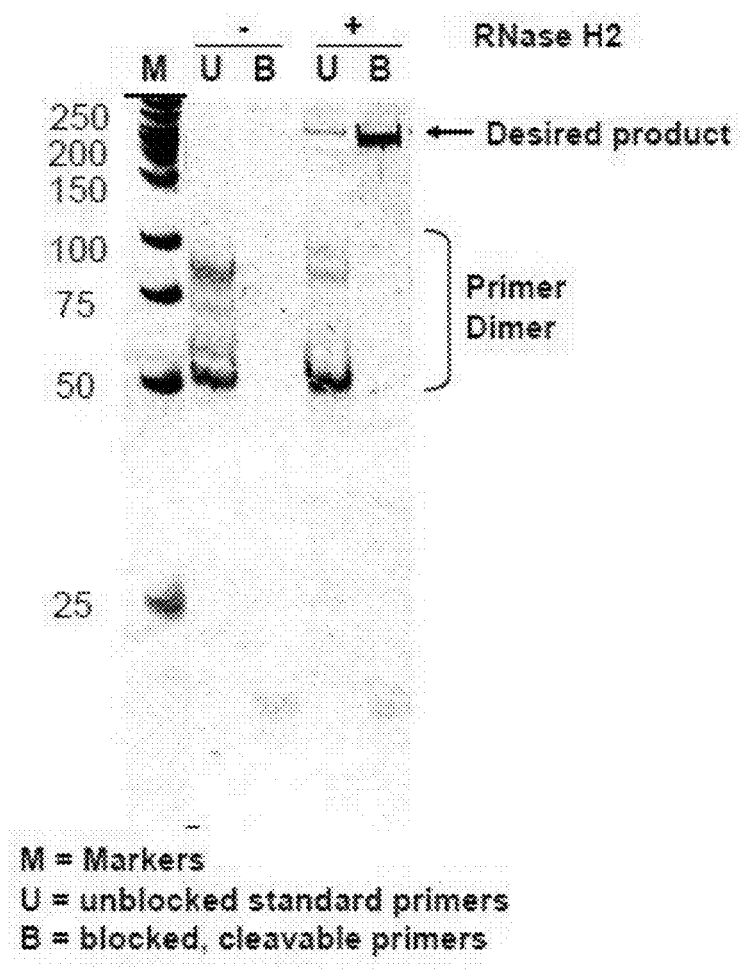
FIG. 25 shows a photograph of a polyacrylamide gel used to separate products from PCR reactions done using standard and blocked/cleavable primers on a HCV amplicon showing that use of standard primers results in formation of undesired small primer-dimer species while use of blocked primers results in specific amplification of the desired product. The nucleic acids were imaged using fluorescent staining and the image was inverted for clarity.

PCR reactions were done in 384 well format using a Roche Lightcycler® 480 platform. Reactions comprised 1× New England Biolabs (Beverly, Mass.) DyNAmo reaction mix with DyNAmo DNA polymerase, 200 nM of each primer (For+Rev), with or without 1.3 mU of *Pyrococcus abyssi* RNase H2 in 10 µl volume. Template DNA was either 2000 copies of the linearized HCV plasmid amplicon or no target control. Thermal cycling parameters included an initial 2 minutes soak at 95° C. and then 50 cycles were performed of [95° C. for 15 seconds+60° C. for 30 seconds]. Samples were separated on an 8% polyacrylamide non-denaturing gel and visualized using GelStar stain. Results are shown in FIG. 25. The unblocked standard primers produced multiple products having sizes ranging from 55 bp to 90 bp in size and no desired full length product was seen. In the absence of RNase H2, use of the blocked primers did not result in any amplified product. With RNase H2, the blocked primers produced a single strong amplicon of the expected size and no undesired small species were seen.

The DyNAmo is a non hot-start DNA polymerase. Use of RNase H2 blocked primer of the present invention with a hot-start RNase H2 having reduced activity at lower temperatures eliminated undesired primer-dimers from the reaction and resulted in formation of the desired amplicon whereas standard unblocked primers failed and produced only small, undesired species.

Example 18—Use of Detergent in RNase H2 Assay Buffers

The presence of detergent was found to be beneficial to cleavage by the *Pyrococcus abyssi* RNase H2 enzyme. Different detergents were tested at different concentrations to optimize the reaction conditions.

Figure 26:
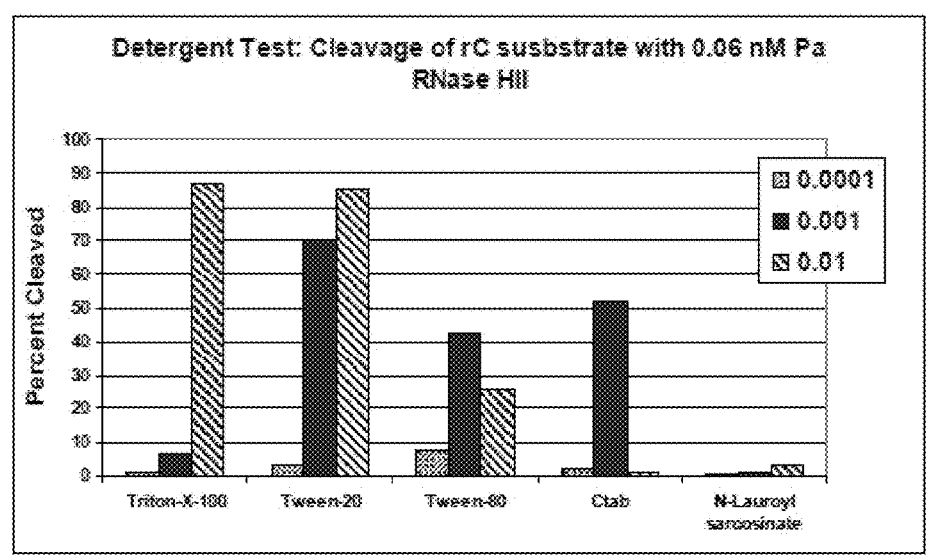
FIG. 26 is a graph quantifying the relative cleavage by *Pyrococcus abyssi* RNase H2 of a radiolabeled rC containing substrate in buffer containing different detergents at different concentrations (expressed as % vol:vol).

Aliquots of each of the recombinant RNase H2 enzymes were incubated with the single-stranded and double-stranded oligonucleotide substrates indicated above in an 80 µl reaction volume in buffer 50 mM NaCl, 10 mM MgCl$_2$, and 10 mM Tris pH 8.0 for 20 minutes at 70° C. Reactions were stopped with the addition of gel loading buffer (formamide/EDTA) and separated on a denaturing 7M urea, 15% polyacrylamide gel. The RNA strand of the substrate SEQ ID NOS: 10 and 11 was radiolabeled with $^{32}$P. Reactions were performed using 100 nM substrate with 100 microunits (µJ) of enzyme in Mg Cleavage Buffer with different detergents at varying concentrations. Detergents tested included Triton-X100, Tween-20, Tween-80, CTAB, and N-lauryol sarcosyl. Results with *Pyrococcus absii* RNase H2 are shown in FIG. 26. Additional experiments were done to more finely titrate CTAB detergent concentration. Optimum levels of detergent to obtain highest enzyme activity were (vol:vol): Triton-X100 0.01%, Tween-20 0.01%, and CTAB 0.0013%. The detergents Tween-80 and N-lauryol sarcosyl did not perform as well as the other detergents tested. Thus both non-ionic (Triton, Tween) and ionic (CTAB) detergents can be employed to stabilize thermophilic RNase H2 enzymes of the present invention.

Example 19—Use of Fluorescence-Quenched (F/Q) Cleavable Primers in qPCR

In Example 9 above, it was demonstrated that cleavable blocked primers function in PCR and further can be employed in real-time quantitative PCR (qPCR) using SYBR green detection. In this example we demonstrate use of fluorescence-quenched cleavage primers where the primer itself generates detectable signal during the course of the PCR reaction.

Figure 27:
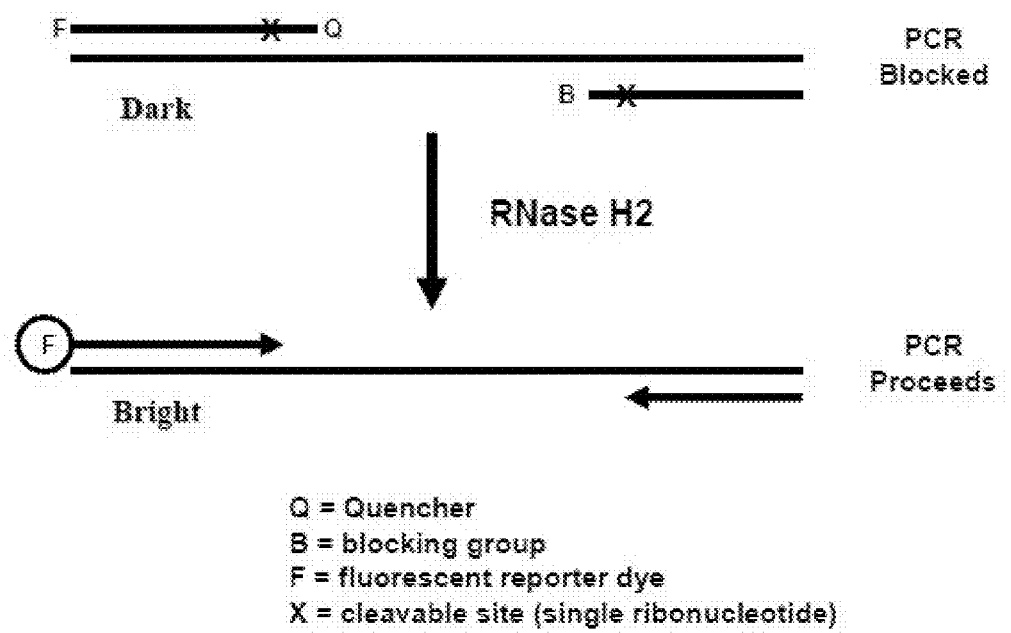
FIG. 27 is a reaction schematic of RNase H2 activation of fluorescence-quenched (F/Q) blocked PCR primers.

FIG. 18 illustrates the scheme for performing PCR using blocked cleavable primers. FIG. 27 illustrates the scheme for performing PCR using fluorescence-quenched cleavable primers. In this case one primer in the pair is detectably labeled with a fluorescent dye. A fluorescence quencher is positioned at or near the 3'-end of the primer and effectively prevents priming and DNA synthesis when the probe is intact. A single ribonucleotide base is positioned between the dye and the quencher. Cleavage at the ribonucleotide by RNase H2 separates the reporter and quencher, removing quenching, resulting in a detectable signal. Concomitantly, cleavage activates the primer and PCR proceeds.

The following synthetic oligonucleotides shown in Table 42, were employed to demonstrate this reaction using a synthetic template. As a control the 5'-nuclease Taqman® assay was performed with unmodified primers and a standard fluorescence-quenched probe. Three variants of the synthetic fluorescence-quenched cleavable primers were compared, having 4, 5, or 6 DNA bases 3' to the RNA base. It was previously established that 4 DNA bases 3' to the RNA base was optimal using oligonucleotide substrates having a C3 spacer or ddC end group. It was possible that the presence of a bulky hydrophobic quencher group at or near the 3'-end might change the optimal number of DNA residues needed in this domain.

TABLE 42

| Name | Sequence | SEQ ID NO: |
|---|---|---|
| Syn-For | 5'-AGCTCTGCCCAAAGATTACCCTG | SEQ ID NO: 68 |
| Syn-Rev | 5'-CTGAGCTTCATGCCTTTACTGT | SEQ ID NO: 69 |
| Syn-Probe | 5'-FAM-TTCTGAGGCCAACTCCACTGC CACTTA-IBFQ | SEQ ID NO: 200 |
| Syn-For F/Q-4D | 5'-FAM-CTGAGCTTCATGCCTTTACTGT uCCCC-IBFQ | SEQ ID NO: 201 |
| Syn-For F/Q-5D | 5'-FAM-CTGAGCTTCATGCCTTTACTGTuC CCCG-IBFQ | SEQ ID NO: 202 |
| Syn-For F/Q-6D | 5'-FAM-CTGAGCTTCATGCCTTTACTGTuC CCCGA-IBFQ | SEQ ID NO: 203 |

DNA bases are shown in uppercase.
RNA bases are shown in lowercase.
FAM is 6-carboxyfluorescein.
IBFQ is Iowa Black FQ, a dark quencher.

Synthetic Template

SEQ ID NO: 75
AGCTCTGCCCAAAGATTACCCTGACAGCTAAGTGGCAGTGGAAGTTGGCC

TCAGAAGTAGTGGCCAGCTGTGTGTCGGGGA<u>ACAGTAAAGGCATGAAG</u>

CTCAG

PCR reactions were performed in 10 µl volume using 200 nM primers, 200 µM of each dNTP (800 µM total), 1 unit of iTaq (BIO-RAD), 50 mM Tris pH 8.3, 50 mM KCl, and 3 mM MgCl$_2$. Reactions were run either with or without varying amounts of Pyrococcus abyssi RNase H2 on a Roche Lightcycler® 480 platform with 2×10$^6$ copies of synthetic template/target oligonucleotide (SEQ ID NO: 75). Reactions were started with a soak at 95° C. for 5 minutes followed by 45 cycles of [95° C. for 10 seconds, 60° C. for 30 seconds, and 72° C. for 1 second]. The For and Rev primers (SEQ ID NOS: 68 and 69) were used with the internally placed DLP (SEQ ID NO: 200). Alternatively, the For primer (SEQ ID NO: 68) was used with the FQ primers (individually) (SEQ ID NOS: 201-203).

Use of the F/Q cleavable primers resulted in detectable fluorescence signal in real time during PCR similar to that obtained using the traditional dual-labeled probe (DLP) (SEQ ID NO: 200) in the 5'-nuclease assay format. Primer SEQ ID NO: 201, with 4 DNA residues 3' to the RNA base, showed delayed amplification relative to the unmodified primers. Primers SEQ ID NOS: 202 and 203, with 5 and 6 DNA bases 3' to the RNA base, were more efficient and performed equally well. It is therefore preferable to use an oligonucleotide design with 5 DNA bases 3' to the RNA base in this assay format as opposed to the 3-4 DNA base design optimal when the 3'-blocking group is smaller. In previous Examples using a SYBR Green assay format, 1.3 mU of RNase H2 resulted in priming efficiency identical to unmodified primers. In the present F/Q assay format, use of 1.3 mU of RNase H2 resulted in delayed amplification whereas use of 2.6 mU of RNase H2 resulted in identical results compared to unmodified primers. Increasing the amount of RNase H2 for the F/Q assay format is therefore preferred. Both amplification and detection of signal was RNase H2 dependent.

Figure 28:
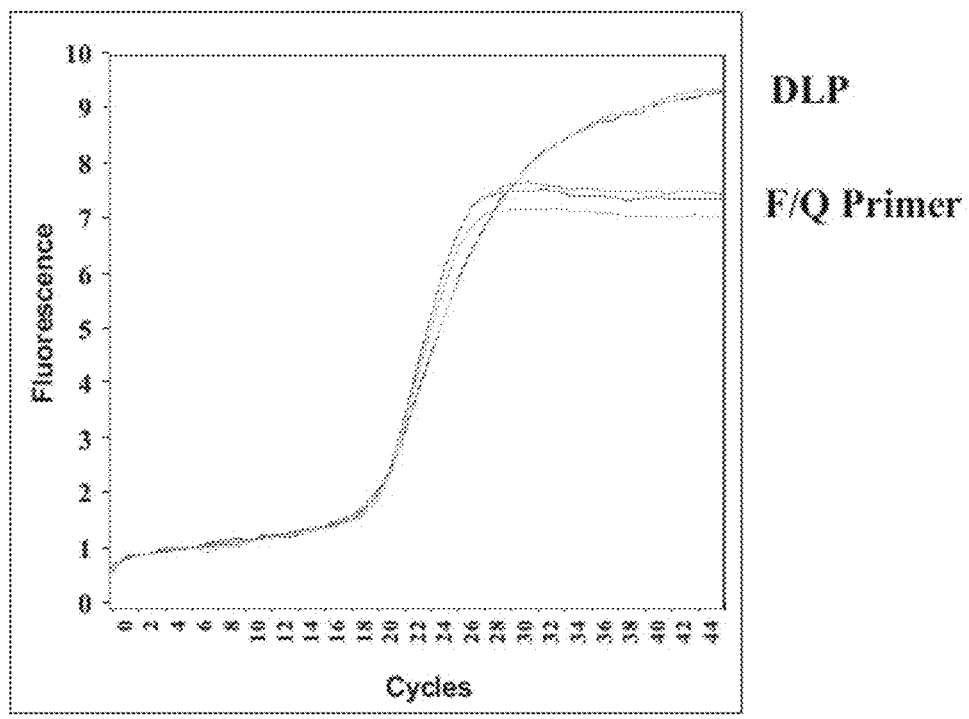
FIG. 28 is an amplification plot showing the fluorescence signal resulting from use of unblocked primers with a fluorescence-quenched dual-labeled probe (DLP) compared with a blocked fluorescence-quenched cleavable primer for a 103 base synthetic amplicon. Cycle number is shown on the X-axis and relative fluorescence intensity is shown on the Y-axis.
Figure 29:
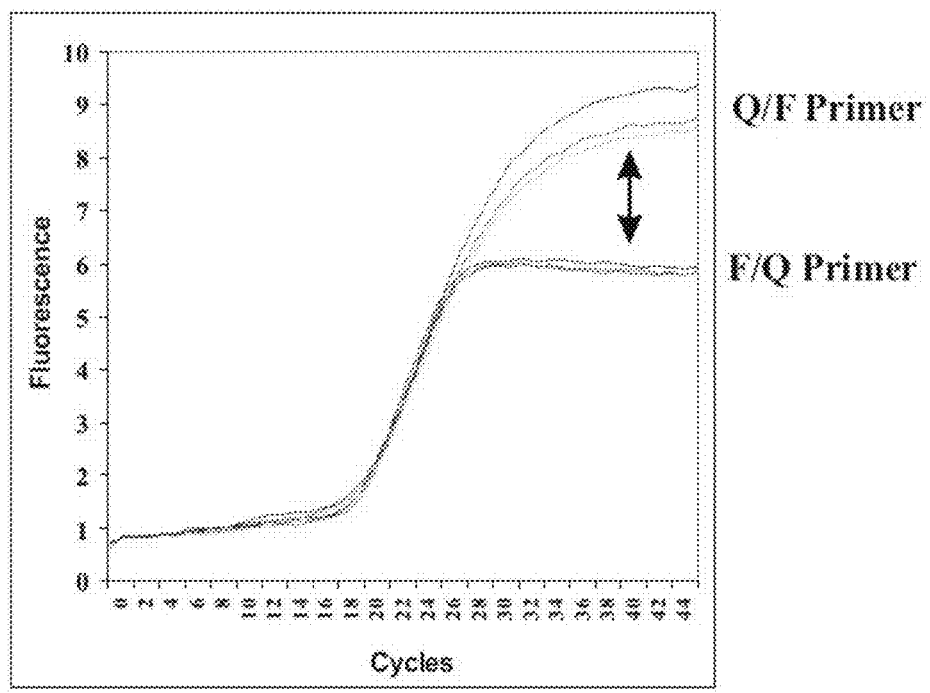
FIG. 29 is an amplification plot showing the fluorescence signal resulting from use of a F/Q configuration blocked fluorescence-quenched cleavable primer compared with a Q/F configuration blocked fluorescence-quenched cleavable primer for a 103 base synthetic amplicon. Cycle number is shown on the X-axis and relative fluorescence intensity is shown on the Y-axis.

Examples of amplification plots for qPCR reactions run using the 5'-nuclease assay DLP (SEQ ID NO: 200) and the F/Q cleavable 5D primer (SEQ ID NO: 202) are shown in FIG. 28. It is evident that amplification efficiency is similar between both methods as the Cp values where fluorescence is first detected is identical (20.0). Interestingly, the ΔRf (the magnitude of fluorescence signal detected) peaked at slightly higher levels using the DLP than the FQ primer.

We therefore tested if changing dye/quencher configuration on the primer would alter the fluorescence signal, comparing F/Q vs. Q/F versions of the same primer. In the synthetic amplicon assay used above, the preferred 5-DNA probe has a "G" residue present at the 3'-end. G residues tend to quenche FAM, whereas other bases have little effect on FAM fluorescence. The amplicon was therefore modified to change this base. The sequences in Table 43, were synthesized and tested in a fluorescent real-time PCR assay format.

TABLE 43

| Name | Sequence | SEQ ID NO: |
|---|---|---|
| Syn-For | 5'-AGCTCTGCCCAAAGATTACCCTG | SEQ ID NO: 68 |
| Syn-For(C) F/Q-5D | 5'-FAM-CTGAGCTTCATGCCTTTACT GTuCCCCC-IBFQ | SEQ ID NO: 204 |
| Syn-For(C) Q/F-5D | 5'-IBFQ-CTGAGCTTCATGCCTTTACTG TuCCCCC-FAM | SEQ ID NO: 205 |

DNA bases are shown in uppercase.
RNA bases are shown in lowercase.
FAM is 6-carboxyfluorescein.
IBFQ is Iowa Black FQ, a dark quencher.

Synthetic Template

SEQ ID NO: 206
AGCTCTGCCCAAAGATTACCCTGACAGCTAAGTGGCAGTGGAAGTTGG

CCTCAGAAGTAGTGGCCAGCTGTGTGTGGGGGA<u>ACAGTAAAGGCATGA</u>

AGCTCAG

PCR reactions were performed in 10 µl volume using 200 nM primers, 200 µM of each dNTP (800 µM total), 1 unit of iTaq (BIO-RAD), 50 mM Tris pH 8.3, 50 mM KCl, and 3 mM MgCl$_2$. Reactions were run with 2.6 mU of Pyrococcus abyssi RNase H2 on a Roche Lightcycler® 480 platform with 2×10$^6$ copies of synthetic template/target oligonucleotide (SEQ ID NO: 206). Reactions were started with a soak at 95° C. for 5 minutes followed by 45 cycles of [95° C. for 10 seconds, 60° C. for 30 seconds, and 72° C. for 1 second]. The For primer (SEQ ID NO: 68) was used with either the FQ primer (SEQ ID NO: 204) or the QF primer (SEQ ID NO: 205).

Use of the F/Q and Q/F cleavable primers resulted in an identical Cp, indicating that both primers performed with equal efficiency in the reaction. As predicted, the Q/F primer showed increased ΔRf relative to the F/Q primer. Both versions of the primer work equally well in the assay.

Example 20—Use of Fluorescence-Quenched (F/Q) Cleavable Primers in Multiplex qPCR Multiplex assays are commonly employed today to streamline experiments and increase throughput. It is particularly common to combine a qPCR assay specific for an experimental gene of interest with a second qPCR assay specific for an internal reference control gene for normalization purposes. One weakness of SYBR Green detection for qPCR is that multiplex reactions are not possible. The use of dye-labeled fluorescence-quenched probes or primers does permit such multiplex reactions to be run. Real time PCR cycling and detection equipment is available today that permits combination of 2, 3, or 4 different fluorophores into the same reaction tube. This example demonstrates the utility of fluorescence-quenched (F/Q) cleavable primers in multiplex qPCR.

The following oligonucleotide reagents shown in Table 44, were synthesized to perform multiplex qPCR using either a dual-labeled probe with the 5'-nuclease assay or an F/Q cleavable primer. One assay was specific for the human MYC gene (NM_002476) and the second assay was specific for the human SFRS9 gene (NM_003769), a splicing factor which is a commonly used internal normalization control gene.

TABLE 44

| Name | Sequence | SEQ ID NO: |
|---|---|---|
| MYC-For | 5'-TCGGATTCTCTGCTCTCCT | SEQ ID NO: 207 |
| MYC-Rev | 5'-CCTCATCTTCTTGTTCCTCC | SEQ ID NO: 208 |
| MYC-Probe | 5'-FAM-CCACCACCAGCAGCGACTCTGA-IBFQ | SEQ ID NO: 209 |
| MYC-For-FQ | 5'-FAM-TCGGATTCTCTGCTCTCCTcGACGG-IBFQ | SEQ ID NO: 210 |
| MYC-Rev-B | 5'-CCTCATCTTCTTGTTCCTCCuCAGA-SpC3 | SEQ ID NO: 211 |
| SFRS9-For | 5'-TGTGCAGAAGGATGGAGT | SEQ ID NO: 212 |
| SFRS9-Rev | 5'-CTGGTGCTTCTCTCAGGATA | SEQ ID NO: 213 |
| SFRS9-Probe | 5'-MAX-TGGAATATGCCCTGCGTAAACTGGA-IBFQ | SEQ ID NO: 214 |
| SFRS9-For-FQ | 5'-MAX-TGTGCAGAAGGATGGAGTgGGGAT-IBFQ | SEQ ID NO: 215 |
| SFRS9-Rev-B | 5'-CTGGTGCTTCTCTCAGGATAaACTC-SpC3 | SEQ ID NO: 216 |

DNA bases are shown in uppercase.
RNA bases are shown in lowercase.
FAM is 6-carboxyfluorescein.
IBFQ is Iowa Black FQ, a dark quencher.
MAX is a red reporter dye.
SpC3 is a C3 spacer.

PCR reactions were performed in 10 µl volume using 200 nM primers (and probe where appropriate), 200 µM of each dNTP (800 µM total), 1 unit of iTaq (BIO-RAD), 50 mM Tris pH 8.3, 50 mM KCl, and 3 mM MgCl$_2$. Reactions were run with 10 mU of *Pyrococcus abyssi* RNase H2 on a Roche Lightcycler® 480 platform with 2 ng of cDNA made from total HeLa cell RNA. Reactions were started with a soak at 95° C. for 5 minutes followed by 45 cycles of [95° C. for 10 seconds, 60° C. for 30 seconds, and 72° C. for 1 second].

The multiplex reactions for the 5'-nuclease assays included the MYC For and Rev primers+MYC probe (SEQ ID NOS: 207-209) and the SFRS9 For and Rev primers+SFRS9 probe (SEQ ID NOS: 212-214). The multiplex reactions for the FQ-cleavable primer assays included the MYC-For-FQ and MYC-Rev-B blocked primers (SEQ ID NOS: 210 and 211) and the SFRS9-For-FQ and SFRS9-Rev-B blocked primers (SEQ ID NOS: 215 and 216). All assays were also run in singleplex format for comparison. The FAM primers and probes were detected in the fluorescein dye channel while the MAX primers and probes were detected in the HEX dye channel. Both the multiplexed DLP 5'-nuclease assays and the multiplexed FQ-cleavable primer assays worked well and resulted in very similar data, which is summarized in Table 45 below.

TABLE 45

Multiplex qPCR reactions for MYC and SFRS9

| Reaction | Cp Value FAM Channel | Cp Value HEX Channel |
|---|---|---|
| MYC FAM DLP | 25.7 | — |
| SFRS9 MAX DLP | — | 24.8 |
| MYC FAM DLP + SFRS9 MAX DLP | 24.6 | 23.9 |
| MYC FAM FQ-Primer | 27.2 | — |
| SFRS9 MAX FQ Primer | — | 28.0 |
| MYC FAM FQ-Primer + SFRS9 MAX FQ Primer | 27.9 | 26.1 |

RNase H concentration was titrated and higher levels of enzyme were needed to maintain reaction efficiency in multiplex format. For example, blocked primers in singleplex SYBR Green detection format required 1.3 mU of enzyme. Blocked FQ primers in singleplex format required 2.6 mU of enzyme. Blocked FQ primers in multiplex format required 10 mU of enzyme. It is therefore important to titrate the amount of RNase H2 enzyme employed when cleavable primers are used in different assay formats.

Another application where use of multiplex probes is common practice is allelic discrimination SNPs. The following assay was designed to distinguish a SNP pair for the SMAD7 gene at a site that is known to be relevant for development of colorectal carcinoma, rs4939827. FQ blocked primers were designed and synthesized at this site using the standard design features taught in the above examples without any further optimization to discriminate between the "C" and "T" alleles in this gene. Sequences are shown below in Table 46.

TABLE 46

| Name | Sequence | SEQ ID NO: |
|---|---|---|
| rs4939827 Rev | 5'-CTCACTCTAAACCCCAGCATT | SEQ ID NO: 217 |
| rs4939827 C-FAM-FQ-For | 5'-FAM-CAGCCTCATCCAAAAGAGG AAAcAGGA-IBFQ | SEQ ID NO: 218 |
| rs4939827 T-HEX-FQ-For | 5'-HEX-CAGCCTCATCCAAAAGAGG AAAuAGGA-IBFQ | SEQ ID NO: 219 |

DNA bases are shown in uppercase. RNA bases are shown in lowercase. FAM is 6-carboxyfluorescein. IBFQ is Iowa Black FQ, a dark quencher. MAX is a red reporter dye.

The above primers target the following 85 bp region of the SMAD7 gene (NM_005904). Primer binding sites are underlined and the SNP location is highlighted as bold italic.

rs4939827 (SMAD7) C allele
(SEQ ID NO: 220)
CAGCCTCATCCAAAAGAGGAAA*C*AGGACCCCAGAGCTCCCTCAGACTCCT -continued

CAGGAAACACAGACAATGCTGGGGTTTAGAGTGAG rs4939827 (SMAD7) T allele
(SEQ ID NO: 221)
CAGCCTCATCCAAAAGAGGAAATAGGACCCCAGAGCTCCCTCAGACTCCT

CAGGAAACACAGACAATGCTGGGGTTTAGAGTGAG

PCR reactions were performed in 10 µl volume using 200 nM FQ-For and unmodified Rev primers, 200 µM of each dNTP (800 µM total), 1 unit of iTaq (BIO-RAD), 50 mM Tris pH 8.3, 50 mM KCl, and 3 mM MgCl$_2$. Reactions were run with 2.6 mU of *Pyrococcus abyssi* RNase H2 on a Roche Lightcycler® 480 platform with 2 ng of target DNA. Target DNA was genomic DNA made from cells homozygous for the two SMAD7 alleles (Coreill 18562 and 18537). The "C" and "T" alleles (SEQ ID NOS: 220 and 221) were tested individually (homozygote) and together (heterozygote). Reactions were started with a soak at 95° C. for 5 minutes followed by 45 cycles of [95° C. for 10 seconds, 60° C. for 30 seconds, and 72° C. for 1 second]. Data acquisition was set for multiplex mode detecting the FAM and HEX channels.

Figure 30:
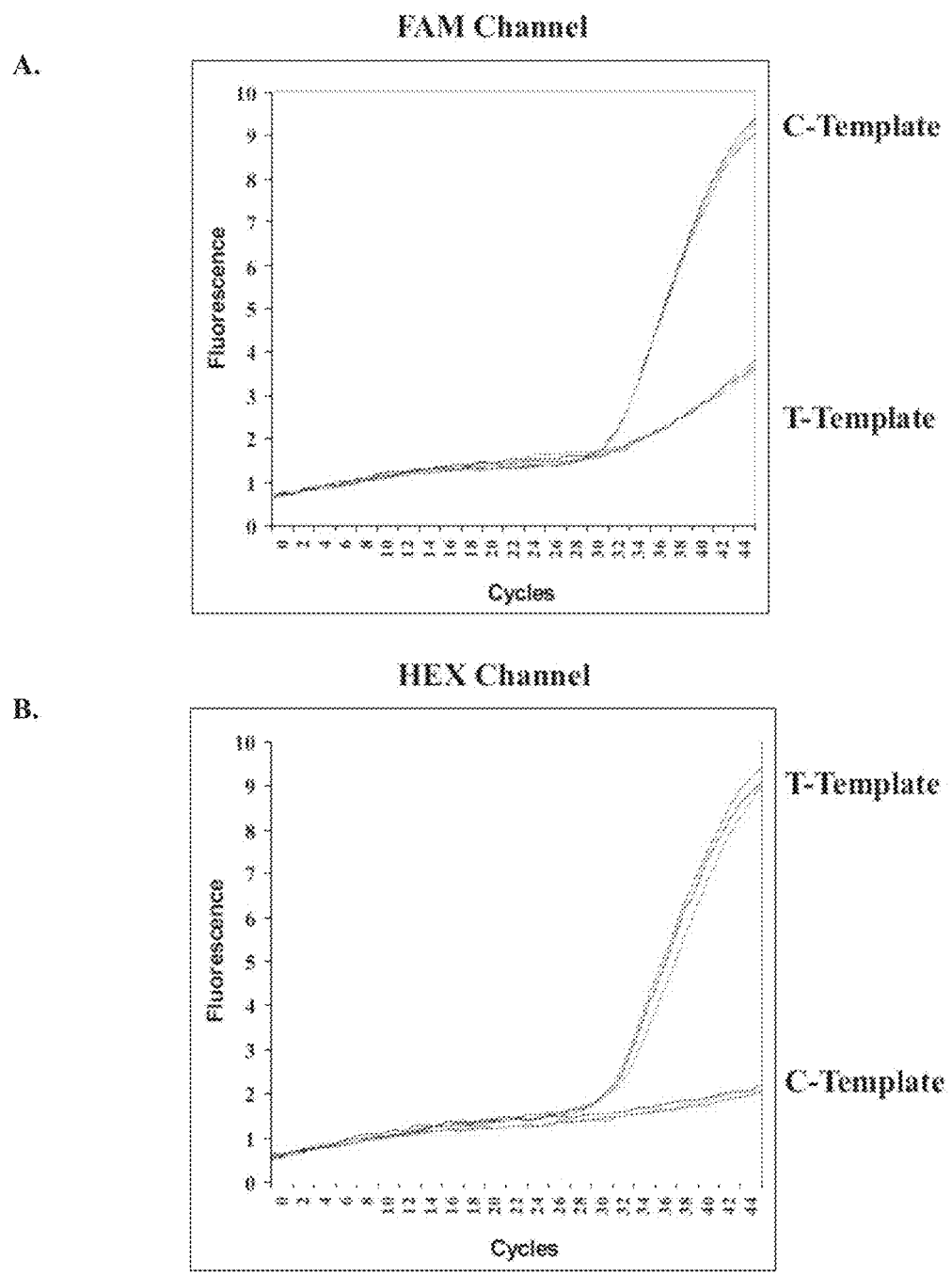
FIG. 30 is an amplification plot showing the fluorescence signal resulting from use of F/Q configuration blocked fluorescence-quenched cleavable primers to distinguish DNA templates that differ at a single base within the SMAD 7 gene. Panel (A) shows results from the FAM channel where the FAM-labeled "C" allele probe was employed. Panel "B" shows results from the HEX channel wherein the HEX-labeled "T" allele probe was employed. Cycle number is shown on the X-axis and relative fluorescence intensity is shown on the Y-axis.

Results are shown in FIG. 30. It is clear that the FAM-labeled "C" probe detected the presence of the "C" target DNA but not the "T" target DNA and that the HEX "T" probe detected the presence of the "T" target DNA but not the "C" target DNA. Thus FQ cleavable primers can be used in multiplex formats to distinguish SNPs.

Figure 31:
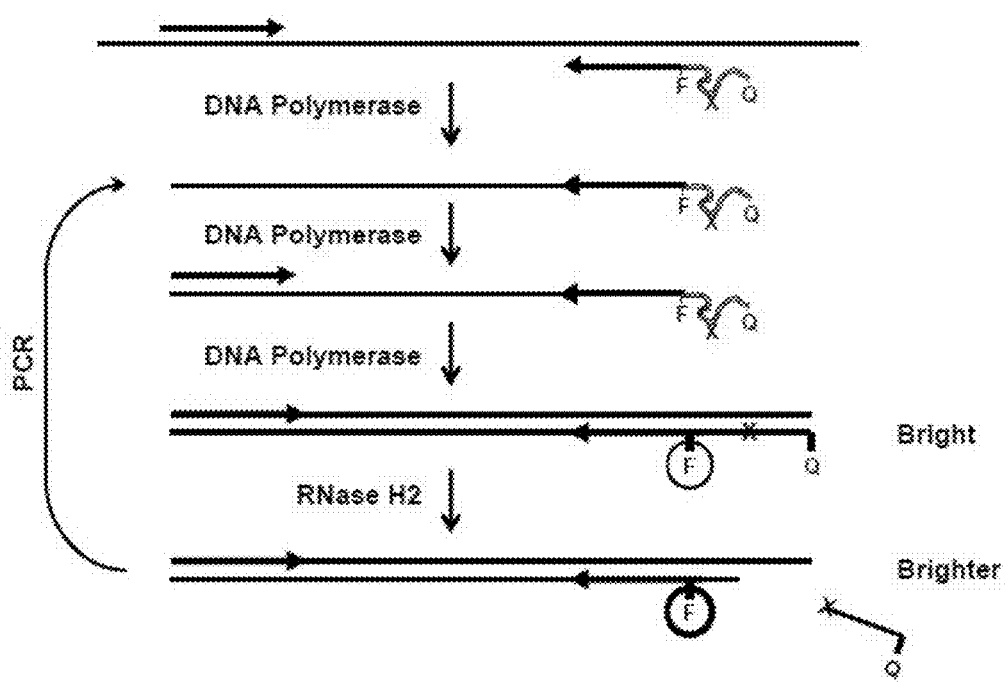
FIG. 31 is a reaction schematic of RNase H2 cleavage of fluorescence-quenched (FQT) primer used in a primer probe assay. The Primer Domain is complementary to the target nucleic acid and serves to primer DNA synthesis. The Reporter Domain is non-complementary to target and contains a RNA base positioned between a reporter dye and a quencher group. The Reporter Domain remains single-stranded until conversion to double-stranded form during PCR where this domain now serves as template. Conversion to double-stranded form converts the Reporter Domain into a substrate for RNase H2; cleavage by RNase H2 separates reporter from quencher and is a detectable event.

Example 21—Use of Fluorescence-Quenched Cleavable Primers in the Primer-Probe Assay We previously described a method of detecting nucleic acid samples using fluorescence quenched primers comprising two distinct but linked elements, a Reporter Domain positioned towards the 5'-end and a Primer Domain, positioned at the 3'-end of the nucleic acid molecule (US patent application US 2009/0068643). The Primer Domain is complementary to and will bind to a target nucleic acid under conditions employed in PCR. It is capable of priming DNA synthesis using the complementary target as template, such as in PCR. The Reporter Domain comprises a sequence which can be complementary to the target or can be unrelated to the target nucleic acid and does not hybridize to the target. Furthermore the Reporter Domain includes a detectable element, such as a fluorescent reporter dye, and a quencher. The reporter dye and quencher are separated by a suitable number of nucleotides such that fluorescent signal from the reporter dye is effective suppressed by the quencher when the Reporter Domain is in single-stranded random coil conformation. During PCR, the Primer Domain will prime DNA synthesis and the FQT synthetic oligonucleotide is thereby incorporated into a product nucleic acid, which itself can is used as template in the next cycle of PCR. Upon primer extension during the next cycle of PCR, the entire FQT probe is converted to double-stranded form, including the Reporter Domain. Formation of a rigid double-stranded duplex physically increases the distance between the fluorophore and the quencher, decreasing the suppression of fluorescence emission (hence increasing fluorescent intensity). Thus conversion of the FQT primer to double-stranded form during PCR constitutes a detectable event. Further increases in fluorescent signal can be achieved by cleavage of the Reporter Domain at a site between the reporter dye and the quencher, such that the reporter dye and the quencher become physically separated and are no longer covalently linked on the same nucleic acid molecule. This cleavage event is dependent upon formation of double-stranded nucleic acid sequence so that cleavage cannot occur if the FQT primer is in its original single-stranded state. Suitable methods to separate reporter and quencher include, for example, use of a restriction endonuclease to cleave at a specific sequence in dsDNA. Alternatively, an RNase H2 cleavage domain can be placed between the fluorophore and quencher. Placement of a single ribonucleotide residue between the fluorophore and the quencher would make the FQT primer a suitable substrate for RNase H2 during PCR. The scheme for this reaction is shown in FIG. 31. The present example demonstrates use of a thermostable RNase H2 to mediate cleavage of a fluorescence-quenched primer in a primer-probe real time PCR assay.

A qPCR assay was designed for the human Drosha gene including unmodified For and Rev primers with an internally positioned dual-labeled probe suitable for use in the 5'-nuclease assay. The For primer was also synthesized as an FQT forward primer using the same Primer Domain sequence as the unmodified For primer and adding a Reporter Domain on the 5'-end comprising a reporter dye (Fluorescein-dT) and a dark quencher (IBFQ) separated by 11 bases including a centrally positioned rU base (cleavage site). Sequences are shown below in Table 47.

TABLE 47

| Name | Sequence | SEQ ID NO: |
|---|---|---|
| Drosha-For | 5'-ACCAACGACAAGACCAAGAG | SEQ ID NO: 222 |
| Drosha-Rev | 5'-TCGTGGAAAGAAGCAGACA | SEQ ID NO: 223 |
| Drosha-probe | 5'-FAM-ACCAAGACCTTGGCGGA CCTTT-IBFQ | SEQ ID NO: 224 |
| Drosha-For-FQT | 5'-IBFQ-TTTCCuGGTTT(Fl-dT) ACCAACGACAAGACCAAGAG | SEQ ID NO: 225 |

DNA bases are shown in uppercase. RNA bases are shown in lowercase. Fl-dT in an internal Fluorescein-dT modified base. IBFQ is Iowa Black FQ, a dark quencher. The portion of the FQT probe that is complementary to the Drosha target is underlined (i.e., the Primer Domain).

The above primers target the following 141 bp region of the human Drosha gene (RNASEN, NM_013235). Primer binding sites are underlined and the internal probe binding site for the 5'-nuclease assay is in bold font.

Drosha amplicon
(SEQ ID NO: 226)
ACCAACGACAAGACCAAGAGGCCTGTGGCGCTTCGCACCAAGACCTTGGC

GGACCTTTTGGAATCATTTATTGCAGCGCTGTACATTGATAAGGATTTGG

AATATGTTCATACTTTCATGAATGTCTGCTTCTTTCCACGA

5'-Nuclease qPCR reactions were performed in 10 µl volume using 200 nM unmodified For and Rev primers with 200 nM probe, 200 µM of each dNTP (800 µM total), 1 unit of iTaq (BIO-RAD), 50 mM Tris pH 8.3, 50 mM KCl, and 3 mM MgCl$_2$. FQT qPCR reactions were performed in 10 µl volume using 200 nM FQT-For primer and 200 nM unmodified Rev primer, 200 µM of each dNTP (800 µM total), 1 unit of iTaq (hot start thermostable DNA polymerase, BIO-RAD), 50 mM Tris pH 8.3, 50 mM KCl, and 3 mM MgCl$_2$. Reactions were run with or without 2.6 mU of *Pyrococcus abyssi* RNase H2 on a Roche Lightcycler® 480 platform. Reactions were run with or without 10 ng of cDNA made from HeLa total cellular RNA. Reactions were started with a soak at 95° C. for 5 minutes followed by 45 cycles of [95° C. for 10 seconds, 60° C. for 30 seconds, and 72° C. for 1 second].

Results for the 5'-nuclease qPCR reaction are shown in FIG. 32A. A positive signal was seen at cycle 26. Results for the FQT primer qPCR reactions are shown in FIG. 32B. A positive signal was seen at cycle 27, nearly identical to the 5'-nuclease assay results. In this case, signal was dependent upon RNase H2 cleavage. Thus cleavage at an internal RNA residue by RNase H2 can be used to generate signal from FQT primers that have a distinct fluorescence-quenched reporter domain.

Example 22—Use of Modified Bases in Cleavable Blocked Primers to Improve Mismatch Discrimination We demonstrated that blocked cleavable primers can be used in qPCR to distinguish single base mismatches in the SYBR Green assay format in Example 13 and in the fluorescence-quenched (FQ) assay format in Example 20. Depending upon the precise base mismatch and the sequence context, detectable signal for the mismatch target occurred from 5 to 15 cycles after detection of the perfect match target. There may be circumstances where greater levels of mismatch discrimination are desired, such as detection of a rare mutant allele in the background of predominantly wild type cells. We demonstrate in this example that selective placement of 2'OMe RNA modified residue within the cleavable primer can improve mismatch discrimination.

Example 5 above demonstrated that modified bases could be compatible with cleavage of a heteroduplex substrate by RNase H2 depending upon the type of modification employed and placement relative to the cleavage site. Here we demonstrate in greater detail use of the 2'OMe modification in blocked primers having a single unmodified ribonucleotide base. The following primers, shown below in Table 48, were synthesized and used in qPCR reactions in the SYBR Green format with a synthetic oligonucleotide template. Blocked cleavable primers having a single rU residue were synthesized either without additional modification (SEQ ID NO: 116) or with a 2'OMe base 5'- to the rU (SEQ ID NO: 228) or with a 2'OMe base 3'- to the rU (SEQ ID NO: 229). If the 2'OMe residue is positioned 5'- to the ribonucleotide, then it will remain in the final primer which results from cleavage by RNase H2. Therefore a Syn-Rev-mU primer was made specific for the synthetic template bearing a 3'-2'OMe U residue at the 3'-end to mimic this reaction product (SEQ ID NO: 227).

TABLE 48

| Name | Sequence | SEQ ID NO: |
|---|---|---|
| Syn-For | 5'-AGCTCTGCCCAAAGATTACCCTG | SEQ ID NO: 68 |
| Syn-Rev | 5'-CTGAGCTTCATGCCTTTACTGT | SEQ ID NO: 69 |
| Syn-Rev-mU | 5'-CTGAGCTTCATGCCTTTA CTG(mU) | SEQ ID NO: 227 |
| Syn-Rev-rU-C3 | 5'-CTGAGCTTCATGCCTTTACTG TuCCCC-SpC3 | SEQ ID NO: 116 |
| Syn-Rev-mUrU-C3 | 5'-CTGAGCTTCATGCCTTTA CTG(mU)uCCCC-SpC3 | SEQ ID NO: 228 |

TABLE 48-continued

| Name | Sequence | SEQ ID NO: |
|---|---|---|
| Syn-Rev-rUmC-C3 | 5'-CTGAGCTTCATGCCTTTA CTGTu(mC)CCC-SpC3 | SEQ ID NO: 229 |

DNA bases are shown in uppercase. RNA bases are shown in lowercase. 2'OMe RNA bases are indicated as (mN).

The following synthetic oligonucleotide was used as template. Primer binding sites are underlined.

Synthetic template, SEQ ID NO: 144:
<u>AGCTCTGCCCAAAGATTACCCTG</u>ACAGCTAAGTGGCAGTGGAAGTTGGCC
TCAGAAGTAGTGGCCAGCTGTGTGTCGGGGA<u>ACAGTAAAGGCATGAAGCT
CAG</u>

PCR reactions were performed in 10 μl volume using 200 nM unmodified For primer pairwise with 200 nM of each of the different Rev primers shown above in Bio-Rad SYBR Green master mix. Reactions were run with or without 1.3-200 mU of *Pyrococcus abyssi* RNase H2 on a Roche Lightcycler® 480 platform with no target or 2×10⁶ copies of the synthetic oligonucleotide template. Reactions were started with a soak at 95° C. for 5 minutes followed by 45 cycles of [95° C. for 10 seconds, 60° C. for 20 seconds, and 72° C. for 30 seconds]. Results are summarized in Table 49.

TABLE 49

Cp values of qPCR reactions comparing blocked primers with or without a 2'OMe base flanking a cleavable ribonucleotide.

| RNase H2 | Syn-Rev SEQ ID NO: 89 | Syn-Rev-mU SEQ ID NO: 227 | Syn-Rev-rU-C3 SEQ ID NO: 116 | Syn-Rev-mUrU-C3 SEQ ID NO: 228 | Syn-Rev-rUmC-C3 SEQ ID NO: 229 |
|---|---|---|---|---|---|
| None | 17.8 | 19.8 | >40 | >40 | >40 |
| 50 mU | 17.8 | 19.8 | 17.2 | 21.6 | >40 |
| 100 mU | 17.8 | 19.6 | 17.2 | 19.7 | >40 |
| 150 mU | 17.8 | 19.9 | 17.2 | 19.5 | >40 |
| 200 mU | 17.8 | 19.8 | 17.2 | 19.1 | >40 |

The unblocked primer with a 3'-terminal 2'OMe base (SEQ ID NO: 227) showed a 2 cycle delay relative to the unmodified primer (SEQ ID NO: 69), indicating that the terminal 2'OMe base slightly decreased priming efficiency but nevertheless was functional as a PCR primer. The blocked primer containing a single rU base (SEQ ID NO: 116) performed as expected (see Example 13) and worked well with low concentrations of RNase H2 (data not shown). For the 2'OMe RNA containing primers a higher concentration of RNase H2 was needed. The primer having a 2'OMe residue 5'- to the ribonucleotide (SEQ ID NO: 228) showed good activity at 50 mU RNase H2 and performed identically to the unblocked 2'OMe control primer (SEQ ID NO: 227) when 100 mU or higher RNase H2 was employed. The primer having a 2'OMe residue 3'- to the ribonucleotide (SEQ ID NO: 229) did not function at any level of RNase H2 tested. The primer having a 2'OMe residue 5'- to the ribonucleotide (SEQ ID NO: 228) was next tested in a mismatch discrimination qPCR assay.

The standard configuration blocked RNase H2 cleavable primer (SEQ ID NO: 116) was compared with the 5'-2'OMe version of this sequence (SEQ ID NO: 228). These two "Rev" primers were used with the unmodified "For" primer (SEQ ID NO: 68) together with 3 different synthetic oligonucleotide templates (originally used in defining mismatch discrimination potential in Example 13). These templates provide a perfect match control (Template SEQ ID NO: 144), a T/U mismatch (Template SEQ ID NO: 137), or a G/U mismatch (Template SEQ ID NO: 158). The 3 templates oligonucleotides are shown below with the cleavable blocked primer (SEQ ID NO: 116) aligned beneath to illustrate the regions of match vs. mismatch.

```
Synthetic template, SEQ ID NO: 144 (A:U match):
AGCTCTGCCCAAAGATTACCCTGACAGCTAAGTGG

CAGTGGAAGTTGGCCTCAGAAGTAGTGGCCAGCT

GTGTGTCGGGGAACAGTAAAGGCATGAAGCTCAG-3'
         ||||||||||||||||||||||||||||
3'-C3-CCCCuTGTCATTTCCGTACTTCGAGTC-5'

Synthetic template, SEQ ID NO: 137 (T:U mismatch):
AGCTCTGCCCAAAGATTACCCTGACAGCTAAGTGG

CAGTGGAAGTTGGCCTCAGAAGTAGTGGCCAGCT

GTGTGTCGGGGTACAGTAAAGGCATGAAGCTCAG-3'
         |||| ||||||||||||||||||||||
3'-C3-CCCCuTGTCATTTCCGTACTTCGAGTC-5'

Synthetic template, SEQ ID NO: 158 (G:U mismatch):
AGCTCTGCCCAAAGATTACCCTGACAGCTAAGTGG

CAGTGGAAGTTGGCCTCAGAAGTAGTGGCCAGCT

GTGTGTCGGGGGACAGTAAAGGCATGAAGCTCAG-3'
         |||| ||||||||||||||||||||||
3'-C3-CCCCuTGTCATTTCCGTACTTCGAGTC-5'
```

PCR reactions were performed in 10 µl volume using 200 nM unmodified For primer with 200 nM of cleavable blocked Rev primer (SEQ ID NO: 116) or 5'mU containing cleavable blocked Rev primer (SEQ ID NO: 228) in Bio-Rad SYBR Green master mix. Reactions were run with 1.3 mU (primer SEQ ID NO: 116) or 100 mU (primer SEQ ID NO: 228) of *Pyrococcus abyssi* RNase H2. Reactions were run on a Roche Lightcycler® 480 platform with 2×10⁶ copies of the different synthetic oligonucleotide templates (SEQ ID NOS: 137, 144, or 158). Reactions were started with a soak at 95° C. for 5 minutes followed by 45 cycles of [95° C. for 10 seconds, 60° C. for 20 seconds, and 72° C. for 30 seconds]. Results are summarized in Table 50 and are shown as ΔCp (ΔCp=Cp mismatch−Cp match).

TABLE 50

Cp values of qPCR reactions comparing mismatch discrimination of blocked primers with or without a 2'OMe base on the 5'-side of an RNA residue.

|  | 1.3 mU RNase H2 SEQ ID NO: 116 rU primer | 100 mU RNase H2 SEQ ID NO: 228 mUrU primer |
|---|---|---|
| Match (A:U) | 0 | 0 |
| Mismatch (T:U) | 5.3 | 12.7 |
| Mismatch (G:U) | 10.9 | 14.4 |

(ΔCp = Cp mismatch − Cp match)

In both cases tested, addition of a 2'OMe residue directly 5' to the cleavable ribonucleotide significantly improved mismatch discrimination. The T/U mismatch improved from a ΔCp of 5.3 to 12.7 and the G/U mismatch improved from a ΔCp of 10.9 to 14.4. This new primer design required use of 100 mU of RNase H2 compared with 1.3 mU (in a 10 ul assay), however the enzyme is inexpensive and the boost in reaction specificity was considerable. We conclude that the use of chemically modified residues in select positions within the cleavable primer can significantly improve the mismatch discrimination capability of the assay.

Example 23—Use of Double-Mismatch Design in Cleavable Blocked Primers to Improve Mismatch Discrimination Some nucleic acid probes that are complementary to a wild type (WT) sequence will bind to both the perfect match WT target and a mutant target bearing a single base mismatch with sufficiently similar affinity that the two sequences (WT and mutant) are not easily distinguished. While a single mismatch introduced between the probe and target sequence may not significantly disrupt binding to the wild type target (which has 1 mismatch with the probe) disrupts binding to the mutant target (which now has 2 mismatches with the probe). This strategy has been used to improve selectivity of hybridization based assays as well as assays dependent upon interaction with nucleic acid binding proteins. The present example demonstrates use of a double-mismatch strategy to improve base discrimination with use of cleavable-blocked primers of the present invention.

For the present study, the SMAD7 qPCR SNP discrimination assay presented in Example 20 was employed as a model system, except that the SYBR Green detection format was used instead of the FQ format. Blocked-cleavable primers were synthesized with the base mismatch in the positioned at the cleavable ribonucleotide. Using the present probe design, any mismatch placed 5'- to the cleavage site (RNA base) will be retained in the primer extension product and thus will be replicated during PCR. In order to maintain the presence of the double-mismatch during PCR, the new mismatch must be positioned 3'- to the cleavable RNA residue in the domain that is cleaved off and is not retained in daughter products. It is desirable that the intentionally added second mismatch not disrupt function of the primer with a perfect match target. It was demonstrated in Example 13 that mismatches present in the "+1 position" (i.e., immediately 3'- to the RNA base) can have a significant impact upon cleavage and functional primer efficiency. The double mismatch was therefore placed at the "+2 position" 3'- to the RNA base with the expectation that this configuration would not be disruptive as a single mismatch but would be disruptive as a double mismatch.

Blocked-cleavable primers were designed and synthesized at this site using standard design features to discriminate between the "C" and "T" alleles in the SMAD7 gene (SNP locus rs4939827). The same unmodified Rev primer was used in all assays (SEQ ID NO: 217). The perfect match "C" allele primer is SEQ ID NO: 231 and the perfect match "T" allele primer is SEQ ID NO: 235. Next, a series of primers were made bearing a mutation at position +2 relative to the ribonucleotide (2 bases 3'- to the RNA residue). It was anticipated that the identity of the base mismatch would alter the relative perturbation that having a mismatch at this position would introduce into the assay. Therefore, perfect match (wild type) and all 3 possible base mismatches were synthesized and studied (SEQ ID NOS: 232-234 and 236-238). Sequences are shown below in Table 51.

TABLE 51

| Name | Sequence | SEQ ID NO: |
|---|---|---|
| rs4939827 Rev | 5'-CTCACTCTAAACCCCAGCATT | SEQ ID NO: 217 |
| rs4939827 For | 5'-CAGCCTCATCCAAAAGAGGAAA | SEQ ID NO: 230 |
| rs4939827 C-For WT | 5'-CAGCCTCATCCAAAAGAGGAAAcAGGA-SpC3 | SEQ ID NO: 231 |
| rs4939827 C-For CAA | 5'-CAGCCTCATCCAAAAGAGGAAAcAAGA-SpC3 | SEQ ID NO: 232 |
| rs4939827 C-For CAC | 5'-CAGCCTCATCCAAAAGAGGAAAcACGA-SpC3 | SEQ ID NO: 233 |
| rs4939827 C-For CAT | 5'-CAGCCTCATCCAAAAGAGGAAAcATGA-SpC3 | SEQ ID NO: 234 |
| rs4939827 T-For WT | 5'-CAGCCTCATCCAAAAGAGGAAAuAGGA-SpC3 | SEQ ID NO: 235 |
| rs4939827 T-For UAA | 5'-CAGCCTCATCCAAAAGAGGAAAuAAGA-SpC3 | SEQ ID NO: 236 |
| rs4939827 T-For UAC | 5'-CAGCCTCATCCAAAAGAGGAAAuACGA-SpC3 | SEQ ID NO: 237 |
| rs4939827 T-For UAT | 5'-CAGCCTCATCCAAAAGAGGAAAuATGA-SpC3 | SEQ ID NO: 238 |

DNA bases are shown in uppercase. RNA bases are shown in lowercase. SpC3 is a spacer C3 used as a 3'-blocking group. Mutations introduced to create double-mismatches are indicated with bold underline.

The above primers target the following 85 bp region of the SMAD7 gene (NM_005904). Primer binding sites are underlined and the SNP location is highlighted as bold italic. Primers are aligned with target in FIG. 33 to help illustrate the scheme of the "double mutant" approach to improve SNP discrimination.

rs4939827 (SMAD7) C allele (SEQ ID NO: 220)

CAGCCTCATCCAAAAGAGGAAA*C*AGGACCCCAGAGCTCCCTCAGACTCCT

CAGGAAACACAGACAATGCTGGGGTTTAGAGTGAG rs4939827 (SMAD7) T allele (SEQ ID NO: 221)

CAGCCTCATCCAAAAGAGGAAA*T*AGGACCCCAGAGCTCCCTCAGACTCCT

CAGGAAACACAGACAATGCTGGGGTTTAGAGTGAG

PCR reactions were performed in 10 μl volume using 200 nM of the unmodified Rev primer (SEQ ID NO: 217) and the series of cleavable blocked For primers (SEQ ID NOS: 231-238) in Bio-Rad SYBR Green master mix. Reactions were run with 2.6 mU of *Pyrococcus abyssi* RNase H2 on a Roche Lightcycler® 480 platform with 2 ng of target DNA. Target DNA was genomic DNA made from cells homozygous for the two SMAD7 alleles (Coreill 18562 and 18537). The "C" and "T" alleles (SEQ ID NOS: 220 and 221) were tested individually. Reactions were started with a soak at 95° C. for 5 minutes followed by 80 cycles of [95° C. for 10 seconds, 60° C. for 30 seconds, and 72° C. for 1 second]. Results are shown in Table 52 below.

TABLE 52

Cp and ΔCp values of qPCR reactions comparing mismatch discrimination of blocked primers with or without a second mutation at position +2 relative to the ribonucleotide.

| | | Cp "C" Allele | Cp "T" Allele | Cp |
|---|---|---|---|---|
| SEQ ID NO: 230 | Unblocked control | 27.5 | 26.5 | — |
| SEQ ID NO: 231 | rCAG (WT) | 29.2 | 39.9 | 10.7 |
| SEQ ID NO: 232 | rCAA | 29.0 | 47.8 | 18.8 |
| SEQ ID NO: 233 | rCAC | 31.6 | 45.4 | 13.8 |
| SEQ ID NO: 234 | rCAT | 30.2 | 42.8 | 12.6 |
| SEQ ID NO: 235 | rUAG (WT) | 42.6 | 29.2 | 13.4 |
| SEQ ID NO: 236 | rUAA | 49.3 | 40.1 | 9.2 |
| SEQ ID NO: 237 | rUAC | 74.1 | 49.9 | 24.2 |
| SEQ ID NO: 238 | rUAT | 62.5 | 45.3 | 17.2 |

(ΔCp = Cp mismatch − Cp match)

For the "C" allele, the standard design perfectly matched probe (SEQ ID NO: 231) showed amplification efficiency similar to unmodified control primers and the mismatch discrimination was 10.7 cycles (ΔCp=10.7) against the "T" target. The mismatch primers showed a minor decrease in detection efficiency with the "C" allele target (a shift of up to 2.4 cycles was observed) but mismatch discrimination at the SNP site increased significantly with a ΔCp of 18.8 cycles seen for the rCAA primer (SEQ ID NO: 232).

For the "T" allele, the standard design perfect match probe (SEQ ID NO: 235) also showed amplification efficiency similar to unmodified control primers and the mismatch discrimination was 13.4 cycles (ΔCp=13.4) against the "C" target. However, unlike the "C" allele, the mismatch primers for the "T" allele showed a large decrease in detection efficiency with the "T" allele target. Shifts as large as 20 cycles were observed. Nevertheless the relative SNP discrimination was improved with a ΔCp of 24.2 cycles seen for the rUAC primer (SEQ ID NO: 237). For this region of the SMAD7 gene, the "T" allele creates an "AT-rich" stretch at the site of the cleavable RNA base and this sequence has low thermal stability. The presence of a mismatch at the +2 position must destabilize the structure in this region much more for the "T" allele than the higher stability "C" allele, which would account for the observed increase Cp for the "T" allele probes against the "T" target. However, this shift in Cp values does not limit utility of the assay. Given the inherent increased specificity of the blocked-cleavable primers (see Example 11), there should be no problem with routinely extending reactions to 60-80 or more cycles. In certain settings, the increased discrimination power of the double-mismatch format will be of sufficient value to accept the lower overall reaction efficiency. In "AT-rich" regions like the SMAD7 "T" allele, it might also be useful to position the double mismatch at the +3 position, removing its disruptive effects further from the cleavable ribonucleotide.

Example 24—Identity of Reaction Products Made by PCR Amplification at SNP Sites Using Cleavable-Blocked Primers For use in PCR or any primer extension application, if a base mismatch (SNP site) is positioned directly at the ribonucleotide residue in blocked-cleavable primers, then a cleavage event that occurs 5'- to the RNA base will result in a primer extension product that reproduces the base variant present in the template nucleic acid. A cleavage event that occurs 3'- to the RNA base will result in a primer extension product that changes the product to the RNA base present in the primer, creating an error that will be replicated in subsequent PCR cycles. Cleavage on the 3'-side of the ribonucleotide is therefore an undesired event. Given the enormous amplification power of PCR, even a small amount of 3'-cleavage could lead to the accumulation of a sizeable amount of products containing a sequence error. For example, cleavage at a rate of 0.1% would lead to 1 out of 1000 molecules having the "wrong" base at the site of the RNA residue which would then be detectable as "perfect match" in subsequent PCR cycles. This would equate to a 10 cycle shift (ΔCp=10) in a qPCR reaction. Using the design parameters taught in Example 13, cycle shifts for SNP discrimination varied from 5-15. Thus a small amount of undesired and unsuspected 3'-cleavage could easily account for the delayed false-positive signals seen in Example 13 during SNP interrogation.

A false positive signal in an allele-specific SNP discrimination reaction could arise from two sources. First, ongoing inefficient cleavage at the "normal" RNase H2 cleavage site at the 5'-side of the RNA base (see FIG. 3) in spite of the mismatch. This reaction will result in primer extension products identical to the starting target. Second, a false positive signal in an allele-specific SNP discrimination reaction could also arise from inefficient cleavage at an "abnormal" position anywhere on the 3'-side of the RNA base. This reaction would produce primer extension products identical to the primer and which would then amplify with high efficiency using this same primer. If the first scenario were correct, then the products from a reaction performed using allele "A" primer with allele "B" target should produce mostly allele "B" products, which would continue to amplify inefficiently with allele "A" primers. If the second scenario were correct, then the products from a reaction performed using allele "A" primer with allele "B" target should produce mostly allele "A" products, which would amplify efficiently with allele "A" primers.

To distinguish between these possibilities, a re-amplification experiment was performed wherein a first round of PCR amplification was performed using a SMAD7 "T" allele primer with SMAD7 "T" allele target DNA or with SMAD7 "C" allele target DNA. The reaction products were diluted $10^8$ fold and re-amplification was performed using the "T" vs. "C" allele primers to determine if the identity of the SNP base present in the reaction products changed during the first round of amplification. The SMAD7 rs4939827 allele system was employed using the following primers and target DNAs, which are shown below in Table 53.

TABLE 53

| Name | Sequence | SEQ ID NO: |
| --- | --- | --- |
| rs4939827 Rev | 5'-CTCACTCTAAACCCCAGCATT | SEQ ID NO: 217 |
| rs4939827 For | 5'-CAGCCTCATCCAAAAGAGGAAA | SEQ ID NO: 230 |
| rs4939827 C-For WT | 5'-CAGCCTCATCCAAAAGAGGA AAcAGGA-SpC3 | SEQ ID NO: 231 |
| rs4939827 T-For WT | 5'-CAGCCTCATCCAAAAGAGGA AAuAGGA-SpC3 | SEQ ID NO: 235 |

DNA bases are shown in uppercase. RNA bases are shown in lowercase. SpC3 is a spacer C3 used as a 3'-blocking group.

The above primers target the following 85 bp region of the SMAD7 gene (NM_005904). Synthetic oligonucleotides were synthesized for use as pure targets in the SMAD7 system and are shown below. Primer binding sites are underlined and the SNP location is highlighted as bold italic.

rs4939827 (SMAD7) C allele
(SEQ ID NO: 220)
CAGCCTCATCCAAAAGAGGAAA*C*AGGACCCCAGAGCTCCCTCAGACTCCT

CAGGAAACACAGACAATGCTGGGGTTTAGAGTGAG rs4939827 (SMAD7) T allele
(SEQ ID NO: 221)
CAGCCTCATCCAAAAGAGGAAA*T*AGGACCCCAGAGCTCCCTCAGACTCCT

CAGGAAACACAGACAATGCTGGGGTTTAGAGTGAG

PCR reactions were performed in 10 μl volume using 200 nM of the unmodified Rev primer (SEQ ID NO: 217) and the "T" allele cleavable blocked For primer (SEQ ID NO: 235) in Bio-Rad SYBR Green master mix. Reactions were run with 2.6 mU of *Pyrococcus abyssi* RNase H2 on a Roche Lightcycler® 480 platform with $6.6 \times 10^5$ copies of synthetic oligonucleotide target SMAD7 "C" allele (SEQ ID NO: 220) or SMAD7 "T" allele (SEQ ID NO: 230). Reactions were started with a soak at 95° C. for 5 minutes followed by 80 cycles of [95° C. for 10 seconds, 60° C. for 30 seconds, and 72° C. for 1 second]. Results of qPCR amplifications done at this SNP site are shown in Table 54 below.

TABLE 54

Cp and ΔCp values of qPCR reactions showing mismatch discrimination of cleavable-blocked primers at a SMAD7 C/T allele.

| | Cp for: "T" Target SEQ ID NO: 221 | Cp for: "C" Target SEQ ID NO: 220 | ΔCp |
|---|---|---|---|
| Primer rs4939827 T-For WT SEQ ID NO: 235 | 32.5 | 18.9 | 13.6 |

The "T" allele primer performed similar to pervious results showing a ΔCp of 13.6 between reactions run using the match "T" allele target DNA and the mismatch "C" allele target DNA.

This experiment was repeated using a $10^8$ dilution of the reaction products from the above PCR amplifications as target DNA. If cleavage at the mismatch site occurred at the expected position 5'- to the ribonucleotide, then the reaction products should remain "true" and "T" allele product would be made from input "T" allele template and "C" allele product would be made for input "C" allele template. However, if any appreciable cleavage occurred 3'- to the ribonucleotide, then the reaction products should be converted to the sequence of the primer at the SNP site. In this case, a "T" allele product would be made from a "C" allele target.

PCR reactions were performed in 10 μl volume using 200 nM of the unmodified Rev primer (SEQ ID NO: 217) and the "T" allele cleavable blocked For primer (SEQ ID NO: 235) or the "C" allele cleavable blocked For primer (SEQ ID NO: 231) in Bio-Rad SYBR Green master mix. Reactions were run with 2.6 mU of *Pyrococcus abyssi* RNase H2 on a Roche Lightcycler® 480 platform. Input target DNA was a $10^8$ dilution of the reaction products shown in Table 54 above. Reactions were started with a soak at 95° C. for 5 minutes followed by 45 cycles of [95° C. for 10 seconds, 60° C. for 30 seconds, and 72° C. for 1 second]. Results of qPCR amplifications done at this SNP site are shown in Table 55 below.

TABLE 55

Cp and ΔCp values of qPCR reactions showing mismatch discrimination of cleavable-blocked primers at a SMAD7 C/T allele.

| | Cp for: "T" Target amplified by "T" primer | Cp for: "C" Target amplified by "T" primer | ΔCp |
|---|---|---|---|
| Primer rs4939827 T-For WT SEQ ID NO: 235 | 27.7 | 29.2 | 1.5 |
| Primer rs4939827 C-For WT SEQ ID NO: 231 | 38.6 | 38.5 | 0.1 |

The reactions products previously made (Table 54) using the "T" allele primer with both the "T" allele target and the "C" allele target now show nearly identical amplification efficiency using the "T" allele primer whereas previously a ΔCp of 13.6 was observed between the two different starting target DNAs. This is most consistent with the product nucleic acids having similar sequence, i.e., both are now predominantly "T" allele. Consistent with this hypothesis, both of these samples now show similar delayed Cp using the "C" allele primer. Thus it appears that the product from the "T" allele primer amplification using the "C" allele target was largely converted to "T" allele, consistent with that product originating with a primer cleavage event occurring 3'- to the ribonucleotide base. The reaction products from the original amplification using the "T" allele primer (Table 54) were subcloned and DNA sequence determined. All clones identified had the "T" allele present, whether the starting template was the "T" allele or the "C" allele, adding further support to this conclusion.

Example 25—Use of Phosphorothioate Modified Internucleotide Linkages in Cleavable Blocked Primers to Improve Mismatch Discrimination The results form Example 24 indicates that PCR performed with a mismatched primer/target combination can produce a product with sequence matching the primer instead of the target. The most likely scenario that would result in this kind of product starts with cleavage of the mismatched primer at a position 3'- to the ribonucleotide residue. Use of chemical modifications that prevent unwanted cleavage in this domain of the primer may improve performance of the cleavable-blocked primers especially in SNP discrimination. The following primers, as shown in below in Table 56, were synthesized with nuclease-resistant phosphorothioate (PS) modified internucleotide linkages placed at positions 3'- to the ribonucleotide as indicated. It was established in Example 15 that placement of a PS bond at the 3'-linkage directly at the RNA base can decrease cleavage efficiency. This modification survey therefore focused on the DNA linkages further 3'- to this site. The synthetic amplicon system previously used in Example 13 was employed.

TABLE 56

| Name | Sequence | SEQ ID NO: |
|---|---|---|
| Syn-For | 5'-AGCTCTGCCCAAAGATTACCCTG | SEQ ID NO: 68 |
| Syn-Rev-rU-C3 | 5'-CTGAGCTTCATGCCTTTACTGTuCCCC-SpC3 | SEQ ID NO: 116 |
| Syn-Rev-rU-C*CCC-C3 | 5'-CTGAGCTTCATGCCTTTACTGTuC*CCC-SpC3 | SEQ ID NO: 301 |
| Syn-Rev-rU-CC*CC-C3 | 5'-CTGAGCTTCATGCCTTTACTGTuCC*CC-SpC3 | SEQ ID NO: 239 |

TABLE 56-continued

| Name | Sequence | SEQ ID NO: |
|---|---|---|
| Syn-Rev-rU-CCC*C-C3 | 5'-CTGAGCTTCATGCCTTTACTGTuCCC*C-SpC3 | SEQ ID NO: 240 |
| Syn-Rev-rU-C*C*C*C-C3 | 5'-CTGAGCTTCATGCCTTTACTGTuC*C*C*C-SpC3 | SEQ ID NO: 241 |

DNA bases are shown in uppercase. RNA bases are shown in lowercase.
"*" indicates a phosphorothioate (PS) modified internucleotide linkage.

The standard configuration blocked RNase H2 cleavable primer (SEQ ID NO: 116) was compared with PS-modified versions of this sequence (SEQ ID NOS: 301 and 239-241). This set of "Rev" primers were used with the unmodified "For" primer (SEQ ID NO: 68) together with two different synthetic oligonucleotide templates (originally used in defining mismatch discrimination potential in Example 13). These templates provide a perfect match control (Template SEQ ID NO: 144) and a T/U mismatch (Template SEQ ID NO: 137). The two templates and oligonucleotides are shown below with the cleavable blocked primer (SEQ ID NO: 116) aligned beneath to illustrate the regions of match vs. mismatch.

```
Synthetic template, SEQ ID NO: 144 (A:U match):
AGCTCTGCCCAAAGATTACCCTGACAGCTAAGTGGCAGTGGAAGTTGGCCTCAGAAGTAGTGGCCAGCT
GTGTGTCGGGGAACAGTAAAGGCATGAAGCTCAG-3'
              ||||||||||||||||||||||||||
          3'-C3-CCCCuTGTCATTTCCGTACTTCGAGTC-5'

Synthetic template, SEQ ID NO: 137 (T:U mismatch):
AGCTCTGCCCAAAGATTACCCTGACAGCTAAGTGGCAGTGGAAGTTGGCCTCAGAAGTAGTGGCCAGCT
GTGTGTCGGGGTACAGTAAAGGCATGAAGCTCAG-3'
              |||| |||||||||||||||||||||
          3'-C3-CCCCuTGTCATTTCCGTACTTCGAGTC-5'
```

PCR reactions were performed in 10 µl volume using 200 nM of the unmodified For primer (SEQ ID NO: 68) and the different cleavable blocked Rev primers shown above (SEQ ID NOS: 116, 301 and 239-241) in Bio-Rad SYBR Green master mix. Reactions were run with 1.3 mU of *Pyrococcus abyssi* RNase H2 on a Roche Lightcycler® 480 platform. Input target DNA was 2×10⁶ copies of the synthetic target sequences shown above (SEQ ID NOS: 137 and 144). Reactions were started with an incubation at 95° C. for 5 minutes followed by 45 cycles of [95° C. for 10 seconds, 60° C. for 30 seconds, and 72° C. for 1 second]. Results of qPCR amplifications done at this SNP site are shown in Table 57 below.

TABLE 57

Cp values of qPCR reactions comparing mismatch discrimination of blocked primers with or without PS linkages 3'- to the cleavable ribonucleotide.

| | Match Target (A:U) SEQ ID NO: 144 | Mismatch Target (T:U) SEQ ID NO: 137 | ΔCp |
|---|---|---|---|
| SEQ ID NO: 116 CCCC Primer | 18.5 | 26.2 | 7.7 |
| SEQ ID NO: 301 C*CCC Primer | 19.5 | 31.9 | 12.4 |
| SEQ ID NO: 239 CC*CC Primer | 18.2 | 26.7 | 8.5 |
| SEQ ID NO: 240 CCC*C Primer | 18.4 | 26.3 | 7.9 |

TABLE 57-continued

Cp values of qPCR reactions comparing mismatch discrimination of blocked primers with or without PS linkages 3'- to the cleavable ribonucleotide.

| | Match Target (A:U) SEQ ID NO: 144 | Mismatch Target (T:U) SEQ ID NO: 137 | ΔCp |
|---|---|---|---|
| SEQ ID NO: 241 C*C*C*C Primer | 18.5 | 29.1 | 10.6 |

(ΔCp = Cp mismatch − Cp match)

Placement of a PS modified linkage at the 3' "+1" position (rUC*CCC) led to almost a 5 cycle improvement in SNP discrimination in this assay (SEQ ID NO: 241 vs. 116), demonstrating that increasing nuclease stability in the domain 3'- to the ribonucleotide can significantly improve assay performance. Modification o the linkages further 3' from the ribonucleotide had minimal impact. Modification of all of the linkages in this area (rUC*C*C*C, nucleotides 23-27 of SEQ ID NO: 241) also showed benefit, improving relative SNP discrimination by 3 cycles, but unexpectedly showed less benefit than using just a single modification at the 3'+1 linkage. This may relate to the lowered binding affinity Tm that also results from the PS modification.

Thus, adding nuclease resistant modifications at the linkages 3'- to the cleavable ribonucleotide can increase SNP discrimination for the RNase H2 mediated cleavable-blocked primer PCR assay. Typically, only one of the two stereoisomers at a PS linkage (the Rp or Sp isomer) confers benefit. Improved activity might therefore be realized by isolation a chirally pure PS compound here, as was demonstrated in Example 15. Other nuclease resistant modifications may be suitable in this area, such as the non-chiral phosphorodithioate linkage, the methyl phosphonate linkage, the phosphoramidate linkage, a boranophosphate linkage, and abasic residues such as a C3 spacer to name a few.

Example 26—Use of Cleavable Primers Having an Unblocked 3'-Hydroxyl in a qPCR Assay In the above Examples, a blocking group was placed at the 3'-end of the primer to prevent primer extension from occurring prior to RNase H2 cleavage. For certain primer designs and applications, it may not be necessary or even desirable to employ a 3'-blocking group. We have previously described a method of nucleic acid amplification termed polynomial amplification that employs primers that are chemically modified in ways that block template function while retaining primer function. A variety of groups can be used for this purpose, including internal C3 spacers and internal 2'OMe RNA bases. Using nested primers, high specificity is achieved and amplification power is dependent upon the number of nested primers employed, with amplification occurring according to a polynomial expansion instead of the exponential amplification seen in PCR (see U.S. Pat. No. 7,112,406 and pending US Patent applications 2005/0255486 and 2008/0038724). Combining elements of the polynomial amplification primers with an RNase H2 cleavable domain of the present invention results in a novel primer design that has an unblocked 3'-hydroxyl and is capable of supporting primer extension yet cannot support PCR. Upon cleavage, the template blocking groups are removed and primer function for use in PCR is restored. The present example demonstrates use of cleavable template-blocked primers having a 3'-hydroxyl in qPCR.

The following primers, as shown below in Table 58, were synthesized for use with the artificial synthetic amplicon used in previous Examples.

TABLE 58

| Name | Sequence | SEQ ID NO: |
|---|---|---|
| Syn-For | 5'-AGCTCTGCCCAAAGATTACCCTG | SEQ ID NO: 68 |
| Syn-Rev | 5'-CTGAGCTTCATGCCTTTACTGT | SEQ ID NO: 69 |
| Syn-For-rA-C3 | 5'-AGCTCTGCCCAAAGATTA CCCTGaCAGC-SpC3 | SEQ ID NO: 242 |
| Syn-For-rA-iC3-D1 | 5'-AGCTCTGCCCAAAGATTAA CCCTGaCAGC(SpC3-SpC3) | SEQ ID NO: 243 |
| Syn-For-rA-iC3-D2 | 5'-AGCTCTGCCCAAAGATTA CCCTGaCAGC(SpC3-SpC3)AG | SEQ ID NO: 244 |
| Syn-For-rA-iC3-D4 | 5'-AGCTCTGCCCAAAGATTA CCCTGaCAGC(SpC3-SpC3)AGTG | SEQ ID NO: 245 |
| Syn-For-rA-iC3-D5 | 5'-AGCTCTGCCCAAAGATTA CCCTGaCAGC(SpC3-SpC3)AGTGG | SEQ ID NO: 246 |

DNA bases are shown in uppercase. RNA bases are shown in lowercase.
SpC3 is a Spacer C3 group, positioned either internal within the primer or at the 3'-end.

The synthetic amplicon oligonucleotide template (SEQ ID NO: 143) is shown below with the unmodified and various modified cleavable For primers shown aligned above and the unmodified Rev primer aligned below. DNA bases are uppercase, RNA bases are lowercase, and "x" indicates a Spacer-C3 group.

```
5'AGCTCTGCCCAAAGATTACCCTG                         SEQ ID NO: 68   unmodified 5'AGCTCTGCCCAAAGATTACCCTGaCAGC-x                  SEQ ID NO: 242  3'-block 5'AGCTCTGCCCAAAGATTACCCTGaCAGCxxA                 SEQ ID NO: 243  Int D1

5'AGCTCTGCCCAAAGATTACCCTGaCAGCxxAG                SEQ ID NO: 244  Int D2

5'AGCTCTGCCCAAAGATTACCCTGaCAGCxxAGTG              SEQ ID NO: 245  Int D4

5'AGCTCTGCCCAAAGATTACCCTGaCAGCxxAGTGG             SEQ ID NO: 246  Int D5
  |||||||||||||||||||||||||||||  |||||
5'AGCTCTGCCCAAAGATTACCCTGACAGCTAAGTGGCAGTGGAAGTTGGCCTCAGAAGTAGTGGCCAG

CTGTGTGTCGGGGAACAGTAAAGGCATGAAGCTCAG-3'
  ||||||||||||||||||||||||
  TGTCATTTCCGTACTTCGAGTC-5'                       SEQ ID NO: 69
```

PCR reactions were performed in 10 µl volume using 200 nM of the individual For primers (SEQ ID NOS: 68, 242-246) and the unmodified Rev primer (SEQ ID NO: 69) in Bio-Rad SYBR Green master mix. Reactions were run with or without 1.3 mU of *Pyrococcus abyssi* RNase H2 on a Roche Lightcycler® 480 platform. Input target DNA was $2 \times 10^6$ copies of the synthetic target shown above (SEQ ID NO: 144). Reactions were started with an incubation at 95° C. for 5 minutes followed by 60 cycles of [95° C. for 10 seconds, 60° C. for 30 seconds, and 72° C. for 1 second]. Results of qPCR amplifications are shown in Table 59 below.

TABLE 59

Cp values of qPCR reactions comparing performance of cleavable primers having a 3'-blocking group vs. cleavable primers having internal template blocking groups.

| | Without RNase H2 | +1.3 mU RNase H2 |
|---|---|---|
| Unblocked For SEQ ID NO: 68 Unblocked Rev SEQ ID NO: 69 | 17.0 | 17.2 |
| 3'-blocked For SEQ ID NO: 242 Unblocked Rev SEQ ID NO: 69 | >60 | 17.1 |
| Int-blocked For SEQ ID NO: 243 (D1) Unblocked Rev SEQ ID NO: 69 | >60 | 17.1 |
| Int-blocked For SEQ ID NO: 244 (D2) Unblocked Rev SEQ ID NO: 69 | >60 | 17.1 |
| Int-blocked For SEQ ID NO: 245 (D4) Unblocked Rev SEQ ID NO: 69 | >60 | 17.1 |
| Int-blocked For SEQ ID NO: 246 (D5) Unblocked Rev SEQ ID NO: 69 | >60 | 17.9 |

The unblocked primers gave detectable signal at around cycle 17 in this assay system. Using the unblocked Rev primer with the 3'-blocked For primer, no signal was detected within the 60 cycle PCR run without RNase H2, however with RNase H2 a similar cycle detection time of around 17 was seen. The internally blocked For primers that had a free 3'-hydroxyl group behaved identically to the 3'-modified primer. In spite of the unblocked 3'-hydroxyl, primer cleavage with RNase H2 was required for function in PCR, presumably due to the loss of template function imposed by the internal C3 spacers. C3 spacers placed near the 3'-end may also inhibit primer extension to a certain degree. No signal was detected in the absence of RNase H2; with RNase H2, cleavage and amplification proceeded normally.

This example demonstrates that cleavable primers do not need to be modified at the 3'-terminal residue to function in a cleavable-primer PCR assay and that primers having internal modifications that disrupt template function can perform equally well. Given the significance of this finding to primer design, a similar experiment was performed using an endogenous human gene target using human genomic DNA to ensure that these results could be generalized.

The following primers, as shown below in Table 60, were synthesized based upon the human SMAD7 gene used in previous Examples, using only the "C" allele.

TABLE 60

| Name | Sequence | SEQ ID NO: |
|---|---|---|
| rs4939827 Rev | 5'-CTCACTCTAAACCCCAGCATT | SEQ ID NO: 217 |
| rs4939827 For | 5'-CAGCCTCATCCAAAAGAGGAAA | SEQ ID NO: 230 |
| rs4939827 C-For-C3 | 5'-CAGCCTCATCCAAAAGAGGAAAcAGGA-SpC3 | SEQ ID NO: 231 |
| rs4939827 C-For-iC3-D1 | 5'-CAGCCTCATCCAAAAGAGGAAAcAGGA(SpC3-SpC3)C | SEQ ID NO: 247 |
| rs4939827 C-For-iC3-D2 | 5'-CAGCCTCATCCAAAAGAGGAAAcAGGA(SpC3-SpC3)CC | SEQ ID NO: 248 |
| rs4939827 C-For-iC3-D4 | 5'-CAGCCTCATCCAAAAGAGGAAAcAGGA(SpC3-SpC3)CCAG | SEQ ID NO: 249 |
| rs4939827 C-For-iC3-D5 | 5'-CAGCCTCATCCAAAAGAGGAAAcAGGA(SpC3-SpC3)CCAGA | SEQ ID NO: 250 |

DNA bases are shown in uppercase. RNA bases are shown in lowercase.
SpC3 is a Spacer C3 group, positioned either internal within the primer (template block) or at the 3'-end (primer block).

The SMAD7 amplicon sequence (SEQ ID NO: 220) is shown below with the unmodified and various modified cleavable For primers shown aligned above. DNA bases are uppercase, RNA bases are lowercase, and "x" indicates a Spacer-C3 group.

```
5'CAGCCTCATCCAAAAGAGGAAA                    SEQ ID NO: 230 unmodified

5'CAGCCTCATCCAAAAGAGGAAAcAGGA-x             SEQ ID NO: 231 3'-block

5'CAGCCTCATCCAAAAGAGGAAAcAGGAxxC            SEQ ID NO: 247 Int-block

5'CAGCCTCATCCAAAAGAGGAAAcAGGAxxCC           SEQ ID NO: 248 Int-block

5'CAGCCTCATCCAAAAGAGGAAAcAGGAxxCCAG         SEQ ID NO: 249 Int-block

5'CAGCCTCATCCAAAAGAGGAAAcAGGAxxCCAGA        SEQ ID NO: 250 Int-block
             ||||||||||||||||||||||||  |||||
5'CAGCCTCATCCAAAAGAGGAAACAGGACCCCAGAGCTCCCTCAGACTCCTCAGGAAACACAGACAAT

GCTGGGGTTTAGAGTGAG-3'
```

PCR reactions were performed in 10 µl volume using 200 nM of the individual For primers (SEQ ID NOS: 230-231, 247-250) and the unmodified Rev primer (SEQ ID NO: 217) in Bio-Rad SYBR Green master mix. Reactions were run with or without 2.6 mU of *Pyrococcus abyssi* RNase H2 on a Roche Lightcycler® 480 platform. Input target DNA was 2 ng of genomic DNA from a human cell line (Coreill 18562, SMAD7 "C" allele). Reactions were started with an incubation at 95° C. for 5 minutes followed by 60 cycles of [95° C. for 10 seconds, 60° C. for 30 seconds, and 72° C. for 1 second]. Results of qPCR amplifications are shown in Table 61 below.

TABLE 61

Cp values of qPCR reactions comparing performance of cleavable primers having a 3'-blocking group vs. cleavable primers having internal template blocking groups.

|  | Without RNase H2 | +2.6 mU RNase H2 |
|---|---|---|
| Unblocked For SEQ ID NO: 230 Unblocked Rev SEQ ID NO: 217 | 25.8 | 25.5 |
| 3'-blocked For SEQ ID NO: 231 Unblocked Rev SEQ ID NO: 217 | >60 | 26.3 |
| Int-blocked For SEQ ID NO: 247 (D1) Unblocked Rev SEQ ID NO: 217 | >60 | 26.3 |
| Int-blocked For SEQ ID NO: 248 (D2) Unblocked Rev SEQ ID NO: 217 | >60 | 26.2 |
| Int-blocked For SEQ ID NO: 249 (D4) Unblocked Rev SEQ ID NO: 217 | >60 | 26.2 |
| Int-blocked For SEQ ID NO: 250 (D5) Unblocked Rev SEQ ID NO: 217 | >60 | 26.7 |

The unblocked primers gave detectable signal around cycle 26 in this assay system using human genomic DNA. Using the unblocked Rev primer with the 3'-blocked For primer, no signal was detected within the 60 cycle PCR run without RNase H2, however with RNase H2 a similar cycle detection time of around 26 was seen. All of the internally blocked For primers that had a free 3'-hydroxyl group behaved identically to the 3'-modified primer. No signal was detected in the absence of RNase H2; with RNase H2, cleavage and amplification proceeded normally with detection occurring around 26 cycles.

This example further demonstrates that cleavable primers do not need to be modified at the 3'-end to function in the cleavable primer qPCR assay. Primers having internal modifications that disrupt template function still require a primer cleavage event to function as primers in the assay. When cleavage is done using RNase H2 at an internal cleavable residue, like a single RNA base, amplification efficiency is identical to that seen using unmodified primers. This novel version of template-blocked cleavable primers can be employed to perform PCR in complex nucleic acid samples like human genomic DNA.

Example 27—Cleavable Primers with Internal Template Blocking Groups and a 3'-Hydroxyl can Prime DNA Synthesis The cleavable template-blocked primers disclosed in Example 26 have an unblocked 3'-hydroxyl group that should permit the oligonucleotides to function as primers in linear primer extension reactions but the internal template-blocking groups prevent function in PCR as most of the primer cannot be replicated. Consequently, no primer binding site exists in the daughter products. Cleavage of the primer by RNase H2 removes the domain containing the template-blocking groups and restores normal primer function. The present example demonstrates that these compositions can function to prime DNA synthesis.

The following primers shown below in Table 62 were employed to perform linear primer extension reactions using the artificial synthetic amplicon system used in previous Examples.

TABLE 62

| Name | Sequence | SEQ ID NO: |
|---|---|---|
| Syn-For | 5'-AGCTCTGCCCAAAGATTACCCTG | SEQ ID NO: 68 |
| Syn-For-rA-C3 | 5'-AGCTCTGCCCAAAGATTA CCCTGaCAGC-SpC3 | SEQ ID NO: 242 |
| Syn-For-rA-iC3-D1 | 5'-AGCTCTGCCCAAAGA TTACCCTGaCAGC(SpC3-SpC3)A | SEQ ID NO: 243 |
| Syn-For-rA-iC3-D2 | 5'-AGCTCTGCCCAAAGA TTACCCTGaCAGC(SpC3-SpC3)AG | SEQ ID NO: 244 |
| Syn-For-rA-iC3-D4 | 5'-AGCTCTGCCCAAAGATTA CCCTGaCAGC(SpC3-SpC3)AGTG | SEQ ID NO: 245 |
| Syn-For-rA-iC3-D5 | 5'-AGCTCTGCCCAAAGATTA CCCTGaCAGC(SpC3-SpC3)AGTGG | SEQ ID NO: 246 |

DNA bases are shown in uppercase. RNA bases are shown in lowercase.
SpC3 is a Spacer C3 group, positioned either internal within the primer or at the 3'-end.

A newly synthesized 103mer oligonucleotide template was made which was complementary to the Syn-For primers above (SEQ ID NO: 251), which is shown below with the unmodified and various modified cleavable For primers aligned above. DNA bases are uppercase, RNA bases are lowercase, and "x" indicates a Spacer-C3 group.

```
5'AGCTCTGCCCAAAGATTACCCTG                      SEQ ID NO: 68  unmodified

5'AGCTCTGCCCAAAGATTACCCTGaCAGC-x               SEQ ID NO: 242 3'-block

5'AGCTCTGCCCAAAGATTACCCTGaCAGCxxA              SEQ ID NO: 243 Int D1

5'AGCTCTGCCCAAAGATTACCCTGaCAGCxxAG             SEQ ID NO: 244 Int D2

5'AGCTCTGCCCAAAGATTACCCTGaCAGCxxAGTG           SEQ ID NO: 245 Int D4

5'AGCTCTGCCCAAAGATTACCCTGaCAGCxxAGTGG          SEQ ID NO: 246 Int D5
  ||||||||||||||||||||||||||||  |||||
3'TCGAGACGGGTTTCTAATGGGACTGTCGATTCACCGTCACCTTCAACCGGAGTCTTCATCACCGGTC

GACACACAGCCCCTTGTCATTTCCGTACTTCGAGTC-5'
```

Figure 34:
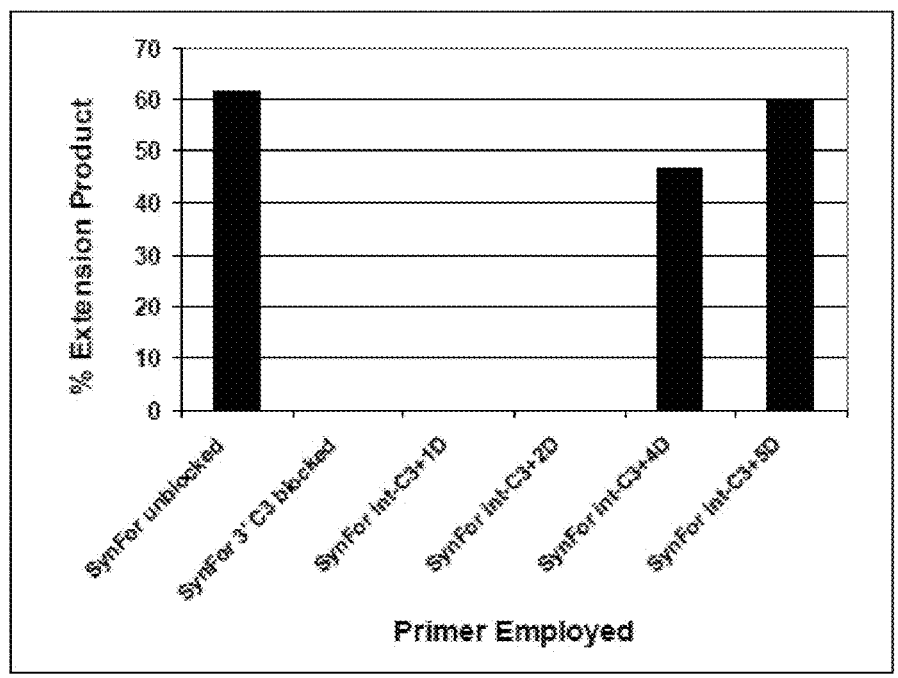
FIG. 34 is a graph that shows the relative functional activity of different oligonucleotide compositions to prime DNA synthesis in a linear primer extension reaction.

The six For primers shown above were radiolabeled with $^{32}$P as described above. Primer extension reactions were performed in a 20 µL volume using 0.8 U iTaq polymerase (Bio-Rad), 800 µM dNTPs, 3 mM MgCl$_2$, in 1× iTaq buffer (20 mM Tris pH 8.4, 50 mM KCl) and 2 nM primer and template (40 fmole of each oligonucleotide in the 20 µL reaction). Reactions were started with an incubation at 95° C. for 5 minutes followed by 35 cycles of [95° C. for 10 seconds, 60° C. for 30 seconds, and 72° C. for 1 second] on an MJ Research PTC-100 thermal cycler. Reactions were stopped with the addition of cold EDTA containing formamide gel loading buffer. Reaction products were separated using denaturing 7M urea, 15% polyacrylamide gel electrophoresis (PAGE) and visualized using a Packard Cyclone™ Storage Phosphor System (phosphorimager). The relative intensity of each band was quantified as above and results plotted as a fraction of total radioactive material present in the band representing the primer extension product. Results are shown in FIG. 34.

Under these reaction conditions, 61% of the control unblocked primer (SEQ ID NO: 68) was converted into a higher molecular weight primer extension product. As expected, the 3'-end blocked cleavable primer (SEQ ID NO: 242) did not show any primer extension product. Similarly, the D1 and D2 cleavable primers with internal C3 groups and a 3'-hydroxyl (SEQ ID NOS: 243-244) also did not support primer extension. The cleavable primers having a slightly longer terminal DNA domains (the D4 and D5 sequences, SEQ ID NOS: 245-246) did support primer extension with the D4 showing 47% conversion and the D5 showing 60% conversion of the primer into an extension product, a reaction efficiency identical to the unmodified control primer. Thus when internal C3 spacers are placed very near the 3'-end both priming and template function are disrupted. When placed more than 4 residues from the 3'-end only template function is blocked.

Example 28—Use of Cleavable Primers with Internal Template Blocking Groups and a 3'-Hydroxyl to Improve Mismatch Discrimination Example 24 demonstrated that cleavage of an RNA-containing primer on the 3'-side of the RNA base by RNase H2 is an undesired event that can contribute to late arising false positive signals in a qPCR SNP discrimination assay. Example 25 demonstrated that modifications which confer nuclease resistance to this domain can improve SNP discrimination. The novel compositions described in examples 26 and 27 place internal C3 groups on the 3'-side of the cleavable ribonucleotide which disrupts template function of the primer in a domain that is removed by RNase H2 cleavage. This example demonstrates that positioning the C3 spacer groups close to the RNA base improves performance of the cleavable primer in SNP discrimination using a format that leaves the probe "unblocked", having an unmodified 3'-hydroxyl.

The following primers, as shown below in Table 63, were synthesized for the human SMAD7 gene similar to previous Examples. Primers were made specific for the "C" allele and were tested on both "C" allele and "T" allele genomic DNA targets.

TABLE 63

| Name | Sequence | SEQ ID NO: |
|---|---|---|
| rs4939827 Rev | 5'-CTCACTCTAAACCCCAGCATT | SEQ ID NO: 217 |
| rs4939827 For | 5'-CAGCCTCATCCAAAAGAGGAAA | SEQ ID NO: 230 |
| rs4939827 C-For-C3 | 5'-CAGCCTCATCCAAAAGAGG AAAcAGGA-SpC3 | SEQ ID NO: 231 |
| rs4939827 C-For-A(C3C3)A | 5'-CAGCCTCATCCAAAAGA GGAAAcA(SpC3-SpC3)A | SEQ ID NO: 252 |

DNA bases are shown in uppercase. RNA bases are shown in lowercase.
SpC3 is a Spacer C3 group, positioned either internal within the primer or at the 3'-end.

The SMAD7 amplicon sequence (SEQ ID NO: 220, "C" target) is shown below with the unmodified and two modified cleavable For primers aligned above it. DNA bases are uppercase, RNA bases are lowercase, and "x" indicates a Spacer-C3 group. The site of the rs4939827 C/T SNP is indicated with bold underline.

```
5'CAGCCTCATCCAAAAGAGGAAA                    SEQ ID NO: 230 unmodified

5'CAGCCTCATCCAAAAGAGGAAAcAGGA-x             SEQ ID NO: 231 3'-block

5'CAGCCTCATCCAAAAGAGGAAAcAxxA               SEQ ID NO: 252 Int-block
 ||||||||||||||||||||||| |
5'CAGCCTCATCCAAAAGAGGAAACAGGACCCCAGAGCTCCCTCAGACTCCTCAGGAAACACAGACAAT

GCTGGGGTTTAGAGTGAG-3'
```

The same primers are aligned with the mismatch SMAD7 amplicon sequence (SEQ ID NO: 221, "T" target).

```
5'CAGCCTCATCCAAAAGAGGAAA                    SEQ ID NO: 230 unmodified

5'CAGCCTCATCCAAAAGAGGAAAcAGGA-x             SEQ ID NO: 231 3'-block

5'CAGCCTCATCCAAAAGAGGAAAcAxxA               SEQ ID NO: 252 Int-block
 |||||||||||||||||||||||  |
5'CAGCCTCATCCAAAAGAGGAAATAGGACCCCAGAGCTCCCTCAGACTCCTCAGGAAACACAGACAAT

GCTGGGGTTTAGAGTGAG-3'
```

PCR reactions were performed in 10 µl volume using 200 nM of the individual For primers (SEQ ID NOS: 230-231, 247-250) and the unmodified Rev primer (SEQ ID NO: 217) in Bio-Rad SYBR Green master mix. Reactions were run with or without 2.6 mU of *Pyrococcus abyssi* RNase H2 on a Roche Lightcycler® 480 platform. Input target DNA was 2 ng of genomic DNA from human cell lines homozygous for the SMAD7 "C" and "T" alleles (Coreill 18562 and 18537). Reactions were started with an incubation at 95° C. for 5 minutes followed by 75 cycles of [95° C. for 10 seconds, 60° C. for 30 seconds, and 72° C. for 1 second]. Results of qPCR amplifications are shown in Table 64 below.

TABLE 64

Cp values of qPCR reactions comparing performance of cleavable primers having a 3'-blocking group vs. cleavable primers having internal template blocking groups in a SNP discrimination assay.

| | Unmodified Control SEQ ID NO: 230 | | | 3'-C3 Blocked SEQ ID NO: 231 | | | Int-C3, 3'-unblocked SEQ ID NO: 252 | | |
|---|---|---|---|---|---|---|---|---|---|
| | "C" Allele | "T" Allele | ΔCp | "C" Allele | "T" Allele | ΔCp | "C" Allele | "T" Allele | ΔCp |
| No RNaseH | 27.5 | 25.9 | — | >75 | >75 | — | >75 | >75 | — |
| 2.6 mU RNaseH | 27.3 | 26.1 | — | 27.8 | 37.8 | 10.0 | 41.8 | 68.4 | 26.6 |
| 10 mU RNaseH | 27.1 | 25.8 | — | 27.0 | 40.0 | 13.0 | 29.9 | 53.7 | 23.8 |
| 50 mU RNaseH | 27.1 | 26.0 | — | 27.0 | 28.5 | 1.5 | 27.6 | 53.3 | 25.7 |
| 200 mU RNaseH | 27.1 | 25.8 | — | 27.0 | 26.1 | — | 27.5 | 41.4 | 13.9 |

(ΔCp = Cp mismatch "T" − Cp match "C")

The unmodified primers are designed to be non-discriminatory and amplified both alleles with similar efficiency, producing a detectable signal at around 26-27 cycles. Both cleavable primers were dependent upon RNase H2 for function and did not produce any detectable signal for either allele in the absence of cleaving enzyme. Using low amounts of RNase H2 (2.6-10 mU), the 3'-blocked cleavable primer (SEQ ID NO: 231) produced detectable signal around cycle 27 for the match "C" allele and showed a delayed Cp of 38-40 cycles for the mismatch "T" allele (ΔCp of 10-13). Using higher amounts of RNase H2, specificity was lost and both alleles amplified with similar efficiency. The cleavable primer having two C3 spacers 3'- to the ribonucleotide (SEQ ID NO: 252) required higher levels of RNase H2 for efficient cleavage/priming and showed delayed Cp values even for the perfect match "C" allele using 2.6 and 10 mU of enzyme. It is not surprising that modifications of this kind near the RNA cleavable site require higher amounts of enzyme. Example 22 demonstrated that placing a 2'OMe modification adjacent to the ribonucleotide required 100 mU of RNase H2 to achieve full activity. Using higher amounts of enzyme resulted in efficient cleavage and positive signal was detected at ~27 cycles using 50 or 200 mU of RNase H2. Importantly, SNP discrimination was markedly improved using this primer design, with the ΔCp for the "T" allele being around 25 cycles using RNase H2 in the concentration range of 2.6-50 mU. Mismatch discrimination decreased when using 200 mU of the enzyme; however, SNP discrimination was still almost at a 14 cycle ΔCp. Optimal enzyme concentration was 50 mU, at which point priming efficiency was similar to unmodified primers and SNP discrimination showed a 25.7 cycle ΔCp.

Therefore the present cleavable primer design with two internal C3 spacer groups near the ribonucleotide and an unblocked 3'-hydroxyl, "RDxxD", showed significantly improved mismatch discrimination over the original primer design, "RDDDD-x" (where R=RNA base, D=DNA base, and x=C3 spacer). Related designs, such as "RDDxxD" or "RDxxDD", may show similarly improved function and small optimizations in design may be beneficial depending upon the precise sequence context of the SNP of interest. Utilizing chemical modifying groups like the C3 spacer that disrupt template function but leave the 3'-hydroxyl unmodified can enhance the specificity of cleavage at the ribonucleotide by RNase H2 and improve SNP discrimination.

Example 29—Use of RNase H2-Cleavable Ligation Probes in DNA Sequencing Methods

The previous Examples described the use of RNase H2 cleavable oligonucleotide compositions for applications as primers where the cleavable oligonucleotide primes a DNA synthesis reaction. Applications disclosed in the above Examples include both end-point and real time PCR in several different detection formats. Example 8 showed use of cleavable primers in a DNA sequencing application using the Sanger sequencing method with DNA polymerase and dideoxynucleotide terminators; in this case the RNase H2-cleavable oligonucleotide also functioned as a primer. RNase H2-cleavable oligonucleotides can also be used in ligation format assays as well. One such application is DNA sequencing using cleavable ligation probes. The current Example demonstrates use of RNase H2-cleavable ligation probes in a format suitable for use in DNA sequencing.

The use of ligation probes to sequentially interrogate the identity of bases in an unknown nucleic acid sequence (i.e., DNA sequencing) has been described (see U.S. Pat. No. 5,750,341 and U.S. Pat. No. 6,306,597 and US application 2008/0003571). The basic scheme for sequencing in the 5' to 3' direction by ligation begins with a nucleic acid acceptor molecule hybridized to an unknown nucleic acid sequence. A series of base interrogation probes are hybridized to this sequence which have a known fixed DNA base at the 5'-end followed by random bases or universal bases to permit stable nucleic acid hybridization of the probe to the target nucleic acid of unknown sequence. Hybridization and subsequent ligation reactions are dependent upon perfect or near perfect match between the ligation probe and the target; perfect match is required at the site of ligation. Ligation leads to a detectable event which permits identification of the specific base present at the ligation site. An RNase H2 cleavable site is contained within the ligation probe. Following ligation the probe is cleaved by RNase H2, releasing the bulk of the probe but leaving the newly identified base ligated to the acceptor nucleic acid sequence, which has now been elongated by one residue as a result of the cycle of ligation and cleavage. This series of enzymatic and chemical events is repeated through multiple cycles of ligation, base identification, and cleavage and the unknown nucleic acid sequence is thereby determined.

While the patent references cited above teach methods for sequencing by ligation, the methods suggested therein to achieve cleavage and release of the ligation probe permitting multiple cycles of ligation/detection are inefficient and difficult to perform. RNase H2-cleavable oligonucleotides using the methods of the present invention offer an improvement over pre-existing method and permit construction of less costly, easier to use cleavable ligation probes for DNA sequencing. One scheme for DNA sequencing using RNase H2 cleavable ligation probes is shown in FIG. 35.

The RNase H2 cleavable ligation probes in this method contain a fixed known DNA base (or bases) at the 5'-end. The fixed known base(s) can be the single 5'-most base or can include 2 or 3 or more bases towards the 5'-end. The present Example employs a system wherein only the single DNA base at the 5'-end of the probe is fixed. The synthetic oligonucleotide has a 5'-phosphate to permit enzymatic ligation using a DNA ligase. An activated adenylated form of the probe can also be used. As mentioned, the first base at the 5'-end is fixed (known). Thus four independent probes are needed to perform DNA sequencing, an "A" probe, a "C" probe, a "T" probe, and a "G" probe. Obviously more probes will be needed if the number of fixed bases are greater than one (for example, 16 ligation probes will be needed if the first 2 bases are used as fixed known sequence, one for each possible dinucleotide pair). The first base following the fixed known DNA residue (in this case, the second base from the 5'-end) is a residue which is cleavable by RNase H2. In the present Example, an RNA base is employed, however a 2'-F residue or other cleavable modified base (such as are described in previous Examples) can also be used. The remaining bases in the probe will be random bases (heterogeneous mixes of the 4 DNA bases) and/or universal bases (such as inosine, 5-nitroindole, or other such groups as are well known to those with skill in the art). Total length of the probe will usually be around 8-9 bases, however longer or shorter probe length is possible depending on the particular ligase enzyme employed. When using T4 DNA ligase, a length of 8 is sufficient to achieve efficient hybridization and enzymatic ligation. Longer probes can also be used.

Complexity of the probe population increases according to $4^N$, where N=the number of random bases employed. For example, the probe "pTn" has a fixed "T" base at the 5'-end, a single "n" RNA base, and 6 "N" DNA bases, totaling 7 random residues (p=phosphate, n=RNA, N=DNA). This presents a complexity of $4^7$ molecules (16,384) in the population. The complexity of the probe can be decreased by substituting universal base groups for random N bases. This is particularly effective towards the 3'-end. For example, using 3 inosine residues would convert the above probe to "pTnNNNIII" (as before, with I=inosine). This probe has a complexity of $4^4$ molecules (256). It will require a significantly lower mass input of ligation probe to achieve 100% ligation with a probe having a complexity of 256 than one having a complexity of 16,384. Use of one or more universal bases is generally preferred. Finally, the ligation probe has a dye molecule at or near the 3'-end to provide a detectable signal that can be resolved following ligation. The 3'-modifying group also serves to block ligation at the 3'-end so that the ligation probe itself cannot serve as an acceptor nucleic acid.

Figure 35:
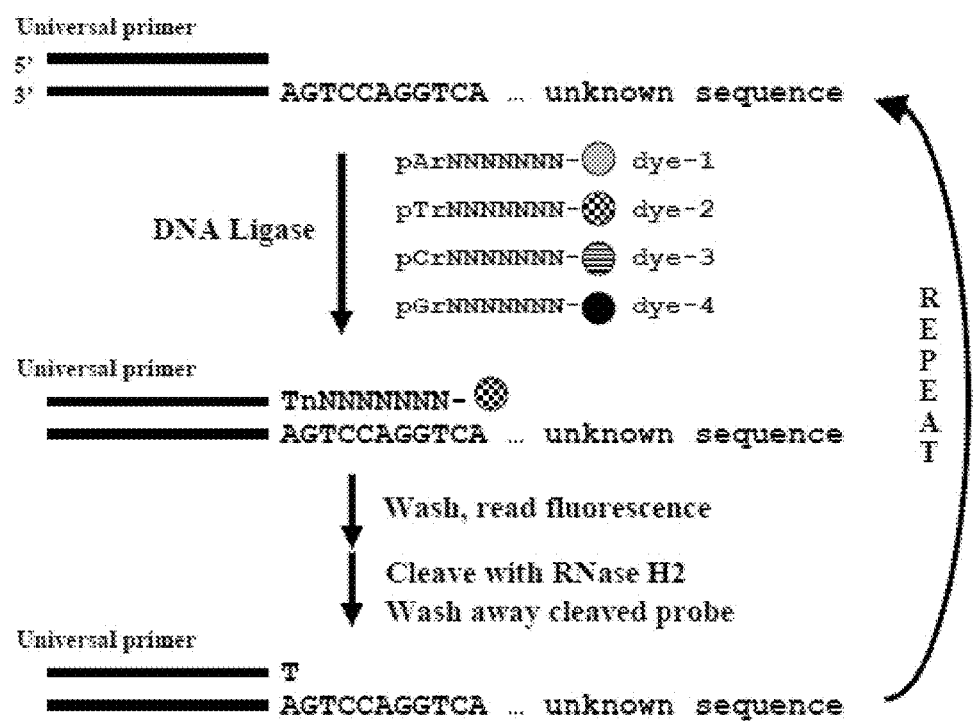
FIG. 35 shows the scheme for performing cycles of DNA sequencing by ligation using RNase H2 cleavable ligation probes FIG. 35 discloses the "3'-AGTCCAGGTCA" sequence as SEQ ID NO: 304.

Use of RNase H2 cleavable ligation probes of this design in DNA sequencing is shown schematically in FIG. 35. A universal primer or acceptor nucleic acid is hybridized to the unknown nucleic acid. Attachment of a universal adaptor sequence on the end of the unknown sequence may be required to permit hybridization of the acceptor molecule, and this strategy permits use of the same acceptor nucleic acid for all reactions. The acceptor nucleic acid must have a 3'-hydroxyl group available for ligation. The mix of ligation probes is introduced into the reaction in molar excess (>256 fold excess for the 8mer inosine containing probe design described above) and T4 DNA ligase is used to perform enzymatic ligation. Free probe is removed by washing and retained fluorescent signal is measured. The color of the dye retained identifies which probe (A vs. G vs. C vs. T) was attached during the ligation reaction. RNase H2 is then used to cleave the probe, removing the "N" bases and universal bases but leaving the known base attached to the acceptor nucleic acid. In this manner the identity of the corresponding base within the template is determined, the acceptor nucleic acid has been extended by one base, and an accessible 3'-hydroxyl is once again available for ligation, permitting cycling of the process.

The following oligonucleotides shown below in Table 65, were made as a representative synthetic system to demonstrate ligation and subsequent cleavage of RNA-containing fluorescent ligation probes using the methods of the present invention. The ligation probes here have a fixed 9 base sequence (without any "N" bases or universal base modifications). The designation "CLP" indicates "cleavable ligation probe". The designation "ANA" indicates an "acceptor nucleic acid" which provides the 3'-hydroxyl acceptor site for a ligation reaction. "Targ-A" is a target nucleic acid, which directs a ligation reaction involving the complementary "T" ligation probe ("CLP-T-Cy3"). "Targ-T" is a target nucleic acid, which directs a ligation reaction involving the complementary "A" ligation probe ("CLP-A-FAM").

TABLE 65

| CLP-C-TR | 5'-pCaGCTGAAG-TR | SEQ ID NO: 253 |
|---|---|---|
| CLP-G-Cy5 | 5'-pGaGCTGAAG-Cy5 | SEQ ID NO: 254 |
| CLP-A-FAM | 5'-pAaGCTGAAG-FAM | SEQ ID NO: 255 |
| CLP-T-Cy3 | 5'-pTaGCTGAAG-Cy3 | SEQ ID NO: 256 |
| ANA | 5'-CCCTGTTTGCTGTTTTTCCTTCTC | SEQ ID NO: 257 |
| Targ-A | 5'-AGTGTTTGCTCTTCAGCTAGAGAA GGAAAAACAGCAAACAGGG | SEQ ID NO: 258 |
| Targ-T | 5'-AGTGTTTGCTCTTCAGCTTGAAA GGAAAAACAGCAAACAGGG | SEQ ID NO: 259 |

DNA bases are shown in uppercase.
RNA bases are shown in lowercase.
"p" is 5'-phosphate.
TR is the fluorescent dye Texas Red.
Cy5 is the fluorescent dye Cyanine-5.
Cy3 is the fluorescent dye Cyanine-3.
FAM is the fluorescent dye 6-carboxyfluorescein.
The position of base variation between Targ-A and Targ-T is underlined, which is complementary to the 5'-base of the corresponding ligation probe.

Figure 36:
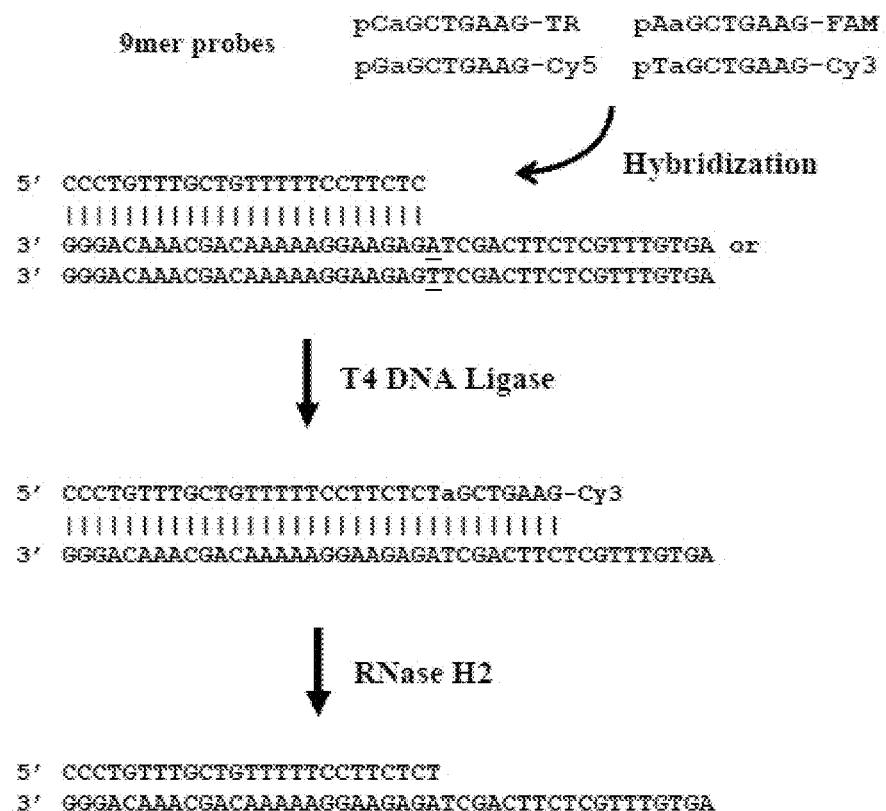
FIG. 36 shows the scheme for hybridization, ligation, and subsequent cleavage by RNase H2 of RNA-containing cleavable ligation probes of a set of specific exemplary synthetic sequences (SEQ ID NOS: 253, 255, 254, 256, 257-259, 305, 258, 306 and 258, respectively, in order of appearance).

FIG. 36 shows the predicted results for a ligation-cleavage reaction cycle using the synthetic oligonucleotide sequences shown above. "Targ-A" (SEQ ID NO: 258) will direct hybridization and ligation of the "CLP-T-Cy3" probe (SEQ ID NO: 256) while "Targ-T" (SEQ ID NO: 259) will direct hybridization and ligation of the "CLP-A-FAM" probe (SEQ ID NO: 255). Assuming that the reactions have high specificity, the remaining two ligation probes do not have a matching target in this experiment and so should not participate in the ligation reaction. Following ligation, the newly formed fusion of the "ANA"+"CLP" product will become a substrate for RNase H2. Cleavage by RNase H2 will result in release of the 3'-end of the ligation probe (including the RNA base and the fluorescent reporter dye), leaving the "ANA" molecule longer by one base.

The "T" target nucleic acid (SEQ ID NO: 259) or the "A" target nucleic acid (SEQ ID NO: 258) and the "ANA" acceptor nucleic acid (SEQ ID NO: 257) were mixed at 1.75 µM and all 4 ligation probes (SEQ ID NOS: 253-256) were added to a concentration of 3.5 µM (each) in T4 DNA Ligase buffer (50 mM Tris-HCl pH 7.5, 10 mM MgCl$_2$, 10 mM dithiothreitol, 1 mM ATP) in a volume of 80 µL, heated to 70° C. for 3 minutes and cooled slowly to 25° C. Ligation reactions were incubated at 37° C. for 5 minutes with or without 140 units of T4 DNA Ligase. The reactions were stopped by heating at 65° C. for 10 minutes. Reaction volumes were then adjusted to 200 µL with the addition of RNase H2 buffer [Tris-HCl pH 8.0 (final concentration 10 mM), NaCl (final concentration 50 mM), MgCl$_2$ (final concentration 4 mM)] and 20 units of RNase H2 was added to each tube. Reaction mixtures were incubated at 60° C. for 30 minutes, followed by desalting over a Sephadex G25 column, and the samples were lyophilized. Samples were rehydrated in 70 µL of water and 10 µL aliquots were analyzed on a 20% acrylamide, 7M urea, denaturing gel, followed by visualization using GelStar stain (#50535 GelStar Nucleic Acid Gel Stain, Lonza). The remainder of the reactions was saved at −20° C. for future testing, including mass spectrometry or other methods as needed.

Figure 37:
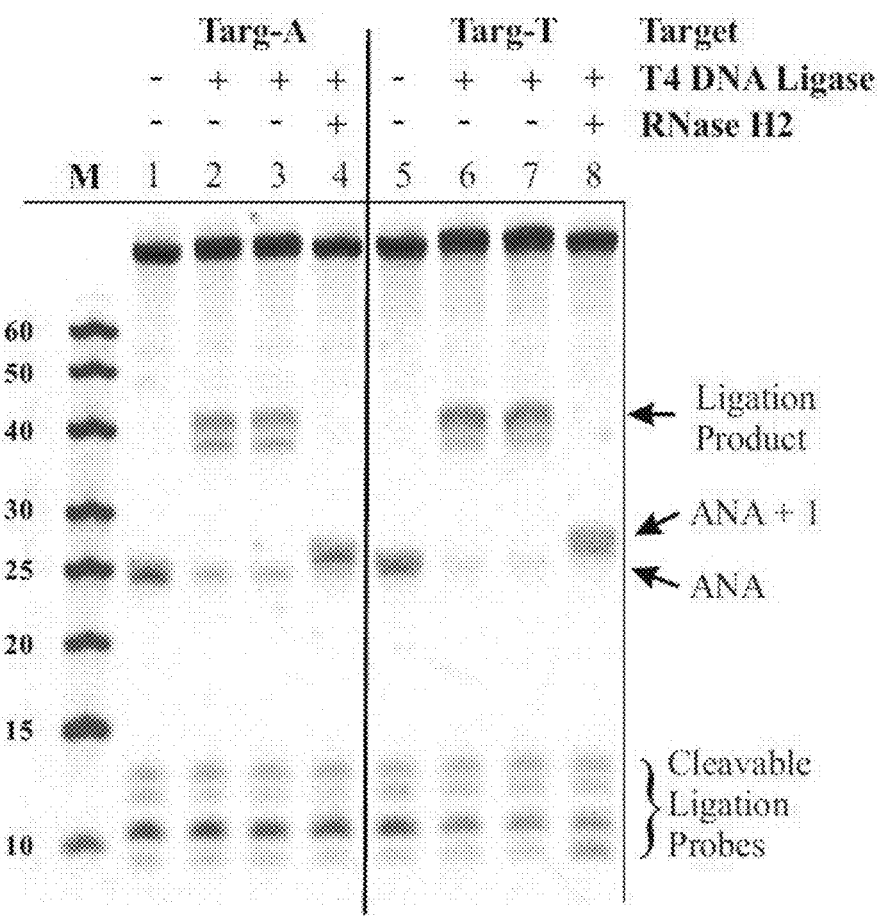
FIG. 37 shows a photograph of a polyacrylamide gel used to separate products from ligation reactions done using cleavable ligation probes on a synthetic template showing that the 9mer probes are efficiently ligated to the acceptor nucleic acid (ANA) and that the ligation product is efficiently cleaved by RNase H2, leaving an ANA species that is lengthened by one base. The nucleic acids were imaged using fluorescent staining and the image was inverted for clarity.

The gel image is shown in FIG. 37. Lanes 1 and 5 show the component oligonucleotides in the absence of enzymes to visualize migration relative to size markers (lane M). Lanes 2 and 3 are duplicate reactions where Targ-A (SEQ ID NO: 258) was incubated with the 4 cleavage ligation probes (SEQ ID NOS: 253-256) in the presence of T4 DNA Ligase. An upward size shift of the acceptor nucleic acid (ANA, SEQ ID NO: 257) is clearly seen which represents ligation with CLP-T-Cy3 (SEQ ID NO: 256) and is identified as the ligation product. Specific ligation with the correct CLP-T-Cy3 probe and not the other 3 probes (mismatched bases) occurred, which was verified by visual inspection of the color of the dye (this cannot be appreciated in the black and white image shown in FIG. 37) and was further verified by mass spectrometry. Similarly, lanes 7 and 8 are duplicate reactions where Targ-T (SEQ ID NO: 259) was incubated with the 4 cleavage ligation probes (SEQ ID NOS: 253-256) in the presence of T4 DNA Ligase. An upward size shift of the acceptor nucleic acid (ANA, SEQ ID NO: 257) is clearly seen which represents ligation with CLP-A-FAM (SEQ ID NO: 255) and is identified as the ligation product. Specific ligation with the correct CLP-A-FAM probe and not the other 3 probes (mismatched bases) occurred, which was verified again by visual inspection of the color of the dye and confirmed by mass spectrometry analysis. Finally, lanes 4 and 8 demonstrate that these ligation products are reduced in size when treated with RNase H2, indicating that cleavage occurred. Note that the resulting bands show slightly reduced mobility compared with the original ANA band, indicating that this new species is longer than the starting material. Mass spectrometry confirmed that actual mass of the reaction products in lanes 4 and 8 were consistent with the predicted 1-base elongation of the starting ANA nucleic acid, that the correct base was inserted, and that the new "ANA+1" species had a 3'-hydroxyl. The new ANA+1 species is now prepared for a second cycle of ligation/cleavage.

This example has therefore demonstrated that short RNA-containing short probes can be specifically ligated to an acceptor nucleic acid in the presence of a complementary target nucleic acid. Ligation is sensitive to the identify of the template base matching the 5'-terminal base of the ligation probe and specific ligation of the correct complementary probe can be detected from within a heterogeneous mix of different probe sequences. Finally, RNase H2 can cleave the ligation probe at the 5'-side of the RNA base, releasing the bulk of the probe, resulting in an acceptor nucleic acid molecule which has been extended by one base in length. The extended acceptor nucleic acid contains a 3'-hydroxyl and can be used in repeated cycles of ligation/cleavage.

Example 30—Use of Universal Bases in RNase H2-Cleavable Ligation Probes

In Example 29 above it was proposed that universal bases, such as 5'-nitroindole or inosine, could be used in cleavable ligation probes. The present example demonstrates use of the universal base 5-nitroindole in a model system where the probe sequence is fixed (does not contain random N-bases). The oligonucleotides, shown below in Table 66, were synthesized based upon the synthetic probe/template system in Example 29. Cleavage ligation probes were designed as 8mers with a 5'-phosphate, an "A" base at the 5'-end (to direct ligation to the "T" target), a single ribonucleotide, and 2 or 3 additional fixed DNA bases. Three or four 5-nitroindole bases were positioned towards the 3'-end. A FAM fluorescent dye was attached at the 3'-end. The same acceptor nucleic acid (ANA) and T-target nucleic acid were employed as in Example 29. A reaction scheme showing alignment of oligonucleotide components for this example is shown in FIG. 38.

TABLE 66

| CLP-A-FAM-3x5NI | 5'-pAaGCTXXX-FAM | SEQ ID NO: 260 |
|---|---|---|
| CLP-A-FAM-4x5NI | 5'-pAaGCXXXX-FAM | SEQ ID NO: 261 |
| ANA | 5'-CCCTGTTTGCTGTTTTCCTTCTC | SEQ ID NO: 257 |
| Targ-T | 5'-AGTGTTTGCTCTTCAGCTTGAG AAGGAAAAACAGCAAACAGGG | SEQ ID NO: 259 |

DNA bases are shown in uppercase.
RNA bases are shown in lowercase.
"p" is 5'-phosphate.
"X" is the universal base 5-nitroindole.
FAM is the fluorescent dye 6-carboxyfluorescein.
The position of base hybridization with the 5'-end of the ligation probe is underlined on the target.

Figure 39:
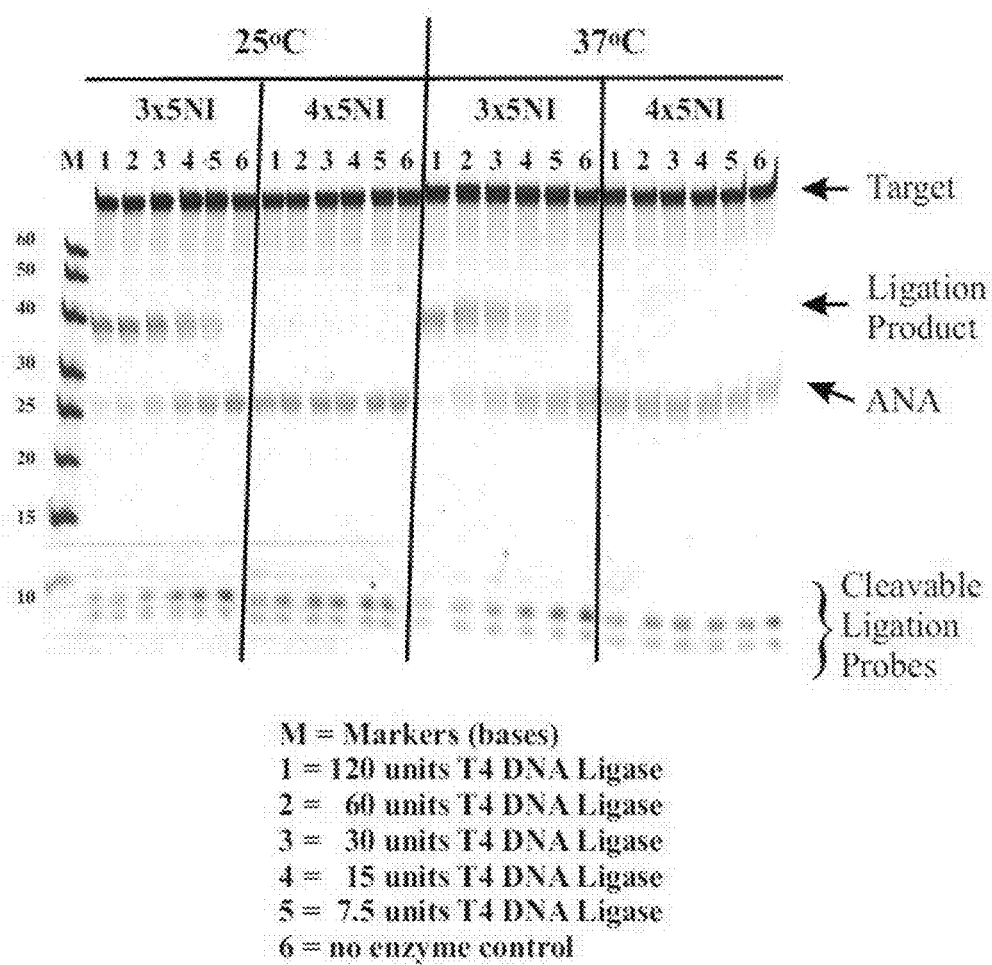
FIG. 39 shows a photograph of a polyacrylamide gel used to separate products from ligation reactions done using cleavable ligation probes on a synthetic template showing that an 8mer probe containing three 5-nitroindole (3×5NI) bases is efficiently ligated to an acceptor nucleic acid (ANA) whereas an 8mer probe containing four 5-nitroindole (4×5NI) bases is not. The nucleic acids were imaged using fluorescent staining and the image was inverted for clarity.

The "T" target nucleic acid (SEQ ID NO: 259) and the "ANA" acceptor nucleic acid (SEQ ID NO: 257) were mixed at 2 µM with the 3× or 4×5'-nitroindole containing CLPs (cleavable ligation probes, SEQ ID NOS: 260-261) in T4 DNA Ligase buffer (50 mM Tris-HCl pH 7.5, 10 mM MgCl$_2$, 10 mM dithiothreitol, 1 mM ATP). The reactions were heated at 70° C. for 5 minutes and cooled slowly to 25° C. T4 DNA Ligase (New England Biolabs) was added at a range of 7.5-120 units and the ligation reactions were incubated at 25 or 37° C. for 5 minutes. The reactions were terminated by the addition of EDTA to a final concentration of 50 mM. Final reaction volumes were 50 µL. An equal volume of 90% formamide, 1×TBE loading buffer was added to each sample, which were then heat denatured at 70° C. for 3 minutes and cooled on ice. Samples were separated on a denaturing 7M urea, 20% polyacrylamide gel. Gels were stained using GelStar' stain and visualized with UV excitation. The gel image is shown in FIG. 39.

The 8mer cleavable ligation probe with three 5-nitroindole universal bases (SEQ ID NO: 260) worked well and showed near 100% ligation efficiency using the higher enzyme amounts (60-120 units T4 DNA Ligase). In contrast, the 8mer cleavable ligation probe with four 5-nitroindole universal bases (SEQ ID NO: 261) did not ligate to the acceptor nucleic acid using any amount of enzyme. The same results were seen at 25° C. and at 37° C. suggesting that this difference in reactivity does not relate to difference in Tm of the two probes. It is more likely that the differential reactivity relates to substrate preferences for the T4 DNA Ligase enzyme. This Example demonstrates that three 5-nitroindole bases can be positioned at the 3'-end of an 8mer ligation probe and retain good function. This same experiment was repeated using 9mer ligation probes. In this case, a probe having "six DNA+three 5-nitroindole bases" and a probe having "five DNA+four 5-nitroindole bases" were both substrates for T4 DNA Ligase but a probe with "four DNA bases+five 5-nitroindole bases" did not (data not shown), consistent with the idea that T4 DNA Ligase requires 5 fixed DNA bases towards the 5'-end of the ligation probe to function well and that 5'-nitroindole bases can be introduced after this requirement is met. The precise optimal probe design can vary with different ligase enzymes.

These findings are significant as it permits synthesis of lower complexity pools of ligation probes.

Example 31—Use of Random Bases and Universal Bases in RNase H2-Cleavable Ligation Probes Examples 29 and 30 demonstrated use of RNase H2-cleavable ligation probes where some or all of the probe sequence was a perfect match to the target. In sequencing a nucleic acid of unknown sequence, it is necessary to use probes that contain primarily random bases so that probe hybridization can occur for any sequence encountered. The present Example demonstrates use of 8mer cleavable ligation probes having a random base (Nmer) domain, a universal base (5-nitroindole) domain and only a single fixed DNA base at the 5'-end. The following oligonucleotides shown in Table 67 were employed:

TABLE 67

| CLP-A-FAM<br>4N + 3x5NI | 5'-pAnNNNXXX-FAM | SEQ ID<br>NO: 262 |
|---|---|---|
| CLP-T-Cy3<br>4N + 3x5NI | 5'-pTnNNNXXX-Cy3 | SEQ ID<br>NO: 263 |
| CLP-G-Cy5<br>4N + 3x5NI | 5'-pGnNNNXXX-Cy5 | SEQ ID<br>NO: 264 |
| ANA | 5'-CCCTGTTTGCTGTTTTTCCTTCTC | SEQ ID<br>NO: 257 |

TABLE 67-continued

| Targ-T | 5'-AGTGTTTGCTCTTCAGCTTGAG<br>AAGGAAAAACAGCAAACAGGG | SEQ ID<br>NO: 259 |
|---|---|---|

DNA bases are shown in uppercase.
RNA bases are shown in lowercase.
"p" is 5'-phosphate.
"N" represents a random mix of the DNA bases A, G, C, and T.
"n" represents a random mix of the RNA bases A, C, G, and U.
"X" is the universal base 5-nitroindole.
FAM is the fluorescent dye 6-carboxyfluorescein. Cy5 is the fluorescent dye Cyanine-5.
Cy3 is the fluorescent dye Cyanine-3.
The position of base hybridization with the 5'-end of the ligation probe is underlined on the target.

Figure 40:
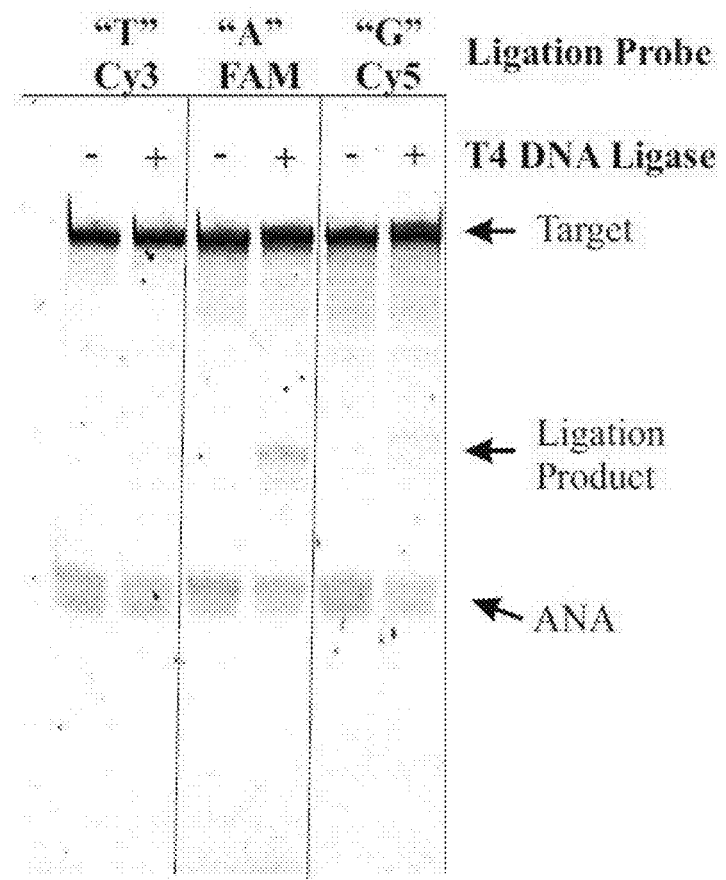
FIG. 40 shows a photograph of a polyacrylamide gel used to separate ligation products from reactions done using cleavable ligation probes on a synthetic template showing that an 8mer probe containing a single fixed DNA base at the 5'-end, four random bases, and 3 universal base 5-nitroindoles can specifically ligate to the target as directed by the single fixed DNA base.

The "T" target nucleic acid (SEQ ID NO: 259) and the "ANA" acceptor nucleic acid (SEQ ID NO: 257) were mixed together at a final concentration of 0.4 µM each and the three cleavable ligation probes (SEQ ID NOS: 262-264) were individually added at a final concentration of 50 µM (125-fold excess over the target and acceptor) in T4 DNA Ligase buffer in a final reaction volume of 50 µL. Reactions were heated to 70° C. for 5 minutes and cooled slowly to 25° C. T4 DNA Ligase was added (400 U) and the ligation reactions were incubated at 37° C. for 30 minutes. The reactions were stopped by heating at 65° C. for 10 minutes followed by desalting over a Sephadex G25 column, after which the samples were lyophilized and rehydrated in 10 µL of water mixed with 10 µL of 90% formamide, 1×TBE loading buffer. Samples were heat denatured at 70° C. for 3 minutes and cooled on ice. Reaction products were separated on a 20% acrylamide 7M urea denaturing gel, followed by visualization using Gel Star stain with UV transillumination (50535 GelStar Nucleic Acid Gel Stain, Lonza). Results are shown in FIG. 40.

The target nucleic acid contained a "T" base at the site complementary to the point of ligation. This template correctly directed ligation of the "A-FAM" ligation probe (SEQ ID NO: 262) but not the mismatch "T-Cy3" (SEQ ID NO: 263) or "G-Cy5" (SEQ ID NO: 264) ligation probes. Ligation specificity was directed by a single fixed DNA base at the 5'-end of the ligation probes which otherwise comprised random "N" bases or universal 5-nitroindole bases. The ligation probes were added to the ligation reactions at 125-fold molar excess over the target and the acceptor nucleic acids. The ligation probes contain a 4-base "N" domain, so the complexity of the nucleic acid mixture was 4$^4$ (256). Thus the reaction theoretically contained sufficient perfect matched probe to ligate with only about 50% of the input acceptor nucleic acid. It is evident from the relative fluorescent images in FIG. 40 that approximate half of the acceptor was present in the longer ligation product species and half was unreacted, indicating that the reaction proceeded as expected. If mismatched sequences ligated to the acceptor with any appreciable efficiency, then the 125-fold excess of ligation probe would most likely have reacted with >50% of the acceptor nucleic acid molecules, which was not observed. Thus ligation reactions using cleavable ligation probes of this design were both efficient and specific.

Example 32—Use of RNase H2-Cleavable Probes in an Oligonucleotide Ligation Assay (OLA)

Use of cleavable ligation probes in DNA sequencing represents just one potential format/application for this general class of assay. The sequencing application is unique in that the target nucleic acid is of unknown sequence. More typically, oligonucleotide ligation assays are employed to determine the presence or absence of a known nucleic acid sequence within a sample nucleic acid of interest. For example, an OLA can be employed to detect the presence of a nucleic acid sequence specific for pathogenic organisms in the background of human DNA. Another example would be to determine the presence or absence of a known, defined polymorphism at a specific target nucleic acid locus (e.g., an allelic discrimination assay or SNP assay). In all of these applications, one ligation probe is positioned so that the 3'-most or 5'-most base aligns with the SNP site and a second perfect-match nucleic acid is positioned adjacent so that if the probe sequence is a match for the SNP base, then a ligation event can occur. If the probe sequence is a mismatch for the SNP base, then ligation is inhibited. The ligation event results in formation of a detectable species.

An allelic discrimination (SNP) assay is shown in this Example to demonstrate utility of the novel RNase H2 cleavable ligation oligonucleotide probes of the present invention. Sequence designs shown herein place the SNP site towards the 3'-end of the acceptor ligation probe.

Figure 41B:
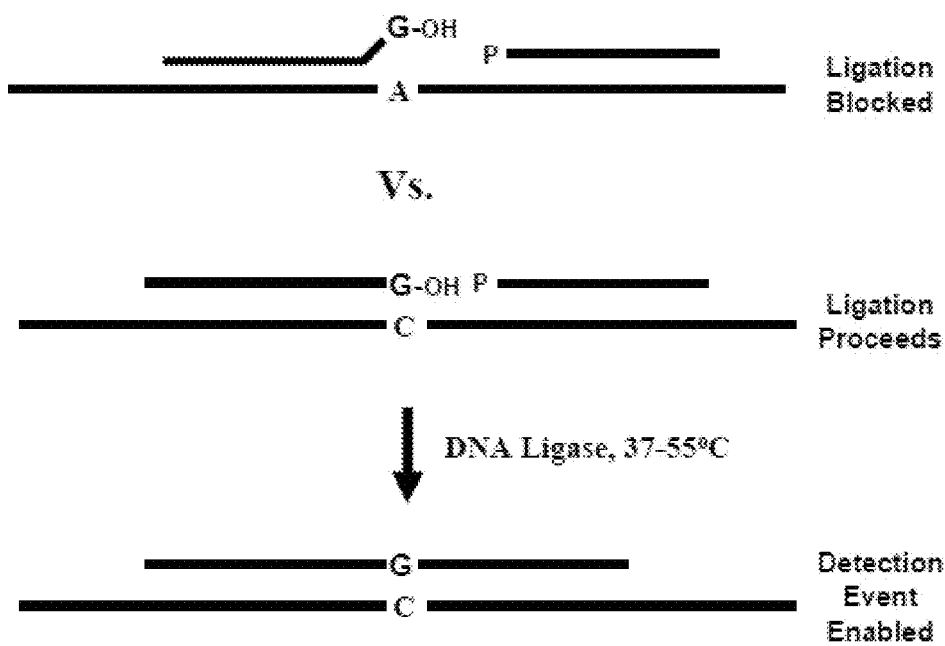
FIG. 41 shows the scheme for a traditional oligonucleotide ligation assay (OLA). Panel A shows the three oligonucleotides needed to interrogate a two allele target system. Panel B shows the steps involved in making a ligation product.

A traditional OLA employs three synthetic oligonucleotides to discriminate between two alleles (FIG. 41A). If the SNP site comprises a "C" allele and an "A" allele, then two acceptor oligonucleotides are required, one bearing a "G" base (match for the "C" allele) and one bearing a "T" base (match for the "A" allele). The acceptor oligonucleotides have a free 3'-hydroxyl group. A third oligonucleotide (a donor nucleic acid) is employed that hybridizes to the target so as to place its 5'-end adjacent to the 3'-end of the ligation probe. The acceptor nucleic acid will have a 5'-phosphate; generally the 3'-end of the donor oligonucleotide is blocked so that it cannot participate in a ligation reaction. In this way, perfect match hybridization of both a acceptor and the donor probes on the target will position the two oligonucleotides in a head-to-tail fashion that enables ligation between the 3'-hydroxyl of the acceptor with the 5'-phosphate of the donor (FIG. 41B). In contrast, a mismatch at the SNP site disrupts this structure and inhibits ligation. In the traditional OLA, the identity of the SNP base is interrogated once at the time of hybridization/ligation and specificity is entirely dependent upon the ability of the DNA Ligase to perform ligation on the perfect matched but not the mismatched species. Typically the three oligonucleotides (two ligation probes and the acceptor) have a similar Tm so that they can function together with the target nucleic acid under identical conditions.

The new RNase H2 OLA of the present invention employs four synthetic nucleic acids to discriminate between two alleles (FIG. 42A). If the SNP site comprises a "C" allele and an "A" allele, then two cleavable acceptor ligation probes are required in this embodiment, one bearing a "G" base (match for the "C" allele) and one bearing a "T" base (match for the "A" allele). The cleavable acceptor ligation probes have a single RNA base positioned towards the 3'-end of the molecule that is aligned to be complementary or not (match vs. mismatch) with the base at the target SNP site. Additional DNA bases are positioned 3'- to the RNA base (preferably four DNA bases, all being complementary to the target) and a blocking group is placed at the 3'-end to prevent ligation. The general design and function of the cleavable ligation probe is similar to the cleavable primers demonstrated in Example 13 in a qPCR format SNP discrimination assay. The cleavable ligation probes can also be designed using various chemically modified bases and abasic residues as outlined in the above Examples to improve SNP discrimination at the RNase H2 cleavage site (see Examples 22, 23, 25, and 28). Preferably the cleavable ligation probes will be designed to have a Tm in the range of 60-70° C. (in RNase H2 cleavage buffer) to permit hybridization of the cleavable probe with target in the optimal temperature range for the enzyme.

Unlike the traditional OLA format, the donor oligonucleotides in the RNase H2 OLA format are also SNP interrogation probes. Thus two donor probes are required, one bearing a "G" base (match for the "C" allele) and one bearing a "T" base (match for the "A" allele). Both donor or probes have a phosphate at the 5'-end to enable ligation and optionally are blocked at the 3'-end (FIG. 42A). The two donor ligation probes can have a lower Tm than the RNase H2 cleavable ligation probes so that hybridization of the cleavable ligation probes and the donor ligation probes with the target nucleic acid can be differentially regulated by control of reaction temperature. These donor probes in the assay format do not interact with RNase H2.

Figure 42B:
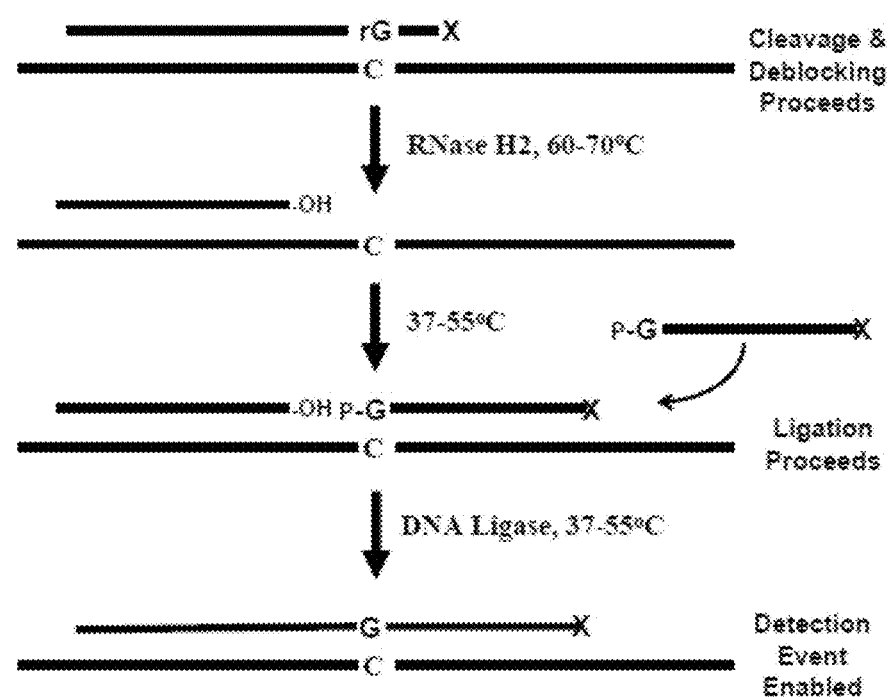
FIG. 42 shows the scheme for the RNase H2 cleavable oligonucleotide ligation assay (OLA) of the present invention. Panel A shows the four oligonucleotides needed to interrogate a two allele target system. Panel B shows the steps involved in making a ligation product using the RNase H2 method. Panel C illustrates how this method tests the identity of the base polymorphism twice.

To perform an RNase H2 OLA, all four OLA probes are mixed in the presence of the target nucleic acid in a buffer compatible with RNase H2 activity (see above examples). Preferably this will be done around 60-70° C. The RNase H2 cleavable acceptor oligonucleotide is complementary to and will hybridize to the target nucleic acid under these conditions. If the RNA base of the acceptor probe and the base at the target SNP site match, then RNase H2 cleavage can occur (FIG. 42B). It is preferred that the donor ligation probe (the non-cleavable probe) has a lower Tm than the cleavable probe. The first stage of the reaction (hybridization of the acceptor oligonucleotide and cleavage by RNase H2) can then be carried out at a temperature that is sufficiently above the Tm of the non-cleavable donor probes that they do not hybridize to target. Cleavage of the acceptor probe by RNase H2 removes the RNA base and uncovers the SNP site, making it available to hybridize with the non-cleavable ligation probe (the donor oligonucleotide).

Figure 42C:
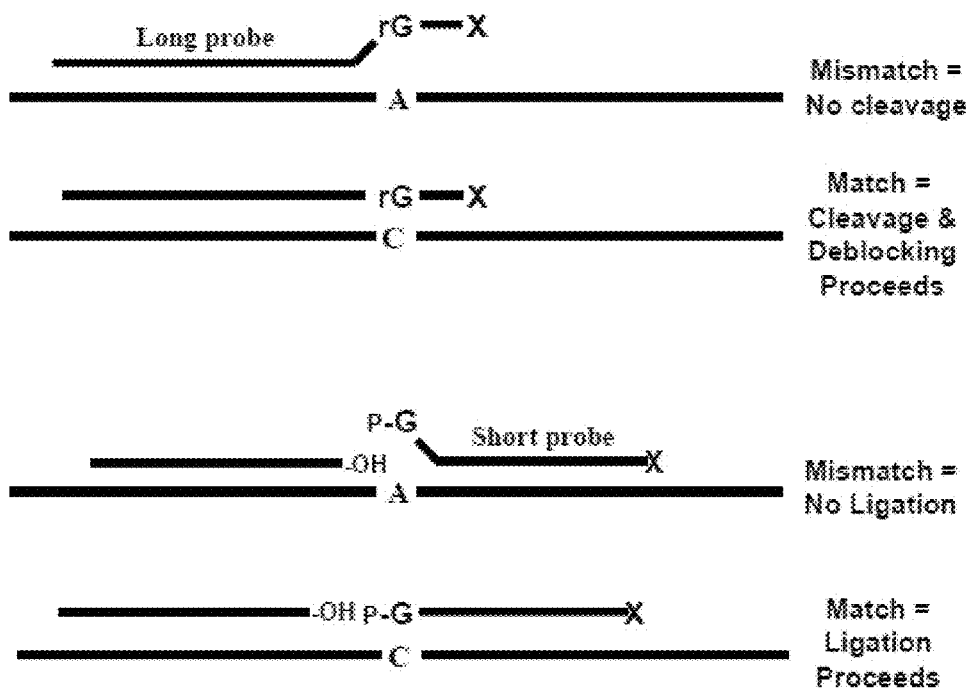

Once the RNase H2 cleavage phase of the OLA is complete, reaction temperature is lowered to permit hybridization of the non-cleavable ligation probe to the target. In the presence of DNA Ligase, the 5'-end of the non-cleavable probe will ligate to the 3'-end of the adjacent cleaved probe (FIG. 42B), if the base at the 5'-end of the donor probe pairs with the base at the SNP site. Thus the RNase H2 OLA assay interrogates the identity of the base at the SNP site twice, once during RNase H2 mediated cleavage of the acceptor oligonucleotide probe and again at the ligation reaction (FIG. 42C). Double interrogation of the identity of the SNP base by two different enzymatic events provides for greater specificity than can be achieved using a traditional OLA.

Example 33—SNP Discrimination Using RNase H2-Cleavable Probes in an OLA

A variety of methods exist that enable detection of OLA products. In the present Example, fluorescence detection is performed in a bead capture assay format to perform an RNase H2 OLA allelic discrimination assay as outlined in Example 32. Sequences were designed that were compatible for use with the Luminex xMAP fluorescent microbead system with detection on a Luminex L100 detection system (Luminex, Austin, Tex.).

Figure 43:
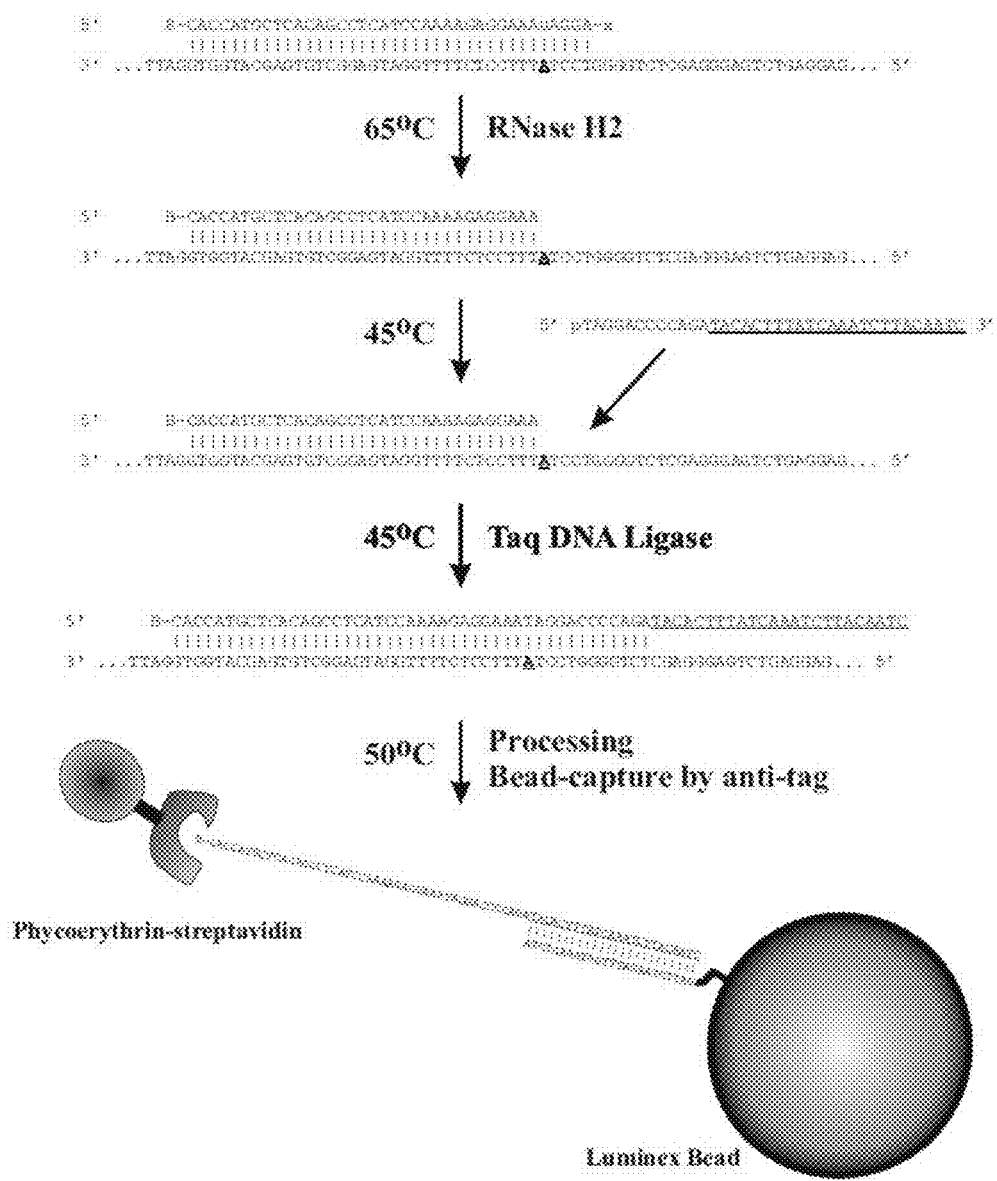
FIG. 43 shows alignment of sequences (SEQ ID NOS: 268, 309-310, 309, 300, 310, 309, 311, 309 and 311-312, respectively, in order of appearance) used in the present Example during each step of the RNase H2 cleavable probe OLA using fluorescence microbeads and a Luminex L100 system to detect the ligation products.

The "OLA-C-antitag" and "OLA-T-antitag" sequences (SEQ ID NOS: 265-266) were made with a 5'-amino modifier to permit conjugation to carboxylate xMAP fluorescent beads using carbodiimide coupling chemistry. The "OLA-T-Tag" and "OLA-C-Tag" sequences (SEQ ID NOS: 269-270) which serve as donor oligonucleotides in the ligation reaction have a 12-base sequence towards the 5'-end which is complementary to the target sequence and positions the SNP site (C/T base) at the 5'-end. Tm for these 12-base domains is estimated to be 50-53° C. (in 10 mM Mg$^{++}$ containing buffer). Both sequences have a 5'-phosphate to permit ligation. The 3'-end of these sequences is a "tag" sequence which is complementary to the "antitag" sequence and permits capture to antitag bearing beads by hybridization. The "OLA-C" and "OLA-T" probes (SEQ ID NOS: 267-268) serve as the acceptor fragment and are complementary to the target and position the single ribonucleotide base (rC or rU) at the SNP site. Tm for the cleavable ligation probes is estimated to be ~75° C. (in 10 mM Mg$^{++}$ containing buffer). Both of the oligonucleotide probes have a biotin at the 5'-end which will enable binding of a reporter dye, Streptavidin-phycoerythrin, for detection by the Luminex L100 system. Synthetic 98mer oligonucleotide targets corresponding to the "C" allele (G base in the target, SEQ ID NO: 271) and "T" allele (A base in the target, SEQ ID NO: 272) were employed in this Example. The sequences corresponding to SEQ ID NOS: 265-272 are shown below in Table 68. Alignment and interaction of the different probe, target, tag, and antitag sequences during the various step in this assay are shown in FIG. 43.

tersville, Ill.). Successful coupling was determined by hybridizing 25-250 fmoles of complementary oligonucleotides containing a 5' biotin modification and detecting the hybrids with 2 µg/mL streptavidin R-phycoerythrin conjugate (S866 1 mg/mL, Invitrogen, Carlsbad, Calif.). Mean fluorescence intensity had to increase in a concentration dependent manner. No cross hybridization was observed between the two anti-tag sequences.

OLA Assay.

RNase H2 digestion mixtures (10 µL) were prepared containing rs4939827 OLA C and rs4939827 OLA T oligos (SEQ ID NOS: 267-268) at a final concentration of 250 nM, and either C, T or C/T mix template oligonucleotides (SEQ ID NOS: 271-272) at 125 nM in a 20 mM Tris-HCl (pH 7.6 at 25° C.), 25 mM KAc, 10 mM MgAc, 10 mM DTT, 1 mM NAD, and 0.1% Triton X-100 buffer (Taq DNA Ligase buffer, New England Biolabs, Ipswitch, Mass.). Samples were incubated for 30 minutes at 65° C. with or without 5 mU of *Pyrococcus abyssi* RNase H2. For each RNase H2 digestion reaction, the volume was increased to 25 µL by adding 2.5 pmoles of rs4939827 OLA 12C Tag and 2.5 pmoles rs4939827 OLA 12T Tag oligonucleotides (SEQ ID NOS: 269-270) (100 nM final concentration for each oligo),

TABLE 68

| | | |
|---|---|---|
| OLA-C antitag | 5' aminoC12-GATTTGTATTGATTGAGATTAAAG | SEQ ID NO: 265 |
| OLA-T antitag | 5' aminoC12-GATTGTAAGATTTGATAAAGTGTA | SEQ ID NO: 266 |
| rs4939827 OLA C | 5' Biotin-CACCATGCTCACAGCCTCATCCAAAAGAGGAAAcAGGA-x | SEQ ID NO: 267 |
| rs4939827 OLA T | 5' Biotin-CACCATGCTCACAGCCTCATCCAAAAGAGGAAAuAGGA-x | SEQ ID NO: 268 |
| rs4939827 OLA C Tag | 5' pCAGGACCCCAGA<u>CTTTAATCTCAATCAATACAAATC</u>-x | SEQ ID NO: 269 |
| rs4939827 OLA T Tag | 5' pTAGGACCCCAGA<u>TACACTTTATCAAATCTTACAATC</u>-x | SEQ ID NO: 270 |
| Targ-C | 5' CCCAGCATTGTCTGTGTTTCCTGAGGAGTCTGAGGGAGCTCTGGGGTC CT<u>G</u>TTTCCTCTTTTGGATGAGGCTGTGAGCATGGTGGATTAGAGACAGCC | SEQ ID NO: 271 |
| Targ-T | 5' CCCAGCATTGTCTGTGTTTCCTGAGGAGTCTGAGGGAGCTCTGGGGTC CT<u>A</u>TTTCCTCTTTTGGATGAGGCTGTGAGCATGGTGGATTAGAGACAGCC | SEQ ID NO: 272 |

DNA bases are uppercase.
RNA bases are lowercase.
Biotin is a Biotin-TEG group.
X represents a C3 spacer.
For the OLA C/T Tag oligonucleotides, the portion of the sequence which is the "tag" and binds the "antitag" sequence is underline.
The site of the SNP with the target sequence under interrogation is underlined and in bold.

Coupling of Antitag Oligos to xMAP Microspheres.

Anti-tag oligonucleotides containing a 5' amino group were coupled to 1.25×10$^7$ xMAP Multi-Analyte COOH Microspheres (L100-C127-01 and L100-C138-01, Luminex, Austin, Tex.) using 3 mg/mL N-(3-Dimethylaminopropyl)-N'-ethylcarbodiimide hydrochloride (03449-1G, Sigma Aldrich), in 0.1 M MES, pH 4.5 buffer (M-8250 Sigma-Aldrich) at room temperature for 90 minutes in the dark (modified manufacturer's protocol). After coupling, the microspheres were washed once with 0.02% Tween20, and then once with 0.1% SDS. Microspheres were re-suspended in 200 µL of TE pH 7.5. The concentration of microspheres was determined by counting with a hemocytometer under a light microscope (Nikon TMS, Freyer Company, Carpenwith or without 40 U of Taq DNA Ligase (New England Biolabs, Ipswitch, Mass.), maintaining a final buffer composition of 20 mM Tris-HCl (pH 7.6 at 25° C.), 25 mM KAc, 10 mM MgAc, 10 mM DTT, 1 mM NAD, and 0.1% Triton X-100. The ligation reactions were incubated at 45° C. for 30 minutes.

Capture of Ligation Product on Fluorescent Beads and Detection of Signal.

10 µL of each ligation mixture was combined with 15 µL of H$_2$O, and 25 µL of the xMAP bead mixture (Bead sets 127 and 138) at a density of 100 beads of each type/µL. The samples were heated to 70° C. for 90 seconds followed by 50° C. for 30 minutes. The samples were transferred to a Millipore Multiscreen filtration plate (MABVN1250, Millipore, Bedford, Mass.), and washed two times with 100 µL of 50° C. 0.2 M NaCl, 0.1 M Tris pH 8.0, 0.08% Triton X-100 buffer. Microspheres were incubated at 50° C. for 15 minutes with 75 µL of a 2 µg/mL solution of streptavidin-R phycoerythrin (S866 1 mg/mL, Invitrogen, Carlsbad, Calif.). Mean fluorescence was measured on a Luminex L100 detection system (Luminex, Austin, Tex.).

Figure 44:
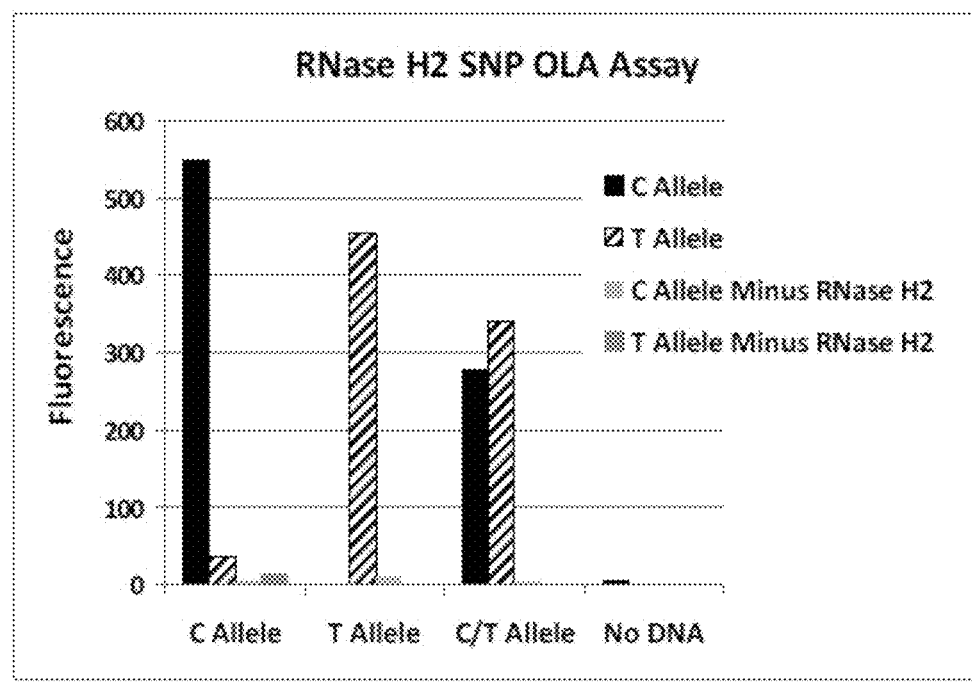
FIG. 44 is a chart that shows the resulting fluorescent signal detected by a Luminex L100 system to assess identity of the reaction products generated from the RNase H2 allelic discrimination OLA shown in FIG. 43.

Results are shown in FIG. 44. Fluorescent beads bearing the "C" allele antitag sequences showed positive fluorescent signal only when the reaction was run in the present of the "C" allele target or the "C/T" mix. Fluorescent beads bearing the "T" allele antitag sequences showed positive fluorescent signal only when the reaction was run in the present of the "T" allele target or the "C/T" mix. Signal was dependent on use of RNase H2 and was not observed in the absence of target DNA. Thus the RNase H2 cleavable oligonucleotide ligation assay of the invention was demonstrated to be effective at distinguishing the presence of a C/T SNP present in a target DNA in a highly specific fashion.

Example 34—Double-Interrogation of Mismatches Through the Use of Forward and Reverse Overlapping, Cleavable Primers with Internal Template Blocking Groups Example 28 demonstrated the utility of internal template blocking groups. The present example demonstrates the utility of combining overlapping forward and reverse cleavable primers with internal template blocking groups to improve mismatch discrimination.

Figure 45A:
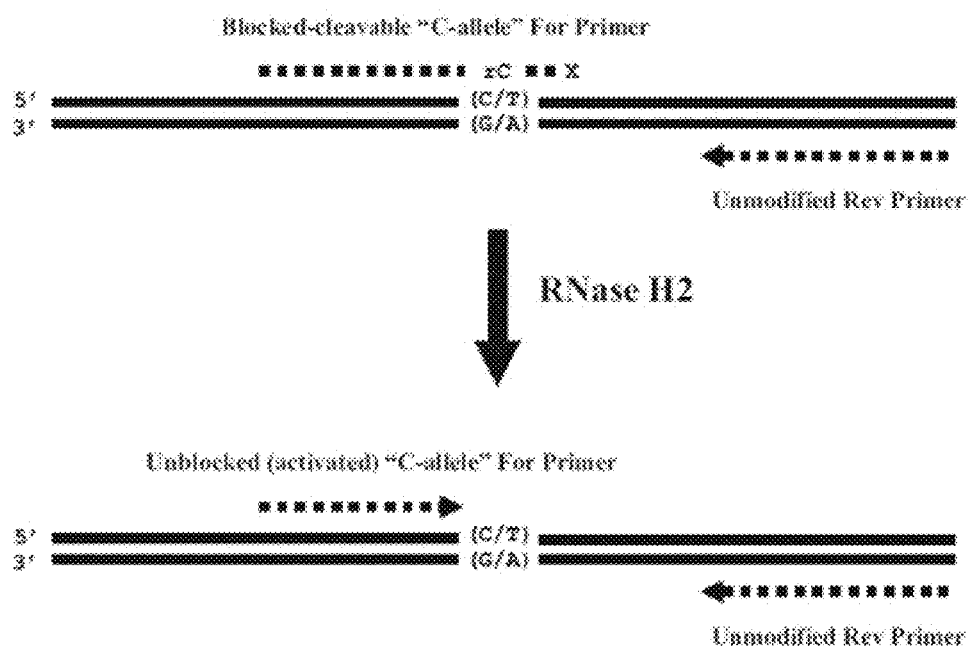
FIG. 45 is a set of schematic figures outlining the single blocked-cleavable primer approach for the "For" orientation is shown in FIG. 45A and for the "Rev" orientation in FIG. 45B.
FIG. 45C is a schematic outlining the dual blocked-cleavable primer approach.
Figure 45B:
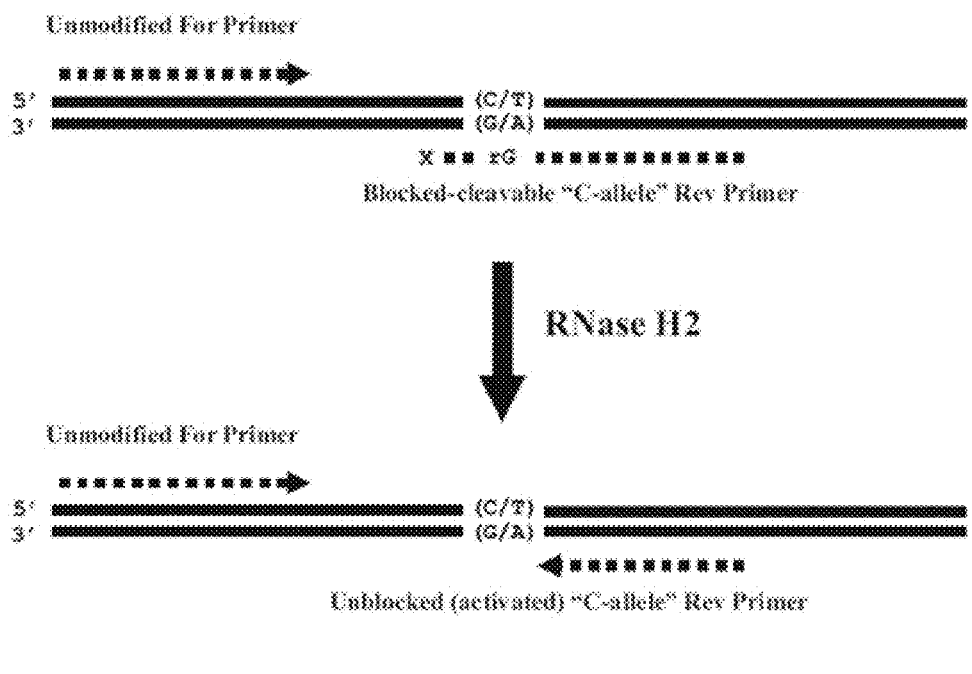
Figure 45C:
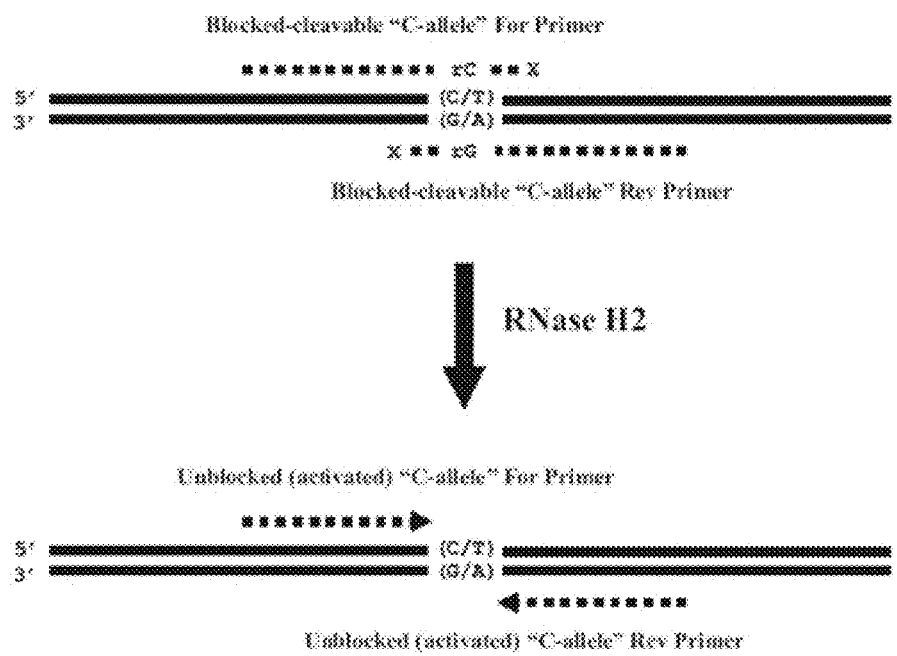

In previous examples, a single blocked-cleavable primer was employed to perform SNP interrogation using PCR with one blocked-cleavable primer positioned with the cleavable RNA residue at the SNP site paired with an unmodified primer. Blocked-cleavable primers can be designed complementary for either the top or bottom (sense or antisense) strand of a double-stranded DNA target. Thus two different SNP discrimination assays of this type can be made for every SNP. A schematic outlining the single blocked-cleavable primer approach for the "For" orientation is shown in FIG. 45a and for the "Rev" orientation in FIG. 45b. An alternative approach is to employ two blocked-cleavable primers which are both specific for the SNP under interrogation, one serving as the "forward" primer and one serving as the "reverse" primer. In this case, the 3'-ends of the two primers will overlap each other when in the inactive blocked state but will not overlap each other when activated following cleavage by RNase H2. A schematic outlining the dual blocked-cleavable primer approach is shown in FIG. 45c. The use of dual allele-specific blocked-cleavable primers will increase specificity of the reaction by providing interrogation for base identity at the SNP site twice for each cycle of PCR.

The following primers, as shown below in Table 69, were synthesized for the human SMAD7 gene similar to previous Examples. Primers were either non-specific and would amplify either allele with similar efficiency or were specific for either the "C" allele or the "T" allele. Primer sets were tested on both "C-allele" and "T-allele" genomic DNA targets.

TABLE 69

| Name | Sequence | SEQ ID NO: |
|---|---|---|
| rs4939827 Rev | 5'-CTCACTCTAAACCCCAGCATT | SEQ ID NO: 217 |
| rs4939827 For | 5'-CAGCCTCATCCAAAAGAGGAAA | SEQ ID NO: 230 |
| rs4939827 C-For-AGGA(C3) | 5'-CAGCCTCATCCAAAAGAGGAAAcAGGA-SpC3 | SEQ ID NO: 231 |
| rs4939827 T-For-AGGA(C3) | 5'-CAGCCTCATCCAAAAGAGGAAAuAGGA-SpC3 | SEQ ID NO: 235 |
| rs4939827 C-For-A(C3C3)A | 5'-CAGCCTCATCCAAAAGAGGAAAcA(SpC3-SpC3)A | SEQ ID NO: 252 |
| rs4939827 T-For-A(C3C3)A | 5'-CAGCCTCATCCAAAAGAGGAAAuA(SpC3-SpC3)A | SEQ ID NO: 273 |
| rs4939827 For v2 | 5'-GGCTGTCTCTAATCCACCAT | SEQ ID NO: 374 |
| rs4939827 Rev v2 | 5'-GAGGGAGCTCTGGGGTCCT | SEQ ID NO: 275 |
| rs4939827 C-Rev-AGGA(C3) | 5'-GAGGGAGCTCTGGGGTCCTgTTTC(SpC3) | SEQ ID NO: 276 |
| rs4939827 T-Rev-AGGA(C3) | 5'-GAGGGAGCTCTGGGGTCCTaTTTC(SpC3) | SEQ ID NO: 277 |
| rs4939827 C-For-A(C3C3)A | 5'-GAGGGAGCTCTGGGGTCCTgT(SpC3-SpC3)C | SEQ ID NO: 278 |
| rs4939827 T-For-A(C3C3)A | 5'-GAGGGAGCTCTGGGGTCCTaT(SpC3-SpC3)C | SEQ ID NO: 279 |

DNA bases are shown in uppercase.
RNA bases are shown in lowercase SpC3 is a Spacer C3 group, positioned either internal within the primer or at the 3'-end.

An 85 base pair SMAD7 amplicon sequence (SEQ ID NO: 280) is shown below. The site of the rs4939827 C/T SNP is indicated in parenthesis.

SEQ ID NO: 280
5'-GGCTGTCTCTAATCCACCATGCTCACAGCCTCATCCAAAAGAGGAAA (C/T)AGGACCCCAGAGCTCCCTCAGACTCCTCAGGAAACACAGACAATG

CTGGGGTTTAGAGTGAG-3'

The relative specificity of allelic discrimination assays using PCR with blocked-cleavable primers was tested in the context of the SMAD7 amplicon shown above. Assays were tested using a single blocked-cleavable primer in the "For" direction, a single blocked-cleavable primer in the "Rev" direction, or dual blocked-cleavable primers in both directions. Primer designs included the "RDDDD-x" and "RDxxD" variants as defined in Example 28 above. As a control, unmodified primers which were not allele-specific were also employed. The "For" orientation primers used are aligned with the SMAD7 target below.

```
SEQ ID NO: 273    5'    CAGCCTCATCCAAAAGAGGAAA u AxxA

SEQ ID NO: 252    5'    CAGCCTCATCCAAAAGAGGAAA c AxxA

SEQ ID NO: 235    5'    CAGCCTCATCCAAAAGAGGAAA u AGGAx

SEQ ID NO: 231    5'    CAGCCTCATCCAAAAGAGGAAA c AGGAx

SEQ ID NO: 230    5'    CAGCCTCATCCAAAAGAGGAAA
                        ::::::::::::::::::::::  :  :::::
5'-GGCTGTCTCTAATCCACCATGCTCACAGCCTCATCCAAAAGAGGAAA(C/T)AGGACCCCAGAGCT

CCCTCAGACTCCTCAGGAAACACAGACAATGCTGGGGTTTAGAGTGAG-3'
   ::::::::::::::::::::::::::
3'-                    TTACGACCCCAAATCTC'ACTC-5'   SEQ ID NO: 217
Where DNA bases are uppercase, RNA bases are lowercase, and "x" is a C3
spacer (propanediol).
```

PCR reactions were performed on a Roche Lightcycler® 480 platform in 10 μl volume using 200 nM of the modified or unmodified For primers (SEQ ID NOS: 230, 231, 235, 252, and 273) paired with the unmodified Rev primer (SEQ ID NO: 217) with 20 ng genomic DNA (Coriell GM07048 homozygous C/C allele or GM18976 homozygous T/T allele). Reactions were run in Bio-Rad SYBR Green master mix with 2.6 mU of *Pyrococcus abyssi* RNase H2 for the "RDDDD-x" primers (SEQ ID NOS: 231 and 235) or 200 mU of *Pyrococcus abyssi* RNase H2 for the "RDxxD" primers (SEQ ID NOS: 252 and 273). Reactions were started with a soak at 95° C. for 5 minutes followed by 45 cycles of [95° C. for 10 seconds and 60° C. for 30 seconds]. Results of qPCR amplifications done at this SNP site are shown in Table 70 below.

TABLE 70

Cp and ΔCp values of qPCR reactions showing mismatch discrimination at a SMAD7 C/T allele using a "For" orientation assay with a single blocked-cleavable primer.

| For Primer Employed | | C/C Target | T/T Target | ΔCp | No Template Control |
|---|---|---|---|---|---|
| SEQ ID NO: 230 | Unmodified control | 23.0 | 23.1 | — | >75 |
| SEQ ID NO: 235 | rU-DDDD-x | 33.4 | 23.4 | 10.0 | >75 |
| SEQ ID NO: 231 | rC-DDDD-x | 22.6 | 31.5 | 8.9 | >75 |
| SEQ ID NO: 273 | rU-DxxD | 47.6 | 23.4 | 24.2 | >75 |
| SEQ ID NO: 252 | rC-DxxD | 22.9 | 41.7 | 18.8 | >75 |

DNA samples homozygous C/C or T/T were readily distinguished using either the "RDDDD-x" or the "RDxxD" design primers, with the "RDxxD" version showing better separation of signal between match and mismatch (larger ΔCp values).

The allele discrimination experiment was next performed using the "Rev" oriented reactions. The "Rev" orientation primers used are aligned with the SMAD7 target below.

SEQ ID NO: 274

```
5'-GGCTGTCTCTAATCCACCAT
   ::::::::::::::::::::
5'-GGCTGTCTCTAATCCACCATGCTCACAGCCTCATCCAAAAGAGGAAA(C/T)AGGACCCCAGAGCT
                                              ::::  :  :::::::::::::
                                                      TCCTGGGGTCTCGA
                                            3'    xCTTT g TCCTGGGGTCTCGA
                                            3'    xCTTT a TCCTGGGGTCTCGA
                                            3'    CxxT g TCCTGGGGTCTCGA
                                            3'    CxxT a TCCTGGGGTCTCGA

CCCTCAGACTCCTCAGGAAACACAGACAATGCTGGGGTTTAGAGTGAG-3'
:::::
```

-continued

GGGAG-5'                              SEQ ID NO: 275

GGGAG-5'                              SEQ ID NO: 276

GGGAG-5'                              SEQ ID NO: 277

GGGAG-5'                              SEQ ID NO: 278

GGGAG-5'                              SEQ ID NO: 279

Where DNA bases are uppercase, RNA bases are lowercase, and "x" is a
C3 spacer (propanediol).

Where DNA bases are uppercase, RNA bases are lowercase, and "x" is a C3 spacer (propanediol).

PCR reactions were performed on a Roche Lightcycler® 480 platform in 10 µl volume using 200 nM of the modified or unmodified Rev primers (SEQ ID NOS: 275, 276, 277, 278, and 279) paired with the unmodified Rev primer (SEQ ID NO: 274) with 20 ng genomic DNA (Coriell GM07048 homozygous C/C allele or GM18976 homozygous T/T allele). Reactions were run in Bio-Rad SYBR Green master mix with 2.6 mU of *Pyrococcus abyssi* RNase H2 for the "RDDDD-x" primers (SEQ ID NOS: 276 and 277) or 50 mU of *Pyrococcus abyssi* RNase H2 for the "RDxxD" primers (SEQ ID NOS: 278 and 279). Reactions were started with a soak at 95° C. for 5 minutes followed by 45 cycles of [95° C. for 10 seconds and 60° C. for 30 seconds]. Results of qPCR amplifications done at this SNP site are shown in Table 71 below.

TABLE 71

Cp and ΔCp values of qPCR reactions showing mismatch discrimination at a SMAD7 C/T allele using a "Rev" orientation assay with a single blocked-cleavable primer.

| Rev Primer Employed | | C/C Target | T/T Target | ΔCp | No Template Control |
|---|---|---|---|---|---|
| SEQ ID NO: 275 | Unmodified control | 24.1 | 24.5 | — | >75 |
| SEQ ID NO: 277 | rA-DDDD-x | 38.0 | 24.4 | 13.6 | >75 |
| SEQ ID NO: 276 | rG-DDDD-x | 22.7 | 35.5 | 12.8 | >75 |
| SEQ ID NO: 279 | rA-DxxD | 42.2 | 25.8 | 16.4 | >75 |
| SEQ ID NO: 278 | rG-DxxD | 24.3 | 46.8 | 22.5 | >75 |

DNA samples homozygous C/C or T/T were readily distinguished using either the "RDDDD-x" or the "RDxxD" design primers, with the "RDxxD" version showing better separation of signal between match and mismatch (larger ΔCp values).

The experiment was next performed using the new dual interrogation "For+Rev" oriented reaction method. The primers used are aligned with the SMAD7 target below.

```
SEQ ID NO: 273  5'-CAGCCTCATCCAAAAGAGGAAA           u AxxA

SEQ ID NO: 252  5'-CAGCCTCATCCAAAAGAGGAAA           c AxxA

SEQ ID NO: 235  5'-CAGCCTCATCCAAAAGAGGAAA           u AGGAx

SEQ ID NO: 231  5'-CAGCCTCATCCAAAAGAGGAAA           c AGGAx

SEQ ID NO: 230  5'-CAGCCTCATCCAAAAGAGGAAA
                  ::::::::::::::::::::::    ::::::
        5'-TAATCCACCATGCTCACAGCCTCATCCAAAAGAGGAAA(C/T)AGGACCCCAGAGCTCCCTCA-3'
                                             :::::  :  ::::::::::::::::::
SEQ ID NO: 275                                          TCCTGGGGTCTCGAGGGAG-5'

SEQ ID NO: 276  3'                      xCTTT     g TCCTGGGGTCTCGAGGGAG-5'

SEQ ID NO: 277  3'                      xCTTT     a TCCTGGGGTCTCGAGGGAG-5'

SEQ ID NO: 278  3'                      CxxT      g TCCTGGGGTCTCGAGGGAG-5'

SEQ ID NO: 279  3'                      CxxT      a TCCTGGGGTCTCGAGGGAG-5'
Where DNA bases are uppercase, RNA bases are lowercase, and "x" is a C3
spacer (propanediol).
```

PCR reactions were performed on a Roche Lightcycler® 480 platform in 10 μl volume using 200 nM of the modified or unmodified For primers (SEQ ID NOS: 230, 231, 235, 252, and 273) paired with the modified or unmodified Rev primers (SEQ ID NOS: 294, 295, 296, 297, and 298) with 20 ng genomic DNA (Coriell GM07048 homozygous C/C allele or GM18976 homozygous T/T allele). Reactions were run in Bio-Rad SYBR Green master mix with 2.6 mU of *Pyrococcus abyssi* RNase H2 for the "RDDDD-x" primers (SEQ ID NOS: 231, 235, 276 and 277), 50 mU of *Pyrococcus abyssi* RNase H2 for the "RDxxD" "C-allele" primers (SEQ ID NOS: 252 and 276), or 200 mU of *Pyrococcus abyssi* RNase H2 for the "RDxxD" "T-allele" primers (SEQ ID NOS: 273 and 279). Reactions were started with a soak at 95° C. for 5 minutes followed by 45 or more cycles of [95° C. for 10 seconds and 60° C. for 30 seconds]. Reactions using the "RDDDD-x" primers were run for 45 cycles. Reactions using the "RDxxD" primers were run for 75 cycles. Results of qPCR amplifications done at this SNP site are shown in Table 72 below.

TABLE 72

Cp and ΔCp values of qPCR reactions showing mismatch discrimination at a SMAD7 C/T allele using a dual interrogation "For + Rev" orientation assay format with two blocked-cleavable primers.

| For Primer Employed | Rev Primer Employed | C/C Target | T/T Target | ΔCp | No Template Control |
|---|---|---|---|---|---|
| SEQ ID NO: 230 Unmodified control | SEQ ID NO: 275 Unmodified control | 24.1 | 23.9 | — | >45 |
| SEQ ID NO: 235 rU-DDDD-x | SEQ ID NO: 277 rA-DDDD-x | 32.0 | 24.2 | 7.8 | 31.1 |
| SEQ ID NO: 231 rC-DDDD-x | SEQ ID NO: 276 rG-DDDD-x | 24.1 | 28.2 | 4.1 | 28.8 |
| SEQ ID NO: 273 rU-DxxD | SEQ ID NO: 279 rA-DxxD | 24.9 | 58.3 | 33.4 | >75 |
| SEQ ID NO: 252 rC-DxxD | SEQ ID NO: 278 rG-DxxD | 25.9 | >75 | >49 | >75 |

The "dual interrogation" assays that employed "RDDDD-x" design blocked-cleavable primers (Table 72) showed reduced mismatch discrimination compared with the single interrogation assay format (Tables 70 and 71). Specificity was limited by background and these primer pairs showed amplification in the absence of template. A "dual interrogation" format has been used previously to increase the specificity of SNP interrogation in a PCR format using the "pyrophosphorolysis activated polymerization" (PAP) method (see Liu and Sommer, BioTechniques 36:156-166, 2004), which did not suffer from background issues. In the PAP format, the blocked For and Rev primers only overlapped by a single base at the 3'-end. The "RDDDD-x" primers overlap by 9 bases, as shown in the alignment below.

```
SEQ ID NO: 231  5'-CAGCCTCATCCAAAAGAGGAAAcAGGAx-3'
                                    ::::::::::
SEQ ID NO: 276  3'             xCTTTgTCCTGGGGTCTCGAGGGAG-5'
Where DNA bases are uppercase, RNA bases are lowercase, and "x"
is a C3 spacer (propanediol).
```

This amount of overlap apparently is sufficient to enable cleavage by RNase H2 of one or both of the blocked-cleavable primers as a "primer-dimer event". Following cleavage and activation of one of the blocked primers, a functional primer-dimer template is formed which could support PCR, as shown below.

```
SEQ ID NO: 230  5'-CAGCCTCATCCAAAAGAGGAAA →
                                     ::::
SEQ ID NO: 276      3'             xCTTTgTCCTGGGGTCTCGAGGGAG-5'
Where DNA bases are uppercase, RNA bases are lowercase, and "x" is a
C3 spacer (propanediol).
```

In contrast, the "dual interrogation" assays that employed "RDxxD" design blocked-cleavable primers (Table 72) showed significantly improved mismatch discrimination compared with the single interrogation assay format (Tables 70 and 71). This format allows for the additive effect from SNP discrimination from both the "For" and the "Rev" primers. Using this blocked-cleavable primer design format only 5 discontinuous bases of overlap exists between the "For" and "Rev" primers, which is insufficient to allow "primer-dimer events" to occur.

typically can only detect the mutant allele at levels of $10^{-1}$ to $10^{-2}$ relative to the wild type allele. Biased amplification methods, where the sequence of interest is selectively amplified relative to related sequences that may differ by as little as a single base, can greatly improve upon these results. The blocked-cleavable primers with RNase H2 cleavage as described herein offers a version of biased amplification that is useful in this application and permits detection of the rare allele at levels or $10^{-4}$ or lower, well within the range needed for utility in medical diagnostic applications.

```
SEQ ID NO: 252  5'-CAGCCTCATCCAAAAGAGGAAAcAxxA-3'
                   :   :::   :
SEQ ID NO: 278       3'          CxxTgTCCTGGGGTCTCGAGGGAG-5'
Where DNA bases are uppercase, RNA bases are lowercase, and "x"
is a C3 spacer (propanediol).
```

Therefore the present double cleavable primer design with two internal C3 spacer groups near the ribonucleotide and an unblocked 3'-hydroxyl, "RDxxD", showed even further improvement over the single forward blocked primer design. This new format should have particular utility in demanding applications such as rare allele detection assays.

Example 35—Improved Detection of a Mutant Allele in a Vast Excess of Wild-Type DNA Using Blocked-Cleavable Primers Previous examples demonstrated the utility of blocked-cleavable primers to discriminate between matched versus mismatched base pairing at the cleavable RNA residue. The present example demonstrates the utility of using this method to detect the presence of a rare mutant allele in the presence of a vast excess of wild-type DNA (rare allele detection).

The ability to detect rare allele(s) in the presence of a high background of the wild-type sequence is of growing importance in both medical diagnostics and basic research. These species may be present at levels of $10^{-2}$ to $10^{-5}$ or lower. With this type of target nucleic acid, unbiased amplification of all alleles present linked to a biased detection probe system does not offer sufficient sensitivity, and such methods Reactions were performed using a Lightcycler 480 in 10 µL 384-well format containing 0.4 U iTaq DNA polymerase, 1× iTaq reaction buffer, 0.01% Triton X-100, 3 mM $MgCl_2$, 800 µM dNTPs, and 200 nM forward and reverse primers. P.a. RNase H2 was added at different concentrations as indicated depending on the design of the primer. Detection was done using a 5'-nuclease assay with the dual-labeled probe (SEQ ID NO: 283) at a concentration of 200 nM. Sequences of the different primers employed and the probe are provided in Table 73 below. The dual-interrogation reactions were run under identical conditions except that BIO-RAD iQ SYBR™ Green Master Mix was employed without use of a 5'-nuclease probe oligonucleotide. Target nucleic acids were human genomic DNAs (GM18562 or GM18537) obtained from the Coriell Institute for Medical Research Cell Repository. Genomic DNA of one genotype was used as background at either 0 or 200 ng (~66,000 copies) and was mixed with genomic DNA of the second genotype at 2 ng (~600 copies), 0.2 ng (~60 copies), 0.02 ng (~6 copies), or 0 ng per reaction. Thermal cycling was performed using an initial 5 minute soak at 95° C. followed by 50 cycles of 10 seconds at 95° C. and 30 seconds at 60° C. Cp and ΔCp values were computed as described in previous example.

TABLE 73

Table 73. Sequeces of primers and probes employed in rare allele detection assays

| Name | Sequence | SEQ ID NO: |
|---|---|---|
| rs4939827 Rev | 5'-CTCACTCTAAACCCCAGCATT | SEQ ID NO: 217 |
| rs4939827 For | 5'-CAGCCTCATCCAAAAGAGGAAA | SEQ ID NO: 230 |
| rs4939827 "C" For | 5'-CAGCCTCATCCAAAAGAGGAAAC | SEQ ID NO: 281 |
| rs4939827 "T" For | 5'-CAGCCTCATCCAAAAGAGGAAAT | SEQ ID NO: 282 |
| rs4939827 C-For-AGGA(C3) | 5'-CAGCCTCATCCAAAAGAGGAAAcAGGA-SpC3 | SEQ ID NO: 231 |
| rs4939827 T-For-AGGA(C3) | 5'-CAGCCTCATCCAAAAGAGGAAAuAGGA-SpC3 | SEQ ID NO: 235 |
| rs4939827 C-For-A(C3C3)A | 5'-CAGCCTCATCCAAAAGAGGAAAcA(SpC3-SpC3)A | SEQ ID NO: 252 |

TABLE 73-continued

Table 73. Sequeces of primers and probes employed in rare allele detection assays

| Name | Sequence | SEQ ID NO: |
|---|---|---|
| rs4939827 T-For-A(C3C3)A | 5'-CAGCCTCATCCAAAAGAGGAAAuA(SpC3-SpC3)A | SEQ ID NO: 273 |
| rs4939827 C-Rev-A(C3C3)A | 5'-GAGGGAGCTCTGGGGTCCTgT(SpC3-SpC3)C | SEQ ID NO: 278 |
| rs4939827 T-Rev-A(C3C3)A | 5'-GAGGGAGCTCTGGGGTCCTaT(SpC3-SpC3)C | SEQ ID NO: 279 |
| rs4939827 probe | FAM-CTCAGGAAACACAGACAATGCTGGG-IBFQ | SEQ ID NO: 283 |

DNA bases are shown in uppercase.
RNA bases are shown in lowercase. SpC3 is a Spacer C3 group, positioned either internal within the primer or at the 3'-end.
FAM is 6-carbocyfluorescein and IBFQ is Iowa Black FQ, a dark fluorescence quencher.

Results are shown in Table 74. Use of the standard unmodified allele-specific primers (For SEQ ID NOS: 281 or 282 paired with Rev SEQ ID NO: 217) resulted in Cp detection values essentially identical to non-specific control primers (For SEQ ID NO: 230 with Rev SEQ ID NO: 217). The "RDDDDx" design primers (For SEQ ID NOS: 231 or 235 paired with Rev SEQ ID NO: 217) were able to detect a 1% level of both the "C" allele in a background of "T" allele and the "T" allele in a background of "C" allele with a 3 cycle detection threshold above background. The "RDxxD" design primers (For SEQ ID NOS: 252 or 273 paired with Rev SEQ ID NO: 217) gave superior results and detected the presence of 0.1% level of both the "C" allele in a background of "T" allele and the "T" allele in a background of "C" allele with a 6 cycle detection threshold above background; detection at a 0.01% level of the rare allele was achieved with a 3 cycle detection threshold above background. The bi-directional assay using "RDxxD" design primers (For SEQ ID NOS: 252 paired with Rev SEQ ID NO: 278 and For SEQ ID NOS: 273 paired with Rev SEQ ID NO: 279) performed at a similar stringency for the "T" allele and was significantly better for the "C" allele. In particular, the "C" allele bidirectional assay (For SEQ ID NOS: 252 paired with Rev SEQ ID NO: 278) showed a greater than 14 cycle detection threshold above background, so it is likely that this assay would be effective at even lower rare allele levels (0.001% or lower).

TABLE 74

Use of blocked-cleavable primers for rare allele detection.
Amplification reactions for the SMAD7 rs4939827 locus were run for 50 cycles using an internal non-discriminatory dual-labeled hydrolysis probe for detection with various primers as indicated (the 3'-end sequence is shown). P.a. RNase H2 was added at the amounts indicated per 10 µL. Human DNA that was a mismatch at the SNP site relative to the primers was either present at 0 or 200 ng (66,000 copies) per reaction; DNA that was a match at the SNP site relative to the primers was present at 2 ng (666 copies), 0.2 ng (66 copies), 0.02 ng (6 copies), or 0.0 ng per reaction. Reactions were run in triplicate and average Cp values are shown. The location of the mismatch in the primer compared to the target nucleic acid is underlined.

| | | Copies Mismatch/Match input human DNA | | | | | | | |
|---|---|---|---|---|---|---|---|---|---|
| 3'-Primer Sequences | mU RNase H2 | 0/ 666 | 0/ 66 | 0/ 6 | 0/ 0 | 66000/ 666 | 66000/ 66 | 66000/ 6 | 66000/ 0 |
| . . . AA | — | 28.7 | 32.2 | 35.9 | >50 | 21.1 | 21.1 | 21.2 | 21.0 |
| . . . AAC | — | 29.4 | 32.9 | 35.4 | >50 | 22.3 | 22.5 | 22.4 | 22.0 |
| . . . AAT | — | 28.5 | 31.6 | 35.7 | >50 | 21.4 | 21.5 | 21.5 | 21.6 |
| . . . AAcAGGA-x | 2.6 | 28.1 | 31.4 | 35.4 | >50 | 28.4 | 30.7 | 31.3 | 31.3 |
| . . . AAuAGGA-x | 20 | 28.1 | 31.3 | 35.7 | >50 | 27.9 | 30.4 | 31.1 | 31.2 |
| . . . AAcAxxA | 50 | 27.9 | 31.4 | 34.6 | >50 | 28.8 | 31.9 | 34.8 | 37.9 |
| . . . AAuAxxA | 400 | 28.2 | 31.9 | 36.1 | >50 | 28.9 | 32.4 | 36.3 | 39.0 |
| "rC/rG" di-primer | 100 | 28.7 | 32.8 | 35.6 | >50 | 28.1 | 32.1 | 35.5 | >50 |
| "rU/rA" di-primer | 400 | 29.6 | 33.0 | 36.7 | >50 | 28.6 | 31.7 | 35.7 | 38.5 |

A person of ordinary skill in the art can appreciate that the double interrogation of 3'-end primer constructs could be varied and still maintain the important functional requirement of preventing self-priming of the forward and reverse primers while still providing an adequate RNase H2 cleavage site. For example, one alternative construct can be "RxDDDD" wherein a spacer is placed next to the ribonucleotide and the ribonucleotide is directly over the mismatched site. In another embodiment, the forward and reverse primers can have different constructs. For example, the For primer can be a "RDxxD" construct while the Rev primer is "RxDDDD". In another embodiment, the mismatch can at a DNA base adjacent to the RNA base. For example, the primer can contain a "RDxxD" construct, wherein the mismatch is located at the underlined DNA base.

Example 36—Optimizing Magnesium Cation Levels can Improve Mismatch Discrimination The present example demonstrates that the mismatch discrimination of allele-specific PCR using blocked-cleavable primers with RNase H2 can be improved by varying concentrations of Mg$^{++}$ ions in the buffer.

It appreciated that varying magnesium levels in PCR buffers can affect the efficiency and specificity of the amplification reaction by effects on the polymerase and on the T$_m$ of primer binding. However, for rhPCR SNP discrimination is mediated by the RNase H2 enzyme and no information is known about how magnesium concentration affects specificity of match versus mismatch cleavage at the RNA base by this enzyme. Pyrococcus abyssi RNase H2 show a broad peak in enzyme activity from 2-10 mM Mg$^{++}$ ion concentration and activity dramatically drops as free Mg$^{++}$ concentration drops below 2 mM; the enzyme is at 50% maximal activity at 1 mM Mg$^{++}$. In rhPCR, dNTPs are typically present at 0.8 mM concentration, and each dNTP binds one molecule of Mg$^{++}$, removing it from availability in the reaction buffer. Thus a buffer that contains 3 mM Mg$^{++}$ with 0.8 mM dNTPs actually has 2.2 mM free Mg$^{++}$. This example examines the effect of varying Mg$^{++}$ ion concentration in rhPCR on reaction efficiency and quality of SNP discrimination.

In previous examples, PCR reactions employing blocked-cleavable primers were performed using 3 mM MgCl$_2$, a concentration which is commonly employed in qPCR to ensure a robust reaction. In the present example, we demonstrate that lowering magnesium levels can increase the specificity of the amplification reaction, as measured by the ΔCp between match vs. mismatch reactions in a SNP genotyping assay. When performing PCR, researchers typically employ either homemade buffers or buy a premade commercial mastermix. It is simple to adjust the magnesium concentration to be higher or lower in a homemade buffer. It is easy to increase the magnesium concentration in a premade buffer, but can be difficult to lower magnesium if the buffer comes with magnesium already added at a set concentration in the mixture. However, it is possible to lower magnesium in a premade mixture by adding nucleotide triphosphates (for example, rNTPs). The rNTPs will chelate a single molecule of magnesium for each nucleotide triphosphate, effectively reducing the concentration of free magnesium in the buffer. In the present example, we demonstrate improvement in PCR specificity using blocked-cleavable primers and RNase H2 by directly adjusting magnesium content of the buffer or by indirectly adjusting free magnesium content of the buffer by adding rNTPs to the reaction mix.

Method: Reduced Magnesium in a Premade Mastermix Having a Fixed MgCl$_2$ Concentration Using rNTPs to Chelate Free Magnesium.

Quantitative real-time PCR (qPCR) was performed with 20 ng of human genomic DNA (GM18562 or GM18537, Coriell Institute for Medical Research, Camden, N.J., USA) using primers specific for a SNP site in the human SMAD7 gene (rs4939827, NM_005904). DNA sample GM18562 is homozygous for the C allele at this locus and DNA sample GM18537 is homozygous for the T allele. Reactions used 1× iQ SYBR™ Green Supermix (Bio-Rad, Hercules, Calif., USA), which is a premade commercial mastermix containing 3 mM MgCl$_2$. Either 0, 5, 96, or 384 fmoles of P.a. RNase H2 (final concentration of 0, 0.5, 9.6, or 38.4 nM in a 10 μL reaction, which equals 0, 2.6, 50, or 200 mU of enzyme). 200 nM of each primer was employed. Control reactions employed unblocked Forward and Reverse primers, rs4939827 For (SEQ ID NO. 217) with rs4939827 Rev (SEQ ID NO. 230). Two different versions of blocked primers specific for each allele were used, either the RDDDDx (see Example 13) or RDxxD designs (see Example 28). Blocked-cleavable forward primers were used in combination with an unmodified reverse primer as follows: rs4939827 C-For RDDDDx (SEQ ID NO. 231) with rs4939827 Rev (SEQ ID #230), rs4939827 T-For RDDDDx (SEQ ID NO. 235) with rs4939827 Rev (SEQ ID #230), rs4939827 C-For RDxxD (SEQ ID NO. 252) with rs4939827 Rev (SEQ ID #230), rs4939827 T-For RDxxD (SEQ ID NO. 273) with rs4939827 Rev (SEQ ID #230). In addition, either 0.5 or 1 mM rATP (diluted in water) was added to some reactions. All oligonucleotides used in this Example are shown in Table 75. Cycling was performed on a Roche LightCycler® 480 (Roche Applied Science, Indianapolis, Ind., USA) as follows: 95° C. for 3 minutes followed by 75 cycles of 95° C. for 10 seconds and 60° C. for 30 seconds. All reactions were performed in triplicate. The initial 3 minute incubation at 95° C. before thermocycling commences allows for reactivation of the hot-start DNA polymerase.

TABLE 75

Synthetic oligonucleotide primers for rs4939827, SMAD7

| Name | Sequence | SEQ ID NO: |
|---|---|---|
| rs4939827 Rev | CTCACTCTAAACCCCAGCATT | SEQ ID NO: 217 |
| rs4939827 For | CAGCCTCATCCAAAAGAGGAAA | SEQ ID NO: 230 |
| rs4939827 C-For RDDDDx | CAGCCTCATCCAAAAGAGGAAA cAGGA-SpC3 | SEQ ID NO: 231 |
| rs4939827 T-For RDDDDx | CAGCCTCATCCAAAAGAGGAAA uAGGA-SpC3 | SEQ ID NO: 235 |
| rs4939827 C-For RDxxD | CAGCCTCATCCAAAAGAGGAAA cA(SpC3-SpC3)A | SEQ ID NO: 252 |
| rs4939827 T-For RDxxD | CAGCCTCATCCAAAAGAGGAAA uA(SpC3-SpC3)A | SEQ ID NO: 273 |

DNA bases are uppercase and RNA bases are lowercase;
SpC3 = C3 spacer (propanediol)

Results are shown in Table 76. Use of unmodified primers resulted in efficient amplification reactions and no difference was seen between reactions containing or not containing rATP or with or without P.a. RNase H2 enzyme. When amplification was performed in the presence of rATP, an increase in mismatch discrimination was observed (increase in ΔCp) that varied with the concentration of rATP present in the reaction for the RDxxD design primers but not the RDDDDx design primers. No amplification occurred when using blocked-cleavable primers if RNase H2 was not added to those reactions (not shown).

TABLE 76

Cp and ΔCp values seen in qPCR with addition of rATP to vary Mg++ concentration using various For primers with an unmodified Rev primer.

| For Primer | [RNase H2] | 0 mM rATP | | | 0.5 mM rATP | | | 1 mM rATP | | |
|---|---|---|---|---|---|---|---|---|---|---|
| | | CC | TT | ΔCp | CC | TT | ΔCp | CC | TT | ΔCp |
| rs4939827 For | 0 mU | 22.7 | 23.7 | — | 22.6 | 23.7 | — | 22.8 | 23.8 | — |
| rs4939827 For | 2.6 mU | 22.7 | 23.8 | — | 22.8 | 23.9 | — | 23.4 | 24.3 | — |
| rs4939827 C-For RDDDDx | 2.6 mU | 23.0 | 34.1 | 11.1 | 23.0 | 33.6 | 10.7 | 23.0 | 35.1 | 12.1 |
| rs4939827 T-For RDDDDx | 2.6 mU | 36.4 | 25.2 | 11.2 | 37.1 | 26.2 | 11.0 | 41.2 | 29.1 | 12.1 |
| rs4939827 C-For RDxxD | 50 mU | 22.8 | 45.5 | 22.7 | 22.9 | 56.2 | 33.4 | 23.3 | 67.4 | 44.1 |
| rs4939827 T-For RDxxD | 200 mU | 45.4 | 24.3 | 21.1 | 49.1 | 24.7 | 24.4 | 59.7 | 25.6 | 34.1 |

Method: reduced magnesium in a premade mastermix having a fixed MgCl$_2$ concentration using rNTPs to chelate free magnesium. Quantitative real-time PCR (qPCR) was performed with 20 ng of human genomic DNA (GM18562 or GM18537, Coriell Institute for Medical Research, Camden, N.J., USA) using primers specific for a SNP site in the human SMAD7 gene (rs4939827, NM_005904). DNA sample GM18562 is homozygous for the C allele at this locus and DNA sample GM18537 is homozygous for the T allele. Reactions used 1× iQ SYBR™ Green Supermix (Bio-Rad, Hercules, Calif., USA), which is a premade commercial mastermix containing 3 mM MgCl$_2$. Either 0, 5, 96, or 384 fmoles of P.a. RNase H2 (final concentration of 0, 0.5, 9.6, or 38.4 nM in a 10 μL reaction, which equals 0, 2.6, 50, or 200 mU of enzyme). 200 nM of each primer was employed. Control reactions employed unblocked Forward and Reverse primers, rs4939827 For (SEQ ID NO: 217) with rs4939827 Rev (SEQ ID NO: 230). Two different versions of blocked primers specific for each allele were used, either the RDDDDx (see Example 13) or RDxxD designs (see Example 28). Blocked-cleavable forward primers were used in combination with an unmodified reverse primer as follows: rs4939827 C-For RDDDDx (SEQ ID NO: 231) with rs4939827 Rev (SEQ ID #230), rs4939827 T-For RDDDDx (SEQ ID NO: 235) with rs4939827 Rev (SEQ ID #230), rs4939827 C-For RDxxD (SEQ ID NO: 252) with rs4939827 Rev (SEQ ID #230), rs4939827 T-For RDxxD (SEQ ID NO: 273) with rs4939827 Rev (SEQ ID #230). In addition, either 0.5 or 1 mM rATP (diluted in water) was added to some reactions. All oligonucleotides used in this Example are shown in Table 75. Cycling was performed on a Roche LightCycler® 480 (Roche Applied Science, Indianapolis, Ind., USA) as follows: 95° C. for 3 minutes followed by 75 cycles of 95° C. for 10 seconds and 60° C. for 30 seconds. All reactions were performed in triplicate. The initial 3 minute incubation at 95° C. before thermocycling commences allows for reactivation of the hot-start DNA polymerase.

TABLE 77

Synthetic oligonucleotide primers

| Name | Sequence | SEQ ID NO: |
|---|---|---|
| rs4939827 Rev | CTCACTCTAAACCCCAGCATT | SEQ ID NO: 217 |
| rs4939827 For | CAGCCTCATCCAAAAGAGGAAA | SEQ ID NO: 230 |
| rs4939827 C-For RDxxD | CAGCCTCATCCAAAAGAGGAAA cA(SpC3-SpC3)A | SEQ ID NO: 252 |
| rs4939827 T-For RDxxD | CAGCCTCATCCAAAAGAGGAAA uA(SpC3-SpC3)A | SEQ ID NO: 273 |
| SMAD7 Probe | FAM-CTCAGGAAACACAGACAA TGCTGGG-IBFQ | SEQ ID NO: 283 |

DNA bases are uppercase and RNA bases are lowercase;
SpC3 = C3 spacer (propanediol);
FAM = 6-carboxyfluorescein;
IBFQ = Iowa Black ™ FQ fluorescence quencher Results are shown in Table 78. When magnesium levels were lowered in the reaction buffer, an increase in mismatch discrimination was observed. As predicted, the increase in mismatch discrimination using 2 mM Mg$^{2+}$ was similar to the increase observed when 1 mM rATP was added to reactions containing 3 mM Mg$^{2+}$. Use of unmodified primers resulted in efficient amplification reactions and no difference was seen between reactions containing varying amounts of the Mg$^{2+}$ or rATP. No amplification occurred when using blocked-cleavable primers if RNase H2 was absent from the reactions (not shown).

TABLE 78

Cp and ΔCp values seen in qPCR with different Mg++ concentrations.

| For Primer | [rATP] | [MgCl$_2$] | C/C | T/T | ΔCq |
|---|---|---|---|---|---|
| rs4939827 For | 1 mM | 3 mM | 24.0 | 24.2 | |
| rs4939827 C-For RDxxD | | | 24.9 | 59.5 | 34.6 |
| rs4939827 T-For RDxxD | | | 78.7 | 30.5 | 48.3 |
| rs4939827 | 0 mM | 3 mM | 24.1 | 23.9 | |

TABLE 78-continued

Cp and ΔCp values seen in qPCR with different Mg++ concentrations.

| For Primer | [rATP] | [MgCl$_2$] | C/C | T/T | ΔCq |
|---|---|---|---|---|---|
| For |  |  |  |  |  |
| rs4939827 |  |  | 24.1 | 44.3 | 20.2 |
| C-For RDxxD |  |  |  |  |  |
| rs4939827 |  |  | 47.6 | 24.7 | 22.9 |
| T-For RDxxD |  |  |  |  |  |
| rs4939827 |  | 2.5 mM | 24.5 | 24.1 |  |
| For |  |  |  |  |  |
| rs4939827 |  |  | 24.7 | 46.0 | 21.2 |
| C-For RDxxD |  |  |  |  |  |
| rs4939827 |  |  | 51.7 | 24.8 | 26.9 |
| T-For RDxxD |  |  |  |  |  |
| rs4939827 |  | 2 mM | 23.9 | 23.7 |  |
| For |  |  |  |  |  |
| rs4939827 |  |  | 25.7 | 71.6 | 45.9 |
| C-For RDxxD |  |  |  |  |  |
| rs4939827 |  |  | 69.5 | 26.9 | 42.6 |
| T-For RDxxD |  |  |  |  |  |
| rs4939827 |  | 1.5 mM | 24.9 | 23.8 |  |
| For |  |  |  |  |  |
| rs4939827 |  |  | 26.0 | 55.4 | 29.5 |
| C-For RDxxD |  |  |  |  |  |
| rs4939827 |  |  | >85 | 51.3 | >33.7 |
| T-For RDxxD |  |  |  |  |  |

Thus magnesium concentration can substantially affect the ΔCp values obtained for SNP discrimination when blocked-cleavable primers are employed in PCR-based genotyping. Titration of magnesium levels may be needed to optimize performance of individual primer pairs between different loci studied, and such experiments can be readily performed by one with skill in the art.

Example 37—Rare-Allele Detection can be Improved with Magnesium Optimization

The present example demonstrates that the ability to detect "rare alleles" in a mixed-allele DNA sample using blocked-cleavable primers in PCR can be improved by optimizing the magnesium concentration present in the reaction buffer.

Example 36 demonstrated that the discrimination achieved between matched and mismatched blocked-cleavable primers in allele-specific PCR assays can be improved by directly lower the magnesium levels or indirectly with the addition of rNTPs, which lowers the free magnesium levels. The present example extends this method to rare allele detection, using RDxxD design primers (see Examples 28 and 35). In this case a commercial SYBR-Green mastermix was employed where magnesium concentration was 3 mM as provided by the manufacturer; rNTPs were added to the reaction mix to lower free magnesium levels.

Blocked-cleavable primers specific for a single-nucleotide polymorphism (SNP) in the human SMAD7 gene (rs4939827, NM_005904) were designed for each allele using the RDxxD design. Control reactions employed unblocked Forward and Reverse primers, rs4939827 For (SEQ ID NO: 217) with rs4939827 Rev (SEQ ID NO: 230). RDxxD design blocked-cleavable For primers were employed with an unmodified Rev primer in the following combinations: rs4939827 C-For RDxxD (SEQ ID NO: 252) with rs4939827 Rev (SEQ ID #230), rs4939827 T-For RDxxD (SEQ ID NO: 273) with rs4939827 Rev (SEQ ID #230). To set up a rare allele detection experiment, DNA for one allele is added at high amounts (to simulate wild type DNA) and small amounts of the second allele are added (to simulate a rare mutant DNA). In this scenario, the "wild type" DNA is a mismatch to the blocked-cleavable For primer while the "mutant" (rare allele) DNA is a match to the blocked-cleavable For primer. Quantitative real-time PCR (qPCR) was performed in the presence of 200 ng (~66,000 genomic equivalent copies) or 0 ng of "wild type" human genomic DNA (either GM18562 or GM18537, Coriell Institute for Medical Research, Camden, N.J., USA) included in the reaction as background. GM18562 and GM18537 are homozygous for two alleles of the rs4939827 SNP (C or T). GM18562 is homozygous for the C allele at the rs4939827 locus and GM18537 is homozygous for the T allele. In addition to the background genomic "wild-type" DNA, 2, 0.2, 0.02 or 0 ng (660, 66, 6, or 0 genomic equivalent copies) of "mutant" human genomic DNA from the allele of the rs4937827 SNP (C or T) opposite to one in the background DNA was added to the reaction. Reactions also contained 1× iQ SYBR™ Green Supermix (Bio-Rad, Hercules, Calif., USA), and either 192 (for rC containing primers) or 768 (for rU containing primers) fmoles of P.a. RNase H2 (final concentration of 19.2 or 76.8 nM in a 10 μL reaction, which is the equivalent of 100 or 400 mU of the RNase H2 enzyme, respectively). 200 nM of each primer was used in each reaction. In addition, either 0 or 1 mM rATP (diluted in water) was added to each reaction. All oligonucleotides used in Example 37 are shown in Table 79. Cycling was performed on a Roche LightCycler® 480 (Roche Applied Science, Indianapolis, Ind., USA) as follows: 95° C. for 3 minutes followed by 65 cycles of 95° C. for 10 seconds and 60° C. for 30 seconds. All reactions were performed in triplicate. The initial 3 minute incubation at 95° C. before thermocycling commences allows for reactivation of the hot-start DNA polymerase.

TABLE 79

Synthetic oligonucleotide primers employed in rare allele detection experiments

| Name | Sequence | SEQ ID NO: |
|---|---|---|
| rs4939827 Rev | CTCACTCTAAACCCCAGCATT | SEQ ID NO: 217 |
| rs4939827 For | CAGCCTCATCCAAAAGAGGAAA | SEQ ID NO: 230 |
| rs4939827 C-For RDxxD | CAGCCTCATCCAAAAGAGGAAA cA(SpC3-SpC3)A | SEQ ID NO: 252 |
| rs4939827 T-For RDxxD | CAGCCTCATCCAAAAGAGGAAA uA(SpC3-SpC3)A | SEQ ID NO: 273 |

DNA bases are uppercase and RNA bases are lowercase;
x = C3 spacer (propanediol)

Results are shown in Tables 80, 81, 82, and 83 below. At the 1:10,000 rare-allele discrimination level (200 ng "wild type or mismatch" template with 0.02 ng "mutant or match" template), the addition of 1 mM rATP increased the ΔCp (in this case defined as the Cp measured in the 1:10,000 samples with the reaction background where no "mutant" T-allele is present) from 7.0 cycles (39.5–32.5=7.0, Table 80) to 12.6 cycles (46.0–33.4, Table 81). When DNAs were switch and the C allele was used as the rare mutant, addition of 1 mM rATP increased the ΔCp from 1.8 cycles (36.7–34.9=1.8, Table 82) to 18.4 cycles (53.6–35.2=18.4, Table 83). Importantly, reaction efficiency was not compromised and the Cp where positive fluorescent signals were first seen were similar between the 3 mM Mg++ and the 3 mM Mg++ plus 1 mM rATP reactions.

Use of unmodified primers resulted in efficient amplification reactions and no significant difference was seen between reactions containing rATP. No amplification occurred when using blocked-cleavable primers if RNase H2 was not added to the reactions (not shown).

TABLE 80

Cps resulting from a PCR rare allele detection experiment using C-allele as wild type with 3 mM Mg$^{++}$.

| | Mismatch template C allele | | | | | | | |
|---|---|---|---|---|---|---|---|---|
| Match | 200 ng (66,000 copies) | | | | 0 ng (0 copies) | | | |
| template T allele | 2 ng (660 copies) | 0.2 ng (66 copies) | 0.02 ng (6 copies) | 0 ng (0 copies) | 2 ng (660 copies) | 0.2 ng (66 copies) | 0.02 ng (6 copies) | 0 ng (0 copies) |
| rs4939827 For | 19.5 | 19.5 | 19.4 | 20.2 | 26.0 | 30.2 | 35.3 | >65 |
| rs4939827 T-For RDxxD | 26.4 | 29.7 | 32.5 | 39.5 | 26.4 | 30.1 | 34.4 | >65 |

TABLE 81

Cps resulting from a PCR rare allele detection experiment using C-allele as wild type with 3 mM Mg$^{++}$ plus 1 mM rATP.

| | Mismatch template C allele | | | | | | | |
|---|---|---|---|---|---|---|---|---|
| Match | 200 ng (66,000 copies) | | | | 0 ng (0 copies) | | | |
| template T allele | 2 ng (660 copies) | 0.2 ng (66 copies) | 0.02 ng (6 copies) | 0 ng (0 copies) | 2 ng (660 copies) | 0.2 ng (66 copies) | 0.02 ng (6 copies) | 0 ng (0 copies) |
| rs4939827 For | 19.4 | 19.3 | 19.4 | 19.4 | 26.1 | 29.5 | 35.2 | >65 |
| rs4939827 T-For RDxxD | 26.9 | 30.7 | 33.4 | 46.0 | 26.4 | 30.0 | 34.9 | >65 |

TABLE 82

Cps resulting from a PCR rare allele detection experiment using T-allele as wild type with 3 mM Mg$^{++}$.

| | Mismatch template T allele | | | | | | | |
|---|---|---|---|---|---|---|---|---|
| Match | 200 ng (66,000 copies) | | | | 0 ng (0 copies) | | | |
| template C allele | 2 ng (660 copies) | 0.2 ng (66 copies) | 0.02 ng (6 copies) | 0 ng (0 copies) | 2 ng (660 copies) | 0.2 ng (66 copies) | 0.02 ng (6 copies) | 0 ng (0 copies) |
| rs4939827 For | 19.8 | 19.8 | 19.8 | 19.9 | 26.2 | 30.0 | 33.9 | >65 |
| rs4939827 C-For RDxxD | 26.6 | 30.0 | 34.9 | 36.7 | 26.5 | 30.0 | 33.9 | >65 |

TABLE 83

Cps resulting from a PCR rare allele detection experiment using C-allele as wild type with 3 mM Mg$^{++}$ plus 1 mM rATP.

| | Mismatch template T allele | | | | | | | |
|---|---|---|---|---|---|---|---|---|
| Match | 200 ng (66,000 copies) T allele | | | | 0 ng (0 copies) T allele | | | |
| template C allele | 2 ng (660 copies) | 0.2 ng (66 copies) | 0.02 ng (6 copies) | 0 ng (0 copies) | 2 ng (660 copies) | 0.2 ng (66 copies) | 0.02 ng (6 copies) | 0 ng (0 copies) |
| rs4939827 For | 20.1 | 20.3 | 20.2 | 20.3 | 27.0 | 30.8 | 33.9 | >65 |
| rs4939827 C-For RDxxD | 27.6 | 30.9 | 35.2 | 53.6 | 27.7 | 31.1 | 34.4 | >65 |

This example demonstrates that adjusting magnesium concentration in the buffer can improve discrimination and detection limits in a PCR rare-allele detection assay using blocked-cleavable primers and RNase H2 and that detection limit can reliably reach levels of 1:10,000.

Example 38—Use of the Non-Ionic Detergent Brij®-58 in PCR with Blocked-Cleavable Primers and RNase H2

Example 18 demonstrated the benefit of including a non-ionic detergent in the reaction mix when performing PCR using blocked-cleavable primers and *Pyrococcus abyssi* (P.a.) RNase H2. The present example demonstrates that the detergent Brij®-58 (also known as either polyethylene glycol hexadecyl ether, or polyoxyethylene (20) cetyl ether) can substitute for other non-ionic detergents, such as Triton X-100, in PCR using blocked-cleavable primers and *Pyrococcus abyssi* (P.a.) RNase H2.

Quantitative real-time PCR (qPCR) was performed in 10 µL reactions with 20 ng of human genomic DNA (GM18562 or GM18537, Coriell Institute for Medical Research, Camden, N.J., USA) using primers specific for a site in the human SMAD7 gene (rs4939827, NM_005904). DNA sample GM18562 is homozygous for the C allele and GM18537 is homozygous for the T allele. Reactions utilized either 0.5 U (10.8 ng/11.1 nM/111 fmol) of native Taq DNA polymerase. Final reaction buffer conditions used were 10 mM Tris-HCL (pH 8.4 at 25° C.), 50 mM KCL, and 3 mM MgCl$_2$. Reactions also used 1 µL of P.a. RNase H2 (5 fmoles; final concentration of 0.5 nM in a 10 µL reaction, or 2.6 mU of the enzyme), diluted in RNase H2 dilution buffer without detergent (20 mM Tris-HCL pH 8.4, 100 mM KCL, 0.1 mM EDTA, and 10% glycerol). One µL of water (no detergent) or one µL of 0.001%, 0.01%, 0.1% Brij-58 or 0.1% Triton X-100 was added to each 10 µL final reaction volume. 200 nM of each primer and a 5' nuclease detection probe were also used in each reaction. Control reactions employed unblocked Forward and Reverse primers, rs4939827 For (SEQ ID NO: 217) with rs4939827 Rev (SEQ ID NO: 230). An RDDDDx design blocked-cleavable forward primer (see Example 13) was used in combination with an unmodified reverse primer as follows: rs4939827 C-For RDDDDx (SEQ ID NO: 231) with rs4939827 Rev (SEQ ID NO: 230). A SMAD7 5'-nuclease fluorescence-quenched probe was included for detection at 200 nM (SEQ ID NO: 283). Oligonucleotides used in this Example are shown in Table 84. Cycling was performed on a Roche LightCycler® 480 (Roche Applied Science, Indianapolis, Ind., USA) as follows: 95° C. for 3 minutes followed by 45 cycles of 95° C. for 10 seconds and 60° C. for 30 seconds. All reactions were performed in triplicate.

TABLE 84

Synthetic oligonucleotide primers and probe

| Name | Sequence | SEQ ID NO: |
|---|---|---|
| rs4939827 Rev | CTCACTCTAAACCCCAGCATT | SEQ ID NO: 217 |
| rs4939827 For | CAGCCTCATCCAAAAGAGGAAA | SEQ ID NO: 230 |
| rs4939827 C-For RDDDDx | CAGCCTCATCCAAAAGAGGAAA cAGGA-SpC3 | SEQ ID NO: 231 |
| SMAD7 Probe | FAM-CTCAGGAAACACAGACAA TGCTGGG-IBFQ | SEQ ID NO: 283 |

DNA bases are uppercase and RNA bases are lowercase;
x = C3 spacer (propanediol);
FAM = 6-carboxyfluorescein;
IBFQ = Iowa Black ™ FQ fluorescence quencher Results are shown in Table 85 below. Cp and ΔCp values were obtained from PCR using either no detergent, 0.0001%, 0.001%, 0.01% final concentration Brij®-58, or 0.01% Triton X-100 detergents. Use of no detergent or 0.0001% Brij®-58 resulted in no amplification with either unmodified or blocked primer designs. Increasing the concentration of Brij®-58 to 0.001% or higher final concentration resulted in efficient amplification reactions with both unmodified and blocked primer designs. Concentrations of Brij®-58 higher than 0.001% showed no significant difference in amplification efficiency between the different Brij®-58 concentrations compared with reactions performed using 0.01% of the non-ionic detergent Triton X-100. This result demonstrates that both the Taq DNA polymerase and the P.a. RNase H2 enzymes are active under these conditions. No amplification occurred when using blocked-cleavable primers if RNase H2 was not added to the reactions (not shown).

TABLE 85

Cp and ΔCp values for quantitative rhPCR reactions using Brij ®-58 or Triton X-100 detergents.

| Detergent | Primers | C/C | T/T | ΔCp* |
|---|---|---|---|---|
| No Detergent | Unblocked Rev | >95 | >95 | |
| | rC DDDDx For | >95 | >95 | |
| 0.0001% Brij-58 | Unblocked Rev | >95 | >95 | |
| | rC DDDDx For | >95 | >95 | |
| 0.001% Brij-58 | Unblocked Rev | 24.2 | 25.0 | |
| | rC DDDDx For | 24.7 | 37.3 | 12.7 |
| 0.01% Brij-58 | Unblocked Rev | 24.2 | 25.1 | |
| | rC DDDDx For | 24.7 | 36.8 | 12.1 |
| 0.1% Triton X-100 | Unblocked Rev | 24.2 | 25.0 | |
| | rC DDDDx For | 24.5 | 36.9 | 12.4 |

*ΔCp = Cp match (C/C) minus Cp mismatch (T/T)

These results demonstrate that the Brij®-58 may be employed as a non-ionic detergent in PCR using blocked-cleavable primers and RNase H2.

Example 39—Use of Blocked-Cleavable Primers with RNase H2 in PCR with a High-Fidelity 3'-Exonuclease DNA Polymerase The present example demonstrates compositions of blocked-cleavable primers that function well with high fidelity proof-reading DNA polymerases.

Many DNA polymerases, like that obtained from *Thermus aquaticus* (Taq DNA polymerase), have a 5'-exonuclease activity but lack 3'-exonuclease activity. These enzymes are often robust but do not have a "proof-reading" function and are generally consider to be "low fidelity". Polymerases in this class are typically employed for routine PCR-based sequence detection assays and were the employed in most of the earlier Examples above. Other polymerases, like those obtained from *Pyrococcus furiosus* (Pfu DNA polymerase), *Thermococcus kodakarensis* (KOD DNA polymerase), etc. lack a 5'-exonuclease activity but have a 3'-exonuclease proofreading activity. These enzymes are considered "high fidelity" polymerases. High fidelity polymerases are often employed in DNA cloning or in Next Generation Sequencing (NGS) applications where even rare mutations introduced by the polymerase are detrimental. However, polymerases with 3'-exonuclease activity can remove the terminal bases at the 3'-end of a primer or end-blocking groups, such as the C3 spacer group employed as a terminal blocking moiety in the RDDDDx primer design; removing the blocking group allows for primer function in the absence of RNase H2 cleavage, thereby eliminating the many benefits obtained from using blocked-cleavable primers as taught herein. It is desirable to have methods that enable use of blocked-cleavable primers for applications such as cloning, gene synthesis, NGS, etc. where high fidelity amplification is desired.

Methods. Quantitative real-time PCR (qPCR) was performed with 2e3 copies of a synthetic oligonucleotide DNA template (SEQ ID NO: 144) using primers specific for this template. Reactions used 1× Phusion®-HF buffer (NEB, Ipswich, Mass., USA), and 0, 2.5, 5, 9.6, 19.2, 192, 288, 384, or 768 fmoles of P.a. RNase H2 (final concentration of 0, 0.25, 0.5, 0.96, 1.92, 19.2, 28.8, 38.4 or 76.8 nM in a 10 µL reaction, or 0, 1.3, 2.6, 5, 10, 100, 150, 200, or 400 mU of the enzyme, respectively). 800 µM deoxynucleotides and 200 nM of each primer were included in each reaction and 1.5 mM of additional $MgCl_2$ was added to each reaction, resulting in a final concentration of 3 mM $MgCl_2$. 0.2 U of the Phusion® DNA polymerase (NEB, Ipswich, Mass., USA) was employed in each amplification reaction. Phusion is a high fidelity DNA polymerase which has 3'-exonuclease activity. For detection, SYBR® Green (Molecular Probes, Eugene, Oreg., USA) was added to a final concentration of 30,000 fold diluted versus the stock reagent (dilutions were made fresh in $dH_2O$). Control reactions employed unmodified primers (Syn-For, SEQ ID NO: 68 and Syn-Rev, SEQ ID NO: 69). Two different types of blocked-cleavable primers were employed, the RDDDDx and RDxxD designs, both perfect match to the target synthetic template. The two blocked-cleavable reverse primers were used in combination with an unmodified forward primer (Syn Rev rU DDDDx, SEQ ID NO: 116 with Syn-For, SEQ ID NO: 68; Syn Rev rU DxxD, SEQ ID NO: 284 with Syn-For, SEQ ID NO: 68). Oligonucleotides used in this experiment are shown in Table 86. PCR was performed on a Bio-Rad® CFX384™ Real Time System (Bio-Rad, Hercules, Calif., USA) as follows: 95° C. for 3 minutes followed by 40 cycles of 95° C. for 10 seconds and 60° C. for 30 seconds. All reactions were performed in triplicate.

TABLE 86

Synthetic oligonucleotides employed in Example 39

| Name | Sequence | SEQ ID NO: |
|---|---|---|
| Synthetic Template | AGCTCTGCCCAAAGATTACCCTG ACAGCTAAGTGGCAGTGGAAGTT GGCCTCAGAAGTAGTGGCCAGCT GTGTGTCGGGGAACAGTAAAGGC ATGAAGCTCAG | SEQ ID NO: 144 |
| Syn-For | AGCTCTGCCCAAAGATTACCCTG | SEQ ID NO: 68 |
| Syn-Rev | CTGAGCTTCATGCCTTTACTGT | SEQ ID NO: 69 |
| Syn Rev rU DDDDx | CTGAGCTTCATGCCTTTACTG TuCCCC-SpC3 | SEQ ID NO: 116 |
| Syn Rev rU DxxD | CTGAGCTTCATGCCTTTACTG TuC (SpC3-SpC3) C | SEQ ID NO: 284 |

DNA bases are uppercase and RNA bases are lowercase;
SpC3 = C3 spacer (propanediol)

Results are shown in Tables 87 and 88 below. As expected, the unmodified control primers performed well with the high-fidelity 3'-exonuclease Phusion® DNA polymerase and showed uniform amplification efficiency with or without added RNase H2 enzyme. The RDDDDx design blocked-cleavable primer (SEQ ID NO: 116) showed full efficiency amplification in the absence of RNase H2 and reduced amplification efficiency when RNase H2 was present. Using Taq DNA polymerase, the reverse is seen: no amplification occurs in the absence of RNase H2 and efficient amplification occurs in the present of even small amounts of RNase H2 (usually 100% efficiency by 2.6 mU enzyme), Example 13). This unexpected observation suggests that the 3'-exonuclease activity of the Phusion DNA polymerase can remove the C3 terminal blocking group on this primer, so primer extension and PCR proceeds without RNase H2 cleavage. Further, there appears to be an adverse interaction between the Phusion DNA polymerase and RNase H2 such that reduced amplification efficiency occurred when both enzymes are present with the RDDDDx class of blocked-cleavable primer (note: no loss of efficiency is seen using unmodified primers when RNase H2 is added).

TABLE 87

Cp values resulting from qPCR performed with an unmodified forward primer and various reverse primers using a high-fidelity DNA polymerase.

| Reverse Primer | SEQ ID | 0 mU RNase H2 | 1.3 mU RNase H2 | 2.6 mU RNase H2 | 5 mU RNase H2 | 10 mU RNase H2 |
|---|---|---|---|---|---|---|
| Syn-Rev | SEQ ID NO: 69 | 25.1 | 25.2 | 25.2 | 25.2 | 25.3 |
| Syn Rev rU DDDDx | SEQ ID NO: 116 | 25.6 | 39.4 | 37.8 | 32.8 | 29.5 |

In contrast to these results, the RDxxD blocked-cleavable primer did not support PCR in the absence of RNase H2. Thus this design of primer is not unblocked by the 3'-exonuclease activity of the Phusion DNA polymerase. Primer cleavage and PCR occurred in the presence of RNase H2. Lower efficiency PCR was seen using low doses of RNase H2 (100 mU per reaction) and near parity with the unblocked control primers was achieved using 400 mU RNase H2 per reaction.

TABLE 88

Cp values resulting from qPCR performed with an unmodified forward primer and various reverse primers using a high-fidelity DNA polymerase.

| Reverse Primer | SEQ ID | 0 mU RNase H2 | 100 mU RNase H2 | 150 mU RNase H2 | 200 mU RNase H2 | 400 mU RNase H2 |
|---|---|---|---|---|---|---|
| Syn-Rev | SEQ ID NO: 69 | 25.1 | 25.2 | 25.2 | 25.2 | 25.3 |
| Syn Rev rU DxxD | SEQ ID NO: 284 | >40 | 31.3 | 29.1 | 27.8 | 26.6 |

We conclude that the RDxxD design of blocked-cleavable primer is preferred over the RDDDDx design when using high fidelity 3'-exonuclease DNA polymerases, such as Phusion. Higher concentrations of RNase H2 may be necessary to achieve reaction efficiencies equal to reactions performed using unmodified primers or is typically seen using Taq DNA polymerase.

Example 40—Improved Design of Blocked-Cleavable Primers for Use in PCR with RNase H2 Using a High Fidelity 3'-Exonuclease DNA Polymerase The present example demonstrates utility of a new design of blocked-cleavable primer, called "RDDDDxxD", in RNase H2-dependent PCR (rhPCR) in combination with a high-fidelity DNA polymerase possessing 3' exonuclease activity.

Previous Example 39 demonstrated that the RDxxD design of blocked-cleavable primer worked well using a high fidelity 3'-exonuclease DNA polymerase while the RDDDDx design did not perform as well. In general, RDxxD blocked-cleavable primers require higher concentrations of RNase H2 in PCR to reach peak amplification efficiency (i.e., to achieve parity with reactions performed using unmodified primers) whereas the RDDDDx design requires use of lower concentrations of RNase H2. At times it can be advantageous to employ RDDDDx type primers with low RNase H2 concentrations. The present example demonstrates performance of a variant of the RDDDDx primer, the new RDDDDxxD primer, which can function well with high fidelity 3'-exonuclease DNA polymerases in PCR using relatively low concentrations of RNase H2. See Example 26 for a description of other properties of this design of blocked-cleavable primer.

Quantitative real-time PCR (qPCR) was performed with 20 ng of human genomic DNA (GM18537, Coriell Institute for Medical Research, Camden, N.J., USA) using primers specific for a site in the human SMAD7 gene (rs4939827, NM_005904). GM18537 DNA is homozygous T/T at this locus. The Phire® DNA polymerase (Thermo Scientific, Pittsburgh, Pa., USA) is a high fidelity 3'-exonuclease DNA polymerase and was employed in the experiments performed in this example. Reactions used 1× Phire® buffer (Thermo Scientific, Pittsburgh, Pa., USA), and 0, 2.5, 9.6, 19.2, 96, 192, 384, 768 or 1152 fmoles of P.a. RNase H2 (final concentration of 0, 0.25, 0.96, 1.92, 9.6, 19.2, 38.4 76.8, or 115.2 nM in a 10 μL reaction, or 0, 1.3, 5, 10, 50, 100, 200, 400, or 600 mU of the enzyme, respectively). 800 mM deoxynucleotides and 200 nM of each primer were included in each reaction. 1.5 mM of supplemental $MgCl_2$ was added to each reaction, resulting in a final concentration of 3 mM $MgCl_2$. 0.1 U of the Phire® DNA polymerase was used in each amplification reaction and SYBR Green (Molecular Probes, Eugene, Oreg., USA) was added to a final concentration of 30,000 fold dilution (from the stock dye) to enable detection. Three types of blocked-cleavable primers were tested, including the RDDDDx, RDxxD, and the new RDDDDxxD designs. Sequences are shown in Table 89 below. Unmodified rs4939827 For and rs4939827 Rev primers (SEQ ID NOS: 217 and 230) served as the control reaction. Blocked-cleavable For primers of the three designs were individually tested in combination with an unmodified Rev primer, including pairs: rs4939827 T-For RDDDDx (SEQ ID NO: 235) with rs4939827 Rev (SEQ ID NO: 217); rs4939827 T-For RDxxD (SEQ ID NO: 273) with rs4939827 Rev (SEQ ID NO: 217); and rs4939827 T-For RDDDDxxD (SEQ ID NO: 285) with rs4939827 Rev (SEQ ID NO: 217). PCR was performed on a Bio-Rad® CFX384™ Real Time System (Bio-Rad, Hercules, Calif., USA) as follows: 98° C. for 3 minutes followed by 40 cycles of 98° C. for 10 seconds and 60° C. for 30 seconds. All reactions were performed in triplicate.

TABLE 89

Synthetic oligonucleotides employed in Example 40

| Name | Sequence | SEQ ID NO: |
|---|---|---|
| rs4939827 Rev | CTCACTCTAAACCCCAGCATT | SEQ ID NO: 217 |
| rs4939827 For | CAGCCTCATCCAAAAGAGGAAA | SEQ ID NO: 230 |
| rs4939827 T-For RDDDDx | CAGCCTCATCCAAAAGAGGAAA cAGGA-SpC3 | SEQ ID NO: 235 |
| rs4939827 T-For RDxxD | CAGCCTCATCCAAAAGAGGAAA uA(SpC3-SpC3)A | SEQ ID NO: 273 |
| rs4939827 T-For RDDDDxxD | CAGCCTCATCCAAAAGAGGAAA uAGGA(SpC3-SpC3)C | SEQ ID NO: 285 |

DNA bases are uppercase and RNA bases are lowercase; SpC3 = C3 spacer (propanediol)

Results are shown in Tables 90 and 91. The RDDDDx blocked-cleavable primer supported PCR with the high fidelity 3'-exonuclease Phire®DNA polymerase in the absence of RNase H2, which suggests that the 3'-block is removed by the 3'-exonuclease proofreading activity of the high fidelity polymerase so that PCR proceeds without the need for RNase H2 cleavage/activation. Identical results were reported in Example 39 using the high fidelity DNA polymerase Phusion®, suggesting that similar behavior could be expected from all DNA polymerases of this class. Also similar to results from the prior Example, reduced amplification efficiency was seen when RNase H2 was added to the amplification reaction, suggesting that some antagonism occurs between the high fidelity DNA polymerase and the RNase H2 enzymes with the RDDDDx design primer. The RDxxD blocked-cleavable primer did not support PCR in the absence of RNase H2. Thus this design of primer cannot readily be unblocked by the 3'-exonuclease activity of the Phire® DNA polymerase. Primer cleavage and PCR occurred in the presence of RNase H2. Lower efficiency PCR was seen using low doses of RNase H2 (100 mU per reaction) and near parity with the unblocked control primers was achieved using 400-600 mU RNase H2 per reaction. Therefore results for both the RDDDDx and RDxxD blocked-cleavable primers were similar when using the two different high fidelity DNA polymerases, Phusion® and Phire®.

The new design RDDDDxxD primer showed no amplification in the absence of RNase H2, indicating that the high fidelity 3'-exonuclease DNA polymerase was unable to remove the 3'-blocking effect present in this primer design. Further, good amplification efficiency was achieved using relatively low concentrations of RNase H2, indicating that there was no or minimal antagonism between the polymerase and the RNase H2 enzymes for this primer design.

ADDITIONAL ACKNOWLEDGEMENTS

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

TABLE 90

Cp values resulting from qPCR performed with an unmodified forward primer and various reverse primers using a high-fidelity DNA polymerase.

| Primer | SEQ ID | 0 mU RNase H2 | 1.3 mU RNase H2 | 5 mU RNase H2 | 10 mU RNase H2 | 50 mU RNase H2 |
|---|---|---|---|---|---|---|
| rs4939827 For | SEQ ID NO: 230 | 23.0 | 23.2 | 23.0 | 23.3 | 22.6 |
| rs4939827 T-For RDDDDx | SEQ ID NO: 235 | 23.7 | >40 | 38.8 | 36.4 | 28.5 |
| rs4939827 T-For RDDDDxxD | SEQ ID NO: 285 | >40 | 33.6 | 28.8 | 25.9 | 24.5 |

TABLE 91

Cp values resulting from qPCR performed with an unmodified forward primer and various reverse primers using a high-fidelity DNA polymerase.

| Primer | SEQ ID | 0 mU RNase H2 | 100 mU RNase H2 | 200 mU RNase H2 | 400 mU RNase H2 | 600 mU RNase H2 |
|---|---|---|---|---|---|---|
| rs4939827 For | SEQ ID NO: 230 | 23.0 | 23.2 | 23.0 | 23.3 | 22.6 |
| rs4939827 T-For RDxxD | SEQ ID NO: 273 | >40 | 29.1 | 25.9 | 24.4 | 23.3 |

We conclude that both RDDDDxxD and RDxxD blocked-cleavable primer designs support PCR when using high fidelity 3'-exonuclease DNA polymerase enzymes. The RDDDDxxD design requires lower input RNase H2 concentrations while the RDxxD requires higher input RNase H2 concentrations. This approach enables use of the blocked-cleavable primer strategy for applications that require high fidelity DNA replication, such as DNA cloning, gene synthesis, or NGS.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and

What is claimed is:

1. A method of improving specificity during amplification of a target DNA sequence, comprising:
   (a) providing a reaction mixture, comprising:
      (i) an oligonucleotide primer having a cleavage domain, which is cleavable by an RNase H enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis,
      (ii) a sample nucleic acid that may or may not include the target sequence,
      (iii) a DNA polymerase, and
      (iv) an RNase H2 enzyme, wherein said RNase H2 enzyme is thermostable and active at 70° C., wherein said RNase H2 enzyme is selected from the group consisting of *Pyrococcus abyssi* RNase H2 enzyme, *Pyrococcus kodakaraensis* RNase H2 enzyme, *Pyrococcus furiosus* RNase H2 enzyme, *Methanocaldococcus jannaschii* RNase H2 enzyme and *Sulfolobus solfataricus* RNase H2 enzyme; and
   (b) hybridizing the oligonucleotide primer to the target DNA sequence to form a double-stranded substrate;
   (c) cleaving the hybridized oligonucleotide primer with said RNase H2 enzyme at a cleavage site within or adjacent to the cleavage domain to remove the blocking group from the oligonucleotide primer; and
   (d) extending the oligonucleotide primer with the DNA polymerase,
wherein the reaction mixture includes a concentration of a divalent cation such that a $\Delta Cp$ of at least about 5.0 or greater or about 50% or greater is obtained for the amplification of the target DNA as adjudged by a 3'-mismatch discrimination assay when comparing Cp values of a perfect matched primer and a mismatched primer.

2. The method of claim 1, wherein the divalent cation is selected from $Mg^{++}$, $Mn^{++}$ and $Co^{++}$.

3. The method of claim 1, wherein the divalent cation comprises $Mg^{++}$.

4. The method of claim 3, wherein a final concentration of $Mg^{++}$ comprises about 2.0 mM free $Mg^{++}$ or less, provided that an amplification of the target DNA sequence occurs.

5. The method of claim 3, wherein the reaction mixture further comprises a divalent cation different from $Mg^{++}$.

6. The method of claim 5, wherein the divalent cation different from $Mg^{++}$ is selected from $Mn^{++}$, $Co^{++}$ or a combination of $Mn^{++}$ and $Co^{++}$.

7. The method of claim 1, wherein the RNase H2 enzyme is encoded by any one of SEQ ID NOS.: 1-5.

8. The method of claim 1, wherein the RNase H2 enzyme is *Pyrococcus abyssi* RNase H2.

9. The method of claim 8, wherein the *Pyrococcus abyssi* RNase H2 is encoded by SEQ ID NO.: 4.

10. The method of claim 1, wherein the RNase H2 enzyme is reversibly inactivated either by chemical modification or by a blocking antibody.

11. The method of claim 1, wherein the blocking group is attached to the 3'-terminal nucleotide of the oligonucleotide primer.

12. The method of claim 1, wherein the blocking group is attached 5' of the 3'-terminal residue and inhibits the oligonucleotide primer from serving as a template for DNA synthesis.

13. The method of claim 12, wherein the blocking group includes one or more abasic residues.

14. The method of claim 13, wherein the one or more abasic residues is a C3 spacer.

15. The method of claim 1, wherein the blocking group comprises one member selected from the group consisting of RDDDDx, RDDDDMx, RDxxD, RDxxDM, RDDDDxxD, RDDDDxxDM and DxxD, wherein R is an RNA residue, D is a DNA residue, M is a mismatched residue and x is a C3 spacer.

16. The method of claim 1, wherein the blocking group includes a label permitting detection of the extension amplification reaction.

17. The method of claim 1, wherein a label permitting detection of the amplification reaction is attached to the oligonucleotide primer 3' from the cleavage site.

18. The method of claim 16, wherein the label is a fluorophore or a mass tag for detection of the amplification reaction by mass spectrometry.

19. The method of claim 1, wherein the cleavage domain comprises one or more of the following moieties: a DNA residue, an abasic residue, a modified nucleoside, or a modified phosphate internucleotide linkage.

20. The method of claim 1, wherein the cleavage domain comprises a single RNA residue.

21. The method of claim 1, wherein the cleavage domain comprises two adjacent RNA residues.

22. The method of claim 1, wherein the cleavage domain comprises a continuous sequence of three or more RNA residues.

23. The method of claim 1, wherein the cleavage domain lacks an RNA residue.

24. The method of claim 1, wherein the cleavage domain comprises one or more 2'-modified nucleosides.

25. The method of claim 24, wherein the one or more 2'-modified nucleosides is selected from the group consisting of 2'-O-alkyl RNA nucleoside, 2'-fluoronucleoside, locked nucleic acid, 2'-ethylene nucleic acid residue, 2'-alkyl nucleoside, 2'-aminonucleoside and 2'-thionucleoside.

26. The method of claim 24, wherein the one or more 2'-modified nucleosides is 2'-O-methyl RNA nucleoside.

27. The method of claim 24, wherein the one or more 2'-modified nucleosides is 2'-fluoronucleoside.

28. The method of claim 1, wherein a sequence flanking the cleavage site contains one or more internucleoside linkages resistant to nuclease cleavage.

29. The method of claim 28, wherein the nuclease resistant linkage is a phosphorothioate.

30. The method of claim 1, wherein the first and second reaction mixtures include a non-ionic detergent.

31. The method of claim 30, wherein the non-ionic detergent comprises polyethylene glycol hexadecyl ether.

32. The method of claim 31, wherein polyethylene glycol hexadecyl ether is present at a final concentration of at least about 0.001% in the first and second reaction mixtures.

33. A method of amplifying a target DNA sequence, comprising:
(a) providing a reaction mixture comprising:
(i) an oligonucleotide primer having a cleavage domain, which is cleavable by an RNase H enzyme, positioned 5' of a blocking group, said blocking group linked at or near the 3'-end of the oligonucleotide primer wherein said blocking group prevents primer extension and/or inhibits the oligonucleotide primer from serving as a template for DNA synthesis,
(ii) a sample nucleic acid that may or may not include the target sequence,
(iii) a DNA polymerase, and
(iv) an RNase H2 enzyme, wherein said RNase H2 enzyme is thermostable and active at 70° C., wherein the RNase H2 enzyme is selected from the group consisting of *Pyrococcus abyssi* RNase H2 enzyme, *Pyrococcus kodakaraensis* RNase H2 enzyme, *Pyrococcus furiosus* RNase H2 enzyme, *Methanocaldococcus jannaschii* RNase H2 enzyme and *Sulfolobus solfataricus* RNase H2 enzyme;
(b) hybridizing the oligonucleotide primer to the target DNA sequence to form a double-stranded substrate;
(c) cleaving the hybridized oligonucleotide primer with said RNase H2 enzyme at a cleavage site within or adjacent to the cleavage domain to remove the blocking group from the oligonucleotide primer; and
(d) extending the oligonucleotide primer with the DNA polymerase,
wherein the reaction mixture includes a divalent cation and a non-ionic detergent comprising polyethylene glycol hexadecyl ether.

34. The method of claim 33, wherein polyethylene glycol hexadecyl ether is present at a final concentration of at least about 0.001% in the reaction mixture.

35. The method of claim 33, wherein the divalent cation is selected from $Mg^{++}$, $Mn^{++}$ and $Co^{++}$.

36. The method of claim 33, wherein the divalent cation comprises $Mg^{++}$.

37. The method of claim 33, wherein the reaction mixture further comprises a divalent cation different from $Mg^{++}$.

38. The method of claim 37, wherein the divalent cation different from $Mg^{++}$ is selected from $Mn^{++}$, $Co^{++}$ or a combination of $Mn^{++}$ and $Co^{++}$.

39. The method of claim 33, wherein the RNase H2 enzyme is encoded by any one of SEQ ID NOS.: 1-5.

40. The method of claim 33, wherein the RNase H2 enzyme is *Pyrococcus abyssi* RNase H2.

41. The method of claim 40, wherein the *Pyrococcus abyssi* RNase H2 is encoded by SEQ ID NO.: 4.

42. The method of claim 33, wherein the RNase H2 enzyme is reversibly inactivated either by chemical modification or by a blocking antibody.

43. The method of claim 33, wherein the blocking group is attached to the 3'-terminal nucleotide of the oligonucleotide primer.

44. The method of claim 33, wherein the blocking group is attached 5' of the 3'-terminal residue and inhibits the oligonucleotide primer from serving as a template for DNA synthesis.

45. The method of claim 33, wherein the blocking group includes one or more abasic residues.

46. The method of claim 45, wherein the one or more abasic residues is a C3 spacer.

47. The method of claim 33, wherein the blocking group comprises one member selected from the group consisting of RDDDDx, RDDDDMx, RDxxD, RDxxDM, RDDDDxxD, RDDDDxxDM and DxxD, wherein R is an RNA residue, D is a DNA residue, M is a mismatched residue and x is a C3 spacer.

48. The method of claim 33, wherein the blocking group includes a label permitting detection of the extension amplification reaction.

49. The method of claim 33, further comprising a label permitting detection of the amplification reaction, wherein the label is attached to the oligonucleotide primer 3' from the cleavage site.

50. The method of claim 48, wherein the label is a fluorophore or a mass tag for detection of the amplification reaction by mass spectrometry.

51. The method of claim 33, wherein the cleavage domain comprises one or more of the following moieties: a DNA residue, an abasic residue, a modified nucleoside, or a modified phosphate internucleotide linkage.

52. The method of claim 33, wherein the cleavage domain comprises one RNA residue, two adjacent RNA residues, or three or more contiguous RNA residues.

53. The method of claim 33, wherein the cleavage domain comprises one or more 2'-modified nucleosides.

54. The method of claim 53, wherein the one or more 2'-modified nucleosides are selected from the group consisting of 2'-O-alkyl RNA nucleoside, 2'-fluoronucleoside, locked nucleic acid, 2'-ethylene nucleic acid residue, 2'-alkyl nucleoside, 2'-aminonucleoside and 2'-thionucleoside.

55. The method of claim 33, wherein a sequence flanking the cleavage site contains one or more internucleoside linkages resistant to nuclease cleavage.

* * * * *

SEQUENCE LISTING

<160> NUMBER OF SEQ ID NOS: 313

<210> SEQ ID NO 1
<211> LENGTH: 697
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 1

```
ggatccgatg aagattgctg gcatcgatga agccggccgt ggcccggtaa ttggtccaat    60
ggttatcgct gcggtagtcg tggacgaaaa cagcctgcca aaactggaag agctgaaagt   120
gcgtgactcc aagaaactga ccccgaagcg ccgtgaaaag ctgtttaacg aaattctggg   180
tgtcctggac gattatgtga tcctggagct gccgcctgat gttatcggca gccgcgaagg   240
tactctgaac gagttcgagg tagaaaactt cgctaaagcg ctgaattccc tgaaagttaa   300
accggacgta atctatgctg atgcggctga cgttgacgag gaacgttttg cccgcgagct   360
gggtgaacgt ctgaactttg aagcagaggt tgttgccaaa cacaaggcgg acgatatctt   420
cccagtcgtg tccgcggcga gcattctggc taaagtcact cgtgaccgtg cggttgaaaa   480
actgaaggaa gaatacggtg aaatcggcag cggttatcct agcgatcctc gtacccgtgc   540
gtttctggag aactactacc gtgaacacgg tgaattcccg ccgatcgtac gtaaaggttg   600
gaaaaccctg aagaaaatcg cggaaaaagt tgaatctgaa aaaaaagctg aagaacgtca   660
agcaactctg gaccgttatt ccgtaaagt gaagctt                              697
```

<210> SEQ ID NO 2
<211> LENGTH: 685
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 2

```
ggatccgatg aagattggtg gcatcgacga agccggccgt ggtccggcga tcggtccgct    60
ggtagtagct actgttgtag tggatgaaaa aaacatcgaa aaactgcgta acatcggcgt   120
aaaagactcc aaacagctga cgccgcacga acgtaaaaac ctgtttttccc agatcacctc   180
cattgcggat gattacaaga tcgtaatcgt gtctccggaa gaaattgaca accgtagcgg   240
taccatgaac gagctggaag ttgaaaaatt cgcgctggcg ctgaactctc tgcagatcaa   300
gccggctctg atctacgcag acgcagcaga tgttgatgca aaccgcttcg catccctgat   360
cgaacgtcgc ctgaactata aagccaaaat catcgcggaa cacaaagcag acgcaaagta   420
cccggtcgtt tctgcggcga gcattctggc gaaggttgtg cgtgacgaag aaatcgaaaa   480
gctgaaaaag caatatggcg actttggcag cggttacccg agcgacccga aacgaagaa   540
atggctggag gagtattaca agaaacataa cagcttccca ccgatcgttc gtcgtacgtg   600
ggaaactgtc cgcaaaattg aagagtccat caaagccaaa agtcccagc tgaccctgga   660
taaattcttc aagaaaccga agctt                                          685
```

<210> SEQ ID NO 3
<211> LENGTH: 703
<212> TYPE: DNA

<213> ORGANISM: Artificial Sequence
<220> FEATURE:
<223> OTHER INFORMATION: SYNTHETIC OLIGONUCLEOTIDE

<400> SEQUENCE: 3

```
ggatccgatg attatcattg gtatcgatga agctggccgt ggtcctgtac tgggcccgat    60
ggttgtatgt gcgttcgcta tcgagaagga acgtgaagaa gaactgaaaa agctgggcgt   120
taaagattct aaagaactga cgaagaataa acgcgcgtac ctgaaaaagc tgctggagaa   180
cctgggctac gtggaaaagc gcatcctgga ggctgaggaa attaaccagc tgatgaacag   240
cattaacctg aacgacattg aaatcaacgc attcagcaag gtagctaaaa acctgatcga   300
aaagctgaac attcgcgacg acgaaatcga aatctatatc gacgcttgtt ctactaacac   360
caaaaagttc gaagactctt tcaaagataa aatcgaagat atcattaaag aacgcaatct   420
gaatatcaaa atcattgccg aacacaaagc agacgccaag tacccagtag tgtctgcggc   480
gagcattatc gcgaaagcag aacgcgacga gatcatcgat tattacaaga aaatctacgg   540
tgacatcggc tctggctacc catctgaccc gaaaaccatc aaattcctgg aagattactt   600
taaaaagcac aagaaactgc cggatatcgc tcgcactcac tggaaaacct gcaaacgcat   660
cctggacaaa tctaaacaga ctaaactgat tatcgaaaag ctt                     703
```

<210> SEQ ID NO 4
<211> LENGTH: 685
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 4

```
ggatccgatg aaagttgcag gtgcagatga agctggtcgt ggtccagtta ttggtccgct    60
ggttattgtt gctgctgttg tggaggaaga caaaatccgc tctctgacta agctgggtgt   120
taaagactcc aaacagctga ccccggcgca acgtgaaaaa ctgttcgatg aaatcgtaaa   180
agtactggat gattactctg tggtcattgt gtccccgcag acattgacg tcgtaaggg    240
cagcatgaac gaactggagg tagaaaactt cgttaaagcc ctgaatagcc tgaaagttaa   300
gccggaagtt atttacattg attccgctga tgttaaagct gaacgtttcg ctgaaaacat   360
tcgcagccgt ctggcgtacg aagcgaaagt tgtagccgaa cataaagcgg atgcgaagta   420
tgagatcgta tccgcagcct ctatcctggc aaaagttatc cgtgaccgcg agatcgaaaa   480
gctgaaagcc gaatacggtg attttggttc cggttacccg tctgatccgc gtactaagaa   540
atggctggaa gaatggtata gcaaacacgg caatttcccg ccgatcgtgc gtcgtacttg   600
ggatactgca agaaaatcg aagaaaaatt caaacgtgcg cagctgaccc tggacaactt   660
cctgaagcgt tttcgcaaca agctt                                         685
```

<210> SEQ ID NO 5
<211> LENGTH: 649
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 5

```
ggatccgatg cgcgttggca tcgatgaagc gggtcgcggt gccctgatcg gccgatgat    60
tgttgctggt gttgtaatct ctgacactaa actgaagttt ctgaaaggca tcggcgtaaa   120
agactctaaa cagctgactc gcgagcgtcg tgaaaagctg tttgatattg ttgctaacac   180
```

```
tgtggaagca ttcactgtcg ttaaagtttt cccttatgaa atcgacaact ataacctgaa    240
tgacctgacc tacgacgcag tttctaaaat catcctgagc ctgtctagct ttaacccaga    300
aattgtaacg gttgataaag tgggcgatga gaaaccggtt atcgaactga ttaataagct    360
gggctacaaa agcaacgtcg tacacaaggc agatgtactg tttgtagaag cctccgctgc    420
tagcatcatt gcgaaagtta ttcgtgataa ctacattgac gaactgaaac aagtatacgg    480
tgactttggt agcggttacc cagctgatcc tcgcactatc aaatggctga atctttcta    540 cgaaaagaat ccgaatccgc cgccaatcat tcgtcgttcc tggaagattc tgcgttctac    600
cgccccgctg tattacattt ccaaagaagg tcgccgtctg tggaagctt               649

<210> SEQ ID NO 6
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (12)..(19)
<223> OTHER INFORMATION: RNA RESIDUE

<400> SEQUENCE: 6
ctcgtgaggt gaugcaggag atgggaggcg                                     30

<210> SEQ ID NO 7
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 7
cgcctcccat ctcctgcatc acctcacgag                                     30

<210> SEQ ID NO 8
<211> LENGTH: 12
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 8
ctcgtgaggt ga                                                        12

<210> SEQ ID NO 9
<211> LENGTH: 12
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (1)..(1)
<223> OTHER INFORMATION: RNA RESIDUE

<400> SEQUENCE: 9
agatgggagg cg                                                        12

<210> SEQ ID NO 10
```

```
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: RNA RESIDUE

<400> SEQUENCE: 10
ctcgtgaggt gatgcaggag atgggaggcg                                    30

<210> SEQ ID NO 11
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 11
cgcctcccat ctcctgcatc acctcacgag                                    30

<210> SEQ ID NO 12
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: RNA RESIDUE

<400> SEQUENCE: 12
ctcgtgaggt gatggaggag atgggaggcg                                    30

<210> SEQ ID NO 13
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 13
cgcctcccat ctcctccatc acctcacgag                                    30

<210> SEQ ID NO 14
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: RNA RESIDUE

<400> SEQUENCE: 14
ctcgtgaggt gatgaaggag atgggaggcg                                    30

<210> SEQ ID NO 15
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 15
```
cgcctcccat ctccttcatc acctcacgag                                      30

<210> SEQ ID NO 16
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 16
ctcgtgaggt gatguaggag atgggaggcg                                      30

<210> SEQ ID NO 17
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 17
cgcctcccat ctcctacatc acctcacgag                                      30

<210> SEQ ID NO 18
<211> LENGTH: 14
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 18
ctcgtgaggt gatg                                                       14

<210> SEQ ID NO 19
<211> LENGTH: 16
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE

<400> SEQUENCE: 19
caggagatgg gaggcg                                                     16

<210> SEQ ID NO 20
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: 2'-LOCKED NUCLEIC ACID MODIFIED RESIDUE

<400> SEQUENCE: 20
ctcgtgaggt gatgcaggag atgggaggcg                                      30

<210> SEQ ID NO 21
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:

<221> NAME/KEY: misc_feature
<222> LOCATION: (15)..(15)
<223> OTHER INFORMATION: 2'-O-METHYL MODIFIED RESIDUE

<400> SEQUENCE: 21
ctcgtgaggt gatgcaggag atgggaggcg           30

<210> SEQ ID NO 22
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: 2'-FLUORO MODIFIED RESIDUE

<400> SEQUENCE: 22
ctcgtgaggt gatgcaggag atgggaggcg           30

<210> SEQ ID NO 23
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: 2'-FLUORO MODIFIED RESIDUE

<400> SEQUENCE: 23
ctcgtgaggt gatguaggag atgggaggcg           30

<210> SEQ ID NO 24
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(16)
<223> OTHER INFORMATION: 2'-FLUORO MODIFIED RESIDUE

<400> SEQUENCE: 24
ctcgtgaggt gatgcuggag atgggaggcg           30

<210> SEQ ID NO 25
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(15)
<223> OTHER INFORMATION: 2'-FLUORO MODIFIED RESIDUE
<220> FEATURE:
<221> NAME/KEY: misc_feature
<222> LOCATION: (14)..(15)
<223> OTHER INFORMATION: N is A, G, C, or T

<400> SEQUENCE: 25
ctcgtgaggt gatnnaggag atgggaggcg           30

<210> SEQ ID NO 26
<211> LENGTH: 30

```
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-FLUORO MODIFIED RESIDUE
<220> FEATURE:
<221> NAME/KEY: misc_feature
<222> LOCATION: (15)..(15)
<223> OTHER INFORMATION: 2'-LOCKED NUCLEIC ACID MODIFIED RESIDUE

<400> SEQUENCE: 26
ctcgtgaggt gatucaggag atgggaggcg                                    30

<210> SEQ ID NO 27
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-O-METHYL MODIFIED RESIDUE
<220> FEATURE:
<221> NAME/KEY: misc_feature
<222> LOCATION: (15)..(15)
<223> OTHER INFORMATION: 2'-FLUORO MODIFIED RESIDUE

<400> SEQUENCE: 27
ctcgtgaggt gatucaggag atgggaggcg                                    30

<210> SEQ ID NO 28
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-O-METHYL MODIFIED RESIDUE
<220> FEATURE:
<221> NAME/KEY: misc_feature
<222> LOCATION: (15)..(15)
<223> OTHER INFORMATION: 2'-LOCKED NUCLEIC ACID MODIFIED RESIDUE

<400> SEQUENCE: 28
ctcgtgaggt gatucaggag atgggaggcg                                    30

<210> SEQ ID NO 29
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-O-METHYL MODIFIED RESIDUE
<220> FEATURE:
<221> NAME/KEY: misc_feature
<222> LOCATION: (14)..(15)
<223> OTHER INFORMATION: 2'-O-METHYL MODIFIED RESIDUE
<220> FEATURE:
<221> NAME/KEY: misc_feature
<222> LOCATION: (15)..(15)
<223> OTHER INFORMATION: N is A, G, C or T

<400> SEQUENCE: 29
```
ctcgtgaggt gatunaggag atgggaggcg					30

<210> SEQ ID NO 30
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-AMINO MODIFIED RESIDUE
<220> FEATURE:
<221> NAME/KEY: misc_feature
<222> LOCATION: (15)..(15)
<223> OTHER INFORMATION: 2'-LOCKED NUCLEIC ACID MODIFIED RESIDUE

<400> SEQUENCE: 30
ctcgtgaggt gatucaggag atgggaggcg					30

<210> SEQ ID NO 31
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: 2'-FLUORO MODIFIED RESIDUE
<220> FEATURE:
<221> NAME/KEY: misc_feature
<222> LOCATION: (15)..(15)
<223> OTHER INFORMATION: N is A, G, C or T

<400> SEQUENCE: 31
ctcgtgaggt gatgnaggag atgggaggcg					30

<210> SEQ ID NO 32
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-O-METHYL MODIFIED RESIDUE
<220> FEATURE:
<221> NAME/KEY: misc_feature
<222> LOCATION: (15)..(15)
<223> OTHER INFORMATION: 2'-AMINO MODIFIED RESIDUE

<400> SEQUENCE: 32
ctcgtgaggt gatucaggag atgggaggcg					30

<210> SEQ ID NO 33
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-LOCKED NUCLEIC ACID MODIFIED RESIDUE
<220> FEATURE:
<221> NAME/KEY: misc_feature
<222> LOCATION: (15)..(15)
<223> OTHER INFORMATION: 2'-FLUORO MODIFIED RESIDUE

<400> SEQUENCE: 33
ctcgtgaggt gattcaggag atgggaggcg                                         30

<210> SEQ ID NO 34
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: 2'-AMINO MODIFIED RESIDUE

<400> SEQUENCE: 34
ctcgtgaggt gatguaggag atgggaggcg                                         30

<210> SEQ ID NO 35
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(15)
<223> OTHER INFORMATION: 2'-LOCKED NUCLEIC ACID MODIFIED RESIDUE

<400> SEQUENCE: 35
ctcgtgaggt gattcaggag atgggaggcg                                         30

<210> SEQ ID NO 36
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-FLUORO MODIFIED RESIDUE
<220> FEATURE:
<221> NAME/KEY: misc_feature
<222> LOCATION: (15)..(15)
<223> OTHER INFORMATION: 2'-O-METHYL MODIFIED RESIDUE

<400> SEQUENCE: 36
ctcgtgaggt gatucaggag atgggaggcg                                         30

<210> SEQ ID NO 37
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-LOCKED NUCLEIC ACID MODIFIED RESIDUE
<220> FEATURE:
<221> NAME/KEY: misc_feature
<222> LOCATION: (15)..(15)
<223> OTHER INFORMATION: 2'-O-METHYL MODIFIED RESIDUE

<400> SEQUENCE: 37
ctcgtgaggt gattcaggag atgggaggcg                                         30

<210> SEQ ID NO 38
<211> LENGTH: 30
<212> TYPE: DNA

```
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: N is A, G, C or U
<220> FEATURE:
<221> NAME/KEY: misc_feature
<222> LOCATION: (15)..(15)
<223> OTHER INFORMATION: RNA RESIDUE

<400> SEQUENCE: 38
ctcgtgaggt gatgnaggag atgggaggcg                                        30

<210> SEQ ID NO 39
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: 2'-FLUORO MODIFIED RESIDUE
<220> FEATURE:
<221> NAME/KEY: misc_feature
<222> LOCATION: (14)..(15)
<223> OTHER INFORMATION: RNA RESIDUE

<400> SEQUENCE: 39
ctcgtgaggt gatucaggag atgggaggcg                                        30

<210> SEQ ID NO 40
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(14)
<223> OTHER INFORMATION: RNA RESIDUE
<220> FEATURE:
<221> NAME/KEY: misc_feature
<222> LOCATION: (15)..(15)
<223> OTHER INFORMATION: 2'-FLUORO MODIFIED RESIDUE

<400> SEQUENCE: 40
ctcgtgaggt gatucaggag atgggaggcg                                        30

<210> SEQ ID NO 41
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(15)
<223> OTHER INFORMATION: 2'-FLUORO MODIFIED RESIDUE

<400> SEQUENCE: 41
ctcgtgaggt gatucaggag atgggaggcg                                        30

<210> SEQ ID NO 42
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
```

```
<220> FEATURE:
<221> NAME/KEY: misc_feature
<222> LOCATION: (14)..(15)
<223> OTHER INFORMATION: 2'-FLUORO MODIFIED RESIDUE

<400> SEQUENCE: 42
ctcgtgaggt gatuuaggag atgggaggcg                                    30

<210> SEQ ID NO 43
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE

<400> SEQUENCE: 43
ctgagcttca tgcctttact gtcctct                                       27

<210> SEQ ID NO 44
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE

<400> SEQUENCE: 44
ctgagcttca tgcctttact gtcctctc                                      28

<210> SEQ ID NO 45
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE

<400> SEQUENCE: 45
ctgagcttca tgcctttact gtcctctcc                                     29

<210> SEQ ID NO 46
<211> LENGTH: 31
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE

<400> SEQUENCE: 46
ctgagcttca tgcctttact gtcctctcct t                                  31

<210> SEQ ID NO 47
<211> LENGTH: 32
<212> TYPE: DNA
<213> ORGANISM: Artificial Sequence
<220> FEATURE:
```

```
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE

<400> SEQUENCE: 47
ctgagcttca tgcctttact gtcctctcct tc                                     32

<210> SEQ ID NO 48
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (2)..(2)
<223> OTHER INFORMATION: RNA RESIDUE

<400> SEQUENCE: 48
cucctgagct tcatgccttt actgtcc                                           27

<210> SEQ ID NO 49
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (3)..(3)
<223> OTHER INFORMATION: RNA RESIDUE

<400> SEQUENCE: 49
ccucctgagc ttcatgcctt tactgtcc                                          28

<210> SEQ ID NO 50
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (4)..(4)
<223> OTHER INFORMATION: RNA RESIDUE

<400> SEQUENCE: 50
tccucctgag cttcatgcct ttactgtcc                                         29

<210> SEQ ID NO 51
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (5)..(5)
<223> OTHER INFORMATION: RNA RESIDUE

<400> SEQUENCE: 51
ttccucctga gcttcatgcc tttactgtcc                                        30

<210> SEQ ID NO 52
<211> LENGTH: 31
<212> TYPE: DNA
<213> ORGANISM: Artificial Sequence
```

```
<220> FEATURE:
<223> OTHER INFORMATION: SYNTHETIC OLIGONUCLEOTIDE
<220> FEATURE:
<221> NAME/KEY: misc_feature
<222> LOCATION: (6)..(6)
<223> OTHER INFORMATION: RNA RESIDUE

<400> SEQUENCE: 52
cttccucctg agcttcatgc ctttactgtc c                            31

<210> SEQ ID NO 53
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (7)..(7)
<223> OTHER INFORMATION: RNA RESIDUE

<400> SEQUENCE: 53
tcttccucct gagcttcatg cctttactgt cc                           32

<210> SEQ ID NO 54
<211> LENGTH: 34
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (9)..(9)
<223> OTHER INFORMATION: RNA RESIDUE

<400> SEQUENCE: 54
tgtcttccuc ctgagcttca tgcctttact gtcc                         34

<210> SEQ ID NO 55
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (11)..(11)
<223> OTHER INFORMATION: RNA RESIDUE

<400> SEQUENCE: 55
cctgtcttcc ucctgagctt catgccttta ctgtcc                       36

<210> SEQ ID NO 56
<211> LENGTH: 38
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (13)..(13)
<223> OTHER INFORMATION: RNA RESIDUE

<400> SEQUENCE: 56
tacctgtctt ccucctgagc ttcatgcctt tactgtcc                     38

<210> SEQ ID NO 57
<211> LENGTH: 40
<212> TYPE: DNA
```

```
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: RNA RESIDUE

<400> SEQUENCE: 57
cttacctgtc ttccucctga gcttcatgcc tttactgtcc                            40

<210> SEQ ID NO 58
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (26)..(26)
<223> OTHER INFORMATION: 3'- SpC3 SPACER MODIFIED RESIDUE

<400> SEQUENCE: 58
ctgagcttca tgcctttact gtuccc                                           26

<210> SEQ ID NO 59
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (28)..(28)
<223> OTHER INFORMATION: 3'- SpC3 SPACER MODIFIED RESIDUE

<400> SEQUENCE: 59
ctgagcttca tgcctttact gtuccccg                                         28

<210> SEQ ID NO 60
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (29)..(29)
<223> OTHER INFORMATION: 3'- SpC3 SPACER MODIFIED RESIDUE
```

<400> SEQUENCE: 60
ctgagcttca tgcctttact gtuccccga                                      29

<210> SEQ ID NO 61
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-AMINO MODIFIED RESIDUE
<220> FEATURE:
<221> NAME/KEY: misc_feature
<222> LOCATION: (30)..(30)
<223> OTHER INFORMATION: 3'- SpC3 SPACER MODIFIED RESIDUE

<400> SEQUENCE: 61
ctgagcttca tgcctttact gtuccccgac                                     30

<210> SEQ ID NO 62
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (32)..(32)
<223> OTHER INFORMATION: 3'- SpC3 SPACER MODIFIED RESIDUE

<400> SEQUENCE: 62
ctgagcttca tgcctttact gtuccccgac ac                                  32

<210> SEQ ID NO 63
<211> LENGTH: 34
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (34)..(34)
<223> OTHER INFORMATION: 3'- SpC3 SPACER MODIFIED RESIDUE

<400> SEQUENCE: 63
ctgagcttca tgcctttact gtuccccgac acac                                34

<210> SEQ ID NO 64

```
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (36)..(36)
<223> OTHER INFORMATION: 3'- SpC3 SPACER MODIFIED RESIDUE

<400> SEQUENCE: 64
ctgagcttca tgcctttact gtuccccgac acacag                                    36

<210> SEQ ID NO 65
<211> LENGTH: 38
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (38)..(38)
<223> OTHER INFORMATION: 3'- SpC3 SPACER MODIFIED RESIDUE

<400> SEQUENCE: 65
ctgagcttca tgcctttact gtuccccgac acacagct                                  38

<210> SEQ ID NO 66
<211> LENGTH: 17
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 66
caggaaacag ctatgac                                                         17

<210> SEQ ID NO 67
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (18)..(18)
<223> OTHER INFORMATION: RNA RESIDUE
<220> FEATURE:
<221> NAME/KEY: misc_feature
<222> LOCATION: (22)..(22)
<223> OTHER INFORMATION: 3'- SpC3 SPACER MODIFIED RESIDUE

<400> SEQUENCE: 67
```
caggaaacag ctatgaccat ga                          22

<210> SEQ ID NO 68
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 68
agctctgccc aaagattacc ctg                         23

<210> SEQ ID NO 69
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 69
ctgagcttca tgcctttact gt                          22

<210> SEQ ID NO 70
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (26)..(26)
<223> OTHER INFORMATION: 2',3'-DIDEOXYCYTIDINE RESIDUE

<400> SEQUENCE: 70
ctgagcttca tgcctttact gtuccc                      26

<210> SEQ ID NO 71
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 2',3'-DIDEOXYCYTIDINE RESIDUE

<400> SEQUENCE: 71
ctgagcttca tgcctttact gtucccc                     27

<210> SEQ ID NO 72
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:

```
<221> NAME/KEY: misc_feature
<222> LOCATION: (28)..(28)
<223> OTHER INFORMATION: 2',3'-DIDEOXYCYTIDINE RESIDUE

<400> SEQUENCE: 72
ctgagcttca tgcctttact gtcccccc                                              28

<210> SEQ ID NO 73
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (29)..(29)
<223> OTHER INFORMATION: 2',3'-DIDEOXYCYTIDINE RESIDUE

<400> SEQUENCE: 73
ctgagcttca tgcctttact gtccccgc                                              29

<210> SEQ ID NO 74
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (30)..(30)
<223> OTHER INFORMATION: 2',3'-DIDEOXYCYTIDINE RESIDUE

<400> SEQUENCE: 74
ctgagcttca tgcctttact gtccccgac                                             30

<210> SEQ ID NO 75
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 75
agctctgccc aaagattacc ctgacagcta agtggcagtg gaagttggcc tcagaagtag           60
tggccagctg tgtgtcgggg aacagtaaag gcatgaagct cag                            103

<210> SEQ ID NO 76
<211> LENGTH: 16
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 76
acctcggcca agaccc                                                           16

<210> SEQ ID NO 77
<211> LENGTH: 22
<212> TYPE: DNA
<213> ORGANISM: Artificial Sequence
```

```
<220> FEATURE:
<223> OTHER INFORMATION: SYNTHETIC OLIGONUCLEOTIDE

<400> SEQUENCE: 77
ccttccttcc ttccttgctt cc                                              22

<210> SEQ ID NO 78
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (17)..(17)
<223> OTHER INFORMATION: RNA RESIDUE
<220> FEATURE:
<221> NAME/KEY: misc_feature
<222> LOCATION: (21)..(21)
<223> OTHER INFORMATION: 3'- SpC3 SPACER MODIFIED RESIDUE

<400> SEQUENCE: 78
acctcggcca agacccggca g                                               21

<210> SEQ ID NO 79
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 79
ccttccttcc ttccttgctt ccgtcct                                         27

<210> SEQ ID NO 80
<211> LENGTH: 320
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 80
acctcggcca agacccggca gggcagccgc tctggctcta gctccagctc cgggaccctc     60
tgggaccccc cgggacccat gtgacccagc ggccctcgc gctggagtgg aggatgcctt    120
ctacacgttg gtgcgtgaga tccggcagca caagctgcgg aagctgaacc ctcctgatga   180
gagtggcccc ggctgcatga gctgcaagtg tgtgctctcc tgacgcagca caagctcagg   240
acatggaggt gccggatgca ggaaggaggt gcagacggaa ggaggaggaa ggaaggacgg   300
aagcaaggaa ggaaggaagg                                               320

<210> SEQ ID NO 81
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 81
```

```
ccctgtttgc tgttttcct tctc                                              24
```

<210> SEQ ID NO 82
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 82

```
cgccgctgtt cctttttgaa g                                                21
```

<210> SEQ ID NO 83
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (25)..(25)
<223> OTHER INFORMATION: RNA RESIDUE
<220> FEATURE:
<221> NAME/KEY: misc_feature
<222> LOCATION: (29)..(29)
<223> OTHER INFORMATION: 3'- SpC3 SPACER MODIFIED RESIDUE

<400> SEQUENCE: 83

```
ccctgtttgc tgttttcct tctcuaaat                                         29
```

<210> SEQ ID NO 84
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (22)..(22)
<223> OTHER INFORMATION: RNA RESIDUE
<220> FEATURE:
<221> NAME/KEY: misc_feature
<222> LOCATION: (26)..(26)
<223> OTHER INFORMATION: 3'- SpC3 SPACER MODIFIED RESIDUE

<400> SEQUENCE: 84

```
cgccgctgtt cctttttgaa gccact                                           26
```

<210> SEQ ID NO 85
<211> LENGTH: 184
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 85

```
ccctgtttgc tgttttcct tctctaaatg aagagcaaac actgcaagaa gtgccaacag       60
gcttggattc catttctcat gactccgcca actgtgaatt gcctttgtta accccgtgca     120
gcaaggctgt gatgagtcaa gccttaaaag ctaccttcag tggcttcaaa aaggaacagc     180
ggcg                                                                   184
```

<210> SEQ ID NO 86
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE

```
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (23)..(23)
<223> OTHER INFORMATION: 2'-FLUORO MODIFIED RESIDUE

<400> SEQUENCE: 86
ctgagcttca tgcctttact gtu                                              23

<210> SEQ ID NO 87
<211> LENGTH: 34
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (23)..(24)
<223> OTHER INFORMATION: 2'-FLUORO MODIFIED RESIDUE
<220> FEATURE:
<221> NAME/KEY: misc_feature
<222> LOCATION: (34)..(34)
<223> OTHER INFORMATION: 3'- SpC3 SPACER MODIFIED RESIDUE

<400> SEQUENCE: 87
ctgagcttca tgcctttact gtuccccgac acac                                  34

<210> SEQ ID NO 88
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 88
ccctgtttgc tgttttttcct tctc                                            24

<210> SEQ ID NO 89
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (25)..(25)
<223> OTHER INFORMATION: RNA RESIDUE
<220> FEATURE:
<221> NAME/KEY: misc_feature
<222> LOCATION: (29)..(29)
<223> OTHER INFORMATION: 3'- SpC3 SPACER MODIFIED RESIDUE

<400> SEQUENCE: 89
ccctgtttgc tgttttttcct tctcuaaat                                       29

<210> SEQ ID NO 90
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 90
```
cgccgctgtt ccttttgaa g                                              21

<210> SEQ ID NO 91
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (22)..(22)
<223> OTHER INFORMATION: RNA RESIDUE
<220> FEATURE:
<221> NAME/KEY: misc_feature
<222> LOCATION: (26)..(26)
<223> OTHER INFORMATION: 3'- SpC3 SPACER MODIFIED RESIDUE

<400> SEQUENCE: 91
cgccgctgtt cctttttgaa gccact                                        26

<210> SEQ ID NO 92
<211> LENGTH: 16
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 92
acctcggcca agaccc                                                   16

<210> SEQ ID NO 93
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (17)..(17)
<223> OTHER INFORMATION: RNA RESIDUE
<220> FEATURE:
<221> NAME/KEY: misc_feature
<222> LOCATION: (21)..(21)
<223> OTHER INFORMATION: 3'- SpC3 SPACER MODIFIED RESIDUE

<400> SEQUENCE: 93
acctcggcca agacccggca g                                             21

<210> SEQ ID NO 94
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 94
ccttccttcc ttccttgctt cc                                            22

<210> SEQ ID NO 95
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature

```
<222> LOCATION: (27)..(27)
<223> OTHER INFORMATION: 3'- SpC3 SPACER MODIFIED RESIDU

<400> SEQUENCE: 95
ccttccttcc ttccttgctt ccgtcct                                   27

<210> SEQ ID NO 96
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 96
gcatttcttc catctccccc tc                                        22

<210> SEQ ID NO 97
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 97
gcatttcttc catctccccc tcugcct                                   27

<210> SEQ ID NO 98
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 98
tccgattctt gctccactgt tg                                        22

<210> SEQ ID NO 99
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 99
tccgattctt gctccactgt tggctga                                   27

<210> SEQ ID NO 100
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
```

```
<400> SEQUENCE: 100
cgcctcccat ctcctacatc acctcacgag                                      30

<210> SEQ ID NO 101
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 101
cgcctcccat ctccttcatc acctcacgag                                      30

<210> SEQ ID NO 102
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 102
cgcctcccat ctcctccatc acctcacgag                                      30

<210> SEQ ID NO 103
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 103
cgcctcccat ctcctgaatc acctcacgag                                      30

<210> SEQ ID NO 104
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 104
cgcctcccat ctcctgtatc acctcacgag                                      30

<210> SEQ ID NO 105
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 105
cgcctcccat ctcctggatc acctcacgag                                      30

<210> SEQ ID NO 106
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 106
cgcctcccat ctccagcatc acctcacgag                                      30

<210> SEQ ID NO 107
<211> LENGTH: 30
```

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 107
cgcctcccat ctcccgcatc acctcacgag                                              30

<210> SEQ ID NO 108
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 108
cgcctcccat ctccggcatc acctcacgag                                              30

<210> SEQ ID NO 109
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 109
ctgagcttca tgcctttact gtacccc                                                 27

<210> SEQ ID NO 110
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 110
ctgagcttca tgcctttact gaacccc                                                 27

<210> SEQ ID NO 111
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 111
```
ctgagcttca tgcctttact gcacccc                                               27

<210> SEQ ID NO 112
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 112
ctgagcttca tgcctttact ggacccc                                               27

<210> SEQ ID NO 113
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 113
ctgagcttca tgcctttact gtatccc                                               27

<210> SEQ ID NO 114
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 114
ctgagcttca tgcctttact gtagccc                                               27

<210> SEQ ID NO 115
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 115
ctgagcttca tgcctttact gtaaccc                                27

<210> SEQ ID NO 116
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 116
ctgagcttca tgcctttact gtucccc                                27

<210> SEQ ID NO 117
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 117
ctgagcttca tgcctttact gaucccc                                27

<210> SEQ ID NO 118
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 118
ctgagcttca tgcctttact gcucccc                                27

<210> SEQ ID NO 119
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

```
<400> SEQUENCE: 119
ctgagcttca tgcctttact ggucccc                                27

<210> SEQ ID NO 120
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 120
ctgagcttca tgcctttact gtutccc                                27

<210> SEQ ID NO 121
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 121
ctgagcttca tgcctttact gtugccc                                27

<210> SEQ ID NO 122
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 122
ctgagcttca tgcctttact gtuaccc                                27

<210> SEQ ID NO 123
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE
```

<400> SEQUENCE: 123
ctgagcttca tgcctttact gtccccc                                              27

<210> SEQ ID NO 124
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA SEQUENCE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 124
ctgagcttca tgcctttact gaccccc                                              27

<210> SEQ ID NO 125
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 125
ctgagcttca tgcctttact gcccccc                                              27

<210> SEQ ID NO 126
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 126
ctgagcttca tgcctttact ggccccc                                              27

<210> SEQ ID NO 127
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)

```
<223> OTHER INFORMATION: 3'- SpC3 SPACER MODIFIED RESIDUE

<400> SEQUENCE: 127
ctgagcttca tgcctttact gtctccc                                              27

<210> SEQ ID NO 128
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 128
ctgagcttca tgcctttact gtcgccc                                              27

<210> SEQ ID NO 129
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 129
ctgagcttca tgcctttact gtcaccc                                              27

<210> SEQ ID NO 130
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 130
ctgagcttca tgcctttact gtgcccc                                              27

<210> SEQ ID NO 131
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 131
ctgagcttca tgcctttact gagcccc                                              27
```

-continued

```
<210> SEQ ID NO 132
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 132
ctgagcttca tgcctttact gcgcccc                                         27

<210> SEQ ID NO 133
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 133
ctgagcttca tgcctttact gggcccc                                         27

<210> SEQ ID NO 134
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 134
ctgagcttca tgcctttact gtgtccc                                         27

<210> SEQ ID NO 135
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 135
ctgagcttca tgcctttact gtggccc                                         27
```

<210> SEQ ID NO 136
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 136
ctgagcttca tgcctttact gtgaccc                               27

<210> SEQ ID NO 137
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 137
agctctgccc aaagattacc ctgacagcta agtggcagtg gaagttggcc tcagaagtag    60
tggccagctg tgtgtcgggg tacagtaaag gcatgaagct cag                    103

<210> SEQ ID NO 138
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 138
agctctgccc aaagattacc ctgacagcta agtggcagtg gaagttggcc tcagaagtag    60
tggccagctg tgtgtcgggg tccagtaaag gcatgaagct cag                    103

<210> SEQ ID NO 139
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 139
agctctgccc aaagattacc ctgacagcta agtggcagtg gaagttggcc tcagaagtag    60
tggccagctg tgtgtcgggg ttcagtaaag gcatgaagct cag                    103

<210> SEQ ID NO 140
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 140
agctctgccc aaagattacc ctgacagcta agtggcagtg gaagttggcc tcagaagtag    60
tggccagctg tgtgtcgggg tgcagtaaag gcatgaagct cag                    103

<210> SEQ ID NO 141
<211> LENGTH: 103

```
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 141
agctctgccc aaagattacc ctgacagcta agtggcagtg gaagttggcc tcagaagtag    60
tggccagctg tgtgtcgggc tacagtaaag gcatgaagct cag                     103

<210> SEQ ID NO 142
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 142
agctctgccc aaagattacc ctgacagcta agtggcagtg gaagttggcc tcagaagtag    60
tggccagctg tgtgtcggga tacagtaaag gcatgaagct cag                     103

<210> SEQ ID NO 143
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 143
agctctgccc aaagattacc ctgacagcta agtggcagtg gaagttggcc tcagaagtag    60
tggccagctg tgtgtcgggt tacagtaaag gcatgaagct cag                     103

<210> SEQ ID NO 144
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 144
agctctgccc aaagattacc ctgacagcta agtggcagtg gaagttggcc tcagaagtag    60
tggccagctg tgtgtcgggg aacagtaaag gcatgaagct cag                     103

<210> SEQ ID NO 145
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 145
agctctgccc aaagattacc ctgacagcta agtggcagtg gaagttggcc tcagaagtag    60
tggccagctg tgtgtcgggg atcagtaaag gcatgaagct cag                     103

<210> SEQ ID NO 146
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 146
agctctgccc aaagattacc ctgacagcta agtggcagtg gaagttggcc tcagaagtag    60
```
tggccagctg tgtgtcgggg accagtaaag gcatgaagct cag                               103

<210> SEQ ID NO 147
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 147
agctctgccc aaagattacc ctgacagcta agtggcagtg gaagttggcc tcagaagtag            60
tggccagctg tgtgtcgggg agcagtaaag gcatgaagct cag                              103

<210> SEQ ID NO 148
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 148
agctctgccc aaagattacc ctgacagcta agtggcagtg gaagttggcc tcagaagtag            60
tggccagctg tgtgtcgggc aacagtaaag gcatgaagct cag                              103

<210> SEQ ID NO 149
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 149
agctctgccc aaagattacc ctgacagcta agtggcagtg gaagttggcc tcagaagtag            60
tggccagctg tgtgtcggga aacagtaaag gcatgaagct cag                              103

<210> SEQ ID NO 150
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 150
agctctgccc aaagattacc ctgacagcta agtggcagtg gaagttggcc tcagaagtag            60
tggccagctg tgtgtcgggt aacagtaaag gcatgaagct cag                              103

<210> SEQ ID NO 151
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 151
agctctgccc aaagattacc ctgacagcta agtggcagtg gaagttggcc tcagaagtag            60
tggccagctg tgtgtcgggg cacagtaaag gcatgaagct cag                              103

<210> SEQ ID NO 152
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 152
agctctgccc aaagattacc ctgacagcta agtggcagtg gaagttggcc tcagaagtag    60
tggccagctg tgtgtcgggg ctcagtaaag gcatgaagct cag    103

<210> SEQ ID NO 153
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 153
agctctgccc aaagattacc ctgacagcta agtggcagtg gaagttggcc tcagaagtag    60
tggccagctg tgtgtcgggg cccagtaaag gcatgaagct cag    103

<210> SEQ ID NO 154
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 154
agctctgccc aaagattacc ctgacagcta agtggcagtg gaagttggcc tcagaagtag    60
tggccagctg tgtgtcgggg cgcagtaaag gcatgaagct cag    103

<210> SEQ ID NO 155
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 155
agctctgccc aaagattacc ctgacagcta agtggcagtg gaagttggcc tcagaagtag    60
tggccagctg tgtgtcggga cacagtaaag gcatgaagct cag    103

<210> SEQ ID NO 156
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 156
agctctgccc aaagattacc ctgacagcta agtggcagtg gaagttggcc tcagaagtag    60
tggccagctg tgtgtcgggt cacagtaaag gcatgaagct cag    103

<210> SEQ ID NO 157
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 157
agctctgccc aaagattacc ctgacagcta agtggcagtg gaagttggcc tcagaagtag    60
tggccagctg tgtgtcgggc cacagtaaag gcatgaagct cag    103

<210> SEQ ID NO 158

```
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 158
agctctgccc aaagattacc ctgacagcta agtggcagtg gaagttggcc tcagaagtag      60
tggccagctg tgtgtcgggg gacagtaaag gcatgaagct cag                       103

<210> SEQ ID NO 159
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 159
agctctgccc aaagattacc ctgacagcta agtggcagtg gaagttggcc tcagaagtag      60
tggccagctg tgtgtcgggg gtcagtaaag gcatgaagct cag                       103

<210> SEQ ID NO 160
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 160
agctctgccc aaagattacc ctgacagcta agtggcagtg gaagttggcc tcagaagtag      60
tggccagctg tgtgtcgggg gccagtaaag gcatgaagct cag                       103

<210> SEQ ID NO 161
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 161
agctctgccc aaagattacc ctgacagcta agtggcagtg gaagttggcc tcagaagtag      60
tggccagctg tgtgtcgggg ggcagtaaag gcatgaagct cag                       103

<210> SEQ ID NO 162
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 162
agctctgccc aaagattacc ctgacagcta agtggcagtg gaagttggcc tcagaagtag      60
tggccagctg tgtgtcggga gacagtaaag gcatgaagct cag                       103

<210> SEQ ID NO 163
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 163
agctctgccc aaagattacc ctgacagcta agtggcagtg gaagttggcc tcagaagtag      60
```

```
tggccagctg tgtgtcgggt gacagtaaag gcatgaagct cag              103
```

<210> SEQ ID NO 164
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 164

```
agctctgccc aaagattacc ctgacagcta agtggcagtg aagttggcc tcagaagtag   60 tggccagctg tgtgtcgggc gacagtaaag gcatgaagct cag              103
```

<210> SEQ ID NO 165
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 165

```
cgcctcccat ctcctgaatc acctcacgag                              30
```

<210> SEQ ID NO 166
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 166

```
cgcctcccat ctcctcaatc acctcacgag                              30
```

<210> SEQ ID NO 167
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 167

```
cgcctcccat ctccttaatc acctcacgag                              30
```

<210> SEQ ID NO 168
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 168

```
cgcctcccat ctccttcatc acctcacgag                              30
```

<210> SEQ ID NO 169
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 169

```
cgcctcccat ctcctggatc acctcacgag                              30
```

<210> SEQ ID NO 170

```
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 170
cgcctcccat ctcctccatc acctcacgag                                    30

<210> SEQ ID NO 171
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 171
cgcctcccat ctcctttatc acctcacgag                                    30

<210> SEQ ID NO 172
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 172
cgcctcccat ctcctaactc acctcacgag                                    30

<210> SEQ ID NO 173
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 173
cgcctcccat ctcctaagtc acctcacgag                                    30

<210> SEQ ID NO 174
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 174
cgcctcccat ctcctaattc acctcacgag                                    30

<210> SEQ ID NO 175
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 175
cgcctcccat ctccgaaatc acctcacgag                                    30

<210> SEQ ID NO 176
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 176
```
cgcctcccat ctcccaaatc acctcacgag                                    30

<210> SEQ ID NO 177
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 177
cgcctcccat ctccaaaatc acctcacgag                                    30

<210> SEQ ID NO 178
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 178
cgcctcccat ctcctgtatc acctcacgag                                    30

<210> SEQ ID NO 179
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 179
cgcctcccat ctcctgcatc acctcacgag                                    30

<210> SEQ ID NO 180
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 180
cgcctcccat ctcctggatc acctcacgag                                    30

<210> SEQ ID NO 181
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 181
cgcctcccat ctccttaatc acctcacgag                                    30

<210> SEQ ID NO 182
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 182
cgcctcccat ctcctcaatc acctcacgag                                    30

<210> SEQ ID NO 183
<211> LENGTH: 30
<212> TYPE: DNA

```
<213> ORGANISM: Artificial Sequence
<220> FEATURE:
<223> OTHER INFORMATION: SYNTHETIC OLIGONUCLEOTIDE

<400> SEQUENCE: 183
cgcctcccat ctcctaaatc acctcacgag                                30

<210> SEQ ID NO 184
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 184
cgcctcccat ctcctctatc acctcacgag                                30

<210> SEQ ID NO 185
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 185
cgcctcccat ctcctgattc acctcacgag                                30

<210> SEQ ID NO 186
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 186
cgcctcccat ctcctgattc acctcacgag                                30

<210> SEQ ID NO 187
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 187
cgcctcccat ctcctgagtc acctcacgag                                30

<210> SEQ ID NO 188
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 188
cgcctcccat ctccagaatc acctcacgag                                30

<210> SEQ ID NO 189
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 189
cgcctcccat ctcccgaatc acctcacgag                                30
```

<210> SEQ ID NO 190
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 190
cgcctcccat ctccggaatc acctcacgag                               30

<210> SEQ ID NO 191
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (14)..(15)
<223> OTHER INFORMATION: RNA RESIDUE
<220> FEATURE:
<221> NAME/KEY: misc_feature
<222> LOCATION: (14)..(15)
<223> OTHER INFORMATION: 2'-FLUORO MODIFIED RESIDUE
<220> FEATURE:
<221> NAME/KEY: misc_feature
<222> LOCATION: (14)..(14)
<223> OTHER INFORMATION: 3'-PHOSPHOROTHIOATE MODIFIED RESIDUE

<400> SEQUENCE: 191
ctcgtgaggt gatucaggag atgggaggcg                               30

<210> SEQ ID NO 192
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: RNA RESIDUE
<220> FEATURE:
<221> NAME/KEY: misc_feature
<222> LOCATION: (15)..(15)
<223> OTHER INFORMATION: 3'-PHOSPHOROTHIOATE MODIFIED RESIDUE

<400> SEQUENCE: 192
ctcgtgaggt gattcaggag atgggaggcg                               30

<210> SEQ ID NO 193
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (27)..(27)
<223> OTHER INFORMATION: 3'-IBFQ MODIFIED RESIDUE

<400> SEQUENCE: 193
ttctgaggcc aactccactg ccactta                                  27

<210> SEQ ID NO 194

```
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (14)..(14)
<223> OTHER INFORMATION: RNA RESIDUE
<220> FEATURE:
<221> NAME/KEY: misc_feature
<222> LOCATION: (27)..(27)
<223> OTHER INFORMATION: 3'-IBFQ MODIFIED RESIDUE

<400> SEQUENCE: 194
ttctgaggcc aacuccactg ccactta                                           27

<210> SEQ ID NO 195
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 195
gcagaaagcg tctagccatg gcgtta                                            26

<210> SEQ ID NO 196
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 196
gcaagcaccc tatcaggcag taccacaa                                          28

<210> SEQ ID NO 197
<211> LENGTH: 31
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (27)..(27)
<223> OTHER INFORMATION: RNA RESIDUE
<220> FEATURE:
<221> NAME/KEY: misc_feature
<222> LOCATION: (31)..(31)
<223> OTHER INFORMATION: 3'- SpC3 SPACER MODIFIED RESIDUE

<400> SEQUENCE: 197
gcagaaagcg tctagccatg gcgttagtat g                                      31

<210> SEQ ID NO 198
<211> LENGTH: 33
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (29)..(29)
<223> OTHER INFORMATION: RNA RESIDUE
<220> FEATURE:
<221> NAME/KEY: misc_feature
```

```
<222> LOCATION: (33)..(33)
<223> OTHER INFORMATION: 3'- SpC3 SPACER MODIFIED RESIDUE

<400> SEQUENCE: 198
gcaagcaccc tatcaggcag taccacaagg cct                                 33

<210> SEQ ID NO 199
<211> LENGTH: 242
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 199
gcagaaagcg tctagccatg gcgttagtat gagtgtcgtg cagcctccag gacccccct     60 cccgggagag ccatagtggt ctgcggaacc ggtgagtaca ccggaattgc caggacgacc   120
gggtcctttc ttggactaaa cccgctcaat gcctggagat ttgggcgtgc cccgcgaga   180 ctgctagccg agtagtgttg ggtcgcgaaa ggccttgtgg tactgcctga tagggtgctt   240
gc                                                                  242

<210> SEQ ID NO 200
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (27)..(27)
<223> OTHER INFORMATION: 3'-IBFQ MODIFIED RESIDUE

<400> SEQUENCE: 200
ttctgaggcc aactccactg ccactta                                        27

<210> SEQ ID NO 201
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-IBFQ MODIFIED RESIDUE

<400> SEQUENCE: 201
ctgagcttca tgcctttact gtccccc                                        27

<210> SEQ ID NO 202
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
```

<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (28)..(28)
<223> OTHER INFORMATION: 3'-IBFQ MODIFIED RESIDUE

<400> SEQUENCE: 202
ctgagcttca tgcctttact gtccccg         28

<210> SEQ ID NO 203
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (29)..(29)
<223> OTHER INFORMATION: 3'-IBFQ MODIFIED RESIDUE

<400> SEQUENCE: 203
ctgagcttca tgcctttact gtccccga        29

<210> SEQ ID NO 204
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (28)..(28)
<223> OTHER INFORMATION: 3'-IBFQ MODIFIED RESIDUE

<400> SEQUENCE: 204
ctgagcttca tgcctttact gtccccc         28

<210> SEQ ID NO 205
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-IBFQ MODIFIED RESIDUE
<220> FEATURE:
<221> NAME/KEY: misc_feature
<222> LOCATION: (23)..(23)
<223> OTHER INFORMATION: RNA RESIDUE

```
<220> FEATURE:
<221> NAME/KEY: misc_feature
<222> LOCATION: (28)..(28)
<223> OTHER INFORMATION: 3'-FAM MODIFIED RESIDUE

<400> SEQUENCE: 205
ctgagcttca tgcctttact gtcccccc                                          28

<210> SEQ ID NO 206
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 206
agctctgccc aaagattacc ctgacagcta agtggcagtg gaagttggcc tcagaagtag       60
tggccagctg tgtgtggggg aacagtaaag gcatgaagct cag                         103

<210> SEQ ID NO 207
<211> LENGTH: 19
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 207
tcggattctc tgctctcct                                                    19

<210> SEQ ID NO 208
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 208
cctcatcttc ttgttcctcc                                                   20

<210> SEQ ID NO 209
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (22)..(22)
<223> OTHER INFORMATION: 3'-IBFQ MODIFIED RESIDUE

<400> SEQUENCE: 209
ccaccaccag cagcgactct ga                                                22

<210> SEQ ID NO 210
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
```

```
<221> NAME/KEY: misc_feature
<222> LOCATION: (20)..(20)
<223> OTHER INFORMATION: RNA RESIDUE
<220> FEATURE:
<221> NAME/KEY: misc_feature
<222> LOCATION: (25)..(25)
<223> OTHER INFORMATION: 3'-IBFQ MODIFIED RESIDUE

<400> SEQUENCE: 210
tcggattctc tgctctcctc gacgg                                              25

<210> SEQ ID NO 211
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (21)..(21)
<223> OTHER INFORMATION: RNA RESIDUE
<220> FEATURE:
<221> NAME/KEY: misc_feature
<222> LOCATION: (25)..(25)
<223> OTHER INFORMATION: 3'- SpC3 SPACER MODIFIED RESIDUE

<400> SEQUENCE: 211
cctcatcttc ttgttcctcc ucaga                                              25

<210> SEQ ID NO 212
<211> LENGTH: 18
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 212
tgtgcagaag gatggagt                                                      18

<210> SEQ ID NO 213
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 213
ctggtgcttc tctcaggata                                                    20

<210> SEQ ID NO 214
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-MAX MODIFIED RESIDUE
<220> FEATURE:
<221> NAME/KEY: misc_feature
<222> LOCATION: (25)..(25)
<223> OTHER INFORMATION: 3'-IBFQ MODIFIED RESIDUE

<400> SEQUENCE: 214
tggaatatgc cctgcgtaaa ctgga                                              25

<210> SEQ ID NO 215
<211> LENGTH: 24
```

```
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-MAX MODIFIED RESIDUE
<220> FEATURE:
<221> NAME/KEY: misc_feature
<222> LOCATION: (19)..(19)
<223> OTHER INFORMATION: RNA RESIDUE
<220> FEATURE:
<221> NAME/KEY: misc_feature
<222> LOCATION: (242)..(24)
<223> OTHER INFORMATION: 3'-IBFQ MODIFIED RESIDUE

<400> SEQUENCE: 215
tgtgcagaag gatggagtgg ggat                                          24

<210> SEQ ID NO 216
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (21)..(21)
<223> OTHER INFORMATION: RNA RESIDUE
<220> FEATURE:
<221> NAME/KEY: misc_feature
<222> LOCATION: (25)..(25)
<223> OTHER INFORMATION: 3'- SpC3 SPACER MODIFIED RESIDUE

<400> SEQUENCE: 216
ctggtgcttc tctcaggata aactc                                         25

<210> SEQ ID NO 217
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 217
ctcactctaa accccagcat t                                             21

<210> SEQ ID NO 218
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-IBFQ MODIFIED RESIDUE

<400> SEQUENCE: 218
cagcctcatc caaaagagga aacagga                                       27

<210> SEQ ID NO 219
```

-continued

```
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-HEX MODIFIED RESIDUE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'-IBFQ MODIFIED RESIDUE

<400> SEQUENCE: 219
cagcctcatc caaaagagga aauagga                                             27

<210> SEQ ID NO 220
<211> LENGTH: 85
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 220
cagcctcatc caaaagagga aacaggaccc cagagctccc tcagactcct caggaaacac        60
agacaatgct ggggtttaga gtgag                                               85

<210> SEQ ID NO 221
<211> LENGTH: 85
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 221
cagcctcatc caaaagagga aataggaccc cagagctccc tcagactcct caggaaacac        60
agacaatgct ggggtttaga gtgag                                               85

<210> SEQ ID NO 222
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 222
accaacgaca agaccaagag                                                     20

<210> SEQ ID NO 223
<211> LENGTH: 19
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 223
tcgtggaaag aagcagaca                                                      19

<210> SEQ ID NO 224
<211> LENGTH: 22
<212> TYPE: DNA
<213> ORGANISM: Artificial Sequence
```

```
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (22)..(22)
<223> OTHER INFORMATION: 3'-IBFQ MODIFIED RESIDUE

<400> SEQUENCE: 224
accaagacct tggcggacct tt                                              22

<210> SEQ ID NO 225
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-IBFQ MODIFIED RESIDUE
<220> FEATURE:
<221> NAME/KEY: misc_feature
<222> LOCATION: (6)..(6)
<223> OTHER INFORMATION: RNA RESIDUE
<220> FEATURE:
<221> NAME/KEY: modified_base
<222> LOCATION: (12)..(12)
<223> OTHER INFORMATION: FLUORESCEIN-MODIFIED BASE

<400> SEQUENCE: 225
tttccuggtt ttaccaacga caagaccaag ag                                   32

<210> SEQ ID NO 226
<211> LENGTH: 141
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 226
accaacgaca agaccaagag gcctgtggcg cttcgcacca agaccttggc ggacclttttg     60 gaatcattta ttgcagcgct gtacattgat aaggatttgg aatatgttca tactttcatg    120
aatgtctgct tctttccacg a                                              141

<210> SEQ ID NO 227
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (22)..(22)
<223> OTHER INFORMATION: 2'-O-METHYL MODIFIED RESIDUE
<220> FEATURE:
<221> NAME/KEY: misc_feature
<222> LOCATION: (22)..(22)
<223> OTHER INFORMATION: RNA RESIDUE

<400> SEQUENCE: 227
ctgagcttca tgcctttact gu                                              22

<210> SEQ ID NO 228
<211> LENGTH: 27
<212> TYPE: DNA
```

```
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (22)..(23)
<223> OTHER INFORMATION: RNA RESIDUE
<220> FEATURE:
<221> NAME/KEY: misc_feature
<222> LOCATION: (22)..(22)
<223> OTHER INFORMATION: 2'-O-METHYL MODIFIED RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 228
ctgagcttca tgcctttact guuccccc                                          27

<210> SEQ ID NO 229
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(24)
<223> OTHER INFORMATION: RNA RESIDUE
<220> FEATURE:
<221> NAME/KEY: misc_feature
<222> LOCATION: (24)..(24)
<223> OTHER INFORMATION: 2'-O-METHYL MODIFIED RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 229
ctgagcttca tgcctttact gtucccc                                           27

<210> SEQ ID NO 230
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 230
cagcctcatc caaaagagga aa                                                22

<210> SEQ ID NO 231
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 231
cagcctcatc caaaagagga aacagga                                           27

<210> SEQ ID NO 232
<211> LENGTH: 27
```

```
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 232
cagcctcatc caaaagagga aacaaga                                         27

<210> SEQ ID NO 233
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 233
cagcctcatc caaaagagga aacacga                                         27

<210> SEQ ID NO 234
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 234
cagcctcatc caaaagagga aacatga                                         27

<210> SEQ ID NO 235
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 235
cagcctcatc caaaagagga aauagga                                         27

<210> SEQ ID NO 236
```

-continued

```
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 236
cagcctcatc caaaagagga aauaaga                                          27

<210> SEQ ID NO 237
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 237
cagcctcatc caaaagagga aauacga                                          27

<210> SEQ ID NO 238
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 238
cagcctcatc caaaagagga aauatga                                          27

<210> SEQ ID NO 239
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (25)..(25)
<223> OTHER INFORMATION: 3'-PHOSPHOROTHIOATE MODIFIED RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 239
```
ctgagcttca tgcctttact gtccccc                                              27

<210> SEQ ID NO 240
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (26)..(26)
<223> OTHER INFORMATION: 3'-PHOSPHOROTHIOATE MODIFIED RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 240
ctgagcttca tgcctttact gtccccc                                              27

<210> SEQ ID NO 241
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(26)
<223> OTHER INFORMATION: 3'-PHOSPHOROTHIOATE MODIFIED RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 241
ctgagcttca tgcctttact gtccccc                                              27

<210> SEQ ID NO 242
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (24)..(24)
<223> OTHER INFORMATION: RNA RESIDUE
<220> FEATURE:
<221> NAME/KEY: misc_feature
<222> LOCATION: (28)..(28)
<223> OTHER INFORMATION: 3'- SpC3 SPACER MODIFIED RESIDUE

<400> SEQUENCE: 242
agctctgccc aaagattacc ctgacagc                                             28

<210> SEQ ID NO 243
<211> LENGTH: 103
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 243
agctctgccc aaagattacc ctgacagcta agtggcagtg aagttggcc tcagaagtag    60 tggccagctg tgtgtcgggg aacagtaaag gcatgaagct cag    103

<210> SEQ ID NO 244
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (24)..(24)
<223> OTHER INFORMATION: RNA RESIDUE
<220> FEATURE:
<221> NAME/KEY: misc_feature
<222> LOCATION: (28)..(28)
<223> OTHER INFORMATION: 3'- SpC3-SpC3 SPACER MODIFIED RESIDUE

<400> SEQUENCE: 244
agctctgccc aaagattacc ctgacagcag    30

<210> SEQ ID NO 245
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (24)..(24)
<223> OTHER INFORMATION: RNA RESIDUE
<220> FEATURE:
<221> NAME/KEY: misc_feature
<222> LOCATION: (28)..(28)
<223> OTHER INFORMATION: 3'- SpC3-SpC3 SPACER MODIFIED RESIDUE

<400> SEQUENCE: 245
agctctgccc aaagattacc ctgacagcag tg    32

<210> SEQ ID NO 246
<211> LENGTH: 33
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (24)..(24)
<223> OTHER INFORMATION: RNA RESIDUE
<220> FEATURE:
<221> NAME/KEY: misc_feature
<222> LOCATION: (28)..(28)
<223> OTHER INFORMATION: 3'- SpC3-SpC3 SPACER MODIFIED RESIDUE

<400> SEQUENCE: 246
agctctgccc aaagattacc ctgacagcag tgg    33

<210> SEQ ID NO 247
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3-SpC3 SPACER MODIFIED RESIDUE

<400> SEQUENCE: 247
cagcctcatc caaaagagga aacaggac                                           28

<210> SEQ ID NO 248
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3-SpC3 SPACER MODIFIED RESIDUE

<400> SEQUENCE: 248
cagcctcatc caaaagagga aacaggacc                                          29

<210> SEQ ID NO 249
<211> LENGTH: 31
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3-SpC3 SPACER MODIFIED RESIDUE

<400> SEQUENCE: 249
cagcctcatc caaaagagga aacaggacca g                                       31

<210> SEQ ID NO 250
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3-SpC3 SPACER MODIFIED RESIDUE

<400> SEQUENCE: 250
cagcctcatc caaaagagga aacaggacca ga                                      32

<210> SEQ ID NO 251
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:

```
<221> NAME/KEY: misc_feature
<222> LOCATION: (24)..(24)
<223> OTHER INFORMATION: 3'- SpC3-SpC3 SPACER MODIFIED RESIDUE

<400> SEQUENCE: 251
cagcctcatc caaaagagga aacaa                                              25

<210> SEQ ID NO 252
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(24)
<223> OTHER INFORMATION: 3'- SpC3-SpC3 SPACER MODIFIED RESIDUE

<400> SEQUENCE: 252
cagcctcatc caaaagagga aacaa                                              25

<210> SEQ ID NO 253
<211> LENGTH: 9
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (9)..(9)
<223> OTHER INFORMATION: 3'- TEXAS RED MODIFIED RESIDUE

<400> SEQUENCE: 253 cagctgaag                                                                 9

<210> SEQ ID NO 254
<211> LENGTH: 9
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (9)..(9)
<223> OTHER INFORMATION: 3'-CY5 MODIFIED RESIDUE

<400> SEQUENCE: 254 gagctgaag                                                                 9

<210> SEQ ID NO 255
<211> LENGTH: 9
```

```
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (9)..(9)
<223> OTHER INFORMATION: 3'- FAM MODIFIED RESIDUE

<400> SEQUENCE: 255 aagctgaag                                                          9

<210> SEQ ID NO 256
<211> LENGTH: 9
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (9)..(9)
<223> OTHER INFORMATION: 3'-CY3 MODIFIED RESIDUE

<400> SEQUENCE: 256 tagctgaag                                                          9

<210> SEQ ID NO 257
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 257
ccctgtttgc tgttttcct tctc                                         24

<210> SEQ ID NO 258
<211> LENGTH: 43
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 258
agtgtttgct cttcagctag agaaggaaaa acagcaaaca ggg                   43

<210> SEQ ID NO 259
<211> LENGTH: 43
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 259
```

```
agtgtttgct cttcagcttg agaaggaaaa acagcaaaca ggg                      43
```

<210> SEQ ID NO 260
<211> LENGTH: 8
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (6)..(8)
<223> OTHER INFORMATION: 5-NITROINDOLE RESIDUE
<220> FEATURE:
<221> NAME/KEY: misc_feature
<222> LOCATION: (8)..(8)
<223> OTHER INFORMATION: 3'-FAM MODIFIED RESIDUE

<400> SEQUENCE: 260

```
aagctnnn                                                              8
```

<210> SEQ ID NO 261
<211> LENGTH: 8
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (5)..(8)
<223> OTHER INFORMATION: 5-NITROINDOLE RESIDUE
<220> FEATURE:
<221> NAME/KEY: misc_feature
<222> LOCATION: (8)..(8)
<223> OTHER INFORMATION: 3'-FAM MODIFIED RESIDUE

<400> SEQUENCE: 261

```
aagcnnnn                                                              8
```

<210> SEQ ID NO 262
<211> LENGTH: 8
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (2)..(2)
<223> OTHER INFORMATION: N is A, G, C or U
<220> FEATURE:
<221> NAME/KEY: misc_feature

```
<222> LOCATION: (3)..(5)
<223> OTHER INFORMATION: N is A, G, C or T
<220> FEATURE:
<221> NAME/KEY: misc_feature
<222> LOCATION: (6)..(8)
<223> OTHER INFORMATION: N is 5-NITROINDOLE RESIDUE
<220> FEATURE:
<221> NAME/KEY: misc_feature
<222> LOCATION: (8)..(8)
<223> OTHER INFORMATION: 3'-FAM MODIFIED RESIDUE

<400> SEQUENCE: 262 annnnnnn                                                                        8

<210> SEQ ID NO 263
<211> LENGTH: 8
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA  RESIDUE
<220> FEATURE:
<221> NAME/KEY: misc_feature
<222> LOCATION: (2)..(2)
<223> OTHER INFORMATION: N is A, G, C or U
<220> FEATURE:
<221> NAME/KEY: misc_feature
<222> LOCATION: (3)..(5)
<223> OTHER INFORMATION: N is A, G, C or T
<220> FEATURE:
<221> NAME/KEY: misc_feature
<222> LOCATION: (6)..(8)
<223> OTHER INFORMATION: N is 5-NITROINDOLE  RESIDUE
<220> FEATURE:
<221> NAME/KEY: misc_feature
<222> LOCATION: (8)..(8)
<223> OTHER INFORMATION: 3'-CY3 MODIFIED RESIDUE

<400> SEQUENCE: 263 tnnnnnnn                                                                        8

<210> SEQ ID NO 264
<211> LENGTH: 8
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (2)..(2)
<223> OTHER INFORMATION: RNA RESIDUE
<220> FEATURE:
<221> NAME/KEY: misc_feature
<222> LOCATION: (2)..(2)
<223> OTHER INFORMATION: N is A, G, C or U
<220> FEATURE:
<221> NAME/KEY: misc_feature
<222> LOCATION: (3)..(5)
<223> OTHER INFORMATION: N is A, G, C or T
<220> FEATURE:
<221> NAME/KEY: misc_feature
<222> LOCATION: (6)..(8)
<223> OTHER INFORMATION: N is 5-NITROINDOLE RESIDUE
<220> FEATURE:
```

```
<221> NAME/KEY: misc_feature
<222> LOCATION: (8)..(8)
<223> OTHER INFORMATION: 3'-CY5 MODIFIED RESIDUE

<400> SEQUENCE: 264 gnnnnnnn                                                                       8

<210> SEQ ID NO 265
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-AMINO-C12 MODIFIED RESIDUE

<400> SEQUENCE: 265
gatttgtatt gattgagatt aaag                                                    24

<210> SEQ ID NO 266
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-AMINO-C12 MODIFIED RESIDUE

<400> SEQUENCE: 266
gattgtaaga tttgataaag tgta                                                    24

<210> SEQ ID NO 267
<211> LENGTH: 38
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-BIOTIN MODIFIED RESIDUE
<220> FEATURE:
<221> NAME/KEY: misc_feature
<222> LOCATION: (34)..(34)
<223> OTHER INFORMATION: RNA RESIDUE
<220> FEATURE:
<221> NAME/KEY: misc_feature
<222> LOCATION: (38)..(38)
<223> OTHER INFORMATION: 3'- SpC3 SPACER MODIFIED RESIDUE

<400> SEQUENCE: 267
caccatgctc acagcctcat ccaaaagagg aaacagga                                     38

<210> SEQ ID NO 268
<211> LENGTH: 38
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-BIOTIN MODIFIED RESIDUE
<220> FEATURE:
<221> NAME/KEY: misc_feature
<222> LOCATION: (34)..(34)
<223> OTHER INFORMATION: RNA RESIDUE
```

```
<220> FEATURE:
<221> NAME/KEY: misc_feature
<222> LOCATION: (38)..(38)
<223> OTHER INFORMATION: 3'- SpC3 SPACER MODIFIED RESIDUE

<400> SEQUENCE: 268
caccatgctc acagcctcat ccaaaagagg aaauagga                             38

<210> SEQ ID NO 269
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (36)..(36)
<223> OTHER INFORMATION: 3'- SpC3 SPACER MODIFIED RESIDUE

<400> SEQUENCE: 269
caggacccca gactttaatc tcaatcaata caaatc                               36

<210> SEQ ID NO 270
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE
<220> FEATURE:
<221> NAME/KEY: misc_feature
<222> LOCATION: (36)..(36)
<223> OTHER INFORMATION: 3'- SpC3 SPACER MODIFIED RESIDUE

<400> SEQUENCE: 270
taggacccca gatacacttt atcaaatctt acaatc                               36

<210> SEQ ID NO 271
<211> LENGTH: 98
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 271
cccagcattg tctgtgtttc ctgaggagtc tgagggagct ctggggtcct gtttcctctt     60
ttggatgagg ctgtgagcat ggtggattag agacagcc                             98

<210> SEQ ID NO 272
<211> LENGTH: 98
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 272
cccagcattg tctgtgtttc ctgaggagtc tgagggagct ctggggtcct atttcctctt     60
ttggatgagg ctgtgagcat ggtggattag agacagcc                             98

<210> SEQ ID NO 273
```

<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(24)
<223> OTHER INFORMATION: 3'- SpC3-SpC3 SPACER MODIFIED RESIDUE

<400> SEQUENCE: 273
cagcctcatc caaaagagga aauaa                                         25

<210> SEQ ID NO 274
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 274
ggctgtctct aatccaccat                                               20

<210> SEQ ID NO 275
<211> LENGTH: 19
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 275
gagggagctc tggggtcct                                                19

<210> SEQ ID NO 276
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (20)..(20)
<223> OTHER INFORMATION: RNA RESIDUE
<220> FEATURE:
<221> NAME/KEY: misc_feature
<222> LOCATION: (24)..(24)
<223> OTHER INFORMATION: 3'- SpC3 SPACER MODIFIED RESIDUE

<400> SEQUENCE: 276
gagggagctc tggggtcctg tttc                                          24

<210> SEQ ID NO 277
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (20)..(20)
<223> OTHER INFORMATION: RNA RESIDUE
<220> FEATURE:
<221> NAME/KEY: misc_feature
<222> LOCATION: (24)..(24)
<223> OTHER INFORMATION: 3'- SpC3 SPACER MODIFIED RESIDUE

<400> SEQUENCE: 277
gagggagctc tggggtccta tttc                                              24

<210> SEQ ID NO 278
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (20)..(20)
<223> OTHER INFORMATION: RNA RESIDUE
<220> FEATURE:
<221> NAME/KEY: misc_feature
<222> LOCATION: (21)..(21)
<223> OTHER INFORMATION: 3'- SpC3-SpC3 SPACER MODIFIED RESIDUE

<400> SEQUENCE: 278
gagggagctc tggggtcctg tc                                                22

<210> SEQ ID NO 279
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (20)..(20)
<223> OTHER INFORMATION: RNA RESIDUE
<220> FEATURE:
<221> NAME/KEY: misc_feature
<222> LOCATION: (21)..(21)
<223> OTHER INFORMATION: 3'- SpC3-SpC3 SPACER MODIFIED RESIDUE

<400> SEQUENCE: 279
gagggagctc tggggtccta tc                                                22

<210> SEQ ID NO 280
<211> LENGTH: 62
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (48)..(48)
<223> OTHER INFORMATION: Y is T or C.

<400> SEQUENCE: 280
ggctgtctct aatccaccat gctcacagcc tcatccaaaa gaggaaayag gacccagag       60 ct                                                                      62

<210> SEQ ID NO 281
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 281
cagcctcatc caaaagagga aa                                                22

<210> SEQ ID NO 282
<211> LENGTH: 23
<212> TYPE: DNA
<213> ORGANISM: Artificial Sequence
<220> FEATURE:

<223> OTHER INFORMATION: SYNTHETIC OLIGONUCLEOTIDE

<400> SEQUENCE: 282
cagcctcatc caaaagagga aat                                               23

<210> SEQ ID NO 283
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-FAM MODIFIED RESIDUE
<220> FEATURE:
<221> NAME/KEY: misc_feature
<222> LOCATION: (25)..(25)
<223> OTHER INFORMATION: 3'-IBFQ MODIFIED RESIDUE

<400> SEQUENCE: 283
ctcaggaaac acagacaatg ctggg                                             25

<210> SEQ ID NO 284
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (25)..(25)
<223> OTHER INFORMATION: 3'- SpC3-SpC3 SPACER MODIFIED RESIDUE

<400> SEQUENCE: 284
ctgagcttca tgcctttact gtucc                                             25

<210> SEQ ID NO 285
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3-SpC3 SPACER MODIFIED RESIDUE

<400> SEQUENCE: 285
cagcctcatc caaaagagga aauaggac                                          28

<210> SEQ ID NO 286
<211> LENGTH: 31
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 286
aaggacagga cagtaaaggc atgaagctca g                                      31

```
<210> SEQ ID NO 287
<211> LENGTH: 32
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 287
gaaggacagg acagtaaagg catgaagctc ag                              32

<210> SEQ ID NO 288
<211> LENGTH: 50
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 288
atgcaggaca gtaaaggcat gaagctcagg aggaagacag gtaagatgca           50

<210> SEQ ID NO 289
<211> LENGTH: 39
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 289
gagctgtgtg tcggggaaca gtaaaggcat gaagctcag                       39

<210> SEQ ID NO 290
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 290
ctgagcttca tgcctttact g                                          21

<210> SEQ ID NO 291
<211> LENGTH: 105
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 291
agctctgccc aaagattacc ctgacagcta agtggcagtg gaagttggcc tcagaagtag  60
tggccagctg tgtgtgtcgg ggaacagtaa aggcatgaag ctcag                105

<210> SEQ ID NO 292
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 292
```
ctgagcttca tgcctttact gtacccc                                                27

<210> SEQ ID NO 293
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 293
ggggtacagt aaaggcatga agctcag                                                27

<210> SEQ ID NO 294
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 294
ctgagcttca tgcctttact gtucccc                                                27

<210> SEQ ID NO 295
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 295
ggggaacagt aaaggcatga agctcag                                                27

<210> SEQ ID NO 296
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 296
ctgagcttca tgcctttact gtucccc                                                27

<210> SEQ ID NO 297
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 297
ggggaacagt aaaggcatga agctcag                                                27

```
<210> SEQ ID NO 298
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 298
cgcctcccat ctcctgaatc acctcacgag                                     30

<210> SEQ ID NO 299
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 299
cgcctcccat ctcctgaatc acctcacgag                                     30

<210> SEQ ID NO 300
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-PHOSPHATE MODIFIED RESIDUE

<400> SEQUENCE: 300
taggacccca gatacacttt atcaaatctt acaatc                              36

<210> SEQ ID NO 301
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (23)..(23)
<223> OTHER INFORMATION: RNA RESIDUE
<220> FEATURE:
<221> NAME/KEY: misc_feature
<222> LOCATION: (24)..(24)
<223> OTHER INFORMATION: 3'-PHOSPHOROTHIOATE MODIFIED RESIDUE
<220> FEATURE:
<221> NAME/KEY: misc_feature
<222> LOCATION: (27)..(27)
<223> OTHER INFORMATION: 3'- SpC3 SPACER MODIFIED RESIDUE

<400> SEQUENCE: 301
ctgagcttca tgcctttact gtccccc                                        27

<210> SEQ ID NO 302
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (15)..(15)
<223> OTHER INFORMATION: RNA RESIDUE
<220> FEATURE:
<221> NAME/KEY: misc_feature
<222> LOCATION: (15)..(15)
<223> OTHER INFORMATION: 3'-PHOSPHOROTHIOATE MODIFIED RESIDUE
```

<400> SEQUENCE: 302
ctcgtgaggt gattcaggag atgggaggcg    30

<210> SEQ ID NO 303
<211> LENGTH: 33
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (11)..(11)
<223> OTHER INFORMATION: R is A or G.

<400> SEQUENCE: 303
ctggggtcct rtttcctctt ttggatgagg ctg    33

<210> SEQ ID NO 304
<211> LENGTH: 11
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 304
actggacctg a    11

<210> SEQ ID NO 305
<211> LENGTH: 33
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE
<220> FEATURE:
<221> NAME/KEY: misc_feature
<222> LOCATION: (33)..(33)
<223> OTHER INFORMATION: 3'- CY3 MODIFIED RESIDUE

<400> SEQUENCE: 305
ccctgtttgc tgttttcct tctctagctg aag    33

<210> SEQ ID NO 306
<211> LENGTH: 25
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 306
ccctgtttgc tgttttcct tctct    25

<210> SEQ ID NO 307
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE
<220> FEATURE:
<221> NAME/KEY: misc_feature
<222> LOCATION: (29)..(29)
<223> OTHER INFORMATION: 3'- SpC3-SpC3-SpC3 SPACER-FAM MODIFIED RESIDUE

<400> SEQUENCE: 307
ccctgtttgc tgtttttcct tctcaagct                              29

<210> SEQ ID NO 308
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (26)..(26)
<223> OTHER INFORMATION: RNA RESIDUE
<220> FEATURE:
<221> NAME/KEY: misc_feature
<222> LOCATION: (28)..(28)
<223> OTHER INFORMATION: 3'-- SpC3-SpC3 SpC3-SpC3 SPACER-FAM MODIFIED
      RESIDUE

<400> SEQUENCE: 308
ccctgtttgc tgtttttcct tctcaagc                               28

<210> SEQ ID NO 309
<211> LENGTH: 66
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 309
gaggagtctg agggagctct ggggtcctat ttcctcttttt ggatgaggct gtgagcatgg    60
tggatt                                                               66

<210> SEQ ID NO 310
<211> LENGTH: 33
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-BIOTIN MODIFIED RESIDUE

<400> SEQUENCE: 310
caccatgctc acagcctcat ccaaaagagg aaa                         33

<210> SEQ ID NO 311
<211> LENGTH: 69
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-BIOTIN MODIFIED RESIDUE

<400> SEQUENCE: 311
caccatgctc acagcctcat ccaaaagagg aaataggacc ccagatacac tttatcaaat    60
cttacaatc                                                            69

<210> SEQ ID NO 312
<211> LENGTH: 24
<212> TYPE: DNA
<213> ORGANISM: Artificial Sequence

```
<220> FEATURE:
<223> OTHER INFORMATION: SYNTHETIC OLIGONUCLEOTIDE
<220> FEATURE:
<221> NAME/KEY: misc_feature
<222> LOCATION: (1)..(1)
<223> OTHER INFORMATION: 5'-LUMINEX BEAD MODIFIED RESIDUE

<400> SEQUENCE: 312
gattgtaaga tttgataaag tgta                                          24

<210> SEQ ID NO 313
<211> LENGTH: 6
<212> TYPE: PRT
<213> ORGANISM: Artificial Sequence
<220> FEATURE:
<223> OTHER INFORMATION: SYNTHETIC OLIGOPEPTIDE

<400> SEQUENCE: 313

His His His His His His
1               5
```